US011680101B2

(12) United States Patent
De Abreu Carvalho et al.

(10) Patent No.: US 11,680,101 B2
(45) Date of Patent: Jun. 20, 2023

(54) ANTI-OPG ANTIBODIES

(71) Applicant: Kymab Limited, Cambridge (GB)

(72) Inventors: Joana De Abreu Carvalho, Cambridge (GB); Steve Holmes, Cambridge (GB); Allan Lawrie, Yorkshire (GB)

(73) Assignee: KYMAB LIMITED, Cambridge (GB)

( * ) Notice: Subject to any disclaimer, the term of this patent is extended or adjusted under 35 U.S.C. 154(b) by 497 days.

(21) Appl. No.: 16/480,903

(22) PCT Filed: Jan. 26, 2018

(86) PCT No.: PCT/EP2018/052017
§ 371 (c)(1),
(2) Date: Jul. 25, 2019

(87) PCT Pub. No.: WO2018/138297
PCT Pub. Date: Aug. 2, 2018

(65) Prior Publication Data
US 2019/0352413 A1 Nov. 21, 2019

(30) Foreign Application Priority Data

Jan. 27, 2017 (GB) .................................. 1701416
Oct. 16, 2017 (GB) .................................. 1717006

(51) Int. Cl.
C07K 16/00 (2006.01)
A61K 39/00 (2006.01)
C07K 16/28 (2006.01)
A61P 9/12 (2006.01)
A61K 39/395 (2006.01)
A61K 45/06 (2006.01)

(52) U.S. Cl.
CPC ...... C07K 16/2878 (2013.01); A61K 39/3955 (2013.01); A61K 45/06 (2013.01); A61P 9/12 (2018.01); A61K 2039/505 (2013.01); C07K 2317/21 (2013.01); C07K 2317/31 (2013.01); C07K 2317/52 (2013.01); C07K 2317/565 (2013.01); C07K 2317/732 (2013.01); C07K 2317/734 (2013.01); C07K 2317/76 (2013.01); C07K 2317/92 (2013.01); C07K 2319/30 (2013.01)

(58) Field of Classification Search
None
See application file for complete search history.

(56) References Cited

U.S. PATENT DOCUMENTS

| 4,675,187 A | 6/1987 | Konishi et al. |
| 4,880,078 A | 11/1989 | Inoue et al. |
| 5,290,540 A | 3/1994 | Prince et al. |
| 5,843,678 A | 12/1998 | Boyle |
| 5,855,913 A | 1/1999 | Hanes et al. |
| 5,874,064 A | 2/1999 | Edwards et al. |
| 5,934,272 A | 8/1999 | Lloyd et al. |
| 5,985,309 A | 11/1999 | Edwards et al. |
| 5,985,320 A | 11/1999 | Edwards et al. |
| 6,015,938 A | 1/2000 | Boyle et al. |
| 6,019,968 A | 2/2000 | Platz et al. |
| 6,087,555 A | 7/2000 | Dunstan et al. |
| 6,284,728 B1 | 9/2001 | Boyle et al. |
| 6,284,740 B1 | 9/2001 | Boyle et al. |
| 6,316,408 B1 | 11/2001 | Boyle |
| 6,613,544 B1 | 9/2003 | Boyle et al. |
| 6,919,434 B1 | 7/2005 | Goto et al. |
| 9,334,327 B2 * | 5/2016 | Lawrie ................. A61K 31/713 |
| 9,334,331 B2 * | 5/2016 | Igawa ..................... C07K 16/36 |
| 10,421,807 B2 * | 9/2019 | Gonzales ................ A61P 17/08 |
| 11,168,128 B2 | 11/2021 | Corti et al. |
| 2003/0207827 A1 | 11/2003 | Boyle et al. |
| 2011/0311995 A1 | 12/2011 | Mouthon et al. |
| 2013/0129725 A1 * | 5/2013 | Fachin ....................... A61P 3/04 424/134.1 |
| 2013/0266974 A1 | 10/2013 | Heidecke et al. |
| 2014/0255404 A1 * | 9/2014 | Lawrie ............... G01N 33/6893 424/135.1 |
| 2017/0202918 A1 | 7/2017 | Yung et al. |
| 2018/0008672 A1 | 1/2018 | Chalothorn et al. |
| 2018/0057580 A1 | 3/2018 | Chalothorn et al. |
| 2018/0155434 A1 | 6/2018 | Ikutani et al. |

FOREIGN PATENT DOCUMENTS

| WO | WO 1992/019244 A2 | 11/1992 |
| WO | WO 97/23614 A1 | 7/1997 |
| WO | WO 1997/032572 A2 | 9/1997 |
| WO | WO 1997/044013 A1 | 11/1997 |
| WO | WO 1998/031346 A1 | 7/1998 |

(Continued)

OTHER PUBLICATIONS

Al Qaraghuli et al. Antibody-protein binding and conformational changes: identifying allosteric signaling pathways to engineer a better effector response. Nature Scientific Reports 10:13969 (2020). (Year: 2020).*
Tokuriki et al. Stability effects of mutations and protein evolvability, Current Opinion in Structural Biology, 19:596-604 (2009). (Year: 2009).*
Bhattacharya et al. Impact of genetic variation on three dimensional structure and function of proteins; PLOS One 12(3): e0171355, pp. 1-22 (Mar. 2017). (Year: 2017).*
Edwards et al. The remarkable flexibility of the human antibody repertoire; isolation of over one thousand different antibodies to a single protein, BLyS. Journal of Molecular Biology 334:103-118 (2003). (Year: 2003).*
Lloyd et al. Modelling the human immune response: performance of a 10(11) human antibody repertoire against a broad panel of therapeutically relevant antigens. Protein Engineering, Eng. Design & Selection 22(3): 159-168 (2009) (Year: 2009).*

(Continued)

Primary Examiner — Elizabeth C. Kemmerer
Assistant Examiner — Regina M DeBerry
(74) Attorney, Agent, or Firm — Lathrop GPM LLP; James H. Velema, Esq.

(57) ABSTRACT

The present invention relates to anti-OPG antibodies, and to methods of treatment, uses and pharmaceutical compositions comprising such antibodies, for example in the treatment and prevention of PAH.

17 Claims, 28 Drawing Sheets

Specification includes a Sequence Listing.

(56) References Cited

FOREIGN PATENT DOCUMENTS

| WO | WO 98/46751 A1 | 10/1998 |
|----|----|----|
| WO | WO 1999/066903 A2 | 12/1999 |
| WO | WO 01/83560 A1 | 11/2001 |
| WO | WO 2003/037913 A2 | 5/2003 |
| WO | WO 2003/038043 A2 | 5/2003 |
| WO | WO 2008/003103 A2 | 1/2008 |
| WO | WO 2011/004192 A1 | 1/2011 |
| WO | WO 2011/158009 A1 | 12/2011 |
| WO | WO 2013/06481 | 5/2013 |
| WO | WO 2013/061098 A2 | 5/2013 |
| WO | WO 2014/042981 A2 | 3/2014 |
| WO | WO 2014/174254 A2 | 10/2014 |
| WO | WO 2015/036737 A1 | 3/2015 |
| WO | WO 2015/103072 A1 | 7/2015 |
| WO | WO 2018/138297 A1 | 8/2018 |
| WO | WO 2021/158413 A1 | 8/2021 |

OTHER PUBLICATIONS

Goel et al. Plasticity within the antigen-combining site may manifest as molecular mimicry in the humoral immune response. J. Immunol. 173: 7358-7367 (2004). (Year: 2004).*
Khan et al. Adjustable locks and flexible keys: plasticity of epitope-paratope interactions in germline antibodies. J. Immunol. 192: 5398-5405 (2014) . (Year: 2014).*
Poosarla et al. Computational De Novo Design of Antibodies Binding to a Peptide With High Affinity. Biotechn. Bioeng. 114(6): 1331-1342 (2017). (Year: 2017).*
Rabia, et al. Understanding and overcoming trade-offs between antibody affinity, specificity, stability and solubility. Biochemical Engineering Journal 137:365-374 (2018) . (Year: 2018).*
Wakabayashi et al. Prevention of metastasis by a polyamine synthesis inhibitor in an animal bone metastasis model. Oncology, 59: 75-80 (2000). (Year: 2000).*
Turkbeyler et al. "Prolidase Could Aetas a Diagnosis and Treatment Mediator in Lung Fibrosis" Inflammation, vol. 35, No. 5:1747-1752 (Oct. 2012). (Year: 2012).*
Morel. Mouse models of human autoimmune diseases: Essential tools that require proper controls, Plos Biology vol. 2/No. 8:1061-1064 (Aug. 2004). (Year: 2004).*
Justice et al. Using the mouse to model human disease: increasing validity and reproducibility, Disease, Models & Mechanisms 9:101-103 (2016). (Year: 2016).*
Wong. Apoptosis in cancer: from pathogenesis to treatment. Journal of Experimental & Clinical Cancer Research vol. 30:87 (2011). (Year: 2011).*
Bucay et al., "Osteoprotegerin-deficient mice develop early onset osteoporosis and arterial calcification," Genes & Development 12:1260-1268 (1998).
Condliffe et al., "Serum osteoprotegerin is increased and predicts survival in idiopathic pulmonary arterial hypertension," Pulmonary Circulation 2(1):21-27 (2012).
Dawson et al., "TRAIL Deficient Mice Are Protected from Sugen/Hypoxia Induced Pulmonary Arterial Hypertension," Diseases 2:260-273 (2014).
Emery et al., "Osteoprotegerin Is a Receptor for the Cytotoxic Ligand TRAIL," Journal of Biological Chemistry 273(23):14363-14367 (1998).
Hameed et al., "Inhibition of tumor necrosis factor-related apoptosis-inducing ligand (TRAIL) reverses experimental pulmonary hypertension," Journal of Experimental Medicine 209(11):1919-1935 (2012).
Holen et al., "Role of osteoprotegerin (OPG) in cancer," Clinical Science 110: 279-291 (2006).
Humbert et al., "Treatment of Pulmonary Arterial Hypertension," New England Journal of Medicine 351(14):1425-1436 (2014).
Kook et al., "Mechanical Force Inhibits Osteoclastogenic Potential of Human Periodontal Ligament Fibroblasts Through OPG Production and ERK-Mediated Signaling," Journal of Cellular Biochemistry 106:1010-1019 (2009).

Lawrie et al., "Evidence of a Role for Osteoprotegerin in the Pathogenesis of Pulmonary Arterial Hypertension," American Journal of Pathology 172(1):256-264 (2008).
Moran et al., "Osteoprotegerin deficiency limits angiotensin II-induced aortic dilation and rupture in the apolipoprotein E-knockout mouse," Arteriosclerosis Thrombosis and Vascular Biology 34(12):2609-2616 (2014).
Simonet et al., "Osteoprotegerin: A Novel Secreted Protein Involved in the Regulation of Bone Density," Cell 89:309-319 (1997).
Alvarez et al., "Serum osteoprotegerin and its ligand in Paget's disease of bone: relationship to disease activity and effect of treatment with bisphosphonates", Arthritis Rheum., 2003, vol. 48, No. 3, pp. 824-8280.
Arnold et al., "A therapeutic antibody targeting osteoprotegerin attenuates severe experimental pulmonary arterial hypertension", Nat Commun., Nov. 15, 2019, 10: 5183.
Baud'Huin et al., "Osteoprotegerin: Multiple partners for multiple functions", Cytokine & Growth Factor Reviews, 2013, vol. 24, pp. 401-409.
Caidahl et al., "Osteoprotegerin: a biomarker with many faces", Arterioscler. Thromb. Vasc. Biol., 2010, vol. 30, No. 9, pp. 1684-1686.
Chemla, "New formula for predicting mean pulmonary artery pressure (mPAP) using systolic pulmonary artery pressure", Chest, 2004, vol. 126, pp. 1313-1317.
Chen et al., "Arthritogenic aiphaviruses: new insights into arthritis and bone pathology", Trends in Microbiology, Jan. 2015, vol. 23, No. 1, pp. 35-43.
Dall'Acqua, et al., "Properties of Human IgG1s Engineered for Enhanced Binding to the Neonatal Fc Receptor (FcRn)", Journal of Biology Chemistry, vol. 281, No. 33, pp. 23514-23524, Aug. 18, 2006.
De Ciriza et al., "Circulating osteoprotegerin is increased in the metabolic syndrome and associates with subclinical atherosclerosis and coronary arterial calcification", Clin Biochem., Dec. 2014, 47(18): 272-278.
De Ciriza et al., "Osteoprotegerin in Cardiometabolic Disorders", Int J Endocrinol., 2015, 2015: 564934.
Hurdman et al., "ASPIRE registry: assessing the Spectrum of Pulmonary hypertension Identified at a REferral centre", European Respiratory Journal, 2012, 39: 945-955.
Idusogie et al., Engineered antibodies with increased activity to recruit complement. J. Immunol., 2001,166: 2571-2575.
Igawa et al., "Antibody recycling by engineered pH-dependent antigen binding improves the duration of antigen neutralization", Nature Biotechnology, 2010, vol. 24, No. 11, pp. 1203-1207.
Jia, "Osteoprotegerin Disruption Attenuates HySu-Induced Pulmonary Hypertension Through Integrin avp3/FAK/AKT Pathway Suppression", Circulation: Cardiovascular Genetics, 2017, vol. 10, p. e001591.
Kabat et al., "Attempts to locate complementarity-determining residues In the variable positions of light and heavy chains", Ann. NY Acad. Sci., 1971, vol. 190, pp. 382-391.
Lazar et al., Engineered antibody Fc variants with enhanced effector function, Proc. Natl. Acad. Sci. U.S.A., Mar. 14, 2006; 103(11): 4005-4010.
Lee et al., Complete humanization of the mouse immunoglobulin loci enables efficient therapeutic antibody discovery, Nature Biotechnology, Mar. 16, 2014; 32: 356-363.
Malyankar et al., "Osteoprotegerin Is an alpha vbeta 3-induced, NF-kappa β-dependent Survival Factor for Endothelial Cells", Journal of Biological Chemistry, 2000, vol. 275, pp. 20959-20962.
Mathis, "Probing molecular interactions with homogeneous techniques based on rare earth cryptates and fluorescence energy transfer", Clinical Chemistry, 1995, vol. 41, No. 9, pp. 1391-1397.
Morrell et al., "Cellular and molecular basis of pulmonary arterial hypertension", J. Am. Coll. Cardiol., Jun. 30, 2009, 54(1 Suppl): S20-S31.
Natsume et al., 2008, Engineered Antibodies of IgG1/IgG3 Mixed Isotype with Enhanced Cytotoxic Activities, Cancer Res., 68: 3863-3872.

(56) References Cited

OTHER PUBLICATIONS

Natsume et al., Improving effector functions of antibodies for cancer treatment: Enhancing ADCC and CDC, 2009, Drug Des. Devel. Then, 3: 7-16.

NHS, Treatment—Pulmonary Hypertension, Jan. 23, 2020, obtained from url: https://www.nhs.uk/conditions/pulmonary-hypertension/treatment/.

O'Regan et al., "Marked elevation in plasma osteoprotegerin constitutes an early and consistent feature of cerebral malaria", Thrombosis and Haemostasis, 2016, vol. 115, No. 4, pp. 773-780.

Pulmonary Heart Association, "Scientists Hope to Expand Pre-Clinical Studies of Antibody to Protein Increased in PAH", Nov. 21, 2019, obtained from url: https://phassociation.org/scientists-hope-to-expand-pre-clinical-studies-of-antibody-to-protein-increased-in-pah/.

Rothman et al., "MicroRNA-140-5p and SMURF1 regulate pulmonary arterial hypertension", J. Clin. Invest, 2016, vol. 126, No. 7, pp. 2495-1508.

Said, "Moderate pulmonary arterial hypertension in male mice lacking the vasoactive intestinal peptide gene", Circulation, 2007, 115: 1260-1268.

Shields et al., High resolution mapping of the binding site on human IgG1 for Fc gamma RI, Fc gamma RII, Fc gamma RiII, and FcRn and design of IgG1 variants with improved binding to the Fc gamma R., J. Biol. Chem., Mar. 2, 2001, 276(9): 6591-6604.

Stępień et al., "Increased levels of bone remodeling biomarkers (osteoprotegerin and osteopontin) in hypertensive individuals", Clin Biochem., Jul. 2011, 44(10-11): 826-831.

Wu, "Receptor-mediated in vitro gene transformation by a soluble DNA carrier system", Journal of Biol. Chem., 1987, vol. 262, No. 10, pp. 4429-4432.

Zhou, "Development of a simple and rapid method for producing non-fucosylated oligomannose containing antibodies with increased effector function", Biotechnol. Bioeng., Feb. 15, 2008, vol. 99, No. 3, pp. 652-665.

Bharti et al., "Evidence that receptor activator of nuclear factor (NF)-kappaB ligand can suppress cell proliferation and induce apoptosis through activation of a NF-kappaB-independent and TRAF6-dependent mechanism", Journal of Biological Chemistry, Feb. 13, 2004, 279(7): 6065-6076.

Chen et al., "Arthritogenic alphaviral infection perturbs osteoblast function and triggers pathologic bone loss", PNAS, Apr. 22, 2014, 111(16): 6040-6045.

Chothia et al., "Canonical structures for the hypervariable regions of immunoglobulins", Journal of Molecular Biology, Aug. 20, 1987, 196(4): 901-917.

Digiammarino et al., "Design and generation of DVD-Ig™ molecules for dualspecific targeting", Methods in Molecular Biology, Jan. 1, 2012, 899: 145-156.

Gül et al., "Antibody-Dependent Phagocytosis of Tumor Cells by Macrophages: A Potent Effector Mechanism of Monoclonal Antibody Therapy of Cancer", Cancer Research, Dec. 1, 2015, 75(23): 5008-5013.

Hoeper et al., "Definitions and Diagnosis of Pulmonary Hypertension", Journal of the American College of Cardiology, Dec. 16, 2013, 62(25).

Hofbauer et al., "Osteoprotegerin: a link between osteoporosis and arterial calcification?", The Lancet, Jul. 28, 2001, 358(9278): 257-259.

International Preliminary Report on Patentability for PCT International Patent Application No. PCT/EP2018/052017, dated Mar. 29, 2018.

International Search Report and Written Opinion for PCT International Patent Application No. PCT/EP2018/052017, dated Jul. 30, 2019.

Kilpatrick et al., "Rapid Development of Affinity Matured Monoclonal Antibodies Using RIMMS", Hybridoma, Aug. 1997, 16(4): 381-389.

Lane et al., "Osteoprotegerin (OPG) activates integrin, focal adhesion kinase (FAK), and Akt signaling in ovarian cancer cells to attenuate TRAIL-induced apoptosis", Journal of Ovarian Research, Nov. 23, 2013, 6(1): 82.

Lawrie et al., "Evidence of a Role for Osteoprotegerin in the Pathogenesis of Pulmonary Arterial Hypertension", The American Journal of Pathology, Jan. 1, 2008, 172(1): 256-264.

Lefranc et al., "Unique database numbering system for immunogenetic analysis", Immunology Today, Nov. 1, 1997, 18(11): 509.

McMurtry et al., "Gene therapy targeting survivin selectively induces pulmonary vascular apoptosis and reverses pulmonary arterial hypertension", The Journal of Clinical Investigation, Jun. 2005, 115(6): 1479-1491.

Neiderfellner et al., "Epitope characterization and crystal structure of GA101 provide insights into the molecular basis for type I/II distinction of CD20 antibodies", Blood, Jul. 14, 2011, 118(2): 358-367.

Schermuly et al., "Mechanisms of disease: Pulmonary arterial hypertension", Nature Reviews Cardiology, Aug. 1, 2011, 8(8): 443-455.

Suckau et al., "Molecular epitope identification by limited proteolysis of an immobilized antigen-antibody complex and mass spectrometric peptide mapping", Biochemistry Naser, J. Immunol., Dec. 1, 1990, 87(141): 9848-9852.

Tuder et al., "Relevant Issues in the Pathology and Pathobiology of Pulmonary Hypertension", Journal of the American College of Cardiology, 62(25), (2013).

* cited by examiner

Scale bar = 20μm

ANTI-OPG ANTIBODIES

This application is a national stage filing under 35 U.S.C. § 371 of International Application No. PCT/EP2018/052017, filed Jan. 26, 2018, which claims priority of British Patent Application No. 1701416.8, filed Jan. 27, 2017, and British Patent Application No. 1717006.9, filed Oct. 16, 2017. The contents of these applications are each incorporated herein by reference.

FIELD OF THE INVENTION

Antibodies and methods of using the antibodies are described. In particular, antibodies that specifically bind human OPG antigen and their use in treating various diseases are described.

INTRODUCTION

Pulmonary Hypertension [PH] covers a variety of conditions that result in abnormally high blood pressure in the lungs. PH can be in the form of pulmonary arterial hypertension (PAH), which may be idiopathic (IPAH), hereditable (hPAH), drug and toxin induced or associated (APAH) with other conditions, such as connective tissue disease. PAH is a devastating disease driven by a sustained pulmonary specific vasoconstriction which triggers a progressive pulmonary vasculopathy that leads to right heart failure (Hoeper, M. M. et al, "Definitions and diagnosis of pulmonary hypertension", J. Am. Coll. Cardiol., 62, D42-50, 2013). Early endothelial cell dysfunction is thought to be an initiating event in the development of PAH. The subsequent proliferation of multiple resident cell types including pulmonary artery smooth muscle cells (PASMC) and endothelial cells (PAEC) is critical to the vascular remodelling. The infiltration of circulating inflammatory and mesenchymal cells is also thought to play an important role in regulating disease pathogenesis (Tuder, R. M. et al, "Relevant issues in the pathology and pathobiology of pulmonary hypertension", J. Am. Coll. Cardiol., 62, D4-12, 2013 and Morrell, N. W. et al, "Cellular and molecular basis of pulmonary arterial hypertension", J. Am. Coll. Cardiol., 54, 520-31, 2009). The prognosis for patients suffering from PH is poor and varies between disease groups. Current therapies for PAH, including calcium channel blockers, diuretics, enthothelin receptor antagonists, prostacyclins, soluble guanalate cyclase and phosphodiesterase inhibitors, are effective in relieving symptoms primarily through vasodilatory mechanisms, however their effects are often transient and importantly do not provide a cure to this fatal condition (Hurdman, J. et al., "ASPIRE registry: assessing the Spectrum of Pulmonary hypertension Identified at a REferral centre", European Respiratory Journal, 39, 945-955, 2012). The side effect profiles of these treatments can result in further reduced quality of life and unsatisfactory disease control. Therefore, there is a continuing need to identify new therapeutic agents that are effective at slowing progression and/or reversing PH and which do not have the problems associated with current treatments.

The molecular and cellular mechanisms involved in the pathogenesis of PAH are complex and involve cross-talk between several signalling pathways including the transforming growth factor beta (TGF-β)/bone morphogenetic protein (BMP) axis, growth factors (e.g. PDGF), vasoactive proteins (e.g. vasoactive intestinal peptide [Said, S. I. et al, "Moderate pulmonary arterial hypertension in male mice lacking the vasoactive intestinal peptide gene", Circulation, 115, 1260-1268, 2007] and endothelin-1 (ET-1) [Schermuly, R. T. et al, "Mechanisms of disease: pulmonary arterial hypertension", Nature Reviews: Cardiology, 8, 443-455, 2011]). It was recently reported that Tumor necrosis factor (TNF) related apoptosis inducing-ligand (TRAIL), a TNF-like cell surface molecule involved in the induction of apoptosis in cancer cells, is also a critical mediator of PAH in experimental models (Hameed, A. G. et al, "Inhibition of tumor necrosis factor-related apoptosis-inducing ligand (TRAIL) reverses experimental pulmonary hypertension", Journal of Experimental Medicine, 209, 1919-1935, 2012). It has also previously been reported that osteoprotegerin (OPG, tnfrsf11b), a secreted glycoprotein belonging to the tumor necrosis factor (TNF) receptor superfamily and capable of binding to TRAIL, is elevated in the lungs and sera from patients with idiopathic PAH (IPAH) (see Lawrie, A. et al, "Evidence of a role for osteoprotegerin in the pathogenesis of pulmonary arterial hypertension", Am. J. Pathol., 172, 256-264, 2008 and Condliffe, R. et al, "Serum osteoprotegerin is increased and predicts survival in idiopathic pulmonary arterial hypertension", Pulm. Circ., 2, 21-27, 2012), transiently in healthy volunteers exposed to altitude induce hypoxia (Supplemental FIG. 1), and can induce the proliferation and migration of PASMCs in vitro.

With regards to TRAIL, OPG is seen as one of a number of decoy receptors for TRAIL, acting to modulate its ability to target cancer cells. Furthermore, in addition to TRAIL, OPG is able to bind receptor activator of NFkB ligand [RANKL] which is expressed on osteoclast precursors, dendritic cells, T-cells and haematopoietic precursors. RANKL interacts with RANK on cell surfaces to stimulate the production and activity of osteoclasts, the principal cells involved in bone turnover. The interaction of OPG with RANKL inhibits RANKL's ability to bind to RANK and stimulate osteoclasts and it is this activity of OPG that confers its ability to reduce bone loss. Therefore, OPG might be expected to enhance cancer cell survival if present at a relevant site and its ability to increase the survival of tumour cells has been documented.

The discovery of the RANKL/RANK/OPG system in the mid 1990s, and its association in the regulation of bone resorption has led to major advances in the understanding of how bone modeling and remodeling are regulated. It was previously known that osteoblastic stromal cells regulated osteoclast formation, but it had not been anticipated that they would do this through expression of RANKL and OPG, or that these cytokines and signalling through receptor activator of RANK would have extensive functions beyond regulation of bone remodeling. RANK/RANKL signaling regulates osteoclast formation, activation and survival in normal bone modeling and remodeling and in a variety of pathologic conditions characterized by increased bone turnover. OPG protects bone from excessive resorption by binding to RANKL and preventing it from binding to RANK. Thus, the relative concentration of RANKL and OPG in bone is a major determinant of bone mass and strength, see Boyce and Xing, "Functions of RANKL/RANK/OPG in bone modelling and remodelling", Arch Biochem Biophys., 2008, 473, 139-146.

The activity of OPG in bone metabolism is well known in the art. U.S. Pat. No. 6,015,938 discloses a transgenic non-human animal that expresses OPG and its use in analysing the involvement of OPG in bone metabolism. U.S. Pat. No. 6,284,740 discloses a gene therapy method for increasing the amount of OPG produced by a mammal thereby increasing bone density. U.S. Pat. Nos. 6,284,728 and 6,613,544 disclose and claims an OPG polypeptide and a nucleic acid molecule that encodes OPG respectively. U.S. Pat. No. 6,316,408 discloses a method to treat or prevent a bone disease by administration of an osteoclast activation and differentiation factor Transgenic mice lacking expression of OPG are described in U.S. Pat. No. 6,087,555. In all cases OPG and its involvement in bone metabolism is taught. WO2013/064810 discloses polyclonal goat anti-mouse OPG antibodies for use in preventing the development of PAH in the monocrotaline rat model and their use in treating established PAH in a mouse model.

SUMMARY OF THE INVENTION

In a first configuration, there is provided an antibody or fragment thereof which specifically binds to human osteoprotegerin (hOPG) (Seq ID No:1) and inhibits (e.g. neutralises) the interaction of hOPG with human RANKL (hRANKL) and/or human TRAIL (hTRAIL).

In a second configuration, there is provided an antibody or fragment thereof which specifically binds to hOPG and which comprises a $V_H$ domain comprising a CDRH3 of from 10 to 23 amino acids and which is derived from the recombination of a human $V_H$ gene segment, a human D gene segment and a human $J_H$ gene segment, wherein the human $J_H$ gene segment is IGHJ4 (e.g. IGHJ4*02).

In a third configuration, there is provided a multispecific (e.g. bispecific) antibody or fusion protein comprising an antibody or fragment thereof as defined elsewhere herein.

In a fourth configuration, there is provided an antibody or fragment thereof as defined elsewhere herein for use in treating or preventing a hOPG-mediated disease or condition.

In a fifth configuration, there is provided the use of an antibody or fragment thereof as defined elsewhere herein in the manufacture of a medicament for administration to a human for treating or preventing a hOPG-mediated disease or condition.

In a sixth configuration, there is provided a method of treating or preventing a hOPG-mediated disease or condition in a human, comprising administering to said human a therapeutically effective amount of an antibody or fragment thereof as defined in any one of claims 1 to 52, wherein the hOPG-mediated disease or condition is thereby treated or prevented.

In a seventh configuration, there is provided a pharmaceutical composition comprising an antibody or fragment thereof as defined elsewhere herein and a pharmaceutically acceptable excipient, diluent or carrier.

In an eighth configuration, there is provided a method of modulating TRAIL/OPG and/or RANKL/OPG interaction in a patient, comprising administering an effective amount of an antibody or fragment as defined elsewhere herein.

In a ninth configuration, there is provided a method of inhibiting OPG activity in a patient, comprising administering an effective amount of an antibody or fragment as defined elsewhere herein.

In a tenth configuration, there is provided a nucleic acid that encodes the CDRH3 of an antibody or fragment thereof as defined elsewhere herein.

In an eleventh configuration, there is provided a vector comprising the nucleic acid as defined elsewhere herein.

In a twelfth configuration, there is provided a host comprising the nucleic acid as defined elsewhere herein.

DESCRIPTION OF THE FIGURES

(FIG. 2) Bar graph shows the increase in the right ventricular systolic pressure (RVSP) from baseline (week 0) at 2 and 3 weeks post treatment with antibodies Ky3 (15F11) or control human IgG4-PE.

Figure 4A:
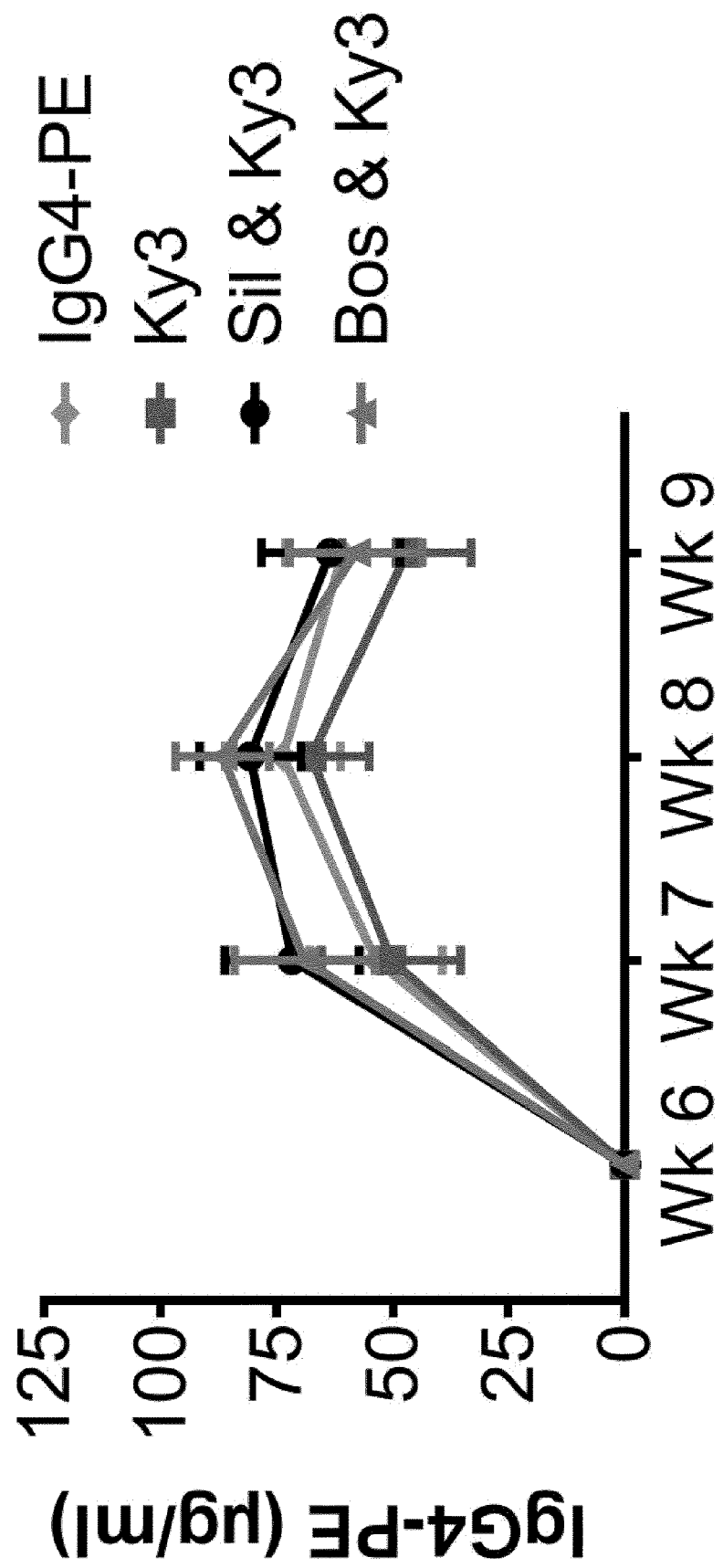
FIG. 4: Therapeutic delivery of monoclonal human anti-human OPG attenuates development of established severe SuHx PAH in rats. Plasma concentrations of antibody and control human IgG4-PE from Batch 1, 2 and 3 (FIG. 4a). Bar graphs show Pulmonary Artery Acceleration Time (PA AT, FIG. 4b), cardiac output (CO, FIG. 4c), right ventricular systolic pressure (RVSP, FIG. 4d), right ventricular arterial elastance (RV Ea, FIG. 4e), right ventricular hypertrophy (RVH, FIG. 4f), estimated pulmonary vascular resistance (ePVRi, FIG. 4g), left ventricular end-systolic pressure (LVESP, FIG. 4h); data are from Batches 1, 2 and 3. Bar graphs show the degree of medial wall thickness as a ratio of total vessel size (Media/CSA) (FIG. 4i) and the relative percentage of muscularised small pulmonary arteries and arterioles in <50 μm vessels (FIG. 4j); data from Batches 1, 2 and 3. Currently, only 2 of 8 Bosentan and Ky3 (15F11) combination & only 2 of 8 Bosentan monotherapy-treated rats have been scored for pulmonary vascular remodelling (FIGS. 4i & 4j). Representative photomicrographs of serial lung sections (FIG. 4k and FIG. 4k-1). Sections were stained for Alcian Blue Elastic van Gieson (ABEVG, FIG. 4k), immunostained for α-smooth muscle actin (α-SMA, FIG.
Figure 4B:
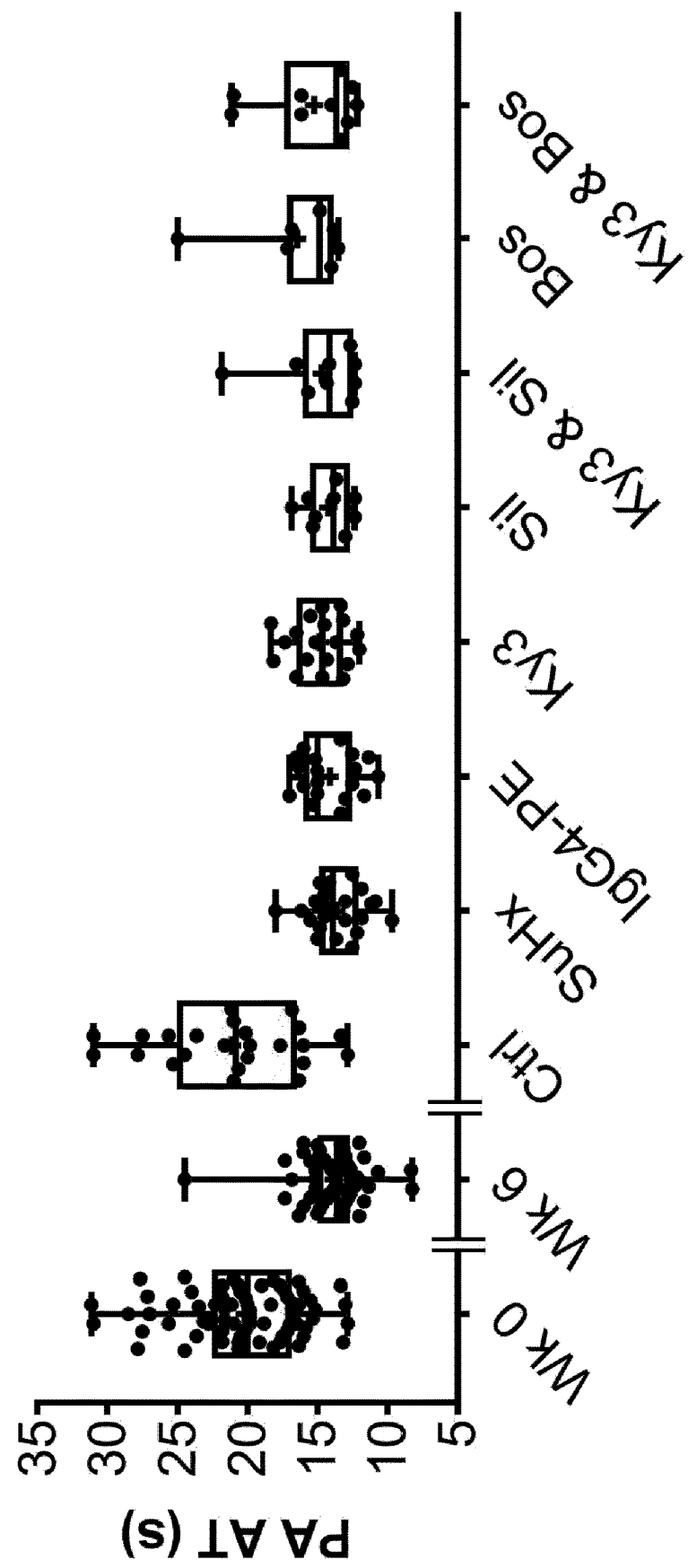
Figure 4C:
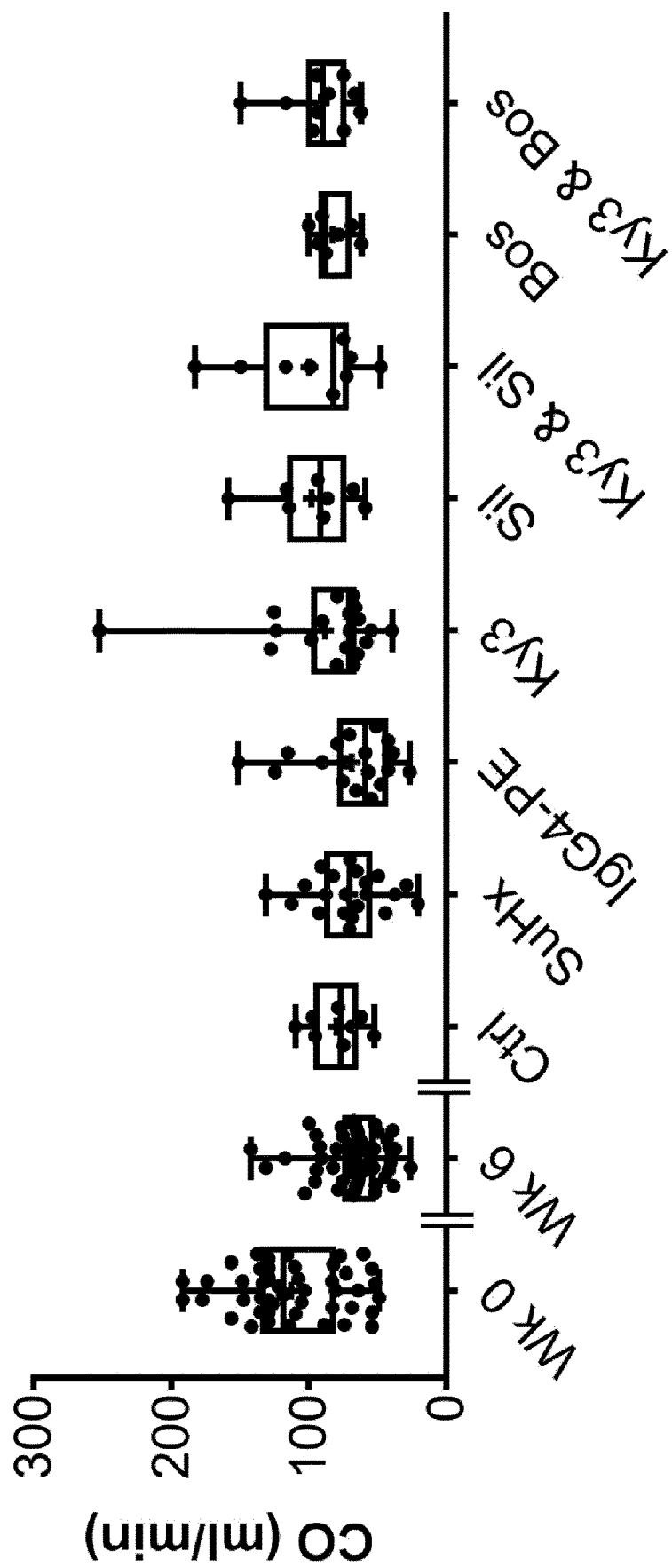
Figure 4D:
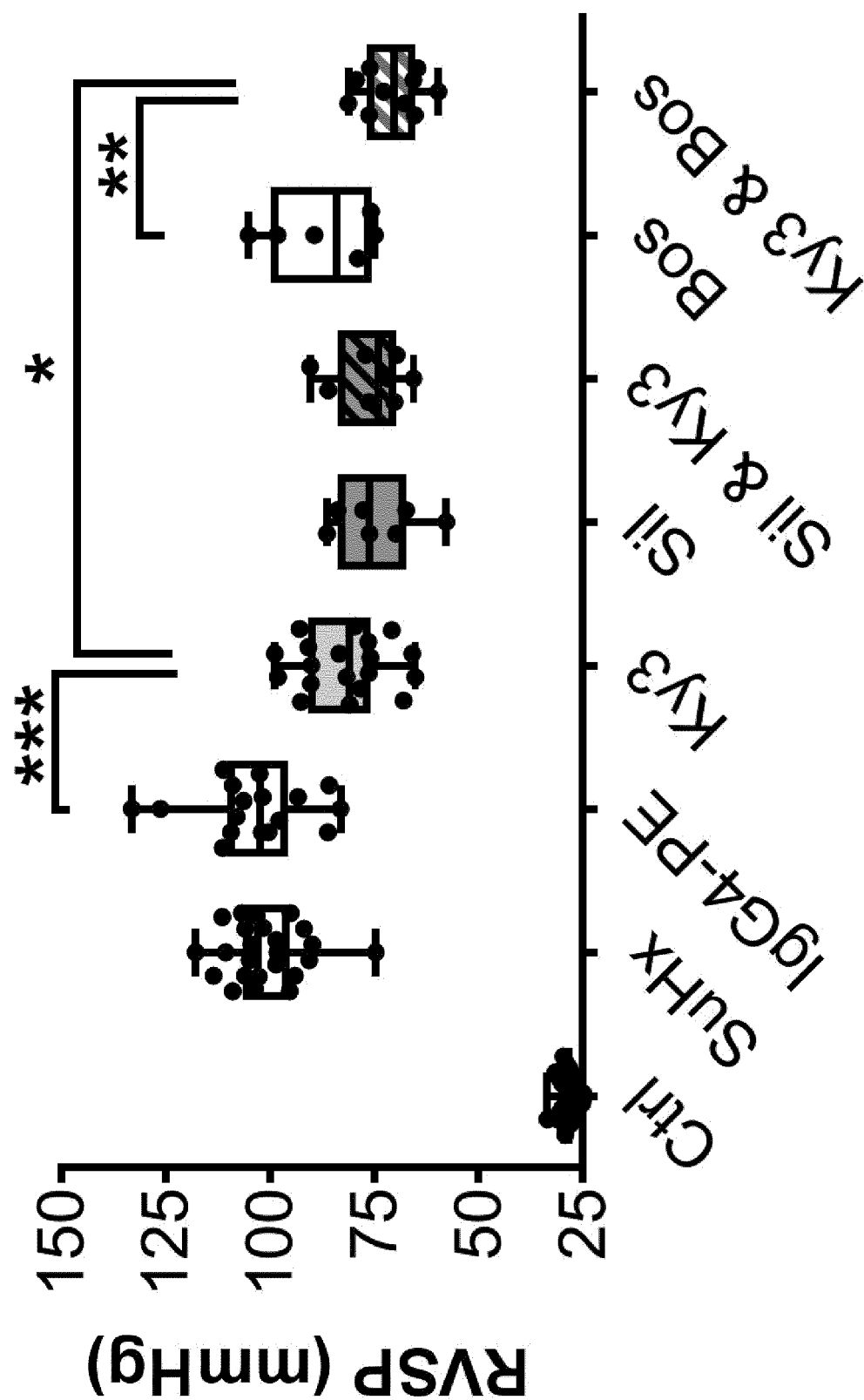
Figure 4E:
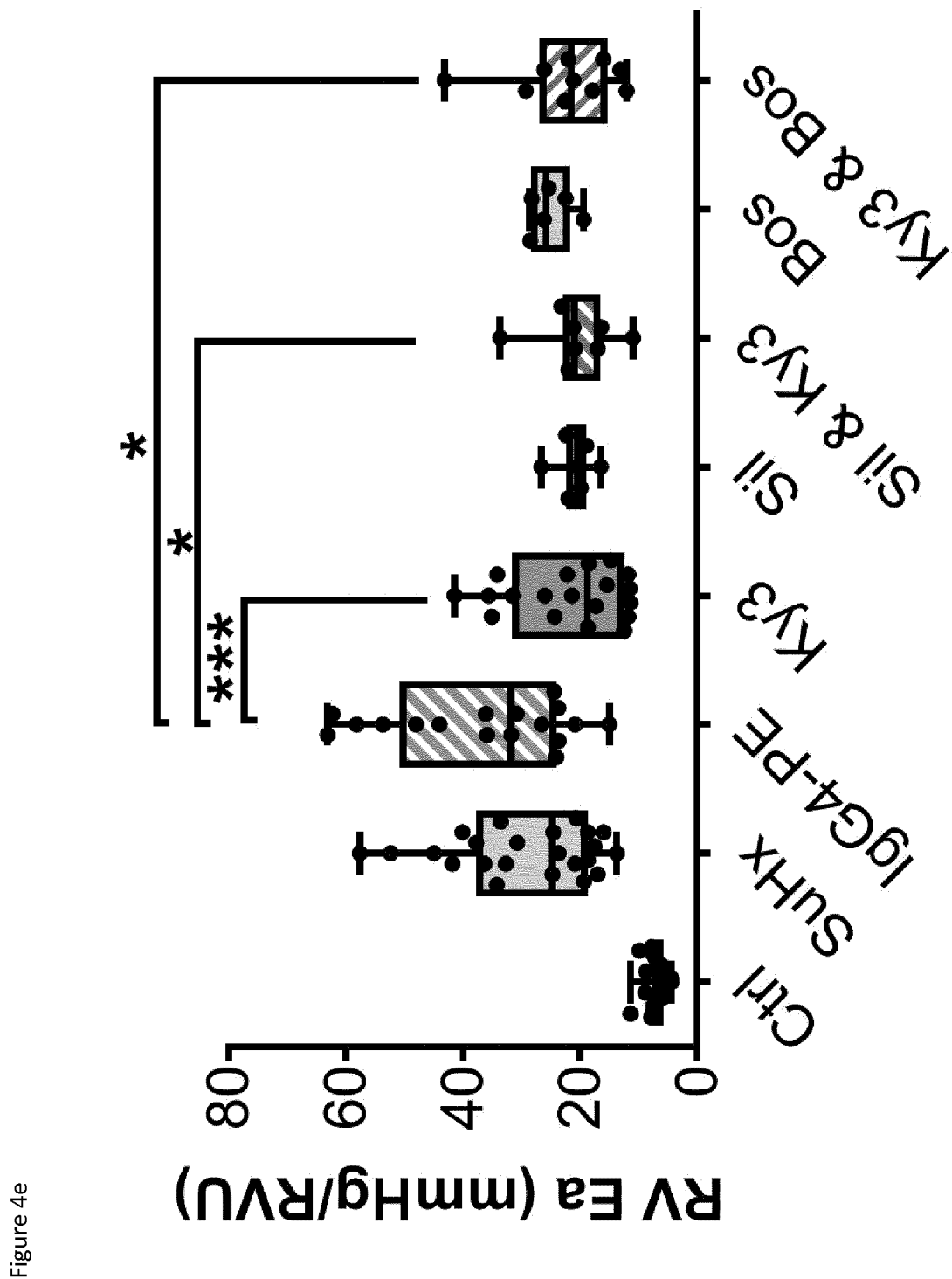
Figure 4F:
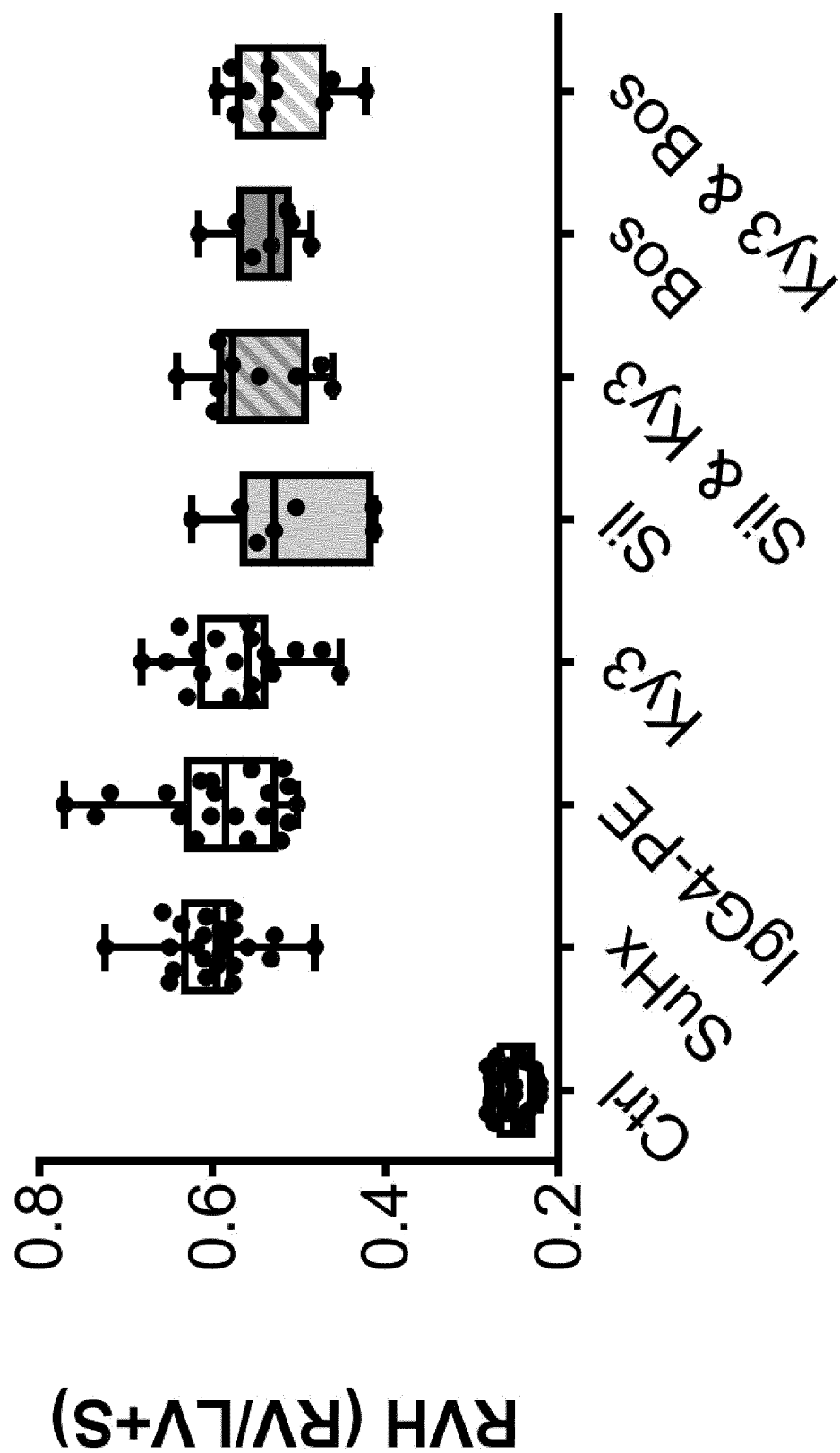
Figure 4G:
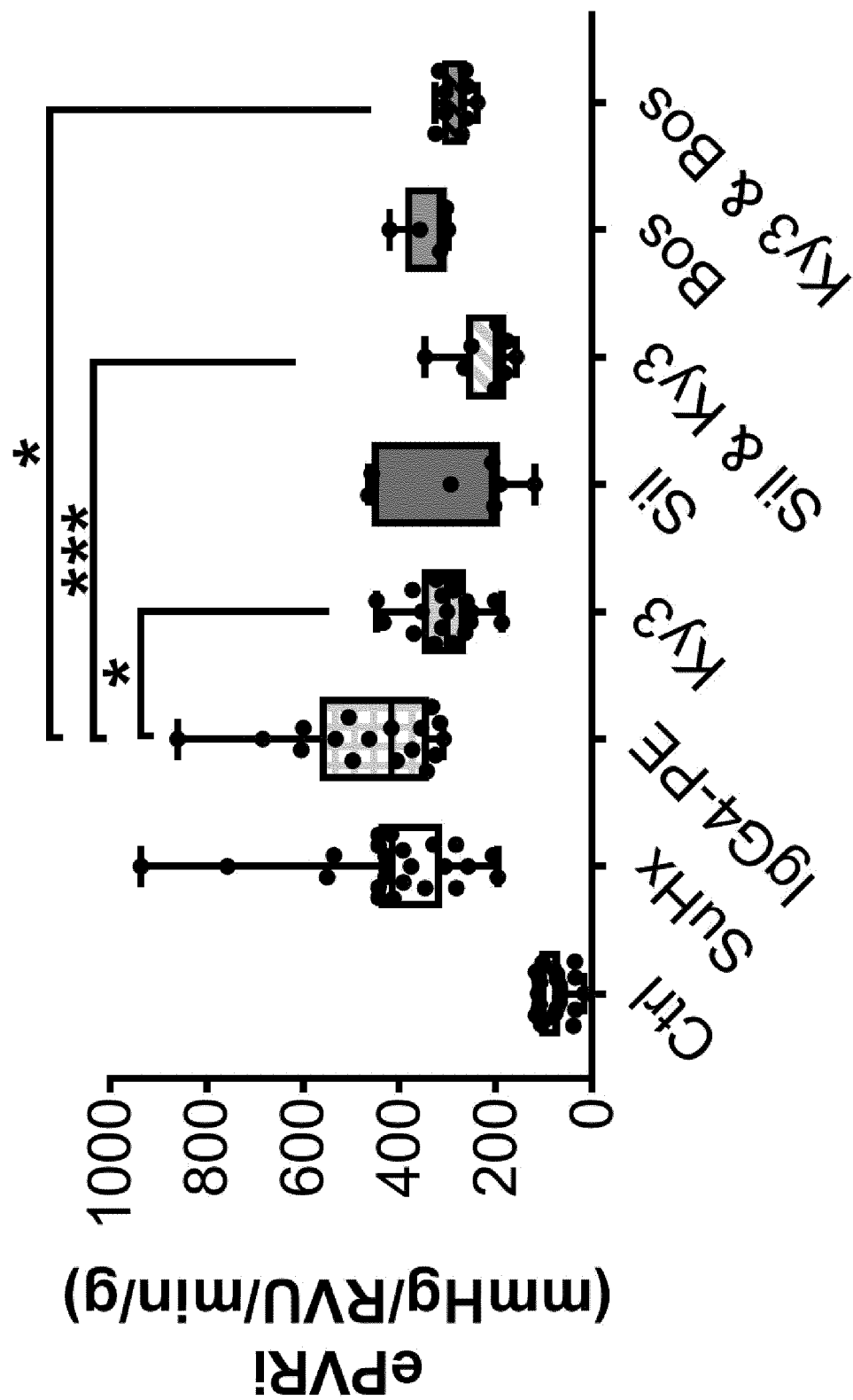
Figure 4H:
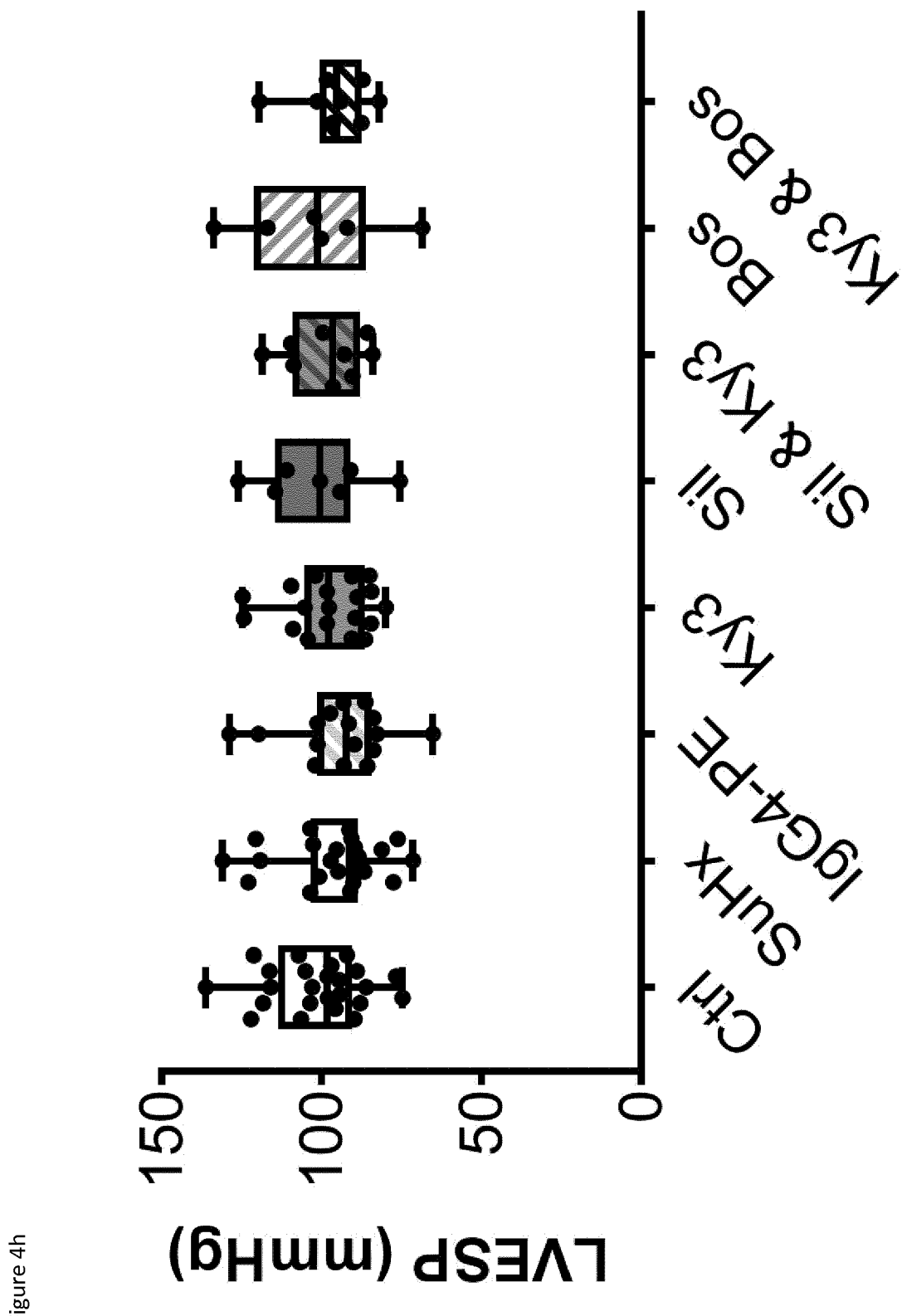
Figure 4I:
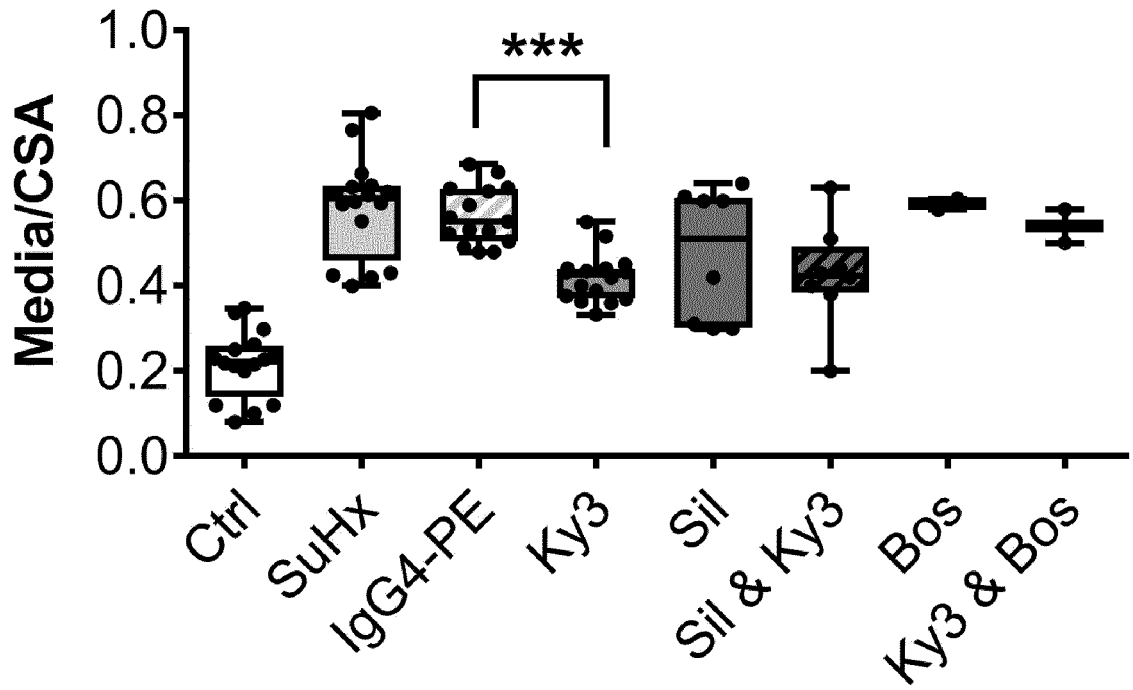
Figure 4J:
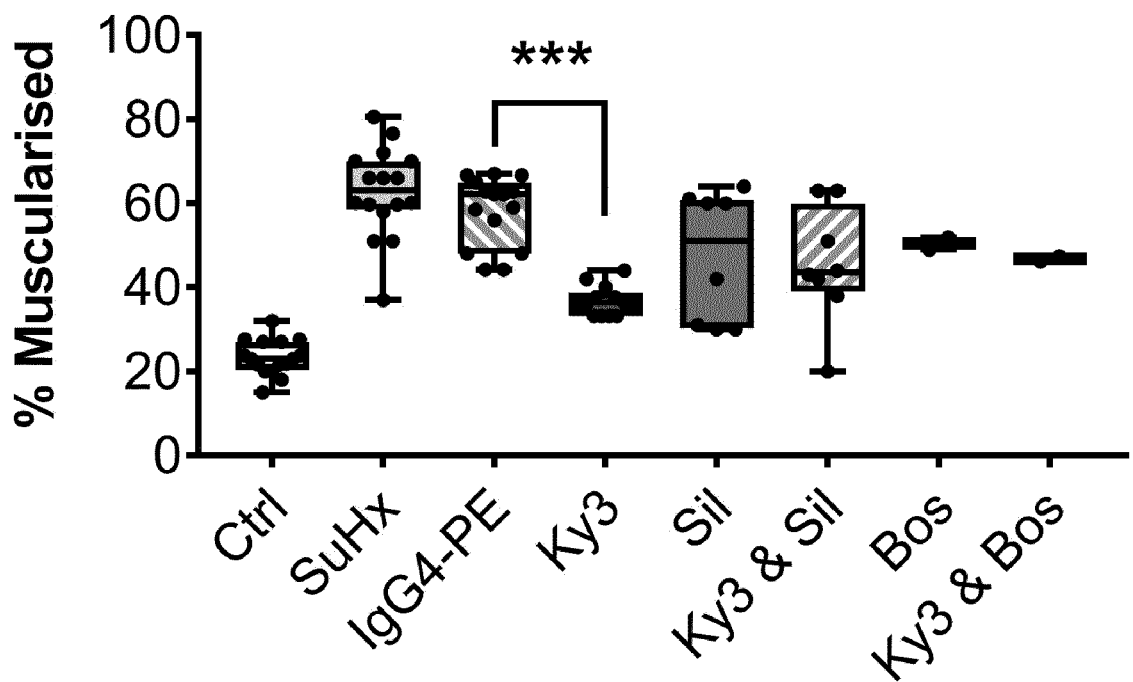
Figure 4K:
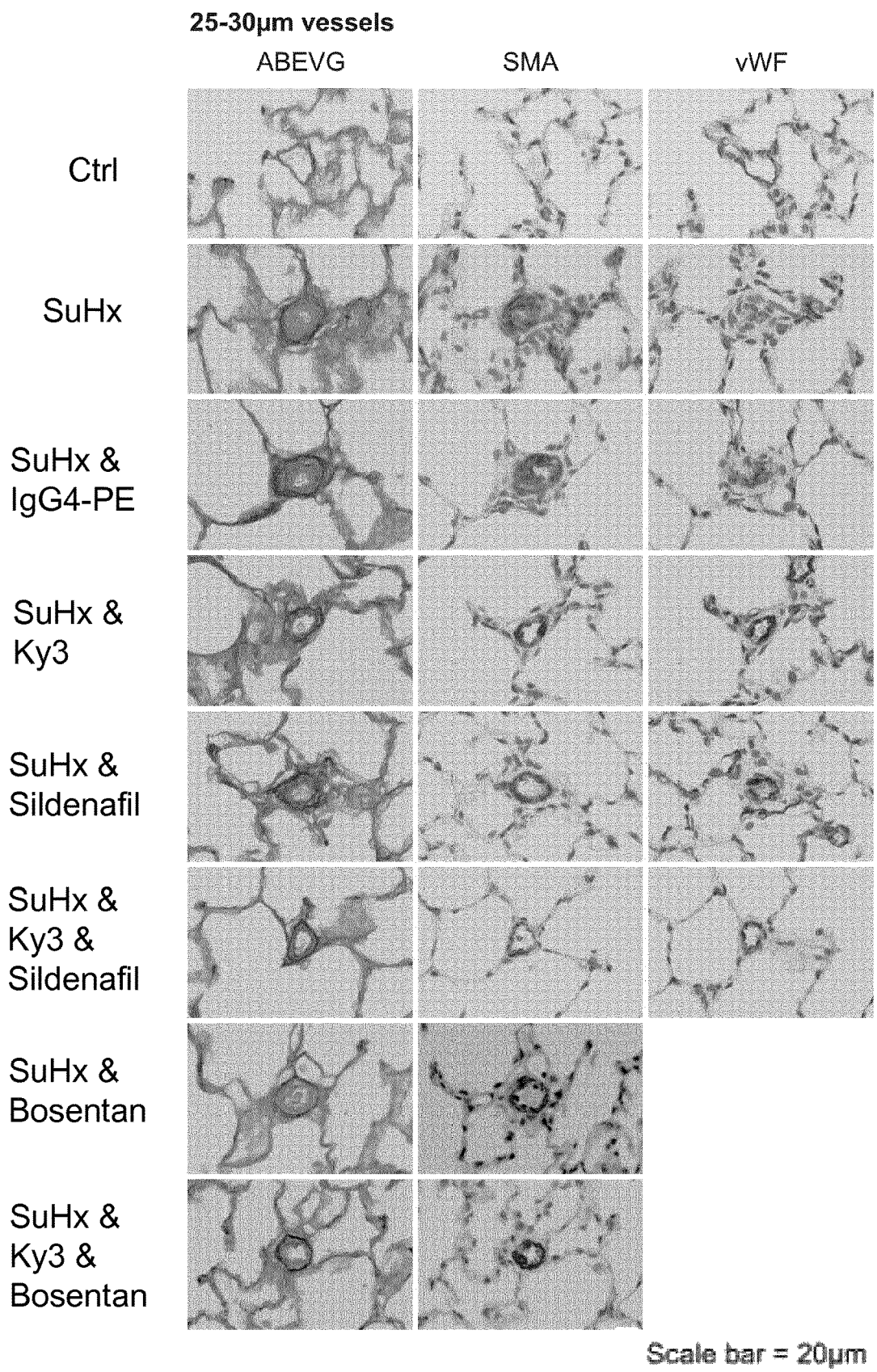
Figures 1, 4K:
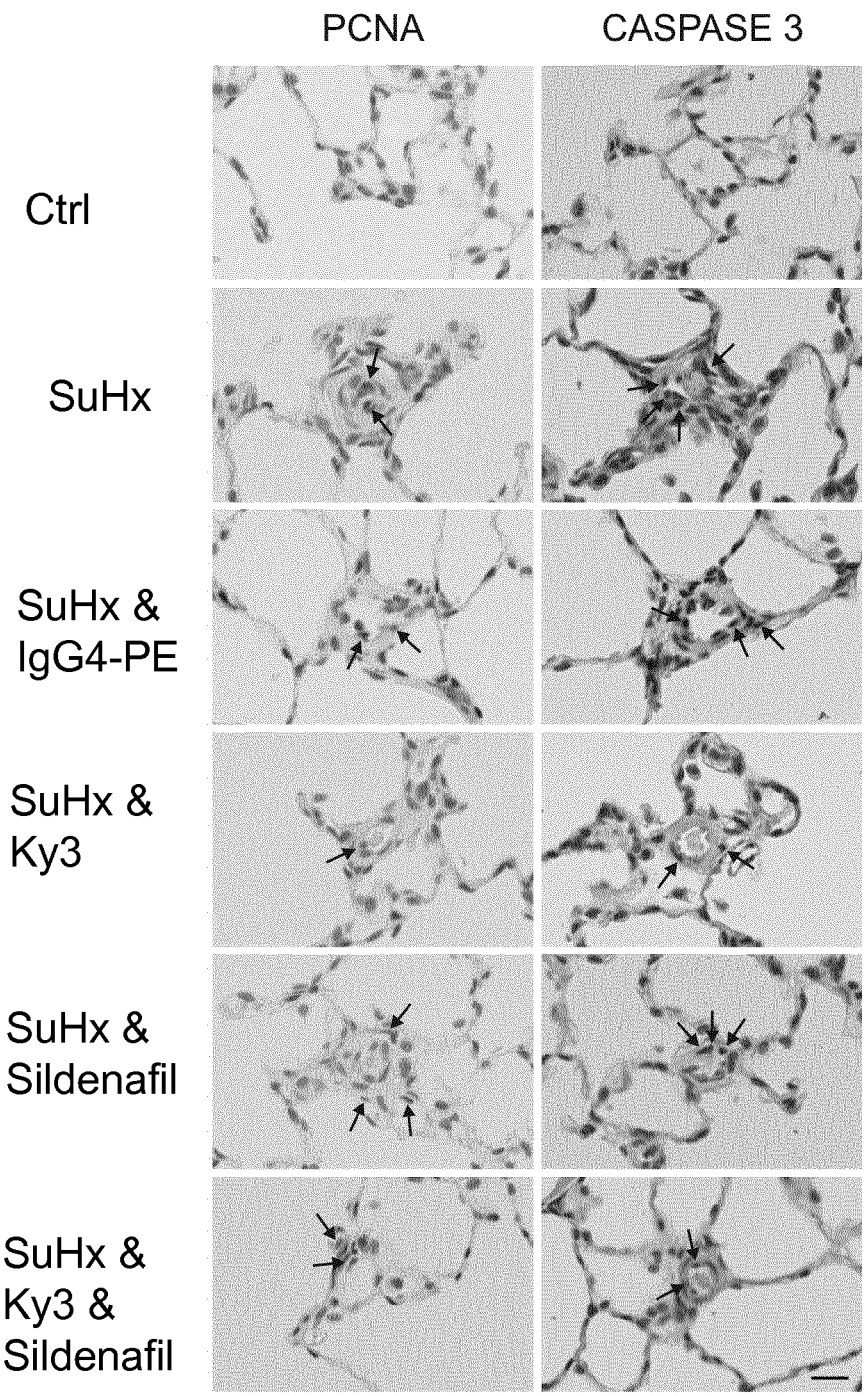
Figure 4L:
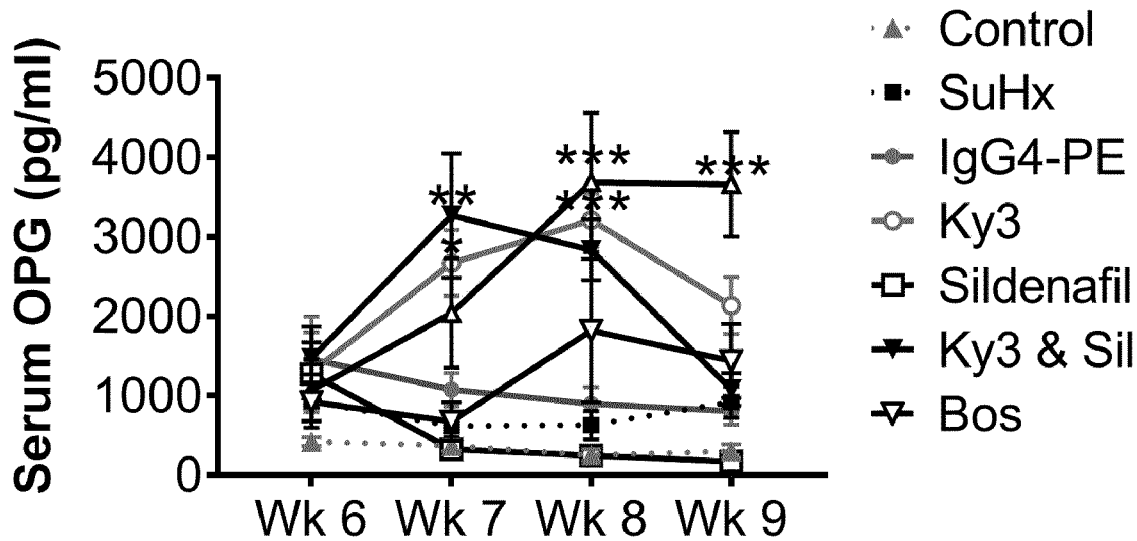
Figure 4M:
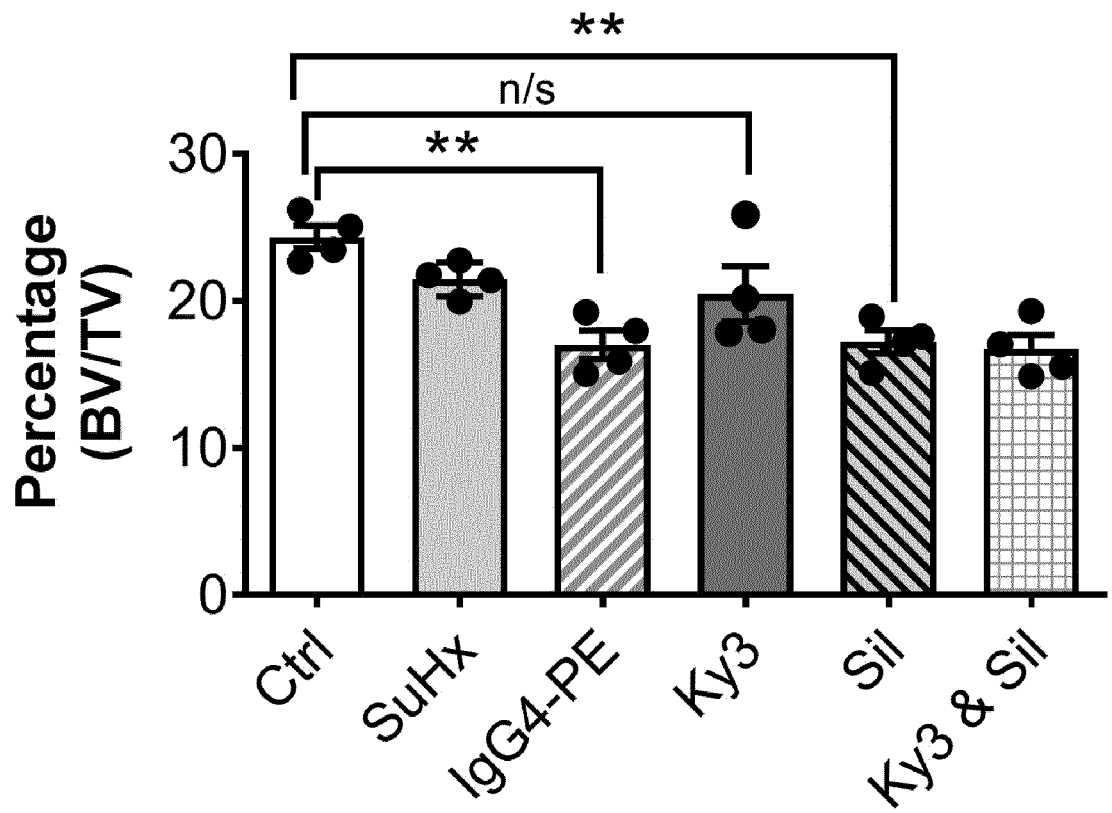
Figure 4N:
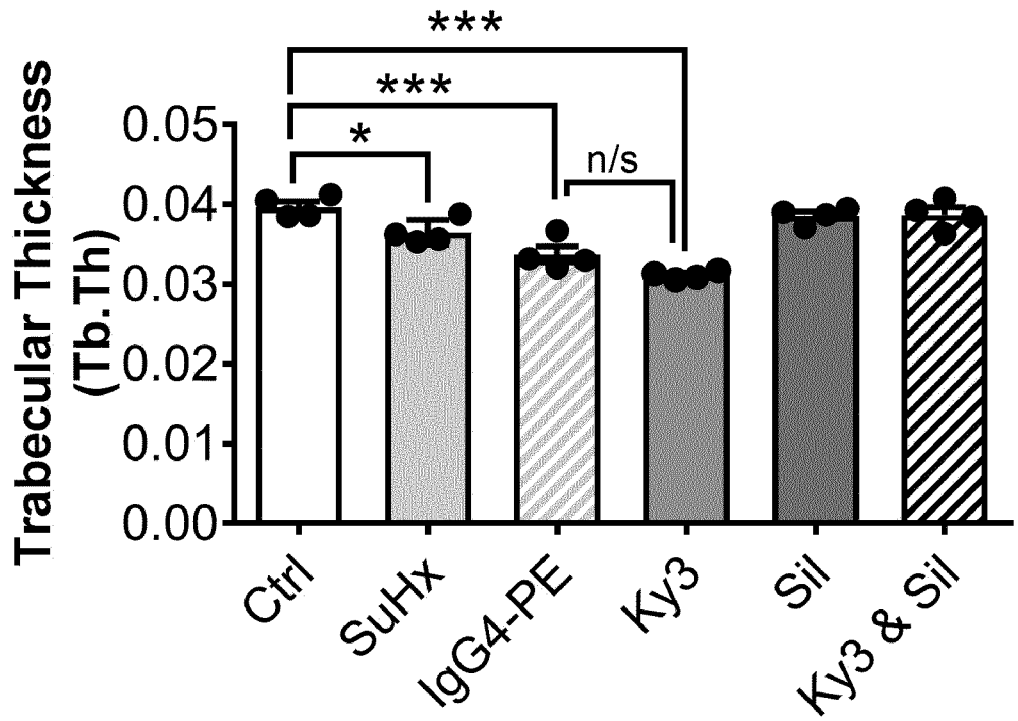
Figure 4O:
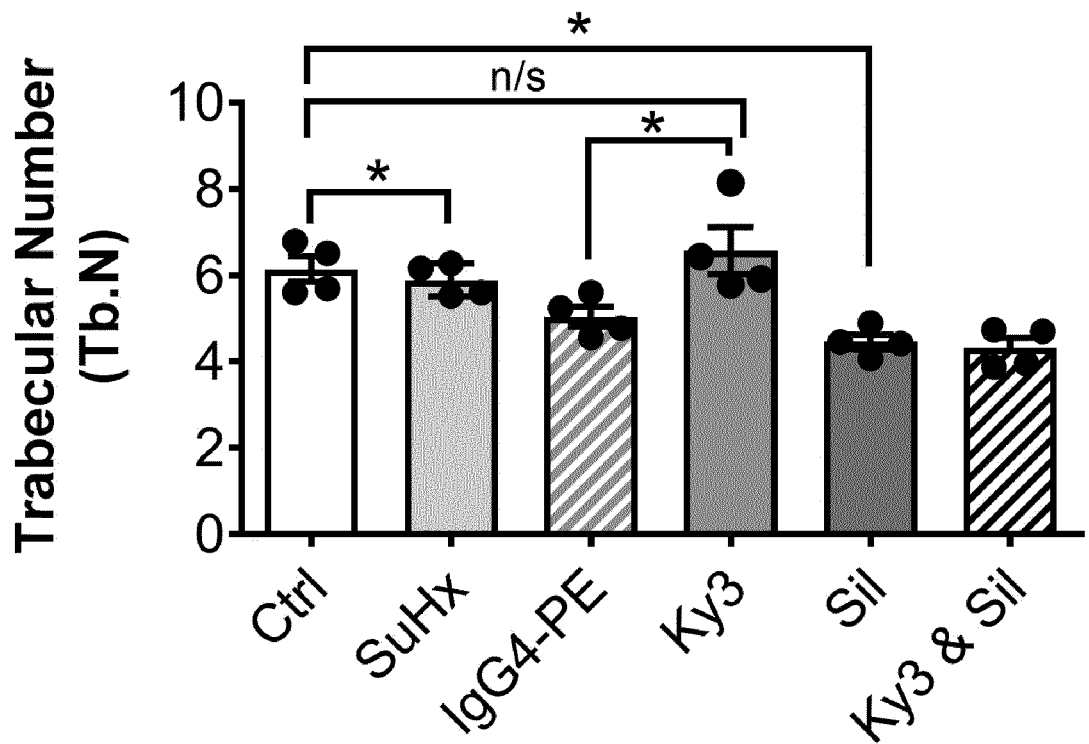

4k), or von Willebrand Factor (vWF, FIG. 4k), proliferating cell nuclear antigen (PCNA, FIG. 4k-1) or cleaved Caspase 3 (FIG. 4k-1). Circulating level of OPG is shown in FIG. 4l; data from Batches 1, 2 and 3. Quantification of femoral trabecular bone volume (%, FIG. 4m), trabecular thickness (mm, FIG. 4n), trabecular number (mm$^{-1}$, FIG. 4o); data from Batches 1 and 2. Statistical analysis of FIGS. 4m, 4n and 4o was performed on control, SuHx, IgG4-PE, Ky3 (15F11) and Sildenafil monotherapy data. Bars represent mean+/−SEM, n=8-14 animals per group, n/s=not significant, *=p<0.05, =p<0.01, *=p<0.001 compared to IgG4-PE treated rats. All images are presented at their original magnification ×400, scale bar represents 50 μm.

Figure 5:
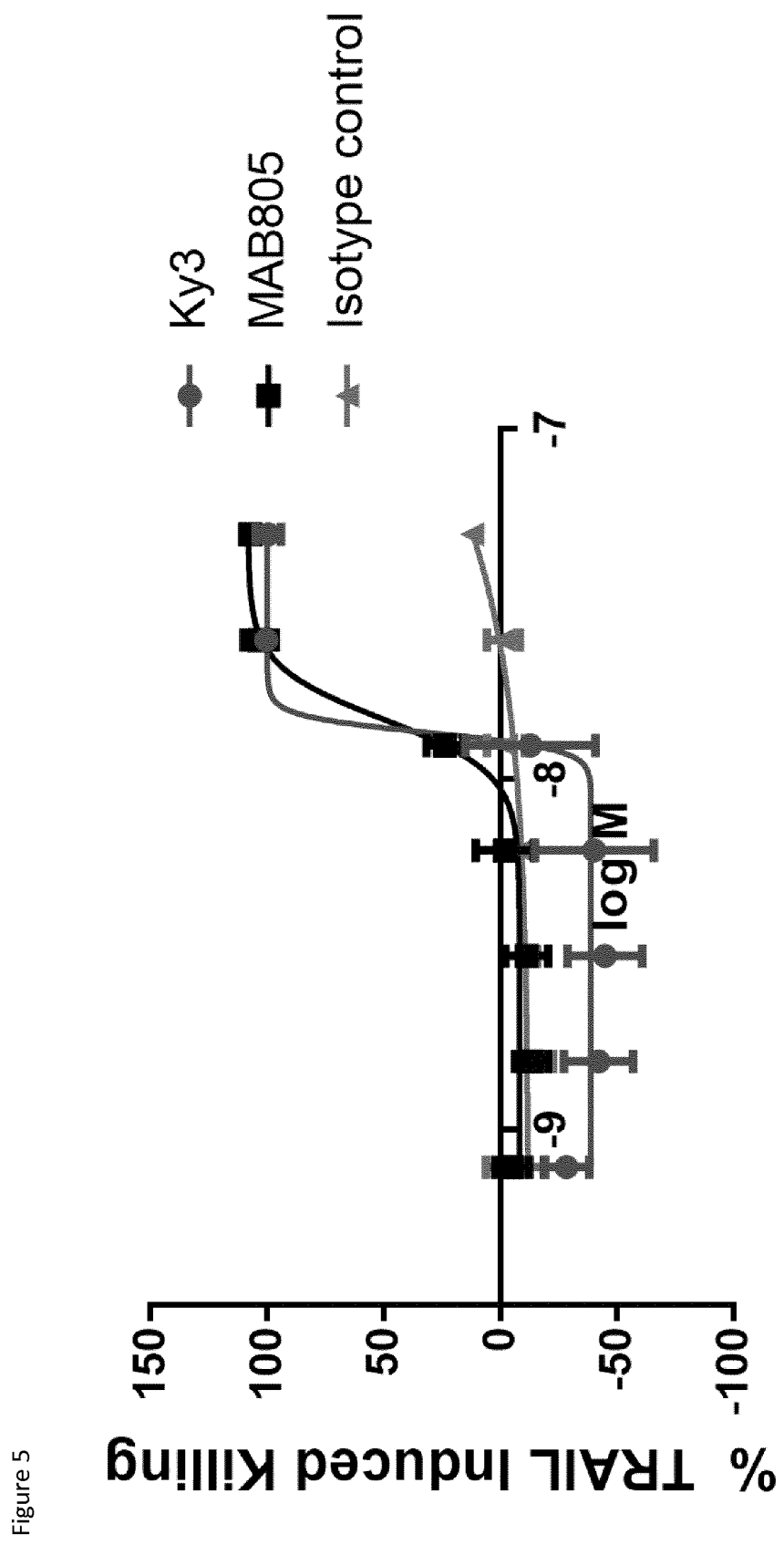

FIG. 5: TRAIL-induced killing of HT1080 cells is restored by Ky3 (15F11) and MAB805 in a concentration dependent manner. HT1080 cells were treated antibodies, 1 nM of TRAIL and 50 nM OPG for 72 hours. At the end-point of the experiment, cell viability was measured by quantification of ATP using Cell Titer Glo (Promega).

DETAILED DESCRIPTION

1. Definitions

Unless otherwise defined herein, scientific and technical terms shall have the meanings that are commonly understood by those of ordinary skill in the art. Further, unless otherwise required by context, singular terms shall include pluralities and plural terms shall include the singular.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example".

In the specification and claims, the term "about" is used to modify, for example, the quantity of an ingredient in a composition, concentration, volume, process temperature, process time, yield, flow rate, pressure, and like values, and ranges thereof, employed in describing the embodiments of the disclosure. The term "about" refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to ageing of a formulation with a particular initial concentration or mixture, and amounts that differ due to mixing or processing a formulation with a particular initial concentration or mixture. Where modified by the term "about" the claims appended hereto include equivalents to these quantities.

As used herein, "administer" or "administration" refers to the act of injecting or otherwise physically delivering a substance as it exists outside the body (e.g., an anti-hOPG antibody provided herein) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

The term "antibody", "immunoglobulin" or "Ig" may be used interchangeably herein and means an immunoglobulin molecule that recognises and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')$_2$, and Fμ fragments), single chain Fμ (scFv) mutants, multispecific antibodies such as bispecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. The term "antibody" can also refer to a Y-shaped glycoprotein with a molecular weight of approximately 150 kDa that is made up of four polypeptide chains: two light (L) chains and two heavy (H) chains. There are five types of mammalian Ig heavy chain isotypes denoted by the Greek letters alpha (α), delta (δ), epsilon (ε), gamma (γ), and mu (μ). The type of heavy chain defines the class of antibody, i.e., IgA, IgD, IgE, IgG, and IgM, respectively. The γ and α classes are further divided into subclasses on the basis of differences in the constant domain sequence and function, e.g., IgG1, IgG2A, IgG2B, IgG3, IgG4, IgA1 and IgA2. In mammals there are two types of immunoglobulin light chains, λ and κ. The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The antibodies described herein may be oligoclonal, polyclonal, monoclonal (including full-length monoclonal antibodies), camelised, chimeric, CDR-grafted, multi-specific, bi-specific (including dual-binding antibodies), catalytic, chimeric, humanized, fully human, anti-idiotypic, including antibodies that can be labelled in soluble or bound form as well as fragments, variants or derivatives thereof, either alone or in combination with other amino acid sequences provided by known techniques. An antibody may be from any species. Antibodies described herein can be naked or conjugated to other molecules such as toxins, radioisotopes, etc.

The term "antigen binding domain," "antigen binding region," "antigen binding fragment," and similar terms refer to that portion of an antibody which comprises the amino acid residues that interact with an antigen and confer on the binding agent its specificity and affinity for the antigen (e.g., the complementarity determining regions (CDRs)). The antigen binding region can be derived from any animal species, such as rodents (e.g., rabbit, rat or hamster) and humans. Preferably, the antigen binding region will be of human origin.

Antigen binding fragments described herein can include single-chain Fvs (scFv), single-chain antibodies, single domain antibodies, domain antibodies, Fv fragments, Fab fragments, F(ab') fragments, F(ab')$_2$ fragments, antibody fragments that exhibit the desired biological activity, disulfide-stabilised variable region (dsFv), dimeric variable region (diabody), anti-idiotypic (anti-Id) antibodies (including, e.g., anti-Id antibodies to antibodies), intrabodies, linear antibodies, single-chain antibody molecules and multispecific antibodies formed from antibody fragments and epitope-binding fragments of any of the above. In particular, antibodies and antibody fragments described herein can include immunoglobulin molecules and immunologically active fragments of immunoglobulin molecules, i.e., molecules that contain an antigen-binding site. Digestion of antibodies with the enzyme, papain, results in two identical antigen-binding fragments, known also as "Fab" fragments, and a "Fc" fragment, having no antigen-binding activity but having the ability to crystallize. "Fab" when used herein refers to a fragment of an antibody that includes one constant and one variable domain of each of the heavy and light chains. The term "Fc region" herein is used to define a C-terminal region of an immunoglobulin heavy chain, including native-sequence Fc regions and variant Fc regions. The "Fc fragment" refers to the carboxy-terminal portions of both H chains held together by disulfides. The effector functions of antibodies are determined by sequences in the Fc region, the region which is also recognised by Fc receptors (FcR) found on certain types of cells. Digestion of antibodies with the enzyme, pepsin, results in a F(ab')$_2$ fragment in which the two arms of the antibody molecule remain linked and comprise two-antigen binding sites. The F(ab')$_2$ fragment has the ability to crosslink antigen.

"Fv" when used herein refers to the minimum fragment of an antibody that retains both antigen-recognition and antigen-binding sites. This region consists of a dimer of one heavy and one light chain variable domain in tight, non-covalent or covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognise and bind antigen, although at a lower affinity than the entire binding site.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, and are directed against a single antigenic determinant or epitope. In contrast, polyclonal antibody preparations typically include different antibodies directed against different antigenic determinants (or epitopes). The term "monoclonal antibody" as used herein encompasses both intact and full-length monoclonal antibodies as well as antibody fragments (such as Fab, Fab', F(ab')$_2$, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, hybridoma, phage selection, recombinant expression, and transgenic animals.

The monoclonal antibodies herein can include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies that exhibit the desired biological activity.

The term "humanized antibody" refers to a subset of chimeric antibodies in which a "hypervariable region" from a non-human immunoglobulin (the donor antibody) replaces residues from a hypervariable region in a human immunoglobulin (recipient antibody). In general, a humanized antibody will include substantially all of at least one, and typically two, variable domains, in which all or substantially all of the hypervariable loops correspond to those of a non-human immunoglobulin sequence, and all or substantially all of the framework regions are those of a human immunoglobulin sequence, although the framework regions may include one or more substitutions that improve antibody performance, such as binding affinity, isomerisation, immunogenicity, etc.

The term "bispecific antibody" means an antibody which comprises specificity for two target molecules, and includes formats such as DVD-Ig (see DiGiammarino et al., "Design and generation of DVD-Ig™ molecules for dual-specific targeting", Meth. Mo. Biol., 2012, 889, 145-156), mAb$^2$ (see WO2008/003103), FIT-Ig (see WO2015/103072), mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BITE, diabody, DART, TandAb, scDiabody, scDiabody-CH3, Diabody-CH3, Triple body, Miniantibody, minibody, TriBi minibody, scFv-CH3 KIH, scFv-CH-CL-scFv, F(ab')2-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv, scFv4-Ig and zybody. For a review of bispecific formats, see Spiess, C., et al., Mol. Immunol. (2015). In another embodiment, the bispecific molecule comprises an antibody which is fused to another non-Ig format, for example a T-cell receptor binding domain; an immunoglobulin superfamily domain; an agnathan variable lymphocyte receptor; a fibronectin domain (e.g., an Adnectin™); an antibody constant domain (e.g., a CH3 domain, e.g., a CH2 and/or CH3 of an Fcab™) wherein the constant domain is not a functional CH1 domain; an scFv; an (scFv)2; an sc-diabody; an scFab; a centyrin and an epitope binding domain derived from a scaffold selected from CTLA-4 (Evibody™); a lipocalin domain; Protein A such as Z-domain of Protein A (e.g., an Affibody™ or SpA); an A-domain (e.g., an Avimer™ or Maxibody™); a heat shock protein (such as and epitope binding domain derived from GroEI and GroES); a transferrin domain (e.g., a trans-body); ankyrin repeat protein (e.g., a DARPin™); peptide aptamer; C-type lectin domain (e.g., Tetranectin™); human γ-crystallin or human ubiquitin (an affilin); a PDZ domain; scorpion toxin; and a kunitz type domain of a human protease inhibitor.

The term "hypervariable region", "CDR region" or "CDR" refers to the regions of an antibody variable domain which are hypervariable in sequence and/or form structurally defined loops. Generally, antigen binding sites of an antibody include six hypervariable regions: three in the $V_H$ (CDRH1, CDRH2, CDRH3), and three in the $V_L$ (CDRL1, CDRL2, CDRL3). These regions of the heavy and light chains of an antibody confer antigen-binding specificity to the antibody. CDRs may be defined according to the Kabat system (see Kabat, E. A. et al., 1991, "Sequences of Proteins of Immunological Interest", 5th edit., NIH Publication no. 91-3242, U.S. Department of Health and Human Services). Other systems may be used to define CDRs, which as the system devised by Chothia et al., (see Chothia, C. & Lesk, A. M., 1987, "Canonical structures for the hypervariable regions of immunoglobulins", J. Mol. Biol., 196, 901-917) and the IMGT system (see Lefranc, M. P., 1997, "Unique database numbering system for immunogenetic analysis", Immunol. Today, 18, 50). An antibody typically contains 3 heavy chain CDRs and 3 light chain CDRs. The term CDR or CDRs is used here to indicate one or several of these regions. A person skilled in the art is able to readily compare the different systems of nomenclature and determine whether a particular sequence may be defined as a CDR.

A "human antibody" is an antibody that possesses an amino-acid sequence corresponding to that of an antibody produced by a human and/or has been made using any of the techniques for making human antibodies and specifically excludes a humanized antibody comprising non-human antigen-binding residues. The term "specifically binds to" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA).

An antagonist (e.g. antibody or fragment thereof) that specifically binds to a hOPG antigen may be cross-reactive with related antigens. Preferably, an antagonist (e.g. antibody or fragment thereof) that specifically binds to a hOPG antigen does not cross-react with other antigens (but may optionally cross-react with OPG of different species, e.g., rhesus, rat or murine). An antagonist (e.g. antibody or fragment thereof) that specifically binds to a hOPG antigen can be identified, for example, by immunoassays, SPR (e.g. BIAcore™), or other techniques known to those of skill in the art. An antagonist (e.g. antibody or fragment thereof) binds specifically to an hOPG antigen when it binds to a hOPG antigen with higher affinity than to any cross-reactive antigen as determined using experimental techniques, such as radioimmunoassays (RIA) and enzyme-linked immunosorbent assays (ELISAs). Typically, a specific or selective reaction will be at least twice background signal or noise and more typically more than 10 times (such as more than 15 times, more than 20 times, more than 50 times or more than 100 times) background. See, e.g., Paul, ed., 1989, Fundamental Immunology Second Edition, Raven Press, New York at pages 332-336 for a discussion regarding antibody specificity The term "aliphatic amino acid" means that the amino acid R groups are nonpolar and hydrophobic. Hydrophobicity increases with increasing number of C atoms in the hydrocarbon chain. Glycine, Alanine, Valine, Leucine and Isoleucine are aliphatic amino acids.

The term "aromatic amino acid" means that the amino acid R groups contain an aromatic ring system. Phenylalanine, Tyrosine and Tryptophan are aromatic amino acids.

The term "hydroxyl-containing amino acid" means that the amino acid R groups contain a hydroxyl group, and are hydrophilic. Serine, Cysteine, Threonine and Methionine are hydroxyl-containing amino acids.

The term "basic amino acid" means that the amino acid R groups are nitrogen containing and are basic at neutral pH. Histidine, Lysine and Arginine are basic amino acids.

The term "cyclic amino acid" means that the amino acid R groups have an aliphatic cyclic structure. Proline is the only cyclic aliphatic amino acid.

The term "acidic amino acid" means that the amino acid R groups are polar and are negatively charged at physiological pH. Aspartate and Glutamate are acidic amino acids.

The term "amide amino acid" means that the amino acid R groups contain an amide group. Asparagine and Glutamine are amide amino acids.

As used herein, "authorisation number" or "marketing authorisation number" refers to a number issued by a regulatory agency upon that agency determining that a particular medical product and/or composition may be marketed and/or offered for sale in the area under the agency's jurisdiction. As used herein "regulatory agency" refers to one of the agencies responsible for evaluating, e.g., the safety and efficacy of a medical product and/or composition and controlling the sales/marketing of such products and/or compositions in a given area. The Food and Drug Administration (FDA) in the US and the European Medicines Agency (EPA) in Europe are but two examples of such regulatory agencies. Other non-limiting examples can include SDA, MPA, MHPRA, IMA, ANMAT, Hong Kong Department of Health-Drug Office, CDSCO, Medsafe, and KFDA.

As used herein, the term "biomarker" refers to a gene, protein, transcript or other marker that is differentially expressed or produced in individuals having a disease of interest, for example, a gene, protein, transcript of other marker that is differentially expressed or produced in individuals having hypertension or cancer. In one embodiment, OPG may be a biomarker whose expression in OPG-mediated diseases, such as those described elsewhere herein, e.g. hypertension or cancer, may be indicative as to whether or not a patient would respond to a particular type of treatment, in particular, whether a patient would response to treatment targeting OPG, for example, therapy using anti-OPG antibodies.

As used herein, a "buffer" refers to a chemical agent that is able to absorb a certain quantity of acid or base without undergoing a strong variation in pH.

As used herein, the term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

The term "chemotherapeutic agent" or "chemotherapy" refers to a therapeutic agent whose primary purpose is to destroy cancer cells, typically by interfering with the tumour cell's ability to grow or multiply. There are many different types of chemotherapeutic agents, with more than 50 approved chemotherapy drugs available. Chemotherapeutic drugs can be classified based on how they work. Alkylating drugs kill cancer cells by directly attacking DNA, the genetic material of the genes. Cyclophosphamide is an alkylating drug. Antimetabolites interfere with the production of DNA and keep cells from growing and multiplying. An example of an antimetabolite is 5-fluorouracil (5-FU). Anti-tumour antibiotics are made from natural substances such as fungi in the soil. They interfere with important cell functions, including production of DNA and cell proteins. Doxorubicin and bleomycin belong to this group of chemotherapy drugs. Plant alkaloids prevent cells from dividing normally. Vinblastine and vincristine are plant alkaloids obtained from the periwinkle plant. Steroid hormones slow the growth of some cancers that depend on hormones. For example, tamoxifen is used to treat breast cancers that depend on the hormone estrogen for growth. DNA damage response (DDR) inhibitors, such as PARP inhibitors, block DNA repair mechanisms following single or double stranded breaks.

Examples of chemotherapeutic agents include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see, U.S. Pat. No. 4,675,187), Melphalan, and other related nitrogen mustards. Suitable toxins and chemotherapeutic agents are described in Remington's Pharmaceutical Sciences, 19$^{th}$ Ed. (Mack Publishing Co., 1995), and in Goodman and Gilman's The Pharmacological Basis of Therapeutics, 7$^{th}$ Ed. (MacMillan Publishing Co., 1985). Other suitable toxins and/or chemotherapeutic agents are known to those of skill in the art.

As used herein, the term "composition" is intended to encompass a product containing the specified ingredients (e.g., an antibody of the invention) in, optionally, the specified amounts, as well as any product which results, directly or indirectly, from combination of the specified ingredients in, optionally, the specified amounts.

As used herein the term "comprising" or "comprises" is used in reference to antibodies, fragments, uses, compositions, methods, and respective component(s) thereof, that are essential to the method or composition, yet open to the inclusion of unspecified elements, whether essential or not.

The term "consisting of" refers to antibodies, fragments, uses, compositions, methods, and respective components thereof as described herein, which are exclusive of any element not recited in that description of the embodiment.

In the context of a polypeptide, the term "derivative" as used herein refers to a polypeptide that comprises an amino acid sequence of a hOPG polypeptide, a fragment of a hOPG polypeptide, or an antibody that specifically binds to a hOPG polypeptide which has been altered by the introduction of amino acid residue substitutions, deletions or additions. The term "derivative" as used herein also refers to a hOPG polypeptide, a fragment of a hOPG polypeptide, or an antibody that specifically binds to a hOPG polypeptide which has been chemically modified, e.g., by the covalent attachment of any type of molecule to the polypeptide. For example, but not by way of limitation, a hOPG polypeptide, a fragment of a hOPG polypeptide, or a hOPG antibody may be chemically modified, e.g., by glycosylation, acetylation, pegylation, phosphorylation, amidation, derivatisation by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a hOPG polypeptide, a fragment of a hOPG polypeptide, or a hOPG antibody may be chemically modified by chemical modifications using techniques known to those of skill in the art, including, but not limited to specific chemical cleavage, acetylation, formulation, metabolic synthesis of tunicamycin, etc. Further, a derivative of a hOPG polypeptide, a fragment of a hOPG polypeptide, or a hOPG antibody may contain one or more non-classical amino acids. A polypeptide derivative possesses a similar or identical function as a hOPG polypeptide, a fragment of a hOPG polypeptide, or a hOPG antibody described herein.

An "effective amount" refers to an amount effective, at dosages and for periods of time necessary, to achieve the desired effect, including a therapeutic or prophylactic result. A "therapeutically effective amount" refers to the minimum concentration required to effect a measurable improvement or prevention of a particular disorder. A therapeutically effective amount herein may vary according to factors such as the disease state, age, sex, and weight of the patient, and the ability of the antibody to elicit a desired response in the individual. A therapeutically effective amount is also one in which toxic or detrimental effects of the antibody are outweighed by the therapeutically beneficial effects. A "prophylactically effective amount" refers to an amount effective, at the dosages and for periods of time necessary, to achieve the desired prophylactic result. In some embodiments, the effective amount of an antibody of the invention is from about 0.1 mg/kg (mg of antibody per kg weight of the subject) to about 100 mg/kg. In certain embodiments, an effective amount of an antibody provided therein is about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg about 90 mg/kg or about 100 mg/kg (or a range therein). In some embodiments, "effective amount" as used herein also refers to the amount of an antibody of the invention to achieve a specified result (e.g., inhibition of a hOPG biological activity of a cell).

The term "epitope" as used herein refers to a localised region on the surface of an antigen, such as hOPG polypeptide or hOPG polypeptide fragment, that is capable of being bound to one or more antigen binding regions of an antibody, and that has antigenic or immunogenic activity in an animal, preferably a mammal, and most preferably in a human, that is capable of eliciting an immune response. An epitope having immunogenic activity is a portion of a polypeptide that elicits an antibody response in an animal. An epitope having antigenic activity is a portion of a polypeptide to which an antibody specifically binds as determined by any method well known in the art, for example, by the immunoassays described herein. Antigenic epitopes need not necessarily be immunogenic. Epitopes usually consist of chemically active surface groupings of molecules such as amino acids or sugar side chains and have specific three dimensional structural characteristics as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, a hOPG epitope is a three-dimensional surface feature of a hOPG polypeptide, which may be a monomer or, more preferably a homodimer (e.g. a cysteine-linked homodimer). In other embodiments, a hOPG epitope is linear feature of a hOPG polypeptide, e.g. homodimer.

The term "excipients" as used herein refers to inert substances which are commonly used as a diluent, vehicle, preservatives, binders, or stabilising agent for drugs and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, Remington's Pharmaceutical Sciences (1990) Mack Publishing Co., Easton, Pa., which is hereby incorporated by reference in its entirety.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, OPG fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a hOPG polypeptide or an antibody that specifically binds to a hOPG polypeptide. In a specific embodiment, a fragment of a hOPG polypeptide or an antibody that specifically binds to a hOPG antigen retains at least 1, at least 2, or at least 3 functions of the polypeptide or antibody.

The term "free" refers to a polypeptide, for example, OPG or fragments and variants thereof, that is combined with a buffer, wherein the polypeptide is not associated with a cell surface or cell membrane. As such, the term "free" can refer to a polypeptide that is capable of surface expression (i.e., includes one or more transmembrane domains or membrane association domains), but that is not, in its present state, expressed on the surface of a cell or bound to a protein that is expressed on the surface of a cell. A free polypeptide can also refer to a free recombinant or native or unbound polypeptide. In the context of phage display, a free antigen can be selected in solution or adsorbed to a surface, for example, adsorbed to the surface of a 96-well plate.

The term "fusion protein" as used herein refers to a polypeptide that comprises an amino acid sequence of an antibody and an amino acid sequence of a heterologous polypeptide or protein (i.e., a polypeptide or protein not normally a part of the antibody (e.g., a non-anti-hOPG antigen antibody)). The term "fusion" when used in relation to hOPG or to an anti-hOPG antibody refers to the joining of a peptide or polypeptide, or fragment, variant and/or derivative thereof, with a heterologous peptide or polypeptide. Preferably, the fusion protein retains the biological activity of the hOPG or anti-hOPG antibody. In certain embodiments, the fusion protein comprises a hOPG antibody $V_H$ domain, $V_L$ domain, $V_H$ CDR (one, two or three $V_H$ CDRs), and/or $V_L$ CDR (one, two or three $V_L$ CDRs), wherein the fusion protein specifically binds to a hOPG epitope.

The term "heavy chain" when used in reference to an antibody refers to five distinct types, called alpha (α), delta (δ), epsilon (ε), gamma (γ) and mu (μ), based on the amino acid sequence of the heavy chain constant domain. These distinct types of heavy chains are well known and give rise to five classes of antibodies, IgA, IgD, IgE, IgG and IgM, respectively, including four subclasses of IgG, namely IgG1, IgG1, IgG3 and IgG4. Preferably the heavy chain is a human heavy chain. In one example, the heavy chain is a disabled IgG isotype, e.g. a disabled IgG4. In certain embodiments, the antibodies of the invention comprise a human gamma 4 constant region. In another embodiment, the heavy chain constant region does not bind Fc-γ receptors, and e.g. comprises a Leu235Glu mutation. In another embodiment, the heavy chain constant region comprises a Ser228Pro mutation to increase stability. In another embodiment, the heavy chain constant region is IgG4-PE.

The term "host" as used herein refers to an animal, preferably a mammal, and most preferably a human.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "inhibits", "inhibition", "inhibiting" and the like, as used herein refers to the ability of an antagonist (e.g. an antibody or fragment thereof) to bind to an epitope which either partially or completely prevents the binding of the ligand (e.g. RANKL or TRAIL) to the receptor (e.g. OPG). If the epitope to which the antagonist binds completely blocks the binding site of the ligand, then ligand binding is completely prevented (which may be a physical blocking—in the case of overlapping epitopes—or steric blocking—where the antagonist is large such that it prevents the ligand binding to its distinct epitope), and the ligand is not removed from circulation. The concentration of circulating ligand may therefore appear to be increased. If the epitope to which the antagonist binds partially blocks the binding site of the ligand, the ligand may be able to bind, but only weakly (in the case of partial inhibition), or in a different orientation to the natural binding interaction. In this case, some of the ligand may be removed from circulation, but not as much as when the ligand binding site is completely free and available for binding. Inhibition thus refers to the physical interaction of ligand and receptor. Inhibition can be measured by HTRF, which is described in more detail elsewhere herein and in Mathis (1995) Clinical Chemistry 41(9), 1391-1397.

As used herein, "injection device" refers to a device that is designed for carrying out injections, an injection including the steps of temporarily fluidically coupling the injection device to a person's tissue, typically the subcutaneous tissue. An injection further includes administering an amount of liquid drug into the tissue and decoupling or removing the injection device from the tissue. In some embodiments, an injection device can be an intravenous device or IV device, which is a type of injection device used when the target tissue is the blood within the circulatory system, e.g., the blood in a vein. A common, but non-limiting example of an injection device is a needle and syringe.

As used herein, "instructions" refers to a display of written, printed or graphic matter on the immediate container of an article, for example the written material displayed on a vial containing a pharmaceutically active agent, or details on the composition and use of a product of interest included in a kit containing a composition of interest. Instructions set forth the method of the treatment as contemplated to be administered or performed.

An "isolated" or "purified" antibody or protein is one that has been identified, separated and/or recovered from a component of its production environment (e.g., natural or recombinant). For example, the antibody or protein is substantially free of cellular material or other contaminating proteins from the cell or tissue source from which the antibody is derived, or substantially free of chemical precursors or other chemicals when chemically synthesised. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). When the antibody is recombinantly produced, it is also preferably substantially free of culture medium, i.e., culture medium represents less than about 20%, 10%, or 5% of the volume of the protein preparation. When the antibody is produced by chemical synthesis, it is preferably substantially free of chemical precursors or other chemicals, i.e. it is separated from chemical precursors or other chemicals which are involved in the synthesis of the protein. Accordingly, such preparations of the antibody have less than about 30%, 20%, 10%, 5% (by dry weight) of chemical precursors or compounds other than the antibody of interest. In a preferred embodiment, antibodies of the invention are isolated or purified.

The terms "Kabat numbering," and like terms are recognised in the art and refer to a system of numbering amino acid residues which are more variable (i.e. hypervariable) than other amino acid residues in the heavy chain variable regions of an antibody, or fragment thereof (Kabat et al., (1971) Ann. NY Acad. Sci. 190:382-391 and, Kabat et al., (1991) Sequences of Proteins of Immunological Interest, Fifth Edition, U.S. Department of Health and Human Services, NIH Publication No. 91-3242). For the heavy chain variable region, the hypervariable region typically ranges from amino acid positions 31 to 35 for CDR1, amino acid positions 50 to 65 for CDR2, and amino acid positions 95 to 102 for CDR3.

"Label" or "labelled" as used herein refers to the addition of a detectable moiety to a polypeptide, for example, a radiolabel, fluorescent label, enzymatic label, chemiluminescent label or a biotinyl group or gold. Radioisotopes or radionuclides may include $^{3}$H, $^{14}$C, $^{15}$N, $^{35}$S, $^{90}$Y, $^{99}$Tc, $^{115}$In, $^{125}$I, $^{131}$I, fluorescent labels may include rhodamine, lanthanide phosphors or FITC and enzymatic labels may include horseradish peroxidase, β-galactosidase, luciferase, alkaline phosphatase. Additional labels include, by way of illustration and not limitation: enzymes, such as glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase; dyes (e.g. cyanine dyes, e.g. Cy5™, Cy5.5™. or Cy7™); additional fluorescent labels or fluorescers include, such as fluorescein and its derivatives", fluorochrome, GFP (GFP for "Green Fluorescent Protein"), other fluorescent proteins (e.g. mCherry, mTomato), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cisbio Assays); chemoluminescent labels or chemiluminescers, such as isoluminol, luminol and the dioxetanes; sensitisers; coenzymes; enzyme substrates; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of Pseudomonas exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEG ALIGN™ (DNASTAR) software. In one embodiment, the % homology is about 70%. In one embodiment, the % homology is about 75%. In one embodiment, the % homology is about 80%. In one embodiment, the % homology is about 85%. In one embodiment, the % homology is about 90%. In one embodiment, the % homology is about 92%. In one embodiment, the % homology is about 95%. In one embodiment, the % homology is about 97%. In one embodiment, the % homology is about 98%. In one embodiment, the % homology is about 99%. In one embodiment, the % homology is 100%.

The term "naturally occurring" or "native" when used in connection with biological materials such as nucleic acid molecules, polypeptides, host cells, and the like, refers to those which are found in nature and not manipulated by a human being.

The term "neutralises", "neutralising" or the like, as used herein refers to the ability of an antagonist (e.g. antibody or fragment thereof) to bind to and block the interaction of one or more binding partners to a target antigen. In the case of OPG, a neutralising antagonist (e.g. antibody or fragment thereof) is able to neutralise the binding of one of the ligands to OPG; e.g. RANKL and/or TRAIL, and therefore may be able to prevent the biological effect of an OPG/TRAIL and/or OPG/RANKL interaction and subsequent signalling, or impact the biological effects of it's ligand individually (e.g. the signalling effects of the RANK/RANKL interaction or the signalling effect of the promiscuous TRAIL ligand). Known ligands of OPG include RANKL and TRAIL, but, especially as the full crystal structure of OPG has not been resolved to date, other ligands of the OPG receptor may not yet have been identified. Recently, Baud'huin M et al, described a number of other potential partners of OPG, see Baud'huin M et al., "Osteoprotegerin: Multiple partners for multiple functions. Cytokine & Growth Factor Reviews", 2013, 24, 401-409, including glycosaminoglycans or proteoglycans. The ligands identified in this paper are incorporated herein by reference. These unknown or recently-identified ligands may include others members of the TNF superfamily, (including lymphotoxin-alpha (LT-α), lymphotoxin-beta (LT-β), CD40L, CD30L, CD27L, FasL, 4-1BBL, OX40L and TRAIL), or the TNF receptor superfamily (including tumor necrosis factor receptor 1 (TNFR1), tumor necrosis factor receptor 2 (TNFR2), lymphotoxin beta receptor (LT-βR), OX40, CD40, Fas receptor, decoy receptor 1 (DR1), decoy receptor 2 (DR2), decoy receptor 3 (DR3), death receptor 3, death receptor 4, death receptor 5, death receptor 6, CD27, CD30, 4-1BB, RANK, TWEAK receptor, TACI, BAFF receptor, herpesvirus entry mediator, nerve growth factor receptor, B-cell maturation antigen, glucocorticoid-induced TNFR-related, TROY and ectodysplasin A2 receptor. Functional activity of OPG may be measured in a disease relevant models of pulmonary artery smooth muscle cell proliferation or migration, or in an apoptosis or proliferation assay (e.g. in a SMC proliferation TRAIL-mediated cytotoxicity), which are well-known to those skilled in the art, and may include the ability of OPG blockade to enhance RANKL-mediated apoptosis (see Alok C. Bharti et al., "Evidence That RANK Ligand Can Suppress Cell Proliferation and Induce Apoptosis Through Activation of a Nuclear Factor-κβ-Independent and TRAF6-Dependent Mechanism", The Journal of Biological Chemistry, 2004, 279, 6065-6076). For example, a proliferation assay may involve measuring the ability of an anti-OPG antagonist (e.g. antibody or fragment thereof) to neutralise OPG-mediated inhibition of cytotoxicity in the L-929 mouse fibroblast cell line. The Neutralisation Dose (ND50) may typically be 0.15-0.3 µg/mL in the presence of 0.1 µg/mL recombinant hOPG Fc Chimera, 50 ng/mL recombinant hTRAIL, and 0.5 µg/mL actinomycin D. Other assays are known to those skilled in the art.

In one embodiment, neutralisation is measured in a homogenous time resolved fluorescence (HTRF) assay as described in more detail herein and in Mathis (1995) Clinical Chemistry 41(9), 1391-1397.

In one embodiment, the term "neutralise", and the like, is interchangeable with the term "inhibits", and the like.

As used herein, "packaging" refers to how the components are organised and/or restrained into a unit fit for distribution and/or use. Packaging can include, e.g., boxes, bags, syringes, ampoules, vials, tubes, clamshell packaging, barriers and/or containers to maintain sterility, labelling, etc.

The term "pharmaceutically acceptable" as used herein means being approved by a regulatory agency of the Federal or a state government, or listed in the U.S. Pharmacopeia, European Pharmacopeia or other generally recognised Pharmacopeia for use in animals, and more particularly in humans.

As used herein, the term "polynucleotide", "nucleotide", nucleic acid", "nucleic acid molecule" and other similar terms are used interchangeable and include DNA, RNA, mRNA and the like.

As used herein, the terms "prevent," "preventing," and "prevention" refer to the total or partial inhibition of the development, recurrence, onset or spread of a hOPG-mediated disease and/or symptom related thereto, resulting from the administration of a therapy or combination of therapies provided herein (e.g., a combination of prophylactic or therapeutic agents, such as an antibody of the invention).

As used herein "prophylaxis" and the like means that a therapy prevents or reduces the risk of an hOPG-mediated disease or disorder.

The term "soluble" refers to a polypeptide, such as OPG and variants or fragments thereof, that is generally found circulating in the plasma or in the tissue but is not bound to a membrane. OPG may be a soluble monomer, or a cysteine-linked homodimer.

The term "subject" or "patient" refers to any animal, including, but not limited to, mammals. As used herein, the term "mammal" refers to any vertebrate animal that suckle their young and either give birth to living young (eutharian or placental mammals) or are egg-laying (metatharian or nonplacental mammals). Examples of mammalian species include, but are not limited to, humans and other primates, including non-human primates such as chimpanzees and other apes and monkey species; farm animals such as cattle, sheep, pigs, goats and horses; domestic mammals such as dogs and cats; laboratory animals including rodents such as mice, rats (including cotton rats) and guinea pigs; birds, including domestic, wild and game birds such as chickens, turkeys and other gallinaceous birds, ducks, geese, and the like. In a particular embodiment, the subject is a human patient.

As used herein "substantially all" or "substantially term" refers to at least about 60%, at least about 70%, at least about 75%, at least about 80%, at least about 85%, at least about 90%, at least about 95%, at least about 98%, at least about 99%, or about 100%.

The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and non-ionic surfactants. Surfactants are often used as wetting, emulsifying, solubilizing, and dispersing agents for various pharmaceutical compositions and preparations of biological materials.

As used herein, the term "tag" refers to any type of moiety that is attached to, e.g., a polypeptide and/or a polynucleotide that encodes a hOPG or hOPG antibody or fragment thereof. For example, a polynucleotide that encodes a hOPG, hOPG antibody or fragment thereof can contain one or more additional tag-encoding nucleotide sequences that encode a, e.g., a detectable moiety or a moiety that aids in affinity purification. When translated, the tag and the antibody can be in the form of a fusion protein. The term "detectable" or "detection" with reference to a tag refers to any tag that is capable of being visualised or wherein the presence of the tag is otherwise able to be determined and/or measured (e.g., by quantitation). A non-limiting example of a detectable tag is a fluorescent tag. Other tags may be, for example, a flag tag or a histidine tag.

As used herein, the term "therapeutic agent" refers to any agent that can be used in the treatment, management or amelioration of a hOPG-mediated disease and/or a symptom related thereto. In certain embodiments, the term "therapeutic agent" refers to an antibody of the invention. In certain other embodiments, the term "therapeutic agent" refers to an agent other than an antibody of the invention. Preferably, a therapeutic agent is an agent which is known to be useful for, or has been or is currently being used for the treatment, management or amelioration of a hOPG-mediated disease or one or more symptoms related thereto, for example a therapeutic agent that is considered by healthcare professionals to be a standard of care. In specific embodiments, the therapeutic agent is a fully human anti-hOPG antibody, such as a fully human anti-hOPG monoclonal anti body.

As used herein, the term "therapy" refers to any protocol, method and/or agent that can be used in the prevention, management, treatment and/or amelioration of a hOPG-mediated disease (e.g. cancer). In certain embodiments, the terms "therapies" and "therapy" refer to a biological therapy, supportive therapy, and/or other therapies useful in the prevention, management, treatment and/or amelioration of a hOPG-mediated disease known to one of skill in the art such as medical personnel.

The terms "treat," "treatment" and "treating" refer to the reduction or amelioration of the progression, severity, and/or duration of a hOPG-mediated disease (e.g., hypertension (for example PAH), cancer or bone disease) resulting from the administration of one or more therapies (including, but not limited to, the administration of one or more prophylactic or therapeutic agents, such as an antibody of the invention or fragment thereof). In specific embodiments, such terms refer to the reduction or inhibition of the binding of hOPG to TRAIL, the reduction or inhibition of the binding of hOPG to RANKL, and/or the inhibition or reduction of one or more symptoms associated with a hOPG-mediated disease, such as hypertension or cancer. In specific embodiments, such terms refer to the reduction or inhibition of the binding of hOPG to TRAIL and/or RANKL, and/or the inhibition or reduction of one or more symptoms associated with a hOPG-mediated disease, such as cancer. In an example, the cell is a human cell. In specific embodiments, a prophylactic agent is a fully human anti-hOPG antibody, such as a fully human anti-hOPG monoclonal antibody.

The term "variable region" or "variable domain" refers to a portion of the OPG and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complimentarily determining regions (CDRs) while the more highly conserved regions in the variable domain are called framework regions (FR). The CDRs of the OPG and heavy chains are primarily responsible for the interaction of the antibody with antigen. Numbering of amino acid positions used herein is according to the EU Index, as in Kabat et al., (1991) Sequences of proteins of immunological interest. (U.S. Department of Health and Human Services, Washington, D.C.) 5th ed. ("Kabat et al.,"). In preferred embodiments, the variable region is a human variable region.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al., (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al., (Eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al, Molecular Cloning: A Laboratory Manual (4 ed.), Cold Spring Harbor Laboratory Press, Cold Spring Harbor, N.Y., USA (2012); Davis et al, Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et al, ed., John Wiley and Sons, Inc.), Current Protocols in Cell Biology (CPCB) (Juan S. Bonifacino et al, ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

2. OPG Antagonists and Antibodies

The complete amino acid sequence for human OPG (hOPG) can be found in NCBI Reference Sequence: NP_002537.3 (Seq ID No:1), which refers to many journal articles, including, for example, D'Abramo A, et al, "Higher Levels of Osteoprotegerin and Immune Activation/Immunosenescence Markers Are Correlated with Concomitant Bone and Endovascular Damage in HIV-Suppressed Patients", PLoS One, 2016, the disclosure of which is hereby incorporated by reference herein in its entirety.

In one embodiment, the antibody is a polyclonal antibody. Methods for generating polyclonal antibodies are known, and include, for example, inoculating a suitable mammal with an antigen to induce the immune system of the animal to produce immunoglobulins (IgGs) that specifically bind the injected antigen. Examples of suitable mammals include, for example, mouse, guinea pig, hamster, rat, rabbit sheep or goat. The polyclonal IgG is then typically purified from the mammal's serum. In one embodiment, the antibody is a polyclonal antibody that specifically binds OPG. In a more particular embodiment, the polyclonal antibody or fragment thereof specifically binds human OPG. Human OPG contains only a signal peptide and a soluble domain. In another embodiment, the antibody is a polyclonal antibody that specifically binds soluble OPG. The term "soluble" refers to a protein, such as OPG which may include it's a signal peptide, but nevertheless lacks one or more transmembrane domain or cytoplasmic domains. In it's native form, soluble hOPG exists as a cysteine-linked homodimer. Thus, in one embodiment, the antibody is a polyclonal antibody that binds dimeric OPG, e.g. hOPG. In another embodiment, the antibody is a polyclonal antibody that binds monomeric OPG, e.g. hOPG. In one embodiment, the antibody is a polyclonal antibody that binds "free" OPG (i.e., OPG that is not associated with any of it's ligands, either directly or indirectly).

In another embodiment, the antibody may be a monoclonal antibody. Methods of making monoclonal antibodies are known and include, for example, fusing myeloma cells with the cells from an animal that was immunized with the desired antigen. In other embodiments, the monoclonal antibodies may be generated using recombinant DNA technology. In one embodiment, the antibody is a monoclonal antibody that specifically binds a surface expressed protein. In one embodiment, the antibody is a fully human monoclonal antibody. In one embodiment, the antibody is a monoclonal antibody that specifically binds OPG. In a more particular embodiment, the monoclonal antibody or fragment thereof specifically binds human OPG. Human OPG contains only a signal peptide and a soluble domain. In another embodiment, the antibody is a monoclonal antibody that specifically binds soluble OPG. The term "soluble" refers to a protein, such as OPG which may include it's a signal peptide, but nevertheless lacks one or more transmembrane domain or cytoplasmic domains. In it's native form, soluble hOPG exists as a cysteine-linked homodimer. Thus, in one embodiment, the antibody is a monoclonal antibody that binds dimeric OPG, e.g. hOPG. In another embodiment, the antibody is a monoclonal antibody that binds monomeric OPG, e.g. hOPG. In one embodiment, the antibody is a monoclonal antibody that binds "free" OPG (i.e., OPG that is not associated with any of it's ligands, either directly or indirectly).

In an example the binding site(s) of the antibody or fragment are selected from a plurality (e.g., library) of binding sites. For example, the plurality of binding sites comprises or consists of a plurality of 4-chain antibodies or fragments thereof, e.g., dAbs, Fabs or scFvs. Suitable methods for producing pluralities of binding sites for screening include phage display (producing a phage display library of antibody binding sites), ribosome display (producing a ribosome display library of antibody binding sites), yeast display (producing a yeast display library of antibody binding sites), or immunisation of a non-human vertebrate (e.g. a rodent, e.g., a mouse or rat, e.g., a Velocimouse™, Kymouse™, Xenomouse™, Aliva Mouse™, HuMab Mouse™, Omnimouse™, Omnirat™ or MeMo Mouse™) with hOPG or a hOPG epitope and isolation of a repertoire of antibody-producing cells (e.g. a B-cell, plasma cell or plasmablast repertoire) and/or a repertoire of isolated antibodies, fragments or binding sites.

OPG binding ability, specificity and affinity ($K_D$ $K_{off}$ and/or $K_{on}$) can be determined by any routine method in the art, e.g., by surface plasmon resonance (SPR). The term "$K_D$", as used herein, is intended to refer to the equilibrium dissociation constant of a particular antibody-antigen interaction. Such binding measurements can be made using a variety of binding assays known in the art, e.g., using surface plasmon resonance (SPR), such as by Biacore™ or using the ProteOn XPR36™ (Bio-Rad®), using KinExA® (Sapidyne Instruments, Inc), or using ForteBio Octet (Pall ForteBio Corp.).

In one embodiment, the surface plasmon resonance (SPR) is carried out at 25° C. In another embodiment, the SPR is carried out at 37° C.

In one embodiment, the SPR is carried out at physiological pH, such as about pH 7 or at pH 7.6 (e.g., using Hepes buffered saline at pH 7.6 (also referred to as HBS-EP)).

In one embodiment, the SPR is carried out at a physiological salt level, e.g., 150 mM NaCl.

In one embodiment, the SPR is carried out at a detergent level of no greater than 0.05% by volume, e.g., in the presence of P20 (polysorbate 20; e.g., Tween-20™) at 0.05% and EDTA at 3 mM.

In one example, the SPR is carried out at 25° C. or 37° C. in a buffer at pH 7.6, 150 mM NaCl, 0.05% detergent (e.g., P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity of the antagonist (e.g. antibody or fragment thereof) is determined using SPR by:

1. Coupling anti-mouse (or other relevant human, rat or non-human vertebrate antibody constant region species-matched) IgG (e.g., Biacore™ BR-1008-38) to a biosensor chip (e.g., GLM chip) such as by primary amine coupling;
2. Exposing the anti-mouse IgG (or other matched species antibody) to a test IgG antibody to capture test antibody on the chip;
3. Passing the test antigen over the chip's capture surface at 1024 nM, 256 nM, 64 nM, 16 nM, 4 nM with a 0 nM (i.e. buffer alone); and
4. And determining the affinity of binding of test antibody to test antigen using surface plasmon resonance, e.g., under an SPR condition discussed above (e.g. at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH 1.7. This removes the captured antibody and allows the surface to be used for another interaction. The binding data can be fitted to 1:1 model inherent using standard techniques, e.g., using a model inherent to the ProteOn XPR36™ analysis software.

Neutralisation and inhibition of OPG interaction with one or more of its ligand (% specific binding of ligand) can be determined by any routine method in the art, e.g., by an HTRF assay (Mathis (1995) Clinical Chemistry 41(9), 1391-1397). The term "% specific binding" refers to the amount of ligand which binds to OPG when in the presence of a test antagonist (e.g. antibody or fragment thereof). A curve can be plotted of % specific binding against antibody concentration to show an $IC_{50}$ (which is the concentration of antibody at the response (or binding) is reduced by 50%, and is a measure of potency of inhibition of binding of ligand to receptor), and a % maximum specific binding, which is where increasing the concentration of antibody no longer results in any increase in binding (i.e. a plateau). An antibody which completely prevents binding of the ligand to receptor has 0% specific binding which correlates to an HTRF assay conducted with no ligand (i.e. no TRAIL or RANKL).

Indirectly, this shows the ability of the antibody to prevent the binding of the ligand to OPG. Such binding measurements can be made using a variety of binding assays known in the art, e.g., using HTRF, AlphaScreen (Perkin Elmer)™ or enzyme-linked immunosorbent assay (ELISA).

In one embodiment, the HTRF assay is carried out at room temperature (e.g. 22 or 25° C.). In another embodiment, the assay is protected from the light, in particular during incubation periods.

In any HTRF assay, appropriate donor-acceptor fluorescent pairs are used. The donor molecule is conjugated to either the receptor of interest (i.e. OPG) or to a ligand of interest (e.g. RANKL or TRAIL). The acceptor molecule is conjugated to the binding partner of the receptor/ligand to which the donor molecule is conjugated. The donor molecule or acceptor molecule may be linked to e.g. anti-mouse Fc antibody, anti-human Fc antibody, anti-Flag antibody, anti-His antibody, directly to streptavidin [each of which is conjugated to either the ligand or receptor of interest (i.e. RANKL, TRAIL or OPG)], or directly to the ligand or receptor of interest (i.e. RANKL, TRAIL or OPG). In one example, the donor is cryptate (620 nm emission) and the acceptor is either D2 (647 nm emission) or Alexaflour647 (emission 647 nm).

In one embodiment, the concentration of test antagonist (e.g. antibody or fragment thereof) is titrated to provide a curve of % specific binding. In one embodiment, the concentration ranges from approximately 50 nM to 1 pM (e.g. 30 nM to 5 pM). In another embodiment, a number of data points are taken, e.g. 6 data points, 7 data points, 8 data points, 9 data points, 10 data points, 11 data points, 12 data points, or 13 data points, in particular 10 or 11 data points.

In an example, the % specific binding of the antagonist (e.g. antibody or fragment thereof) is determined using HTRF by:
1. Combining recombinant hOPG with recombinant hTRAIL or hRANKL in a plate;
2. Allowing a sufficient period of time to reach binding equilibrium (e.g. 30 min);
3. Adding test antagonist (e.g. antibody or fragment thereof) and leaving for a sufficient period of time to equilibrate (e.g. approximately 1 hour);
4. Reading the plate using a reader capable of exciting the donor molecule and capable of measuring the wavelength of emission of both the donor and acceptor fluorescent molecules; and
5. Determining the % specific binding of the test antagonist (e.g. antibody or fragment thereof), for example using Equation 3; and/or
6. Determining the $IC_{50}$ of the antagonist (e.g. antibody or fragment thereof), for example using Equation 4.

Examples of plate readers include EnVision™ (Perkin Elmer), PHERAstar® FSX, CLARIOstar®, and FLUOstar®, and POLARstar® Omega.

In one embodiment, the HTRF assay is carried out in HTRF buffer (e.g. PBS (Sigma)+0.53 M KF (Sigma)+0.1% w/v BSA (Sigma)).

The inhibition (e.g. neutralisation) data (e.g. % specific binding) can be fitted using standard analysis techniques, e.g., using GraphPad/PRISM analysis software.

The present inventors have identified a number of antibodies having specificity for hOPG, which have a number of potential utilities and benefits over existing antibodies. For example, the antibodies described herein may have one or more of the following improved or beneficial properties:
a. Specificity for blocking only one of the ligands of OPG (e.g. blocks RANKL/OPG interaction, but not TRAIL/OPG interaction)
b. Improved or lower immunogenicity/lack of side effects
c. Solubility
d. Stability
e. Ease of formulation
f. Frequency of dosing and/or route of administration
g. Manufacturability (e.g. expression, ease of purification, isoforms)

Ky1 (6D07) has a heavy chain variable region ($V_H$) amino acid sequence of Seq ID No:12, comprising the CDRH1 amino acid sequence of Seq ID No:6 (IMGT) or Seq ID No:9 (Kabat), the CDRH2 amino acid sequence of Seq ID No:7 (IMGT) or Seq ID No:10 (Kabat), and the CDRH3 amino acid sequence of Seq ID No:8 (IMGT) or Seq ID No:11 (Kabat). The heavy chain nucleic acid sequence of the $V_H$ domain is Seq ID No:13. Ky1 (6D07) has a light chain variable region ($V_L$) amino acid sequence of Seq ID No:22, comprising the CDRL1 amino acid sequence of Seq ID No:16 (IMGT) or Seq ID No:19 (Kabat), the CDRL2 amino acid sequence of Seq ID No:17 (IMGT) or Seq ID No:20 (Kabat), and the CDRL3 amino acid sequence of Seq ID No:18 (IMGT) or Seq ID No:21 (Kabat). The light chain nucleic acid sequence of the $V_L$ domain is Seq ID No:23. The $V_H$ domain may be combined with any of the heavy chain constant region sequences described herein, e.g. Seq ID No:107, Seq ID No:109, Seq ID No:111, Seq ID No:113, Seq ID No:117, Seq ID No:118 or Seq ID No:121. The $V_L$ domain may be combined with any of the light chain constant region sequences described herein, e.g. Seq ID No:123, Seq ID No:125, Seq ID No:127, Seq ID No:129, Seq ID No:131, Seq ID No:133, Seq ID No:135, Seq ID No:139, Seq ID No:141, Seq ID No:143, Seq ID No:145, Seq ID No:147, Seq ID No:149, Seq ID No:151, Seq ID No:153 or Seq ID No:163. A full-length heavy chain amino acid sequence is Seq ID No:14 (heavy chain nucleic acid sequence Seq ID No:15). A full-length light chain amino acid sequence is Seq ID No:24 (light chain nucleic acid sequence Seq ID No:25). The heavy chain variable region is made by recombination of human V1-18*01, D1-26*01 and J5*02 gene segments. The light chain variable region is made by recombination of human V1-17*01 and J3*01 gene segments.

Ky2 (8C10) has a heavy chain variable region ($V_H$) amino acid sequence of Seq ID No:32, comprising the CDRH1 amino acid sequence of Seq ID No:26 (IMGT) or Seq ID No:29 (Kabat), the CDRH2 amino acid sequence of Seq ID No:27 (IMGT) or Seq ID No:30 (Kabat), and the CDRH3 amino acid sequence of Seq ID No:28 (IMGT) or Seq ID No:31 (Kabat). The heavy chain nucleic acid sequence of the $V_H$ domain is Seq ID No:33. Ky2 (8C10) has a light chain variable region ($V_L$) amino acid sequence of Seq ID No:42, comprising the CDRL1 amino acid sequence of Seq ID No:36 (IMGT) or Seq ID No:39 (Kabat), the CDRL2 amino acid sequence of Seq ID No:37 (IMGT) or Seq ID No:40 (Kabat), and the CDRL3 amino acid sequence of Seq ID No:38 (IMGT) or Seq ID No:41 (Kabat). The light chain nucleic acid sequence of the $V_L$ domain is Seq ID No:43. The $V_H$ domain may be combined with any of the heavy chain constant region sequences described herein, e.g. Seq ID No:107, Seq ID No:109, Seq ID No:111, Seq ID No:113, Seq ID No:117, Seq ID No:118 or Seq ID No:121. The $V_L$ domain may be combined with any of the light chain constant region sequences described herein, e.g. Seq ID No:123, Seq ID No:125, Seq ID No:127, Seq ID No:129, Seq ID No:131, Seq ID No:133, Seq ID No:135, Seq ID No:139, Seq ID No:141, Seq ID No:143, Seq ID No:145, Seq ID No:147, Seq ID No:149, Seq ID No:151, Seq ID No:153 or Seq ID No:163. A full-length heavy chain amino acid sequence is Seq ID No:34 (heavy chain nucleic acid sequence Seq ID No:35). A full-length light chain amino acid sequence is Seq ID No:44 (light chain nucleic acid sequence Seq ID No:45). The heavy chain variable region is made by recombination of human V3-9*01, D3-9*01 and J4*02 gene segments. The light chain variable region is made by recombination of human V1D-39*01 and J1*01 gene segments.

Ky3 (15F11) has a heavy chain variable region ($V_H$) amino acid sequence of Seq ID No:52, comprising the CDRH1 amino acid sequence of Seq ID No:46 (IMGT) or Seq ID No:49 (Kabat), the CDRH2 amino acid sequence of Seq ID No:47 (IMGT) or Seq ID No:50 (Kabat), and the CDRH3 amino acid sequence of Seq ID No:48 (IMGT) or Seq ID No:51 (Kabat). The heavy chain nucleic acid sequence of the $V_H$ domain is Seq ID No:53. Ky3 (15F11) has a light chain variable region ($V_L$) amino acid sequence of Seq ID No:62, comprising the CDRL1 amino acid sequence of Seq ID No:56 (IMGT) or Seq ID No:59 (Kabat), the CDRL2 amino acid sequence of Seq ID No:57 (IMGT) or Seq ID No:60 (Kabat), and the CDRL3 amino acid sequence of Seq ID No:58 (IMGT) or Seq ID No:61 (Kabat). The light chain nucleic acid sequence of the $V_L$ domain is Seq ID No:63. The $V_H$ domain may be combined with any of the heavy chain constant region sequences described herein, e.g. Seq ID No:107, Seq ID No:109, Seq ID No:111, Seq ID No:113, Seq ID No:117, Seq ID No:118 or Seq ID No:121. The $V_L$ domain may be combined with any of the light chain constant region sequences described herein, e.g.

Seq ID No:123, Seq ID No:125, Seq ID No:127, Seq ID No:129, Seq ID No:131, Seq ID No:133, Seq ID No:135, Seq ID No:139, Seq ID No:141, Seq ID No:143, Seq ID No:145, Seq ID No:147, Seq ID No:149, Seq ID No:151, Seq ID No:153 or Seq ID No:163. A full-length heavy chain amino acid sequence is Seq ID No:54 (heavy chain nucleic acid sequence Seq ID No:55). A full-length light chain amino acid sequence is Seq ID No:64 (light chain nucleic acid sequence Seq ID No:65). The heavy chain variable region is made by recombination of human V3-13*01, D3-10*01 and J4*02 gene segments. The light chain variable region is made by recombination of human V1D-33*01 and J3*01 gene segments.

Ky4 (16G05) has a heavy chain variable region (V$_H$) amino acid sequence of Seq ID No:72, comprising the CDRH1 amino acid sequence of Seq ID No:66 (IMGT) or Seq ID No:69 (Kabat), the CDRH2 amino acid sequence of Seq ID No:67 (IMGT) or Seq ID No:70 (Kabat), and the CDRH3 amino acid sequence of Seq ID No:68 (IMGT) or Seq ID No:71 (Kabat). The heavy chain nucleic acid sequence of the V$_H$ domain is Seq ID No:73. Ky4 (16G05) has a light chain variable region (V$_L$) amino acid sequence of Seq ID No:82, comprising the CDRL1 amino acid sequence of Seq ID No:76 (IMGT) or Seq ID No:79 (Kabat), the CDRL2 amino acid sequence of Seq ID No:77 (IMGT) or Seq ID No:80 (Kabat), and the CDRL3 amino acid sequence of Seq ID No:78 (IMGT) or Seq ID No:81 (Kabat). The light chain nucleic acid sequence of the V$_L$ domain is Seq ID No:83. The V$_H$ domain may be combined with any of the heavy chain constant region sequences described herein, e.g. Seq ID No:107, Seq ID No:109, Seq ID No:111, Seq ID No:113, Seq ID No:117, Seq ID No:118 or Seq ID No:121. The V$_L$ domain may be combined with any of the light chain constant region sequences described herein, e.g. Seq ID No:123, Seq ID No:125, Seq ID No:127, Seq ID No:129, Seq ID No:131, Seq ID No:133, Seq ID No:135, Seq ID No:139, Seq ID No:141, Seq ID No:143, Seq ID No:145, Seq ID No:147, Seq ID No:149, Seq ID No:151, Seq ID No:153 or Seq ID No:163. A full-length heavy chain amino acid sequence is Seq ID No:74 (heavy chain nucleic acid sequence Seq ID No:75). A full-length light chain amino acid sequence is Seq ID No:84 (light chain nucleic acid sequence Seq ID No:85). The heavy chain variable region is made by recombination of human V3-9*01, D3-22*01 and J4*02 gene segments. The light chain variable region is made by recombination of human V1D-39*01 and J1*01 gene segments.

Ky5 (15H06) has a heavy chain variable region (V$_H$) amino acid sequence of Seq ID No:92, comprising the CDRH1 amino acid sequence of Seq ID No:86 (IMGT) or Seq ID No:89 (Kabat), the CDRH2 amino acid sequence of Seq ID No:87 (IMGT) or Seq ID No:90 (Kabat), and the CDRH3 amino acid sequence of Seq ID No:88 (IMGT) or Seq ID No:91 (Kabat). The heavy chain nucleic acid sequence of the V$_H$ domain is Seq ID No:93. Ky5 (15H06) has a light chain variable region (V$_L$) amino acid sequence of Seq ID No:102, comprising the CDRL1 amino acid sequence of Seq ID No:96 (IMGT) or Seq ID No:99 (Kabat), the CDRL2 amino acid sequence of Seq ID No:97 (IMGT) or Seq ID No:100 (Kabat), and the CDRL3 amino acid sequence of Seq ID No:98 (IMGT) or Seq ID No:101 (Kabat). The light chain nucleic acid sequence of the V$_L$ domain is Seq ID No:103. The V$_H$ domain may be combined with any of the heavy chain constant region sequences described herein, e.g. Seq ID No:107, Seq ID No:109, Seq ID No:111, Seq ID No:113, Seq ID No:117, Seq ID No:118 or Seq ID No:121. The V$_L$ domain may be combined with any of the light chain constant region sequences described herein, e.g. Seq ID No:123, Seq ID No:125, Seq ID No:127, Seq ID No:129, Seq ID No:131, Seq ID No:133, Seq ID No:135, Seq ID No:139, Seq ID No:141, Seq ID No:143, Seq ID No:145, Seq ID No:147, Seq ID No:149, Seq ID No:151, Seq ID No:153 or Seq ID No:163. A full-length heavy chain amino acid sequence is Seq ID No:94 (heavy chain nucleic acid sequence Seq ID No:95). A full-length light chain amino acid sequence is Seq ID No:104 (light chain nucleic acid sequence Seq ID No:105). The heavy chain variable region is made by recombination of human V3-15*01, D3-22*01 and J3*02 gene segments. The light chain variable region is made by recombination of human V1D-12*02 and J4*01 gene segments.

The antibodies of the invention are described with respect to the following concepts. Unless otherwise stated, all concepts, are to be read as being able to be combined with any other concept, unless such combination would not make technical sense or is explicitly stated otherwise. In particular, a reference to a particular concept includes a reference to any sub-concept (e.g. a reference to concept 3 in a subsequent concept specifically includes a reference back to concept 3a, concept 3b, etc), unless otherwise apparent from the context.

Concept 1. An antagonist (e.g. antibody or fragment thereof) which specifically binds to human osteoprotegerin (hOPG) (Seq ID No:1) and inhibits (e.g. neutralises) the interaction of hOPG with human RANKL (hRANKL) and/or human TRAIL (hTRAIL).

Concept 1a. An antagonist (e.g. antibody or fragment thereof) which specifically binds to hOPG (Seq ID No:1) and inhibits the interaction of hOPG with hRANKL and/or hTRAIL.

Concept 1b. An antagonist (e.g. antibody or fragment thereof) that specifically binds to hOPG (Seq ID No:1) and neutralises the interaction of hOPG with hRANKL and/or hTRAIL.

Concept 1c. An antagonist (e.g. antibody or fragment thereof) that specifically binds to hOPG (Seq ID No:1) and inhibits (e.g. neutralises) the interaction of hOPG with another ligand, which ligand is a member of the TNF superfamily or a member of the TNF receptor superfamily.

In concept 1c, the ligand may be a member of the TNF superfamily, which may be selected from lymphotoxin-alpha (LT-α), lymphotoxin-beta (LT-β), CD40L, CD30L, CD27L, FasL, 4-1BBL and OX40L. Thus, in one embodiment, the ligand is lymphotoxin-alpha (LT-α). In another embodiment, the ligand is lymphotoxin-beta (LT-β). In another embodiment, the ligand is CD40L. In another embodiment, the ligand is CD30L. In another embodiment, the ligand is CD27L. In another embodiment, the ligand is FasL. In another embodiment, the ligand is 4-1BBL. In another embodiment, the ligand is OX40L.

In concept 1c, the ligand which is a member of the TNF receptor superfamily may be selected from tumor necrosis factor receptor 1 (TNFR1), tumor necrosis factor receptor 2 (TNFR2), lymphotoxin beta receptor (LT-βR), OX40, CD40, Fas receptor, decoy receptor 1 (DR1), decoy receptor 2 (DR2), decoy receptor 3 (DR3), death receptor 3, death receptor 4, death receptor 5, death receptor 6, CD27, CD30, 4-1BB, RANK, TWEAK receptor, TACI, BAFF receptor, herpesvirus entry mediator, nerve growth factor receptor, B-cell maturation antigen, glucocorticoid-induced TNFR-related, TROY and ectodysplasin A2 receptor. Thus, in one embodiment, the ligand is tumor necrosis factor receptor 1 (TNFR1). In another embodiment, the ligand is tumor necrosis factor receptor 2 (TNFR2). In another embodiment, the ligand is lymphotoxin beta receptor (LT-βR). In another embodiment, the ligand is OX40. In another embodiment, the ligand is CD40. In another embodiment, the ligand is Fas receptor. In another embodiment, the ligand is decoy receptor 1 (DR1). In another embodiment, the ligand is decoy receptor 2 (DR2). In another embodiment, the ligand is decoy receptor 3 (DR3). In another embodiment, the ligand is death receptor 3. In another embodiment, the ligand is death receptor 4. In another embodiment, the ligand is death receptor 5. In another embodiment, the ligand is death receptor 6. In another embodiment, the ligand is CD27. In another embodiment, the ligand is CD30. In another embodiment, the ligand is 4-1BB. In another embodiment, the ligand is TWEAK receptor. In another embodiment, the ligand is TACI. In another embodiment, the ligand is BAFF receptor. In another embodiment, the ligand is herpesvirus entry mediator. In another embodiment, the ligand is nerve growth factor receptor. In another embodiment, the ligand is B-cell maturation antigen. In another embodiment, the ligand is glucocorticoid-induced TNFR-related. In another embodiment, the ligand is TROY. In another embodiment, the ligand is ectodysplasin A2 receptor.

Concept 1d. An antagonist (e.g. antibody or fragment thereof) that specifically binds to hOPG (Seq ID No:1) and increases the expression (e.g. the mRNA levels) of BMPRII. It has been observed that the administration of Ky3 (15F11) may result in an increase in the expression of BMPRII in both the prophylactic SuHx model (Example 6, data not shown) and in the therapeutic SuHx model (Example 8, data not shown). This increase of BMRPII is not seen in either the prophylactic or therapeutic MCT model. It is thought that other antibodies (or fragments thereof) or antagonists having the beneficial profile of Ky3 (15F11) (e.g as described in the concepts herein, especially concept 1) may have a similar effect on the expression of BMP receptors (e.g. BMP type II receptors, for example the BMPRII receptor). It has been shown (Lawrie et al. "Evidence of a Role for Osteoprotegerin in the Pathogenesis of Pulmonary Arterial Hypertension" Am. J. Path., 2008, 256-264) that reduced BMPRII expression is associated with increased OPG secretion, while stimulation of PASMC with OPG has a significant impact on the TGFβ pathway signalling. Therefore, without being bound by theory, we envisage that Ky3 and other similar antibodies may have further benefits in the OPG pathway by not only blocking OPG directly, but also by reducing the levels of OPG in the serum through interference with the BMPRII pathway.

Thus, in one embodiment, the antagonist (e.g. antibody or fragment thereof) increases the expression of a BMP receptor (e.g. a BMP type II receptor, for example the BMPRII receptor) by greater than approximately 20% (or greater than approximately 30%, 40% or 50%) compared to the expression of said BMP receptor (e.g. said BMP type II receptor, for example the BMPRII receptor) in untreated individuals. In another embodiment, the antagonist (e.g. antibody or fragment thereof) increases the expression of a BMP receptor (e.g. a BMP type II receptor, for example the BMPRII receptor) by greater than approximately 75% [or doubles, triples or quadruples the expression of a BMP receptor (e.g. a BMP type II receptor, for example the BMPRII receptor)] compared to the expression of said BMP receptor (e.g. said BMP type II receptor, for example the BMPRII receptor) in untreated individuals. In another embodiment, the antagonist (e.g. antibody or fragment thereof) increases the expression of a BMP receptor (e.g. a BMP type II receptor, for example the BMPRII receptor) by a statistically significant amount compared to the expression of said BMP receptor (e.g. said BMP type II receptor, for example the BMPRII receptor) in untreated individuals. Methods for detecting a BMP receptor (e.g. a BMP type II receptor, for example the BMPRII receptor) levels are well known to those skilled in the art, for example as disclosed in Lawrie et al. "Evidence of a Role for Osteoprotegerin in the Pathogenesis of Pulmonary Arterial Hypertension" Am. J. Path., 2008, 256-264.

In one embodiment, the measurement of the BMP receptor (e.g. the BMP type II receptor, for example the BMPRII receptor) is carried out in a prophylatic SuHx model. In another embodiment, the measurement of the BMP receptor (e.g. the BMP type II receptor, for example the BMPRII receptor) is carried out in a therapeutic SuHx model. In another embodiment, the model is a disease model in rats. The model may be any of the models described in more detail in concept 3 hereinbelow.

In any of the concepts hereinbelow, the antagonist (e.g. antibody or fragment thereof) may inhibit (e.g. neutralise) or bind to or otherwise interact with a ligand other than RANKL and/or TRAIL, which may be any of the ligands described above for concept 1c.

Throughout the concepts herein, the OPG may be wild-type human OPG. Additionally, or alternatively, the hOPG is a polymorphic variant, for example, the hOPB comprises 3N and/or 3K. In one embodiment, the OPG is encoded by a nucleotide sequence comprising one or more single nucleotide polymorphisms (SNPs) selected from the group consisting of rs2073618, rs1804854 and rs140782326.

Thus, there is also provided an antagonist (e.g. an antibody or fragment thereof) according to any one of concepts 1 to 52 for use in the treatment of an hOPG-mediated disease or condition (which disease or condition may be any of those described herein) in a subject, wherein the antibody or fragment specifically binds to hOPG expressed by the subject, wherein the hOPG comprises 3N and/or 3K. There is also provided an antagonist (e.g. an antibody or fragment thereof) according to any one of concepts 1 to 52 for use in the treatment of an hOPG-mediated disease or condition (which disease or condition may be any of those described herein) in a subject, wherein the antagonist (e.g. antibody or fragment thereof) specifically binds to hOPG expressed by the subject, wherein the hOPG is encoded by a nucleotide sequence comprising one or more SNPs selected from the group consisting of rs2073618, rs1804854 and rs140782326. Some patients may have hOPG containing this polymorphism, and therefore antibodies which are able to bind and neutralise/inhibit polymorphic hOPG may be useful in treating a different or broader range of patients (if the antibodies are cross reactive between wild type hOPG and polymorphic OPG), and/or may have further, improved inhibition (e.g. neutralisation) ability and/or efficacy and/or specificity.

Throughout the concepts herein, hRANKL may have an amino acid sequence as defined by Seq ID No:5, but may also include polymorphic variants thereof. In another embodiment, the hRANKL is recombinant hRANKL.

Throughout the concepts herein, hTRAIL may have an amino acid sequence as defined by Seq ID No:4, but may also include polymorphic variants thereof. In another embodiment, the hTRAIL is recombinant hTRAIL.

In concept 1, in one embodiment, the antagonist comprises or consists of an antibody (e.g. a human antibody), or a fragment thereof, a bispecific antibody, a multispecific antibody or a non-Ig hOPG binding domain.

The term "neutralises" as used in the concepts herein may be as defined hereinabove. In particular, the ability of an antagonist (e.g. an antibody or fragment thereof) to neutralise hOPG is measured in an HTRF assay. In one embodiment, the antagonist (e.g. antibody or fragment thereof) neutralises hOPG interaction with either hTRAIL and/or hRANKL and has a titration curve which provides a reduction in % specific binding at 50 nM [antagonist] (or at 30 nM [antagonist]) of approximately 20% or more as compared to isotype control. In another embodiment the antagonist (e.g. antibody or fragment thereof) neutralises hOPG interaction with either hTRAIL and/or hRANKL and has a titration curve which provides a reduction in % specific binding at 50 nM [antagonist] (or at 30 nM [antagonist]) of approximately 30% or more as compared to isotype control. In another embodiment the antagonist (e.g. antibody or fragment thereof) neutralises hOPG interaction with either hTRAIL and/or hRANKL and has a titration curve which provides a reduction in % specific binding at 50 nM [antagonist] (or at 30 nM [antagonist]) of approximately 40% or more as compared to isotype control. In another embodiment the antagonist (e.g. antibody or fragment thereof) neutralises hOPG interaction with either hTRAIL and/or hRANKL and has a titration curve which provides a reduction in % specific binding at 50 nM [antagonist] (or at 30 nM [antagonist]) of approximately 50% or more as compared to isotype control.

In another embodiment, the concentration of antagonist (e.g. antibody or fragment thereof) at which the % specific binding is measured is any datapoint which is taken in a concentration range of from 10 nM to 200 nM, for example 10 nM to 150 nM, or 10 nM to 100 nM. In another embodiment, the concentration of antagonist (e.g. antibody or fragment thereof) at which the % specific binding is measures is any datapoint which is taken in a concentration range of from 20 nM to 200 nM, for example 20 nM to 150 nM, or 20 nM to 100 nM. In another embodiment, the lower end point of the range is 10 nM, 20 nM, 30 nM, 40 nM or 50 nM. In another embodiment, the upper end point of the range is 500 nM, 250 nM, 200 nM, 150 nM, 100 nM or 75 nM.

In another embodiment, the antagonist (e.g. antibody or fragment thereof) neutralises hOPG interaction with either hTRAIL and/or hRANKL and has a titration curve which provides a reduction in % specific binding at 50 nM [antagonist] which is more than 3× (such as maybe 4× or even 5×) the standard deviation (SD) of the % specific binding of the isotype control.

In a further embodiment, the antagonist (e.g. antibody or fragment thereof) neutralises hOPG interaction with either hTRAIL and/or hRANKL and has a titration curve which provides a % maximum specific binding which is at least 20% lower as compared to isotype control. In another embodiment, the % maximum specific binding at least 30% lower, or at least 40% lower, or at least 50% lower as compared to isotype control.

In the concepts herein, the isotype control is an antibody generally of the same species (or mixture of species in the case of a chimera), and preferably having the same constant region as the test antibody, but wherein the $V_H$ and $V_L$ domains have either no specificity to the target antigen of interest (i.e. OPG), or have specificity for an antigen which is unrelated to the target antigen of interest (i.e. OPG) or are a non-binding combination of $V_H$ and $V_L$ to any other human target. When testing human variable-mouse constant chimeras, the isotype control may be a commercially available mouse IgG1 isotype control (e.g. available from Sigma Aldrich, catalogue number M9269). When testing a fully-human IgG4-PE formatted antibody, the isotype control is preferably an antibody having a human variable region and a human IgG4-PE constant region. A skilled person will be capable of identifying suitable antibodies as isotype controls.

HTRF assay may be carried out as described hereinabove.

The term "inhibits" as used in the concepts herein may be as defined hereinabove. In particular, the ability of an antagonist (e.g. an antibody or fragment thereof) to inhibit hOPG is measured in an HTRF assay. In one embodiment, the antagonist (e.g. antibody or fragment thereof) inhibits hOPG interaction with either hTRAIL and/or hRANKL and has a titration curve which provides a reduction in % specific binding at 50 nM [antagonist] (or at 30 nM [antagonist]) of approximately 20% or more as compared to isotype control. In another embodiment the antagonist (e.g. antibody or fragment thereof) inhibits hOPG interaction with either hTRAIL and/or hRANKL and has a titration curve which provides a reduction in % specific binding at 50 nM [antagonist] (or at 30 nM [antagonist]) of approximately 30% or more as compared to isotype control. In another embodiment the antagonist (e.g. antibody or fragment thereof) inhibits hOPG interaction with either hTRAIL and/or hRANKL and has a titration curve which provides a reduction in % specific binding at 50 nM [antagonist] (or at 30 nM [antagonist]) of approximately 40% or more as compared to isotype control. In another embodiment the antagonist (e.g. antibody or fragment thereof) inhibits hOPG interaction with either hTRAIL and/or hRANKL and has a titration curve which provides a reduction in % specific binding at 50 nM [antagonist] (or at 30 nM [antagonist]) of approximately 50% or more as compared to isotype control.

In another embodiment, the concentration of antagonist (e.g. antibody or fragment thereof) at which the % specific binding is measured is any datapoint which is taken in a concentration range of from 10 nM to 200 nM, for example 10 nM to 150 nM, or 10 nM to 100 nM. In another embodiment, the concentration of antagonist (e.g. antibody or fragment thereof) at which the % specific binding is measures is any datapoint which is taken in a concentration range of from 20 nM to 200 nM, for example 20 nM to 150 nM, or 20 nM to 100 nM. In another embodiment, the lower end point of the range is 10 nM, 20 nM, 30 nM, 40 nM or 50 nM. In another embodiment, the upper end point of the range is 500 nM, 250 nM, 200 nM, 150 nM, 100 nM or 75 nM.

In another embodiment the antagonist (e.g. antibody or fragment thereof) inhibits hOPG interaction with either hTRAIL and/or hRANKL and has a titration curve which provides a reduction in % specific binding at 50 nM [antagonist] which is more than 3× (such as maybe 4× or even 5×) the standard deviation (SD) of the % specific binding of the isotype control.

In a further embodiment, the antagonist (e.g. antibody or fragment thereof) inhibits hOPG interaction with either hTRAIL and/or hRANKL and has a titration curve which provides a % maximum specific binding which at least 20% lower as compared to isotype control. In another embodiment, the % maximum specific binding is at least 30% lower, or at least 40% lower, or at least 50% lower as compared to isotype control.

The HTRF assay as isotype controls may be as described hereinabove.

In these concepts, antibodies or fragments may include or may not include bispecific antibodies. In one embodiment, in these concepts, antibodies or fragments includes bispecific antibodies. In one embodiment, a bispecific antibody does not include a FIT-Ig format. In one embodiment, a bispecific antibody does not include a mAb$^2$ format. In one embodiment, a bispecific antibody does not include either a FIT-Ig format or a mAb² format. In one embodiment, the antibody or fragment in these concepts includes a bispecific antibody, but does not include a bispecific antibody having a FIT-Ig format. In one embodiment, the antibody or fragment in these concepts includes a bispecific antibody, but does not include a bispecific antibody having a mAb² format. In one embodiment, the antibody or fragment in these concepts includes a bispecific antibody, but does not include a bispecific antibody having a FIT-Ig format or a mAb² format. In another embodiment, in these concepts, antibodies or fragments include dual binding antibodies.

Preferably, an antibody or a fragment thereof that specifically binds to a hOPG antigen does not cross-react with other antigens (but may optionally cross-react with OPG of a different species, e.g., rhesus, cynomolgus, mouse and/or rat). An antibody or a fragment thereof that specifically binds to a hOPG antigen can be identified, for example, by immunoassays, BIAcore™, or other techniques known to those of skill in the art. An antibody or a fragment thereof binds specifically to a hOPG antigen when it binds to a hOPG antigen with higher affinity than to any cross-reactive antigen as determined using experimental techniques, such as radioimmunoassays (RIA) and enzyme-linked immunosorbent assays (ELISAs). Typically, a specific or selective reaction will be at least twice background signal or noise and more typically more than 10 times background. See, e.g., Paul, ed., 1989, Fundamental Immunology Second Edition, Raven Press, New York at pages 332-336 for a discussion regarding antibody specificity.

In one embodiment, the antibody or fragment is a human antibody. In one embodiment, the antibody or fragment is a human antibody or fragment. In one embodiment, the antibody or fragment is a fully human antibody or fragment. In one embodiment, the antibody or fragment is a fully human monoclonal antibody or fragment.

Concept 2. An antagonist (e.g. an antibody or fragment thereof) according to concept 1 which inhibits (e.g. neutralises) both the interaction of hOPG with hRANKL and the interaction of hOPG with hTRAIL.

Concept 2a. An antagonist (e.g. an antibody or fragment thereof) according to concept 1 which inhibits both the interaction of hOPG with hRANKL and the interaction of hOPG with hTRAIL.

Concept 2b. An antagonist (e.g. an antibody or fragment thereof) according to concept 1 which neutralises both the interaction of hOPG with hRANKL and the interaction of hOPG with hTRAIL.

In one embodiment, said antagonist (e.g. antibody or fragment thereof) neutralises the interaction of hOPG with hRANKL simultaneously as neutralising the interaction of hOPG with hTRAIL. In another embodiment, said antagonist (e.g. antibody or fragment thereof) neutralises the interaction of hOPG with hRANKL sequentially to neutralising the interaction of hOPG with hTRAIL.

Concept 3. An antagonist (e.g. an antibody or fragment thereof) according to concept 2, wherein the interaction of hOPG with hTRAIL is fully inhibited (e.g. neutralised) and wherein the interaction of hOPG with hRANKL is partially inhibited (e.g. neutralised).

Concept 3a. An antagonist (e.g. an antibody or fragment thereof) according to concept 2, wherein the interaction of hOPG with hTRAIL is fully inhibited, and wherein the interaction of hOPG with hRANKL is partially inhibited.

Concept 3b. An antagonist (e.g. an antibody or fragment thereof) according to concept 2, wherein the interaction of hOPG with hTRAIL is fully neutralised and wherein the interaction of hOPG with hRANKL is partially neutralised.

In any of the concepts herein, by "fully neutralised", or "fully inhibited" it is meant that the % specific binding at a given concentration or that the % maximum specific binding that is reached is comparable to (or the same as [within standard error]) that achieved when there is no ligand (e.g. RANKL or TRAIL) provided for in the assay. Thus, in one embodiment, full neutralisation or full inhibition provides a reduction of the % specific binding (at either 50 nM or 30 nM [antagonist]) in a range of from 80% to 100%, for example 85% to 100%, or 90% to 100% as compared to isotype control. In another embodiment, the full neutralisation or full inhibition provides a reduction of the % specific binding (at either 50 nM or 30 nM [antagonist]) in a range of from 95% to 100% as compared to isotype control. In another embodiment, the full neutralisation is a 100% reduction in % specific binding as compared to isotype control.

In another embodiment, full neutralisation or full inhibition provides a reduction of the % maximum specific binding in a range of from 80% to 100%, for example 85% to 100%, or 90% to 100% as compared to isotype control. In another embodiment, the full neutralisation or full inhibition provides a reduction of the % maximum specific binding in a range of from 95% to 100% as compared to isotype control. In another embodiment, the full neutralisation is 100% reduction in % maximum specific binding as compared to isotype control.

In any of the concepts herein, by "partially neutralised", or "partially inhibited" it is meant that the % specific binding at a given concentration, or that the % maximum specific binding that is reached, is in between that achieved when there is no ligand (e.g. RANKL or TRAIL) provided for in the assay, and when an isotype control is used in the assay. In one embodiment, the partial neutralisation or partial inhibition provides a reduction in % specific binding (at either 50 nM or 30 nM [antagonist]) or provides a reduction in % maximum specific binding in a range of from 25% to 75%, or 30 to 70%, or from 35% to 65% as compared to isotype control. In another embodiment, the partial neutralisation or partial inhibition provides a reduction in % specific binding (at either 50 nM or 30 nM [antagonist]) or provides a reduction in % maximum specific binding in a range of from 40% to 60% or 45% to 55% as compared to isotype control. In another embodiment, the partial neutralisation or partial inhibition provides a reduction in % specific binding (at either 50 nM or 30 nM [antagonist]) or provides a reduction in % maximum specific binding in a range of from 30% to 75%, or from 40% to 70% as compared to isotype control. In another embodiment, the partial neutralisation or partial inhibition provides a reduction in % specific binding (at either 50 nM or 30 nM [antagonist]) or provides a reduction in % maximum specific binding in of approximately 50% as compared to isotype control.

In another embodiment, the partial inhibition (e.g. neutralisation) has a lower limit of the range of 30%, 35%, 40% or 45%. The upper limit of the range for an antibody or fragment thereof which partially inhibits (e.g. neutralises) an interaction may be 55%, 60%, 65%, 70% or 75%.

Without being bound by theory, it may be that full inhibition (e.g. neutralisation) of hRANKL by the antagonist (e.g. antibody or fragment thereof), because when OPG is inhibited (e.g. neutralised) against RANKL, there is an increase in circulating RANKL, as OPG is not drawing RANKL out of circulation. This possible increase in circulating RANKL is available to bind and signal through its other bind partner, RANK. The signalling through RANK/

RANKL interaction is known to cause bone resorption and decreases bone density [Simonet W S, et al, "Osteoprotegerin: A Novel Secreted Protein Involved in the Regulation of Bone Density", Cell., 1997, 89, 309-319 and Boyce and Xing, "Functions of RANKL/RANK/OPG in bone modelling and remodelling", Arch Biochem Biophys., 2008, 473, 139-146]. It is thought that OPG and the interaction of OPG with RANKL regulates the level of bone resorption at a local level. However, prior art antibodies, mouse anti-human OPG antibody, Mab805 (R&D Systems) and polyclonal goat anti-mouse OPG antibodies, AF459 (R&D Systems) fully inhibit (e.g. neutralise) the OPG interaction with RANKL, and therefore, the antibodies described herein with only partial inhibition (e.g. partial neutralisation) capacity against RANKL may provide further advantages over these antibodies as therapeutics, due to reduced risk of bone-related adverse side-effects.

In one embodiment, the antagonist (e.g. antibody or fragment thereof) results in a reduction in the % of occluded vessels (e.g. muscularised vessels) as compared to an isotype control and/or disease control in an in vivo model of PAH. In another embodiment, the reduction in % of occluded vessels is at least approximately 20% (for example at least approximately 30%, at least approximately 40%, or at least approximately 50% or at least approximately 60%) as compared to an isotype control and/or disease control group in an in vivo model of PAH. The model may be any model as described herein. Without being bound by theory, the % occluded vessels (e.g. muscularised vessels) may be reduced due to apoptosis of smooth muscle cells by increased local availability of TRAIL.

In one embodiment, the antagonist (e.g. antibody or fragment thereof) results in a reduction in the RVSP (mmHg) as compared to an isotype control and/or disease control in an in vivo model of PAH. In one embodiment, the RVSP (mmHg) is between approximately 50 to 100 mmHg, or approximately 60 to 90 mmHg, or approximately 70 to 80 mmHg as compared to an isotype control and/or disease control. The model may be any model as described herein.

In one embodiment, the antagonist (e.g. antibody or fragment thereof) results in a reduction in the RV Ea (mmHg/RVU) as compared to an isotype control and/or disease control group in an in vivo model of PAH. In one embodiment, the RV Ea (mmHg/RVU) is between approximately 10 to 50 mmHg/RVU, or approximately 10 to 40 mmHg/RVU, or approximately 10 to 30 mmHg/RVU as compared to an isotype control and/or disease control. The model may be any model as described herein.

In one embodiment, the antagonist (e.g. antibody or fragment thereof) results in a reduction in the ePVRi (mmHg/RVU/min/g) as compared to an isotype control and/or disease control group in an in vivo model of PAH. In one embodiment, the ePVRi (mmHg/RVU/min/g) is between approximately 150 to 450 mmHg/RVU/min/g, or approximately 200 to 400 mmHg/RVU/min/g, or approximately 250 to 350 mmHg/RVU/min/g as compared to an isotype control and/or disease control. The model may be any model as described herein.

In one embodiment, the in vivo model of PAH is a prophylactic monocrotaline-induced PAH model in rats, for example as described in Example 5. In another embodiment, the in vivo model is a prophylactic sugen hypoxia induced PAH model in rats, for example as described in Example 6. In another embodiment, the in vivo model of PAH is a therapeutic monocrotaline-induced PAH model in rats, for example as described in Example 7. In another embodiment, the in vivo model is a therapeutic sugen hypoxia-induced PAH model in rats, for example as described in Example 8. In one embodiment, the in vivo model is a therapeutic sugen hypoxia-induced PAH model in rats where the rats are treated sub-cutaneously with 20 mg/kg SU5416 and are kept in hypoxia conditions for 3 weeks, then returned to normoxia, and are treated intraperonitally with 3 mg/kg antagonist (e.g. antibody or fragment thereof) at week 6, 7 and 8, and then are euthanased at week 9.

In another embodiment, the measurement is carried out on a rat (or rats) 21 days post-treatment. In another embodiment, the change in the measurement is statistically significant.

Concept 3c. An antagonist (e.g. an antibody or fragment thereof) according to concept 2, wherein the antibody or fragment inhibits or neutralises the interaction of hOPG with hTRAIL to a greater extent than the antibody or fragment inhibits or neutralises the interaction of hOPG with hRANKL.

In concept 3c, the term "greater extent" means at least 50% more than, e.g. the $K_D$ of the antibody or fragment is 50% lower to hTRAIL than to hRANKL. In another embodiment, a greater extent may be at least a 1.5-fold difference in $K_D$, or at least a 2-fold difference, or at least a 2.5-fold difference in $K_D$. In another embodiment, a greater extent may be at least a 3-fold difference in $K_D$, or at least a 4-fold difference, or at least a 5-fold difference in $K_D$.

Concept 3d. An antagonist (e.g. an antibody or fragment thereof) according to claim 2, wherein the antibody or fragment inhibits or neutralises the interaction of hOPG with hTRAIL preferentially to the interaction of hOPG with hRANKL.

In concept 3d, the term "preferentially" means at that the antibody or fragment thereof inhibits or neutralises the interaction of hOPG with hTRAIL better than said antibody or fragment thereof inhibits or neutralises the interaction of hOPG with hRANKL, i.e. the $K_D$ for hTRAIL will be statistically significantly lower than for hRANKL. For example, the antibody or fragment may inhibit or neutralise hTRAIL at least 50% more than it inhibits or neutralises hRANKL, e.g. the $K_D$ of the antibody or fragment is 50% lower to hTRAIL than to hRANKL. In another embodiment, preferentially means that there is at least a 1.5-fold difference in $K_D$, or at least a 2-fold difference, or at least a 2.5-fold difference in $K_D$. In another embodiment, there is at least a 3-fold difference in $K_D$, or at least a 4-fold difference, or at least a 5-fold difference in $K_D$.

Concept 4. An antagonist (e.g. an antibody or a fragment thereof) according to any of concepts 1 to 3, which competes for binding to said hOPG with the antibody Ky3 (15F11).

The antibody Ky3 (15F11) is as described hereinabove, having any of the sequences of CDRs, variable regions and/or full length heavy and light chains as described.

In one embodiment, competition for binding to hOPG may be conducted using SPR. SPR may be carried out as described hereinabove, or as described hereinabove. This applies mutatis mutandis to concepts 7, 9, 24 and 32 hereinbelow.

Concept 5. An antagonist (e.g. an antibody or fragment thereof) according to concept 3 or 4, for treating an OPG-mediated disease or condition in a subject, wherein administration of the antibody or fragment to the subject results in an increase in circulating OPG in said subject.

Concept 5a. An antagonist (e.g. an antibody or fragment thereof) according to concept 3 or 4, for treating an OPG-mediated disease or condition in a subject, wherein administration of the antibody or fragment to the subject is capable of increasing circulating OPG in said subject.

The OPG-mediated disease or condition may be any of the disease or disorders disclosed herein, in particular as specified in any of concepts 52 to 58 hereinbelow.

It has been observed (data not shown) that the antibody Ky3 (15F11), but none of Ky1 (6D07), Ky2 (8C10) or Ky4 (16G05), when administered to a subject (e.g. a rodent such as a rat) results in an increase in circulating OPG.

Figure 1A:
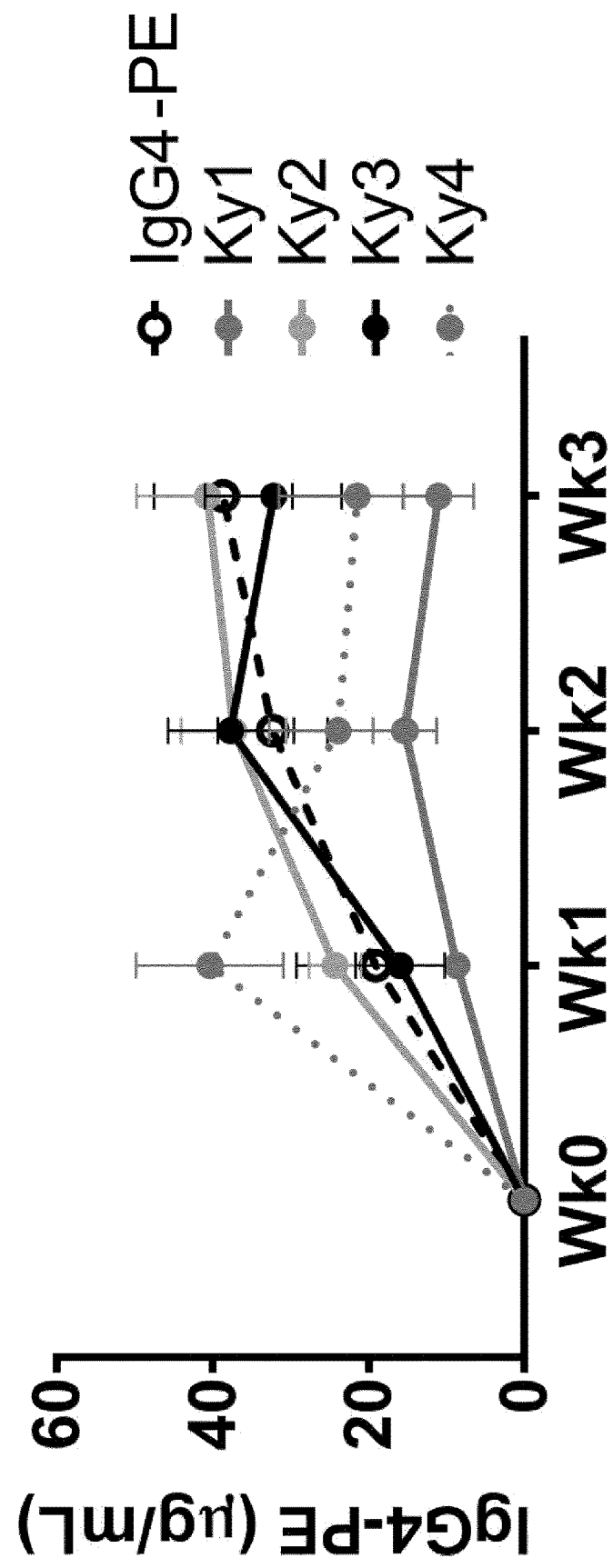
(FIG. 1a) Plasma concentrations of antibodies (Ky1 (6D07), Ky2 (8C10), Ky3 (15F11), Ky4 (16G05) and control human IgG4-PE). Bar graphs show (FIG. 1b) right ventricular systolic pressure (RVSP), (FIG. 1c) right ventricular hypertrophy (RVH), (FIG. 1d) estimated pulmonary vascular resistance (ePVRi) and (FIG. 1e) left ventricular end-systolic pressure (LVESP). Scatter plot (Figure if) demonstrates the media/cross-sectional area by vessel diameter with each vessel analysed depicted as a dot. Bar graphs show (FIG. 1g) the degree of medial wall thickness as a ratio of total vessel size (Media/CSA) and (FIG. 1h) the relative percentage of muscularised small pulmonary arteries and arterioles in <50 μm vessels. (Figure ii) Representative photomicrographs of serial lung sections. Sections were immunostained for α-smooth muscle actin (α-SMA), or von Willebrand Factor (vWF).
Figure 1B:
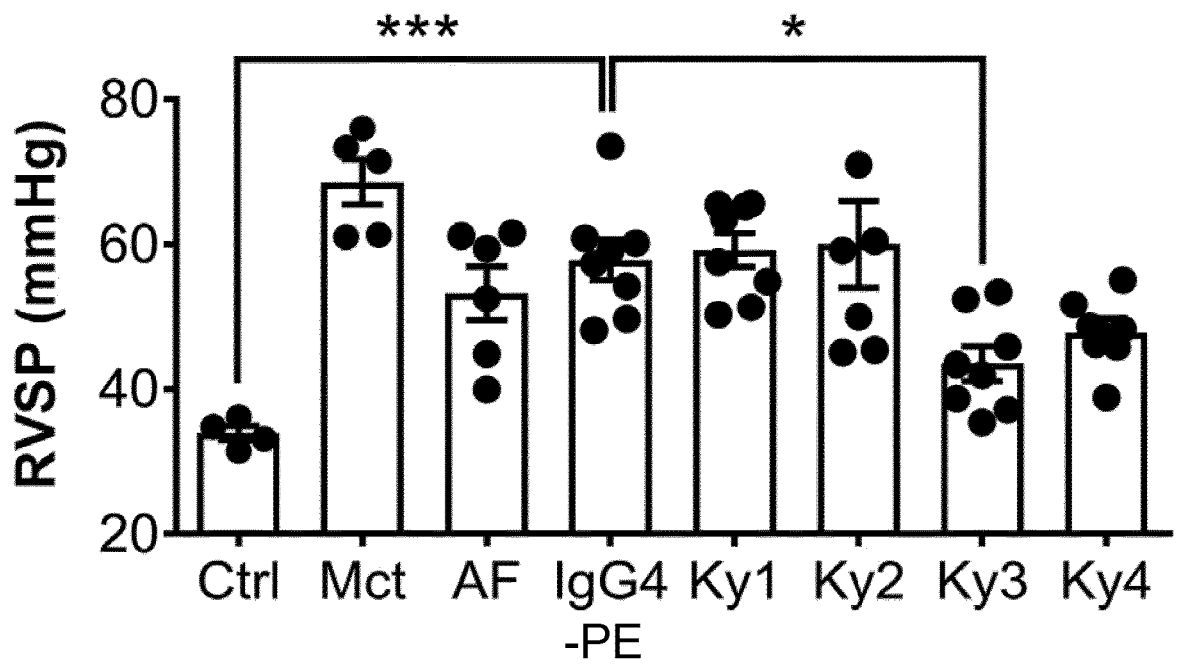
FIG. 1: Monoclonal human anti-human OPG attenuates development of severe PAH induced by monocrotaline in rats.
(FIG. 1j) Circulating plasma levels of OPG. Bars represent mean+/−SEM, dots represent individual animals (Ctrl n=4, Mct n=5, AF n=7, IgG & Ky1-4 n=8 animals per group). *=p<0.05, =p<0.01, *=p<0.001 compared to IgG4-PE treated rats. All images are presented at their original magnification ×400, scale bar represents 50 μm.
Figure 1C:
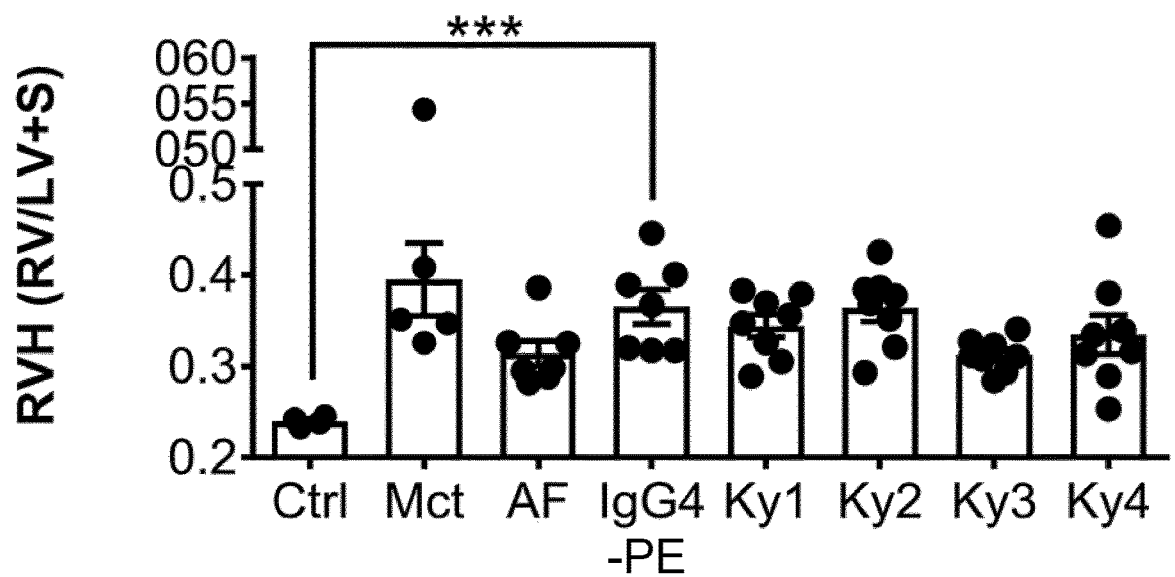
Figure 1D:
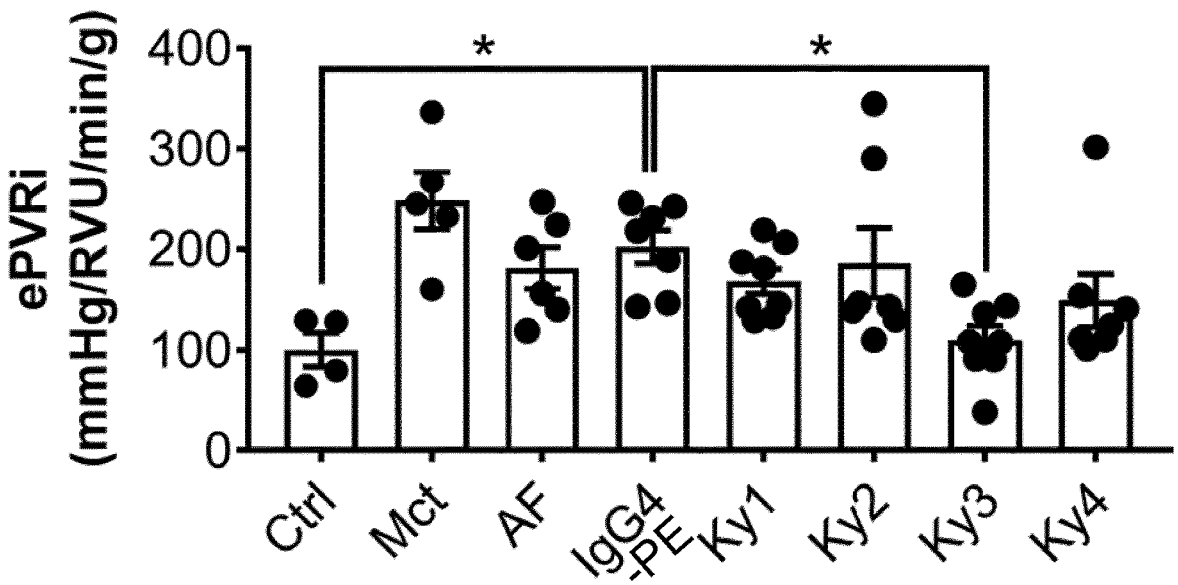
Figure 1E:
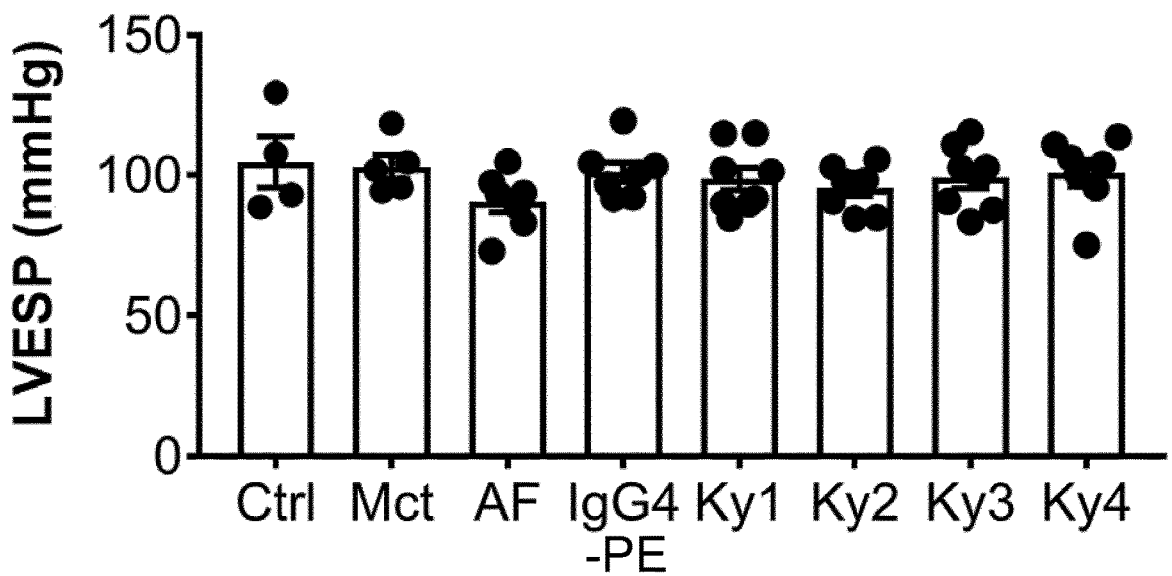
Figure 1F:
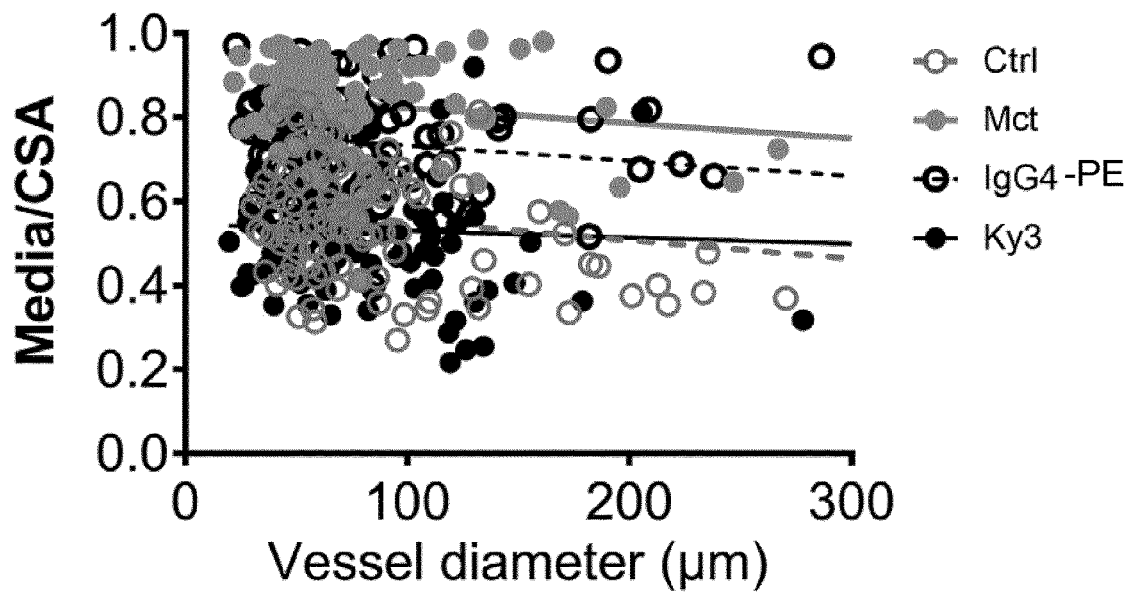
Figure 1G:
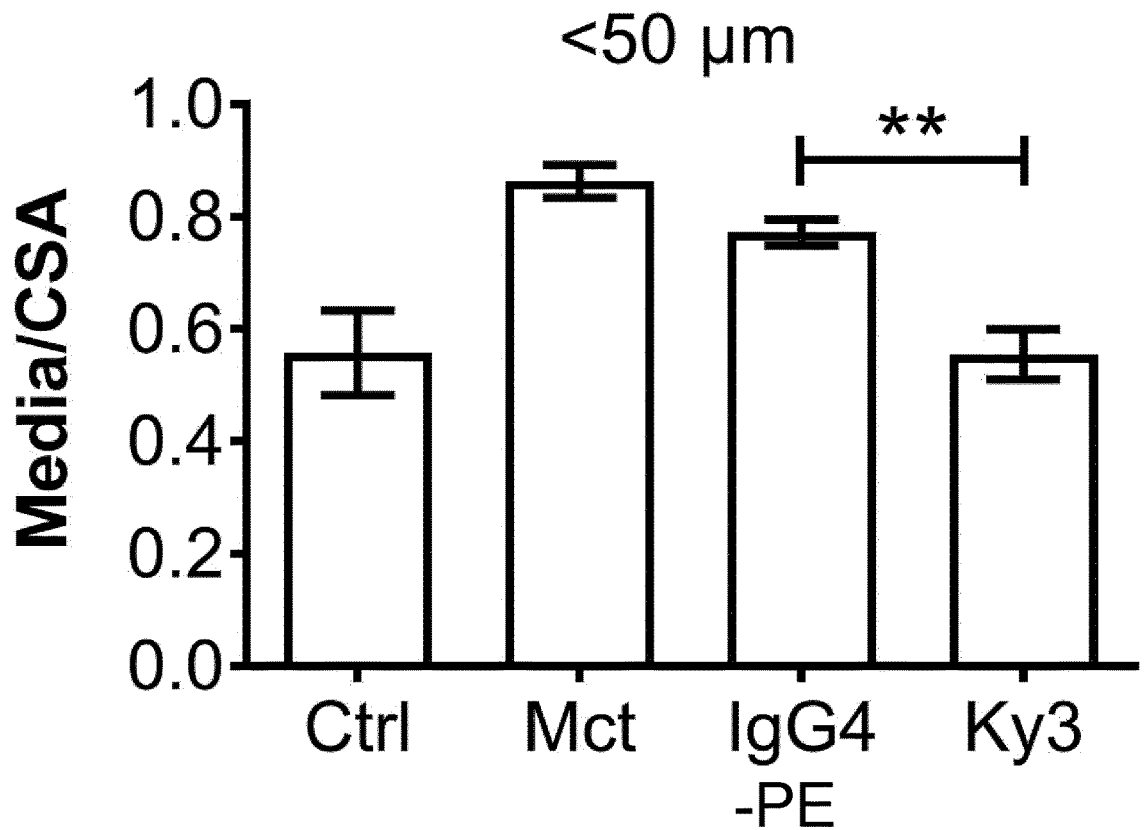
Figure 1H:
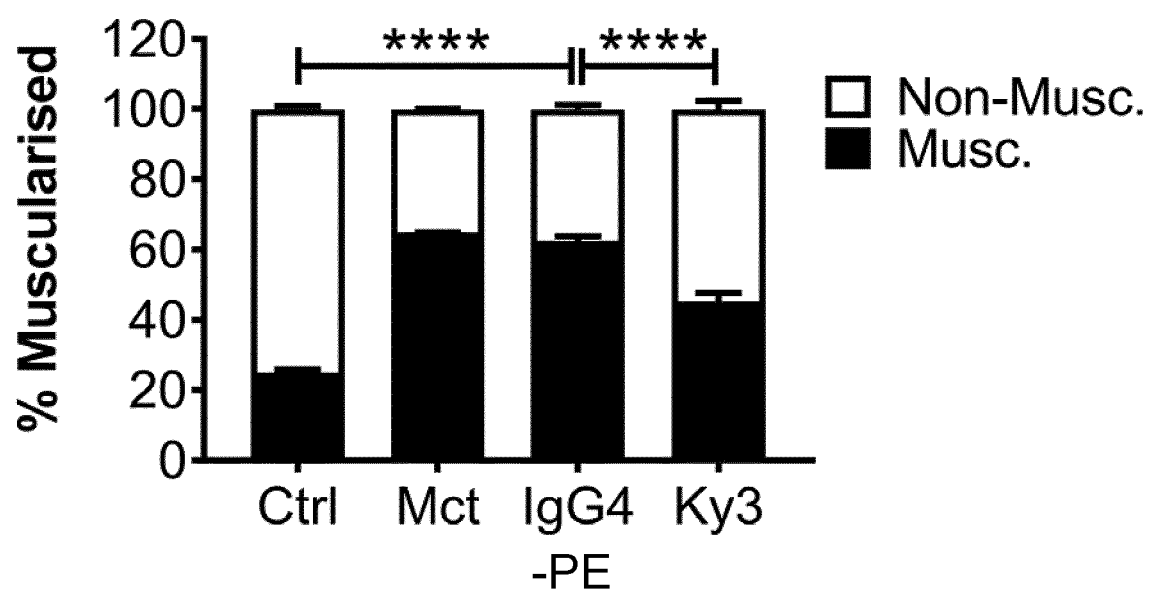
Figure 1I:
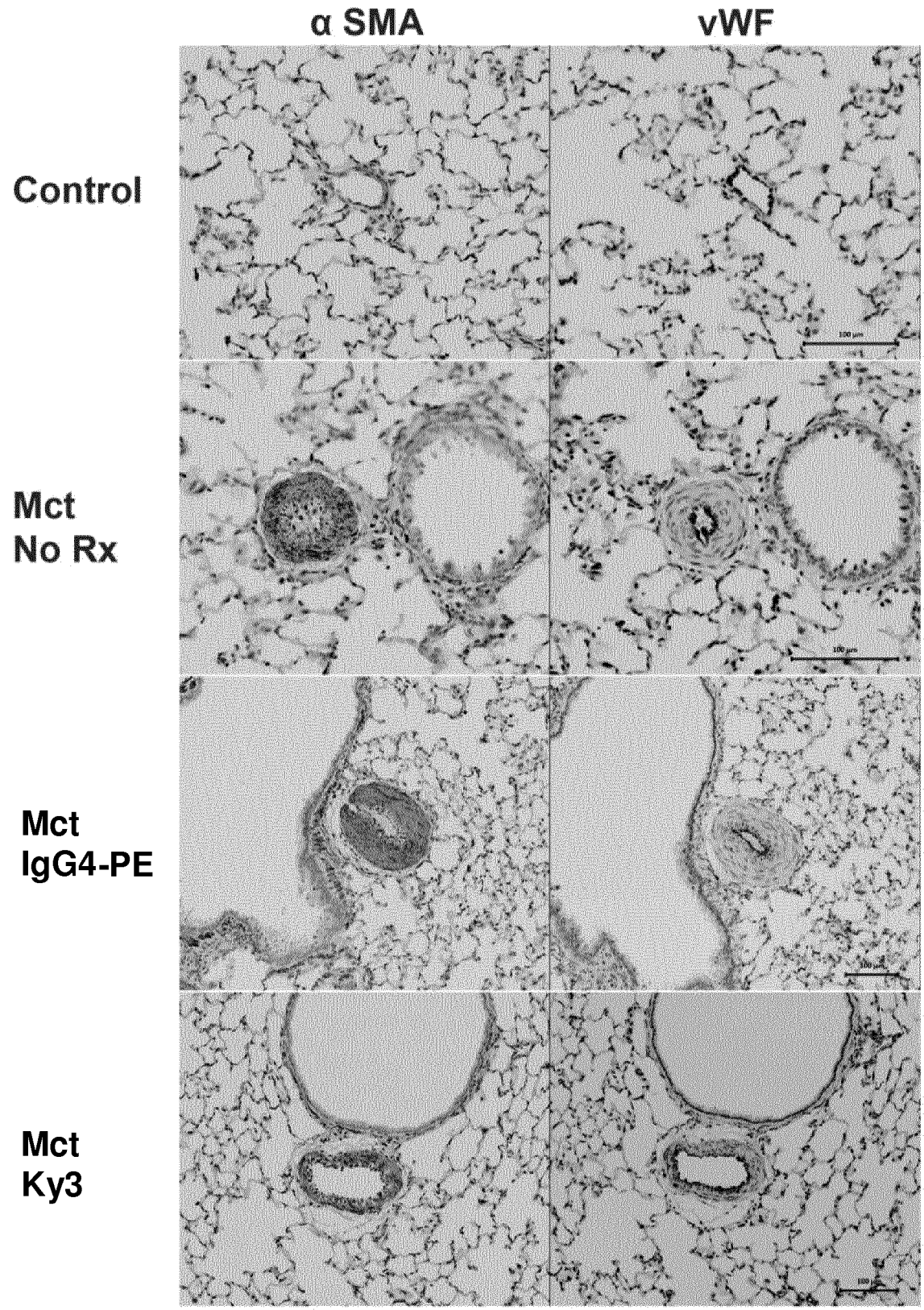
Figure 1J:
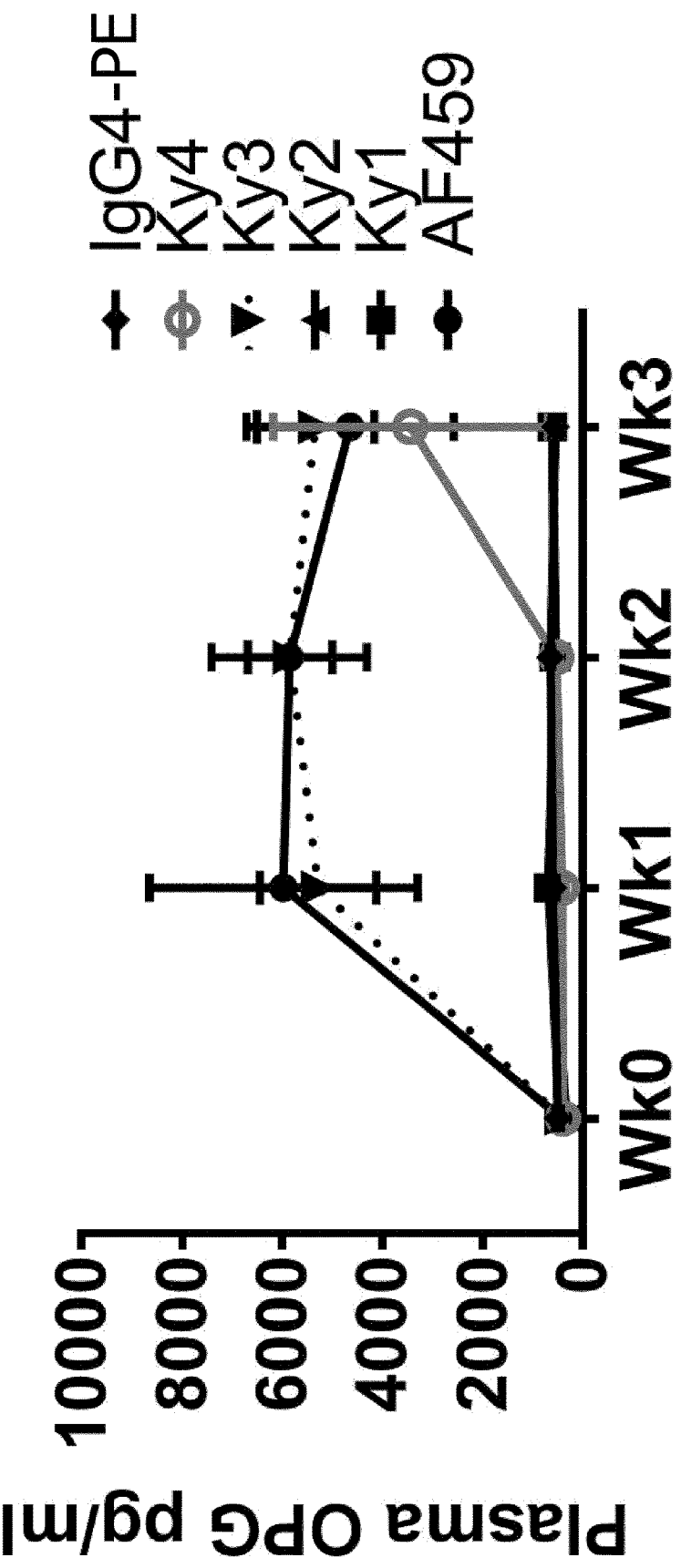

In an ELISA assay, using the Millipore luminex rat OPG assay which quantifies the amount of circulating OPG in plasma taken from rats in the Mct model, Ky3 (15F11) showed an increase of approximately 10-40-fold as compared to isotype control (baseline), and each of Ky1 (6D07), Ky2 (8C10), and Ky4 (16G05), see FIG. 1j hereinbelow. Sustained levels of OPG were observed at week 1, week 2 and week 3 (endpoint) after the first dose during the study, with absolutely values being approximately 5,000-7,000 pg OPG/mL.

In an ELISA assay, using the Millipore luminex rat OPG assay which quantifies the amount of circulating OPG in plasma taken from rats in the SuHx model, Ky3 (15F11) showed an increase of approximately 3-fold as compared to isotype control (baseline). Sustained levels of OPG were observed at week 1, week 2 and week 3 (endpoint) after the first dose during the study, with absolutely values being approximately 3,000-3,500 pg OPG/mL.

Thus, in one embodiment, the plasma levels of OPG in a subject are at least 2-fold increased (e.g. 3-fold, 5-fold, 7-fold or 10-fold increased) after treatment with an anti-OPG antibody of the invention as compared to isotype control, for example in a Mct rat model of PAH, or in a SuHx rat model of PAH. In another embodiment, the plasma levels of OPG in a subject are at least 15-fold increased (e.g. 20-fold, 25-fold, 30-fold or 35-fold increased) after treatment with an anti-OPG antibody of the invention as compared to isotype control, for example in a Mct rat model of PAH, or in a SuHx rat model of PAH.

In another embodiment, the absolute plasma concentration of OPG in a subject is at least 2,000 pg/mL, or at least 2,500 pg/mL, or at least 3,000 pg/mL, after treatment with an anti-OPG antibody of the invention, for example in a Mct rat model of PAH, or in a SuHx rat model of PAH. In another embodiment, the plasma concentration of OPG in a subject is at least 3,500 pg/mL, or at least 4,000 pg/mL, or at least 4,500 pg/mL, or at least 5,000 pg/mL, or at least 5,500 pg/mL, or at least 6,000 pg/mL, or at least 6,500 pg/mL, or at least 7,000 pg/mL, after treatment with an anti-OPG antibody of the invention, for example in a Mct rat model of PAH, or in a SuHx rat model of PAH. The serum levels of OPG may be in a range of approximately 2,500 to 4,000 pg/mL, or from 3,000 to 3,500 pg/mL. The serum levels of OPG may be in a range of approximately 4,000 to 8,000 pg/mL, or from 4,500 to 7,500 pg/mL, or from 5,000 to 7,000 pg/mL, or from 5,500 to 6,500 pg/mL.

In any of the concepts herein, a subject may be as defined hereinabove. In a particular embodiment, the subject is a rodent, e.g. rat or mouse, for example a rat. In a particular embodiment, the subject is a human patient.

In another embodiment, the increase in circulating OPG may be measured in any appropriate model, for example ELISA, Western Blot, PCR or by mRNA detection (e.g. in a microarray). These techniques are well-known to those skilled in the art.

Concept 6. An antagonist (e.g. an antibody or fragment thereof) according to concept 2, wherein the interaction of hOPG with hTRAIL is partially inhibited (e.g. partially neutralised) and wherein the interaction of hOPG with hRANKL is partially inhibited (e.g. partially neutralised).

Concept 6a. An antagonist (e.g. an antibody or fragment thereof) according to concept 2, wherein the interaction of hOPG with hTRAIL is partially inhibited and wherein the interaction of hOPG with hRANKL is partially inhibited.

Concept 6b. An antagonist (e.g. an antibody or fragment thereof) according to concept 2, wherein the interaction of hOPG with hTRAIL is partially neutralised and wherein the interaction of hOPG with hRANKL is partially neutralised.

Partial inhibition (e.g. partial neutralisation) of either hTRAIL or hRANKL may be defined as set out for concept 3 hereinabove.

Concept 6c. An antagonist (e.g. an antibody or fragment thereof) according to concept 2, wherein the antibody or fragment inhibits or neutralises the interaction of hOPG with hTRAIL to a comparable extent than the antibody or fragment neutralises the interaction of hOPG with hRANKL.

A "comparable extent" in the concepts herein means that the difference between the values obtained (e.g. $K_D$ or other measurement of neutralisation or binding) are not statistically significantly different. In one embodiment, the values may be within 2× standard deviation of each other. In another embodiment, the values may be within 3× (e.g. 4× or 5×) standard deviation of each other. In another embodiment, the values are within 2% of each other. In another embodiment, the values are within 5% of each other. In another embodiment, the values are within 10% of each other. In another embodiment, the values are within 12%, 14%, 16%, 18% or 20% of each other.

Concept 7. An antagonist (e.g. an antibody or a fragment thereof) according to concept 1 or concept 6, which competes for binding to said hOPG with the antibody Ky4 (16G05).

The antibody Ky4 (16G05) is as described hereinabove, having any of the sequences of CDRs, variable regions and/or full length heavy and light chains as described.

Concept 8. An antagonist (e.g. an antibody or fragment thereof) according to concept 1, wherein the antagonist (e.g. antibody or fragment thereof) fully inhibits (e.g. fully neutralises) the interaction of OPG with TRAIL, but does not inhibit (e.g. neutralise) the interaction of OPG with RANKL.

Concept 8a. An antagonist (e.g. an antibody or fragment thereof) according to concept 1, wherein the antagonist (e.g. antibody or fragment thereof) fully inhibits the interaction of OPG with TRAIL, but does not inhibit the interaction of OPG with RANKL.

Concept 8b. An antagonist (e.g. an antibody or fragment thereof) according to concept 1, wherein the antagonist (e.g. antibody or fragment thereof) fully neutralises the interaction of OPG with TRAIL, but does not neutralise the interaction of OPG with RANKL.

Concept 9. An antagonist (e.g. an antibody or a fragment thereof) according to concept 8, which competes for binding to said hOPG with the antibody Ky1 (6D07).

Concept 10. An antagonist (e.g. an antibody or fragment thereof) according to any one of concepts 1 to 9, wherein the antagonist (e.g. antibody or fragment thereof) binds to hOPG with a $K_D$ of 0.1 nM or less.

In one embodiment the antagonist (e.g. antibody or fragment thereof) binds to hOPG with a $K_D$ of less than 50 nM, less than 40 nM, less than 30 nM as determined by surface plasmon resonance. Another embodiment, anti-OPG antibody or fragment thereof may bind to OPG, e.g. human OPG with a $K_D$ of less than 20 nM, less than 15 nM, less than 10 nM as determined by surface plasmon resonance. In another embodiment, the anti-OPG antibody or fragment thereof may bind to OPG, e.g. human OPG with a $K_D$ of less than 8 nM, less than 5 nM, less than 4 nM, less than 3 nM, less than 2 nM or less than 1 nM as determined by surface plasmon resonance. The $K_D$ may be 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less.

In another embodiment, the $K_D$ is within a range of 0.01 to 1 nM, or a range of 0.05 to 2 nM, or a range of 0.05 to 1 nM. The $K_D$ may be with regard to hOPG, cynoOPG, ratOPG and/or mouse OPG.

Concept 11. An antagonist (e.g. an antibody or fragment thereof) according to any one of concepts 1 to 10, for treating an OPG-mediated disease or condition in a subject, wherein administration of the antagonist (e.g. antibody or fragment thereof) to the subject results in an increase in circulating TRAIL and/or RANKL in said subject.

Concept 11a. An antagonist (e.g. an antibody or fragment thereof) according to any one of concepts 1 to 10, for treating an OPG-mediated disease or condition in a subject, wherein administration of the antagonist (e.g. antibody or fragment thereof) to the subject is capable of increasing circulating TRAIL and/or RANKL in said subject.

In any of the concepts herein, a subject may be as defined hereinabove. In a particular embodiment, the subject is a rodent, e.g. rat or mouse, for example a rat. In a particular embodiment, the subject is a human patient.

Concept 12. An antagonist (e.g. an antibody or fragment thereof) according to any one of concepts 1 to 11, which specifically binds rat OPG (rOPG) (Seq ID No:3), and optionally inhibits (e.g. neutralises) the interaction of rOPG with rat RANKL and/or rat TRAIL.

Concept 12a. An antagonist (e.g. an antibody or fragment thereof) according to any one of concepts 1 to 11, which specifically binds rat OPG (rOPG) (Seq ID No:3), and optionally inhibits the interaction of rOPG with rat RANKL and/or rat TRAIL.

Concept 12b. An antagonist (e.g. an antibody or fragment thereof) according to any one of concepts 1 to 11, which specifically binds rat OPG (rOPG) (Seq ID No:3), and optionally neutralises the interaction of rOPG with rat RANKL and/or rat TRAIL.

In one embodiment, the antibody or fragment binds to rat OPG with an affinity of less than 1 nM (e.g. from 1 nM to 0.01 pM or from 1 nM to 0.1 pM, or from 1 nM to 1 pM). In one embodiment, the antibody or fragment binds to rat OPG with an affinity of less than 10 nM (e.g. from 10 nM to 0.01 pM or from 10 nM to 0.1 pM, or from 10 nM to 1 pM). In one embodiment, the antibody or fragment binds to rat OPG with an affinity of less than 0.1 nM (e.g. from 0.1 nM to 0.01 pM or from 0.1 nM to 0.1 pM, or from 0.1 nM to 1 pM). In one embodiment, the antibody or fragment binds to rat OPG with an affinity of less than 0.01 nM (e.g. from 0.011 nM to 0.01 pM or from 0.01 nM to 0.1 pM).

In one embodiment, the antibody or fragment binds to rat OPG with an affinity of within 2-fold of the affinity to hOPG. In one embodiment, the antibody or fragment binds to rat OPG with an affinity of within 4-fold of the affinity to hOPG. In one embodiment, the antibody or fragment binds to rat OPG with an affinity of within 5-fold of the affinity to hOPG. In one embodiment, the antibody or fragment binds to rat OPG with an affinity of within 6-fold of the affinity to hOPG. In one embodiment, the antibody or fragment binds to rat OPG with an affinity of within 8-fold of the affinity to hOPG. In one embodiment, the antibody or fragment binds to rat OPG with an affinity of within 10-fold of the affinity to hOPG.

In one embodiment, the antibody or fragment does not detectably bind to rat OPG.

Concept 13. An antagonist (e.g. an antibody or fragment thereof) according to concept 12, wherein the antagonist (e.g. antibody or fragment thereof) binds to rOPG with a $K_D$ of 10 nM or less.

Concept 14. An antagonist (e.g. an antibody or fragment thereof) according to any one of concepts 1 to 13, which specifically binds cynomolgus OPG (cOPG) (Seq ID No:2), and optionally inhibits (e.g. neutralises) the interaction of cOPG with cynomolgus RANKL and/or cynomolgus TRAIL.

Concept 14a. An antagonist (e.g. an antibody or fragment thereof) according to any one of concepts 1 to 13, which specifically binds cynomolgus OPG (cOPG) (Seq ID No:2), and optionally inhibits the interaction of cOPG with cynomolgus RANKL and/or cynomolgus TRAIL.

Concept 14b. An antagonist (e.g. an antibody or fragment thereof) according to any one of concepts 1 to 13, which specifically binds cynomolgus OPG (cOPG) (Seq ID No:2), and optionally neutralises the interaction of cOPG with cynomolgus RANKL and/or cynomolgus TRAIL.

In one embodiment, the antibody or fragment binds to cynomolgus OPG with an affinity of less than 1 nM (e.g. from 1 nM to 0.01 pM or from 1 nM to 0.1 pM, or from 1 nM to 1 pM). In one embodiment, the antibody or fragment binds to cynomolgus OPG with an affinity of less than 10 nM (e.g. from 10 nM to 0.01 pM or from 10 nM to 0.1 pM, or from 10 nM to 1 pM). In one embodiment, the antibody or fragment binds to cynomolgus OPG with an affinity of less than 0.1 nM (e.g. from 0.1 nM to 0.01 pM or from 0.1 nM to 0.1 pM, or from 0.1 nM to 1 pM). In one embodiment, the antibody or fragment binds to cynomolgus OPG with an affinity of less than 0.01 nM (e.g. from 0.011 nM to 0.01 pM or from 0.01 nM to 0.1 pM).

In one embodiment, the antibody or fragment binds to cynomolgus OPG with an affinity of within 2-fold of the affinity to hOPG. In one embodiment, the antibody or fragment binds to cynomolgus OPG with an affinity of within 4-fold of the affinity to hOPG. In one embodiment, the antibody or fragment binds to cynomolgus OPG with an affinity of within 5-fold of the affinity to hOPG. In one embodiment, the antibody or fragment binds to cynomolgus OPG with an affinity of within 6-fold of the affinity to hOPG. In one embodiment, the antibody or fragment binds to cynomolgus OPG with an affinity of within 8-fold of the affinity to hOPG. In one embodiment, the antibody or fragment binds to cynomolgus OPG with an affinity of within 10-fold of the affinity to hOPG.

In one embodiment, the antibody or fragment does not detectably bind to cynomolgus OPG.

Concept 15. An antagonist (e.g. an antibody or fragment thereof) according to concept 14, wherein the antagonist (e.g. antibody or fragment thereof) binds to rOPG with a $K_D$ of 15 nM or less.

Concept 16. An antagonist (e.g. an antibody or fragment thereof) according to any one of concepts 1 to 15, wherein the antagonist is a human antibody or fragment thereof, in particular a fully human complete antibody comprising two full-length heavy chains and two full length light chains.

Concept 17. An antibody or a fragment thereof according to any one of concepts 1 to 16, wherein the antibody or fragment comprises a $V_H$ domain which comprises a CDRH3 comprising the motif $YYYDSX_1X_2Y$ wherein $X_1$ and $X_2$ are independently any amino acid.

Concept 17a. An antibody or a fragment thereof according to any one of concepts 1 to 16, wherein the antibody or fragment comprises a $V_H$ domain which comprises a CDRH3 comprising the motif $X_1$FDY wherein $X_1$ is any amino acid.

In one embodiment, the CDRH3 is as defined by Kabat. In another embodiment, the CDRH3 is as defined by IMGT.

Concept 18. The antibody or fragment thereof according to concept 17, wherein $X_1$ is a hydroxyl-containing amino acid or an aliphatic amino acid.

Concept 18a. The antibody or fragment thereof according to concept 17a, wherein $X_1$ is an aromatic amino acid (e.g. phenylalanine (F)), a cyclic amino acid or an aliphatic amino acid (e.g. alanine (A) or leucine (L)).

In one embodiment, in concept 18a, $X_1$ is an aromatic amino acid selected from Phenylalanine, Tyrosine and Tryptophan. In another embodiment, $X_1$ is an aromatic amino acid selected from Phenylalanine and Tyrosine. In another embodiment, $X_1$ is an aromatic amino acid selected from Phenylalanine and Tryptophan. In another embodiment, $X_1$ is an aromatic amino acid selected from Tryptophan and Tyrosine. In another embodiment, $X_1$ is Phenylalanine. In another embodiment, $X_1$ is Tyrosine. In another embodiment, $X_1$ is Tryptophan.

In one embodiment, in concept 18a, $X_1$ is proline.

In one embodiment, in concept 18a, $X_1$ is an aliphatic amino acid selected from Glycine (G), Alanine (A), Valine (V), leucine (L), and isoleucine (I). In one embodiment, $X_1$ is Glycine (G). In one embodiment, $X_1$ is Alanine (A). In one embodiment, $X_1$ is Valine (V). In one embodiment, $X_1$ is leucine (L). In one embodiment, $X_1$ is isoleucine (I).

In one embodiment, $X_1$ is selected from Glycine and Alanine. In one embodiment, $X_1$ is selected from Glycine and Valine. In one embodiment, $X_1$ is selected from Glycine and Leucine. In one embodiment, $X_1$ is selected from Glycine and Isoleucine. In one embodiment, $X_1$ is selected from Alanine and Valine. In one embodiment, $X_1$ is selected from Alanine and Leucine. In one embodiment, $X_1$ is selected from Alanine and Isoleucine. In one embodiment, $X_1$ is selected from Valine and Leucine. In one embodiment, $X_1$ is selected from Valine and Isoleucine. In one embodiment, $X_1$ is selected from, Leucine and Isoleucine.

In one embodiment, $X_1$ is independently selected from three of each of Glycine, Alanine, Valine, Leucine and Isoleucine. In one embodiment, $X_1$ is independently selected from four of each of Glycine, Alanine, Valine, Leucine and Isoleucine.

Concept 19. The antibody or fragment thereof according to concept 18, wherein $X_1$ is a hydroxyl-containing amino acid, optionally serine (S).

In one embodiment, the hydroxyl-containing amino acid is selected from serine, cysteine, threonine and methionine.

In one embodiment, the hydroxyl-containing amino acid is Serine. In one embodiment, the hydroxyl-containing amino acid is Cysteine. In one embodiment, the hydroxyl-containing amino acid is Threonine. In one embodiment, the hydroxyl-containing amino acid is Methionine.

In one embodiment, the hydroxyl-containing amino acid is Serine or Cysteine. In one embodiment, the hydroxyl-containing amino acid is Serine or Threonine. In one embodiment, the hydroxyl-containing amino acid is Serine or Methionine. In one embodiment, the hydroxyl-containing amino acid is Cysteine or Threonine. In one embodiment, the hydroxyl-containing amino acid is Cysteine or Methionine. In one embodiment, the hydroxyl-containing amino acid is Threonine or Methionine.

Concept 20. The antibody or fragment thereof according to concept 18, wherein $X_1$ is an aliphatic amino acid, optionally glycine (G).

In one embodiment, $X_2$ is selected from Glycine (G), Alanine (A), Valine (V), leucine (L), and isoleucine (I). In one embodiment, $X_2$ is Glycine (G). In one embodiment, $X_2$ is Alanine (A). In one embodiment, $X_2$ is Valine (V). In one embodiment, $X_2$ is leucine (L). In one embodiment, $X_2$ is isoleucine (I).

In one embodiment, $X_2$ is selected from Glycine and Alanine. In one embodiment, $X_2$ is selected from Glycine and Valine. In one embodiment, $X_2$ is selected from Glycine and Leucine. In one embodiment, $X_2$ is selected from Glycine and Isoleucine. In one embodiment, $X_2$ is selected from Alanine and Valine. In one embodiment, $X_2$ is selected from Alanine and Leucine. In one embodiment, $X_2$ is selected from Alanine and Isoleucine. In one embodiment, $X_2$ is selected from Valine and Leucine. In one embodiment, $X_2$ is selected from Valine and Isoleucine. In one embodiment, $X_2$ is selected from, Leucine and Isoleucine.

In one embodiment, $X_2$ is independently selected from three of each of Glycine, Alanine, Valine, Leucine and Isoleucine. In one embodiment, $X_2$ is independently selected from four of each of Glycine, Alanine, Valine, Leucine and Isoleucine.

Concept 21. The antibody or fragment thereof according to any one of concepts 17 to 20, wherein $X_2$ is a hydroxyl-containing amino acid or an aliphatic amino acid.

Concept 22. The antibody or fragment thereof according to concept 21, wherein $X_2$ is a hydroxyl-containing amino acid, optionally serine (S).

The hydroxyl-containing amino acids may be as described for concept 19 hereinabove.

Concept 23. The antibody or fragment thereof according to concept 21, wherein $X_2$ is an aliphatic amino acid, optionally A.

The hydroxyl-containing amino acids may be as described for concept 20 hereinabove.

Concept 24. An antibody or a fragment thereof, optionally according to any one of concepts 1 to 23, which specifically binds to hOPG, and a. competes for binding to said hOPG with the antibody Ky1 (6D07), wherein the antibody Ky1 (6D07) comprises a $V_H$ domain which comprises the CDRH3 sequence of Seq ID No:8 or 11, or the CDRH3 sequence of Seq ID No:8 or 11 comprising 3 or fewer amino acid substitutions; or b. competes for binding to said hOPG with the antibody Ky2 (8C10), wherein the antibody Ky2 (8C10) comprises a $V_H$ domain which comprises the CDRH3 sequence of Seq ID No:28 or 31, or the CDRH3 sequence of Seq ID No:28 or 31 comprising 5 or fewer amino acid substitutions; or c. competes for binding to said hOPG with the antibody Ky3 (15F11), wherein the antibody Ky3 (15F11) comprises a $V_H$ domain which comprises the CDRH3 sequence of Seq ID No:48 or 51, or the CDRH3 sequence of Seq ID No:48 or 51 comprising 6 or fewer amino acid substitutions; or d. competes for binding to said hOPG with the antibody Ky4 (16G05), wherein the antibody Ky4 (16G05) comprises a $V_H$ domain which comprises the CDRH3 sequence of Seq ID No:68 or 71, or the CDRH3 sequence of Seq ID No:68 or 71 comprising 5 or fewer amino acid substitutions; or e. competes for binding to said hOPG with the antibody Ky5 (15H06), wherein the antibody Ky5 (16H06) comprises a $V_H$ domain which comprises the CDRH3 sequence of Seq ID No:88 or 91, or the CDRH3 sequence of Seq ID No:88 or 91 comprising 3 or fewer amino acid substitutions.

In all of concepts 24, 33, 34, 35, 38, 39 and 40, in one embodiment, the CDR comprises one amino acid substitution, which may be a conservative amino acid substitution. In all of concepts 24, 33, 34, 35, 38, 39 and 40, in one embodiment, the CDR comprises two amino acid substitutions, which may be conservative amino acid substitutions. In all of concepts 24, 33, 35, 38 and 40, in one embodiment, the CDR comprises three amino acid substitutions, which may be conservative amino acid substitutions. In all of concepts 24, 33, 35 and 40, in one embodiment, the CDR comprises four amino acid substitutions, which may be conservative amino acid substitutions. In all of concepts 24, 33, 35 and 40, in one embodiment, the CDR comprises five amino acid substitutions, which may be conservative amino acid substitutions. In all of concepts 24, 33 and 35 in one embodiment, the CDR comprises six amino acid substitutions, which may be conservative amino acid substitutions.

Amino acid substitutions include alterations in which an amino acid is replaced with a different naturally-occurring amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g. substituting a charged or hydrophobic amino; acid with alanine), or alternatively, in which a naturally-occurring amino acid is substituted with a non-conventional amino acid.

In one embodiment, the conservative amino acid substitutions are as described herein. For example, the substitution may be of Y with F, T with S or K, P with A, E with D or Q, N with D or G, R with K, G with N or A, T with S or K, D with N or E, I with L or V, F with Y, S with T or A, R with K, G with N or A, K with R, A with S, K or P. In another embodiment, the conservative amino acid substitutions may be wherein Y is substituted with F, T with A or S, I with L or V, W with Y, M with L, N with D, G with A, T with A or S, D with N, I with L or V, F with Y or L, S with A or T and A with S, G, T or V.

Concept 25. An antibody or fragment thereof which specifically binds to hOPG, optionally according to any one of concepts 1 to 24, and which comprises a $V_H$ domain comprising a CDRH3 of from 10 to 23 amino acids and which is derived from the recombination of a human $V_H$ gene segment, a human D gene segment and a human $J_H$ gene segment, wherein the human $J_H$ gene segment is IGHJ4 (e.g. IGHJ4*02).

Concept 25a. An antibody or fragment thereof which specifically binds to hOPG, optionally according to any one of concepts 1 to 24, and which comprises a $V_H$ domain comprising a CDRH3 of from 10 to 23 amino acids and which is derived from the recombination of a human $V_H$ gene segment, a human D gene segment and a human $J_H$ gene segment, wherein the $J_H$ gene segment is IGHJ5 (e.g. IGHJ5*02).

Concept 25b. An antibody or fragment thereof which specifically binds to hOPG, optionally according to any one of concepts 1 to 24, and which comprises a $V_H$ domain comprising a CDRH3 of from 10 to 23 amino acids and which is derived from the recombination of a human $V_H$ gene segment, a human D gene segment and a human $J_H$ gene segment, wherein the $J_H$ gene segment is IGHJ3 (e.g. IGHJ3*02).

In one embodiment, the CDRH3 is of from 15 to 23 amino acids. In another embodiment, the CDRH3 is from 18 to 22 amino acids. In another embodiment, the CDRH3 is from 15 to 19 amino acids. In another embodiment, the CDRH3 is 15, 16, 17, 18, 19, 20 or 21 amino acids. In another embodiment, the CDRH3 is 16 amino acids. In another embodiment, the CDRH3 is 20 amino acids.

Concept 26. The antibody or fragment thereof according to concept 25, 25a or 25b, wherein the human $V_H$ gene segment is IGHV3 (e.g. IGHV3-23, such as IGHV3-23*04, or is IGHV3-13, such as V3-13*01).

There is also provided as concept 26a an antibody or fragment according to concept 25, 25a or 25b, wherein the human $V_H$ gene segment is selected from IGHV1 (e.g. IGHV1-18, such as IGHV1-18*01), or IGHV3 (e.g. IGHV3-9, such as IGHV3-9*01 or e.g. IGHV3-15, such as IGHV3-15*01).

In one embodiment, the human $V_H$ gene segment is IGHV3 (e.g. IGHV3-9, such as IGHV3-9*01). In one embodiment, the human $V_H$ gene segment is IGHV3 (e.g. IGHV3-15, such as IGHV3-15*01).

In one embodiment, the human $V_H$ gene segment is IGHV1 (e.g. IGHV1-18, such as IGHV1-18*01).

In one embodiment, the human $V_H$ gene segment is IGHV3 (e.g. IGHV3-13, such as IGHV3-13*01)

Concept 27. The antibody or fragment thereof according to concept 25, 25a, 25b, 26, or 26a wherein the human $D_H$ gene segment is IGHD2 (e.g. IGHD2-2, such as IGHD2-2*02).

There is also provided as concept 27a an antibody or fragment according to concept 25, 25a, 25b, 26 or 26a, wherein the human D gene segment is selected from IGHD1 (e.g. IGHD1-26, such as IGHD1-26*01), IGHD3 (e.g. IGHD3-9, such as IGHD3-9*01, or e.g. IGHD3-22, such as IGHD3-22*01, or e.g. IGHD3-10, such as IGHD3-10*01).

In one embodiment, the human D gene segment is IGHD1 (e.g. IGHD1-26, such as IGHD1-26*01). In one embodiment, the human D gene segment is IGHD3 (e.g. IGHD3-9, such as IGHD3-9*01). In one embodiment, the human D gene segment is IGHD3 (e.g. IGHD3-22, such as IGHD3-22*01). In one embodiment, the human D gene segment is IGHD3 (e.g. IGHD3-10, such as IGHD3-10*01).

In another embodiment, the human $J_H$ gene segment is IGHJ5 (e.g. IGH5*02), the human D gene segment is IGHD1 (e.g. IGHD1-26, such as IGHD1-26*01) and the human $V_H$ gene segment is IGHV1 (e.g. IGHV1-18, such as IGHV1-18*01).

In another embodiment, the human $J_H$ gene segment is IGHJ4 (e.g. IGH4*02), the human D gene segment is IGHD3 (e.g. IGHD3-9, such as IGHD3-9*01) and the human $V_H$ gene segment is IGHV3 (e.g. IGHV3-9, such as IGHV3-9*01).

In another embodiment, the human $J_H$ gene segment is IGHJ4 (e.g. IGH4*02), the human $D_H$ gene segment is IGHD2 (e.g. IGHD2-2, such as IGHD2-2*02) and the human $V_H$ gene segment is IGHV3 (e.g. IGHV3-23, such as IGHV3-23*04).

In another embodiment, the human $J_H$ gene segment is IGHJ4 (e.g. IGH4*02), the human $D_H$ gene segment is IGHD3 (e.g. IGHD3-10, such as IGHD3-10*01) and the human $V_H$ gene segment is IGHV3 (e.g. IGHV3-13, such as IGHV3-13*01).

In another embodiment, the human $J_H$ gene segment is IGHJ4 (e.g. IGH4*02), the human D gene segment is IGHD3 (e.g. IGHD3-22, such as IGHD3-22*01) and the human $V_H$ gene segment is IGHV3 (e.g. IGHV3-9, such as IGHV3-9*01).

In another embodiment, the $J_H$ gene segment is IGHD3 (e.g. IGHJ3*02), the human D gene segment is IGHD3 (e.g. IGHD3-22, such as IGHD3-22*01) and human $V_H$ gene segment is IGHV3 (e.g. IGHV3-15, such as IGHV3-15*01).

Concept 28. The antibody or fragment thereof according to any one of concepts 25 to 27, wherein the antibody or fragment comprises a $V_L$ domain which is derived from the recombination of a human Vκ gene segment, and a human Jκ gene segment, wherein the human Vκ gene segment is IGκV1D (e.g. IGκV1D-39, such as IGκV1D-39*01).

There is also provided as concept 28a an antibody or fragment according to any of concepts 25, 25a, 25b, 26, 26a, 27 or 27a, wherein the human Vκ gene segment is selected from IGκV1 (e.g. IGκV1-17, such as IGκV1-17*01 or e.g. IGκV1D-33, such as IGκV1D-33*01 or e.g. IGκV1D-12, such as IGκV1D-12*02).

In one embodiment, the human Vκ gene segment is IGκV1 (e.g. IGκV1-17, such as IGκV1-17*01). In one embodiment, the human Vκ gene segment is IGκV1 (e.g. IGκV1D-33, such as IGκV1D-33*01). In one embodiment, the human Vκ gene segment is IGκV1 (e.g. IGκV1D-12, such as IGκV1D-12*02).

There is also provided as concept 28b an antibody or fragment according to any one of concepts 25, 25a, 25b, 26, 26a, 27, 27a, 28 or 28a wherein the human Jκ gene segment is selected from IGκJ1 (e.g. IGκJ1*01), IGκJ3 (e.g. IGκJ3*01) or IGκJ4 (e.g. IGκJ4*01).

In one embodiment, the human Jκ gene segment is IGκJ1 (e.g. IGκJ1*01). In one embodiment, the human Jκ gene segment is IGκJ3 (e.g. IGκJ3*01). In one embodiment, the human Jκ gene segment is IGκJ4 (e.g. IGκJ4*01).

In one embodiment, the human Vκ gene segment is IGκV1 (e.g. IGκV1-17, such as IGκV1-17*01) and the human Jκ gene segment is IGκJ3 (e.g. IGκJ3*01). In another embodiment, the human $J_H$ gene segment is IGHJ5 (e.g. IGH5*02), the human D gene segment is IGHD1 (e.g. IGHD1-26, such as IGHD1-26*01) and the human $V_H$ gene segment is IGHV1 (e.g. IGHV1-18, such as IGHV1-18*01); and the human Vκ gene segment is IGκV1 (e.g. IGκV1-17, such as IGκV1-17*01) and the human Jκ gene segment is IGκJ3 (e.g. IGκJ3*01).

In one embodiment, the human Vκ gene segment is IGκV1D (e.g. IGκV1D-39, such as IGκV1D-39*01) and the human Jκ gene segment is IGκJ1 (e.g. IGκJ1*01). In another embodiment, the human $J_H$ gene segment is IGHJ4 (e.g. IGH4*02), the human D gene segment is IGHD3 (e.g. IGHD3-9, such as IGHD3-9*01) and the human $V_H$ gene segment is IGHV3 (e.g. IGHV3-9, such as IGHV3-9*01); and the human Vκ gene segment is IGκV1D (e.g. IGκV1D-39, such as IGκV1D-39*01) and the human Jκ gene segment is IGκJ1 (e.g. IGκJ1*01).

In one embodiment, the human Vκ gene segment is IGκV1 (e.g. IGκV1D-33, such as IGκV1D-33*01) and the human Jκ gene segment is IGκJ3 (e.g. IGκJ3*01). In another embodiment, the human $J_H$ gene segment is IGHJ4 (e.g. IGH4*02), the human $D_H$ gene segment is IGHD3 (e.g. IGHD3-10, such as IGHD3-10*01) and the human $V_H$ gene segment is IGHV3 (e.g. IGHV3-13, such as IGHV3-13*01); and the human Vκ gene segment is IGκV1 (e.g. IGκV1D-33, such as IGκV1D-33*01) and the human Jκ gene segment is IGκJ3 (e.g. IGκJ3*01)

In one embodiment, the human Vκ gene segment is IGκV1D (e.g. IGκV1D-39, such as IGκV1D-39*01) and the human Jκ gene segment is IGκJ4 (e.g. IGκJ4*01). In another embodiment, the human $J_H$ gene segment is IGHJ4 (e.g. IGH4*02), the human D gene segment is IGHD3 (e.g. IGHD3-22, such as IGHD3-22*01) and the human $V_H$ gene segment is IGHV3 (e.g. IGHV3-9, such as IGHV3-9*01); and the human Vκ gene segment is IGκV1D (e.g. IGκV1D-39, such as IGκV1D-39*01) and the human Jκ gene segment is IGκJ4 (e.g. IGκJ4*01).

In one embodiment, the human Vκ gene segment is IGκV1 (e.g. IGκV1D-12, such as IGκV1D-12*02) and the human Jκ gene segment is IGκJ4 (e.g. IGκJ4*01). In another embodiment, the $J_H$ gene segment is IGHD3 (e.g. IGHJ3*02), the human D gene segment is IGHD3 (e.g. IGHD3-22, such as IGHD3-22*01) and human $V_H$ gene segment is IGHV3 (e.g. IGHV3-15, such as IGHV3-15*01); and the human Vκ gene segment is IGκV1 (e.g. IGκV1D-12, such as IGκV1D-12*02) and the human Jκ gene segment is IGκJ4 (e.g. IGκJ4*01)

Concept 29. An antibody or fragment thereof, optionally according to any one of concepts 1 to 28, which specifically binds to an epitope that is identical to an epitope to which an antibody selected from the group consisting of Ky1 (6D07), Ky2 (8C10), Ky3 (15F11), Ky4 (16G05) and Ky5 (15H06), specifically binds.

In one embodiment, the antibody or fragment thereof specifically binds to an epitope that is identical to an epitope to which the antibody Ky1 (6D07) specifically binds. In one embodiment, the antibody or fragment thereof specifically binds to an epitope that is identical to an epitope to which the antibody Ky2 (8C10) specifically binds. In one embodiment, the antibody or fragment thereof specifically binds to an epitope that is identical to an epitope to which the antibody Ky3 (15F11) specifically binds. In one embodiment, the antibody or fragment thereof specifically binds to an epitope that is identical to an epitope to which the antibody Ky4 (16G05) specifically binds. In one embodiment, the antibody or fragment thereof specifically binds to an epitope that is identical to an epitope to which the antibody Ky5 (15H06) specifically binds.

The antibodies Ky1 (6D07), Ky2 (8C10), Ky3 (15F11), Ky4 (16G05) and Ky5 (15H06) may be as described elsewhere herein.

In one embodiment, there is provided an antibody which specifically bind to an epitope which is substantially similar to an epitope to which any of the antibodies in concept 29 binds.

Contact amino acid residues involved in the interaction of antibody and antigen may be determined by various known methods to those skilled in the art.

In one embodiment, sequential replacement of the amino acids of the antigen sequence (using standard molecular biology techniques to mutate the DNA of the coding sequence of the antigen), in this case hOPG with Alanine (a.k.a Alanine scan), or another unrelated amino acid, may provide residues whose mutation would reduce or ablate the ability of the antibody to recognise the antigen in question. Binding may be assessed using standard techniques, such as, but not limited to, SPR, HTRF, ELISA (which are described elsewhere herein). Other substitutions could be made to enhance the disruption of binding such as changing the charge on the side chain of antigen sequence amino acids (e.g. Lysine change to glutamic acid), switching polar and non-polar residues (e.g. Serine change to leucine). The alanine scan or other amino substitution method may be carried out either with recombinant soluble antigen, or where the target is a cell membrane target, directly on cells using transient or stable expression of the mutated versions.

In one embodiment, protein crystallography may be used to determine contact residues between antibody and antigen (i.e. to determine the epitope to which the antibody binds), crystallography allows the direct visualisation of contact residues involved in the antibody-antigen interaction. As well as standard X-ray crystallography, cryo-electro microscopy has been used to determine contact residues between antibodies and HIV capsid protein (see Lee, Jeong Hyun, et al., "Antibodies to a conformational epitope on gp41 neutralize HIV-1 by destabilizing the Env spike.", Nature communications, 6, (2015)).

In one embodiment, if the antibody recognises a linear epitope, short peptides based on the antigen sequence can be produced and binding of the antibody to these peptides can be assessed using standard techniques, such as, but not limited to, SPR, HTRF, ELISA (which are described elsewhere herein). Further investigation of the epitope could be provided by performing an Alanine scan on any peptides that show binding. Alternative to linear peptides, conformational scans could be carried out using Pepscan technology (website: pepscan.com/) using their chemical linkage of peptides onto scaffolds, which has been used to determine discontinuous epitopes on CD20 targeting antibodies (Niederfellner, Gerhard, et al., "Epitope characterization and crystal structure of GA101 provide insights into the molecular basis for type I/II distinction of CD20 antibodies.", Blood, 118.2, (2011), 358-367.).

In one embodiment, limited proteolytic digestion and mass spectrophotometry can be used to identify binding epitopes. The antibody-antigen complex is digested by a protease, such as, but not limited to, trypsin. The digested complex peptides are compared to antibody-alone and antigen-alone digestion mass spectrophotometry to determine if a particular epitope is protected by the complexation. Further work involving amino acid substitution, competition binding, may then be employed to narrow down to individual amino acid residues involved in the interaction (see, for example, Suckau, Detlev, et al., "Molecular epitope identification by limited proteolysis of an immobilized antigen-antibody complex and mass spectrometric peptide mapping.", Proceedings of the National Academy of Sciences, 87.24, (1990), 9848-9852).

Thus, in one embodiment, the contact residues of the epitope are identified with an unrelated amino acid scan (e.g. alanine scan). In another embodiment, an unrelated amino acid scan (e.g. alanine scan) is carried out using a technique selected from SPR, HTRF, ELISA, X-ray crystallography, cryo-electro microscopy and a combination of limited proteolytic digestion and mass spectrometry. In one embodiment, the unrelated amino acid scan (e.g. alanine scan) is carried out using HTRF. In one embodiment, the unrelated amino acid scan (e.g. alanine scan) is carried out using ELISA.

When the alanine scan is carried out with either ELISA or HTRF, an amino acid residue is identified as contributing to the epitope if the reduction in signal is at least 25%. In one embodiment, the reduction in signal is at least 30%. In one embodiment, the reduction in signal is at least 35%. In one embodiment, the reduction in signal is at least 40%. In one embodiment, the reduction in signal is at least 45%. In one embodiment, the reduction in signal is at least 50%. In one embodiment, the reduction in signal is at least 55%. In one embodiment, the reduction in signal is at least 60%. In one embodiment, the reduction in signal is at least 70%. In one embodiment, the reduction in signal is at least 75%. In one embodiment, the reduction in signal is at least 80%. In one embodiment, the reduction in signal is at least 85%. In one embodiment, the reduction in signal is at least 90%.

When the alanine scan is carried out with SPR, an amino acid residue is identified as contributing to the epitope if there is at least a 10-fold reduction in affinity. In one embodiment, the reduction in affinity is at least 15-fold. In one embodiment, the reduction in affinity is at least 20-fold. In one embodiment, the reduction in affinity is at least 30-fold. In one embodiment, the reduction in affinity is at least 40-fold. In one embodiment, the reduction in affinity is at least 50-fold. In one embodiment, the reduction in affinity is at least 100-fold.

In one embodiment, the contact residues of the epitope are identified by X-ray crystallography. In one embodiment, the contact residues of the epitope are identified by cryo-electro microscopy. In one embodiment, the contact residues of the epitope are identified by a combination of limited proteolytic digestion and mass spectrometry.

Concept 30. The antibody or fragment thereof according to concept 29, wherein the epitope is identified by unrelated amino acid scanning, or by X-ray crystallography.

Concept 31. The antibody or fragment thereof according to concept 30, wherein the contact residues of the epitope are defined by a reduction in affinity of at least 10-fold in an unrelated amino acid scan, e.g. an alanine scan as determined by SPR.

In one embodiment, the reduction in affinity is at least 15-fold. In one embodiment, the reduction in affinity is at least 20-fold. In one embodiment, the reduction in affinity is at least 30-fold. In one embodiment, the reduction in affinity is at least 40-fold. In one embodiment, the reduction in affinity is at least 50-fold. In one embodiment, the reduction in affinity is at least 100-fold.

SPR may be carried out as described hereinabove.

Concept 32. An antibody or fragment thereof, optionally according to any one of concepts 1 to 31, which competes for binding to hOPG with an antibody selected from the group consisting of Ky1 (6D07), Ky2 (8C10), Ky3 (15F11), Ky4 (16G05) and Ky5 (15H06), optionally wherein the competition is determined by SPR.

In one embodiment, the antibody or fragment thereof, optionally according to any one of concepts 1 to 31, competes for binding to hOPG with the antibody Ky1 (6D07), optionally wherein the competition is determined by SPR. In one embodiment, the antibody or fragment thereof, optionally according to any one of concepts 1 to 31, competes for binding to hOPG with the antibody Ky2 (8C10), optionally wherein the competition is determined by SPR. In one embodiment, the antibody or fragment thereof, optionally according to any one of concepts 1 to 31, competes for binding to hOPG with the antibody Ky3 (15F11), optionally wherein the competition is determined by SPR. In one embodiment, the antibody or fragment thereof, optionally according to any one of concepts 1 to 31, competes for binding to hOPG with the antibody Ky4 (16G05), optionally wherein the competition is determined by SPR. In one embodiment, the antibody or fragment thereof, optionally according to any one of concepts 1 to 31, competes for binding to hOPG with the antibody Ky5 (15H06), optionally wherein the competition is determined by SPR.

The antibodies Ky1 (6D07), Ky2 (8C10), Ky3 (15F11), and Ky5 (15H06) may be as described elsewhere herein.

Competition may be determined by surface plasmon resonance (SPR), such techniques being readily apparent to the skilled person. SPR may be carried out using Biacore™, Proteon™ or another standard SPR technique. Such competition may be due, for example, to the antibodies or fragments binding to identical or overlapping epitopes of hOPG. In one embodiment, competition is determined by ELISA, such techniques being readily apparent to the skilled person. In one embodiment, competition is determined by homogenous time resolved fluorescence (HTRF), such techniques being readily apparent to the skilled person. In one embodiment, competition is determined by fluorescence activated cell sorting (FACS), such techniques being readily apparent to the skilled person. In one embodiment, competition is determined by ForteBio Octet® Bio-Layer Interferometry (BLI) such techniques being readily apparent to the skilled person.

In one embodiment, the antibody or fragment competes (e.g., in a dose-dependent manner) with hTRAIL (or a fusion protein thereof) for binding to cell surface-expressed hOPG. In one embodiment, the antibody or fragment competes (e.g., in a dose-dependent manner) with hTRAIL (or a fusion protein thereof) for binding to soluble hOPG.

In one embodiment, the antibody or fragment competes (e.g., in a dose-dependent manner) with hRANKL (or a fusion protein thereof) for binding to cell surface-expressed hOPG. In one embodiment, the antibody or fragment competes (e.g., in a dose-dependent manner) with hRANKL (or a fusion protein thereof) for binding to soluble hOPG.

In one embodiment, the antibody or fragment partially or completely inhibits binding of TRAIL and/or RANKL to cell surface-expressed OPG, such as hOPG. In another embodiment, the antibody or fragment partially or completely inhibits binding of hTRAIL and/or RANKL to soluble hOPG. In some embodiments, the antibody or fragment partially or completely increases the expression and/or concentration of circulating focal adhesion kinase, FAK (see Lane D, et al, "Osteoprotegerin (OPG) activates integrin, focal adhesion kinase (FAK), and Akt signaling in ovarian cancer cells to attenuate TRAIL-induced apoptosis", J. Ovarian Res., 2013, 6, 82, and Jia D et al., "Osteoprotegerin Disruption Attenuates HySu-Induced Pulmonary Hypertension Through Integrin αvβ3/FAK/AKT Pathway Suppression", Circulation: Cardiovascular Genetics, 2017, 10:e001591). In some embodiments, the antibody or fragment partially or significantly increases the expression and/or concentration of circulating integrins, such as αvβ3 (part of the RGD receptor integrin family), see Malyankar U M, et al., "Osteoprotegerin Is an alpha vbeta 3-induced, NF-kappa β-dependent Survival Factor for Endothelial Cells", Journal of Biological Chemistry, 2000, 275, 20959-20962. Integrins are proteins that function mechanically, by attaching the cell cytoskeleton to the extracellular matrix (ECM), and biochemically, by sensing whether adhesion has occurred. The integrin family of proteins consists of alpha and beta subtypes, which form transmembrane heterodimers. Other circulating integrins whose expression and/or concentration may be partially or significantly increase by an antibody or fragment thereof include the RGD receptor integrin family: α5β1, αVβ3, αVβ1, αVβ5, αVβ6, αVβ8, and αIIbβ3.

In one embodiment, the antibody or fragment partially or completely inhibits binding of RANKL to soluble hOPG, but does not show any detectable inhibition of the binding of TRAIL to cell surface-expressed OPG. In one embodiment, the antibody or fragment partially or completely inhibits binding of RANKL to soluble hOPG, but does not show any detectable inhibition of the binding of TRAIL to soluble OPG.

In one embodiment, the antibody or fragment partially or completely inhibits binding of TRAIL to soluble hOPG, but does not show any detectable inhibition of the binding of RANKL to cell surface-expressed OPG. In one embodiment, the antibody or fragment partially or completely inhibits binding of TRAIL to soluble hOPG, but does not show any detectable inhibition of the binding of RANKL to soluble OPG.

Concept 33. The antibody or fragment thereof according to any one of concepts 1 to 32, wherein the antibody or fragment thereof comprises a or said $V_H$ domain, which domain comprises:

a. the CDRH3 sequence of Seq ID No:8 or 11, or the CDRH3 sequence of Seq ID No:8 or 11 comprising 3 or fewer amino acid substitutions; or
b. the CDRH3 sequence of Seq ID No:28 or 31, or the CDRH3 sequence of Seq ID No:28 or 31 comprising 5 or fewer amino acid substitutions; or
c. the CDRH3 sequence of Seq ID No:48 or 51, or the CDRH3 sequence of Seq ID No:48 or 51 comprising 6 or fewer amino acid substitutions; or
d. the CDRH3 sequence of Seq ID No:68 or 71, or the CDRH3 sequence of Seq ID No:68 or 71 comprising 5 or fewer amino acid substitutions; or
e. the CDRH3 sequence of Seq ID No:88 or 91, or the CDRH3 sequence of Seq ID No:88 or 91 comprising 3 or fewer amino acid substitutions.

Concept 34. The antibody or fragment thereof according to any preceding concept, wherein the antibody or fragment thereof comprises a or said $V_H$ domain, which domain comprises:

a. the CDRH1 sequence of Seq ID No:6 or 9, or the CDRH1 sequence of Seq ID No:6 or 9 comprising 2 or 1 amino acid substitution(s); or
b. the CDRH1 sequence of Seq ID No:26 or 29, or the CDRH1 sequence of Seq ID No:26 or 29 comprising 2 or 1 amino acid substitution(s); or
c. the CDRH1 sequence of Seq ID No:46 or 49, or the CDRH1 sequence of Seq ID No:46 or 49 comprising 2 or 1 amino acid substitution(s); or
d. the CDRH1 sequence of Seq ID No:66 or 69, or the CDRH1 sequence of Seq ID No:66 or 69 comprising 2 or 1 amino acid substitution(s); or
e. the CDRH1 sequence of Seq ID No:86 or 89, or the CDRH3 sequence of Seq ID No:86 or 89 comprising 2 or 1 amino acid substitution(s).

Concept 35. The antibody or fragment thereof according to any preceding claim, wherein the antibody or fragment thereof comprises a or said $V_H$ domain, which domain comprises:

a. the CDRH2 sequence of Seq ID No:7 or 10, or the CDRH2 sequence of Seq ID No:7 or 10 comprising 5 or fewer amino acid substitutions; or
b. the CDRH2 sequence of Seq ID No:27 or 30, or the CDRH2 sequence of Seq ID No:27 or 30 comprising 5 or fewer amino acid substitutions; or
c. the CDRH2 sequence of Seq ID No:47 or 50, or the CDRH2 sequence of Seq ID No:47 or 50 comprising 4 or fewer amino acid substitutions; or
d. the CDRH2 sequence of Seq ID No:67 or 70, or the CDRH2 sequence of Seq ID No:67 or 70 comprising 5 or fewer amino acid substitutions; or
e. the CDRH2 sequence of Seq ID No:87 or 90, or the CDRH2 sequence of Seq ID No:87 or 90 comprising 6 or fewer amino acid substitutions.

Concept 36. The antibody or fragment thereof according to any preceding concept, wherein the antibody or fragment thereof comprises a or said $V_H$ domain, which domain comprises:

a. an amino acid sequence of Seq ID No:12, or a heavy chain variable domain amino acid sequence that is at least 80% (e.g. at least 85%, or at least 90%) identical to Seq ID No:12; or
b. an amino acid sequence of Seq ID No:32, or a heavy chain variable domain amino acid sequence that is at least 80% (e.g. at least 85%, or at least 90%) identical to Seq ID No:32; or c. an amino acid sequence of Seq ID No:52, or a heavy chain variable domain amino acid sequence that is at least 80% (e.g. at least 85%, or at least 90%) identical to Seq ID No:52; or d. an amino acid sequence of Seq ID No:72, or a heavy chain variable domain amino acid sequence that is at least 80% (e.g. at least 85%, or at least 90%) identical to Seq ID No:72; or e. an amino acid sequence of Seq ID No:92, or a heavy chain variable domain amino acid sequence that is at least 80% (e.g. at least 85%, or at least 90%) identical to Seq ID No:92.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No.

Concept 37. The antibody or fragment thereof according to any preceding claim comprising first and second copies of a or said $V_H$ domain.

Concept 38. The antibody or fragment thereof according to any preceding concept, comprising a or said $V_L$ domain, which domain comprises:
  a. the CDRL1 sequence of Seq ID No:16 or 19, or the CDRL1 sequence of Seq ID No:16 or 19 comprising 3 or fewer amino acid substitutions; or
  b. the CDRL1 sequence of Seq ID No:36 or 39, or the CDRL1 sequence of Seq ID No:36 or 39 comprising 3 or fewer amino acid substitutions; or
  c. the CDRL1 sequence of Seq ID No:56 or 59, or the CDRL1 sequence of Seq ID No:56 or 59 comprising 3 or fewer amino acid substitutions; or
  d. the CDRL1 sequence of Seq ID No:76 or 79, or the CDRL1 sequence of Seq ID No:76 or 79 comprising 3 or fewer amino acid substitutions; or
  e. the CDRL1 sequence of Seq ID No:96 or 99, or the CDRL1 sequence of Seq ID No:96 or 99 comprising 3 or fewer amino acid substitutions.

Concept 39. The antibody or fragment thereof according to any preceding concept, wherein the antibody or fragment thereof comprises a or said $V_L$ domain, which domain comprises:
  a. the CDRL2 sequence of Seq ID No:17 or 20, or the CDRL2 sequence of Seq ID No:17 or 20 comprising 2 or 1 amino acid substitution(s); or
  b. the CDRL2 sequence of Seq ID No:37 or 40, or the CDRL2 sequence of Seq ID No:37 or 40 comprising 2 or 1 amino acid substitution(s); or
  c. the CDRL2 sequence of Seq ID No:57 or 60, or the CDRL2 sequence of Seq ID No:57 or 60 comprising 2 or 1 amino acid substitution(s); or
  d. the CDRL2 sequence of Seq ID No:77 or 80, or the CDRL2 sequence of Seq ID No:77 or 80 comprising 2 or 1 amino acid substitution(s); or
  e. the CDRL2 sequence of Seq ID No:97 or 100, or the CDRL2 sequence of Seq ID No:97 or 100 comprising 2 or 1 amino acid substitution(s).

Concept 40. The antibody or fragment thereof according to any preceding concept, wherein the antibody or fragment thereof comprises a or said $V_L$ domain, which domain comprises:
  a. the CDRL3 sequence of Seq ID No:18 or 21, or the CDRL3 sequence of Seq ID No:18 or 21 comprising 4 or fewer amino acid substitutions; or
  b. the CDRL3 sequence of Seq ID No:38 or 41, or the CDRL3 sequence of Seq ID No:38 or 41 comprising 5 or fewer amino acid substitutions; or
  c. the CDRL3 sequence of Seq ID No:58 or 61, or the CDRL3 sequence of Seq ID No:58 or 61 comprising 4 or fewer amino acid substitutions; or
  d. the CDRL3 sequence of Seq ID No:78 or 81, or the CDRL3 sequence of Seq ID No:78 or 81 comprising 5 or fewer amino acid substitutions; or
  e. the CDRL3 sequence of Seq ID No:98 or 101, or the CDRL3 sequence of Seq ID No:98 or 101 comprising 5 or fewer amino acid substitutions.

41. The antibody or fragment thereof according to any preceding claim, wherein the antibody or fragment thereof comprises a or said $V_L$ domain, which domain comprises:
  a. an amino acid sequence of Seq ID No:22, or a light chain variable domain amino acid sequence that is at least 80% (e.g. at least 85%, or at least 90%) identical to Seq ID No:22; or
  b. an amino acid sequence of Seq ID No:42, or a light chain variable domain amino acid sequence that is at least 80% (e.g. at least 85%, or at least 90%) identical to Seq ID No:42; or
  c. an amino acid sequence of Seq ID No:62, or a light chain variable domain amino acid sequence that is at least 80% (e.g. at least 85%, or at least 90%) identical to Seq ID No:62; or
  d. an amino acid sequence of Seq ID No:82, or a light chain variable domain amino acid sequence that is at least 80% (e.g. at least 85%, or at least 90%) identical to Seq ID No:82; or
  e. an amino acid sequence of Seq ID No:102, or a light chain variable domain amino acid sequence that is at least 80% (e.g. at least 85%, or at least 90%) identical to Seq ID No:102.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No.

Concept 42. The antibody or fragment thereof according to any one of concepts 38 to 41, comprising first and second copies of said $V_L$ domain.

Concept 43. The antibody or fragment thereof according to any preceding concept, wherein the antibody or fragment comprises a kappa light chain.

Kappa light chain constant region amino acid and nucleotide sequences can be found in Seq ID Nos:122 to 131.

In one embodiment, the light chain may be a lambda light chain. Lambda light chain constant region amino acid and nucleotide sequences can be found in Seq ID Nos:132 to 153 and Seq ID No:162 and Seq ID No:163.

Concept 44. The antibody or fragment thereof according to any one of concepts 24 to 43, wherein the amino acid substitutions are conservative amino acid substitutions, optionally wherein the conservative substitutions are from one of six groups (each group containing amino acids that are conservative substitutions for one another) selected from:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Conservative substitutions may be as described above in concept 24.

Concept 45. The antibody or fragment thereof according to any preceding concept, wherein the antibody or fragment comprises a constant region, such as a human constant region, for example an effector-null human constant region, e.g. an IgG4 constant region or an IgG1 constant region, optionally wherein the constant region is IgG4-PE (Seq ID No:113), or a disabled IgG1 as defined in Seq ID No:121.

In other embodiments, the antibody or fragment is any of the isotypes or constant regions as defined hereinabove. In one embodiment, the constant region is wild-type human IgG1 (Seq ID No:118). For example, the constant region is an effector-enabled IgG1 constant region, optionally having ADCC and/or CDC activity. In one embodiment, the constant region is engineered for enhanced ADCC and/or CDC and/or ADCP.

The IgG4 constant region may be any of the IgG4 constant region amino acid sequences, or encoded by any of the nucleic acid sequences of Seq ID Nos:106 to 117.

The antibody-dependent cell phagocytosis (ADCP) mechanism is discussed in ail et al., "Antibody-Dependent Phagocytosis of Tumor Cells by Macrophages: A Potent Effector Mechanism of Monoclonal Antibody Therapy of Cancer", Cancer Res., 75(23), Dec. 1, 2015.

The potency of Fc-mediated effects may be enhanced by engineering the Fc domain by various established techniques. Such methods increase the affinity for certain Fc-receptors, thus creating potential diverse profiles of activation enhancement. This can be achieved by modification of one or several amino acid residues (e.g. as described in Lazar et al., 2006, Proc. Natl. Acad. Sci. U.S.A., March 14; 103(11):4005-10) or by altering the natural glycosylation profile of the Fc domain by, for example, generating under fucosylated or de-fucosylated variants (as described in Natsume et al, 2009, Drug Des. Devel. Ther., 3:7-16 or by Zhou Q., Biotechnol. Bioeng., 2008, February 15, 99(3):652-65)). For example, to increase ADCC, residues in the hinge region can be altered to increase binding to Fc-gamma RIII (see, for example, Shields et al, 2001, J. Biol. Chem., March 2; 276(9):6591-604). Thus, in one embodiment, the constant region has been engineered to alter the glycosylation profile as compared to WT sequence. In another embodiment, the constant region is defucosylated. In another embodiment, the constant region is modified to increase binding to Fc-γRIII, for example by amino acid substitutions in the hinge region.

The half life of an antibody or fragment may be increased by engineering the Fc domain to increase the binding of IgG to FcRn at pH6. This can be achieved, for example, by changing amino acids M252Y, S254T, T256E (YTE) (Dall'Acqua et al, 2006, Journal of Biological Chemistry, 281(33), 23514-23524). Alternatively, the CDR regions of the variable regions that mediate binding to the target antigen may be engineered or selected to include pH sensitive amino acid residues such as histidines that modify the binding affinity to the target at pH 6, for example as described by Igawa et al, 2010 (Igawa et al, 2010, Nature Biotechnology 24(11), 1203-1207). Thus, in one embodiment, the constant region has been engineered to increase binding to FcRn at pH 6 compared to WT sequence. In another embodiment, the constant region includes M252Y, S254T, T256E (YTE) mutations.

Equally, the enhancement of CDC may be achieved by amino acid changes that increase affinity for C1q, the first component of the classic complement activation cascade (see Idusogie et al, J. Immunol., 2001, 166:2571-2575). Another approach is to create a chimeric Fc domain created from human IgG1 and human IgG3 segments that exploit the higher affinity if IgG3 for C1q (Natsume et al, 2008, Cancer Res., 68: 3863-3872). Thus, in one embodiment, the constant region has been engineered to enhance CDC (compared to WT sequence). In another embodiment, the constant region has been engineered to enhance CDC by increasing affinity for Cq1 as compared to WT sequence. In another embodiment, the constant region is a chimeric Fc domain derived from human IgG1 and human IgG3 segments.

Concept 46. The antibody or fragment thereof according to concept 45, wherein the constant region is a murine constant region.

In other embodiments, the constant region may be of any non-human mammalian origin, e.g. rat, mouse, hamster, guinea pig, dog, cat, horse, chicken, llama, dromedary, etc. In one embodiment, the constant region is a rat constant region. In another embodiment, the constant region is a llama constant region.

Concept 47. The antibody or fragment thereof according to concept 45 or concept 46, wherein the constant region has CDC and/or ADCC activity.

Concept 48. The antibody or fragment thereof according to concept 45 or concept 46, wherein the constant region has no effector function(s).

Concept 49. The antibody or fragment thereof according to any preceding claim wherein the:
a) $V_H$ domain comprises an amino acid sequence of Seq ID No:12 and the $V_L$ domain comprises an amino acid sequence of Seq ID No:22;
b) $V_H$ domain comprises an amino acid sequence that is at least 85% identical to Seq ID No:12, and the $V_L$ domain comprises an amino acid sequence that is at least 85% identical to Seq ID No:22;
c) $V_H$ domain comprises an amino acid sequence of Seq ID No:32 and the $V_L$ domain comprises an amino acid sequence of Seq ID No:42;
d) $V_H$ domain comprises an amino acid sequence that is at least 85% identical to Seq ID No:32, and the $V_L$ domain comprise an amino acid sequence that is at least 85% identical to Seq ID No:42;
e) $V_H$ domain comprises an amino acid sequence of Seq ID No:52 and the $V_L$ domain comprises an amino acid sequence of Seq ID No:62;
f) $V_H$ domain comprises an amino acid sequence that is at least 85% identical to Seq ID No:52, and the $V_L$ domain comprises an amino acid sequence that is at least 85% identical to Seq ID No:62;
g) $V_H$ domain comprises an amino acid sequence of Seq ID No:72 and the $V_L$ domain comprises an amino acid sequence of Seq ID No:82;

h) V$_H$ domain comprises an amino acid sequence that is at least 85% identical to Seq ID No:72, and the V$_L$ domain comprises an amino acid sequence that is at least 85% identical to Seq ID No:82;

i) V$_H$ domain comprises an amino acid sequence of Seq ID No:92 and the V$_L$ domain comprises an amino acid sequence of Seq ID No:102;

j) V$_H$ domain comprises an amino acid sequence that is at least 85% identical to Seq ID No:92, and the V$_L$ domain comprises an amino acid sequence that is at least 85% identical to Seq ID No:102.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No.

Concept 50. The antibody according to any preceding concept wherein the antibody comprises a full-length heavy chain and a full length light chain, and a) the heavy chain amino acid sequence comprises an amino acid sequence of Seq ID No:14 and the light chain amino acid sequence comprises an amino acid sequence of Seq ID No:24;

b) the heavy chain amino acid sequence comprises an amino acid sequence that is at least 85% identical to Seq ID No:14 and the light chain amino acid sequence comprises an amino acid sequence that is at least 85% identical to Seq ID No:24;

c) the heavy chain amino acid sequence comprises an amino acid sequence of Seq ID No:34 and the light chain amino acid sequence comprises an amino acid sequence of Seq ID No:44;

d) the heavy chain amino acid sequence comprises an amino acid sequence that is at least 85% identical to Seq ID No:34, and the light chain amino acid sequence comprises an amino acid sequence that is at least 85% identical to Seq ID No:44;

e) the heavy chain amino acid sequence comprises an amino acid sequence of Seq ID No:54 and the light chain amino acid sequence comprises an amino acid sequence of Seq ID No:64;

f) the heavy chain amino acid sequence comprises an amino acid sequence that is at least 85% identical to Seq ID No:54, and the light chain amino acid sequence comprises an amino acid sequence that is at least 85% identical to Seq ID No:64;

g) the heavy chain amino acid sequence comprises an amino acid sequence of Seq ID No:74 and the light chain amino acid sequence comprises an amino acid sequence of Seq ID No:84;

h) the heavy chain amino acid sequence comprises an amino acid sequence that is at least 85% identical to Seq ID No:74, and the light chain amino acid sequence comprises an amino acid sequence that is at least 85% identical to Seq ID No:84;

i) the heavy chain amino acid sequence comprises an amino acid sequence of Seq ID No:94 and the light chain amino acid sequence comprises an amino acid sequence of Seq ID No:104;

j) the heavy chain amino acid sequence comprises an amino acid sequence that is at least 85% identical to Seq ID No:94, and the light chain amino acid sequence comprises an amino acid sequence that is at least 85% identical to Seq ID No:104.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No.

Concept 51. The antibody or fragment thereof according to any preceding concept, wherein the antibody or fragment is capable of enhancing TRAIL-mediated apoptosis.

Concept 51a. An antibody or fragment thereof according to any preceding concept for use in enhancing TRAIL-mediated apoptosis.

Concept 51b. An antibody or fragment thereof according to any preceding concept for use in treating a proliferative disease or disorder or for use in treating cancer, wherein the antibody or fragment thereof enhances TRAIL mediated apoptosis.

TRAIL-mediated apoptosis may be measured by any technique for measuring apoptosis known to the skilled person. TRAIL-mediated apoptosis may be enhanced by blockade of OPG, as it has been shown that OPG itself attenuates TRAIL-mediated apoptosis, for example via the FAK pathway (see Lane D, et al, "Osteoprotegerin (OPG) activates integrin, focal adhesion kinase (FAK), and Akt signaling in ovarian cancer cells to attenuate TRAIL-induced apoptosis", J. Ovarian Res., 2013, 6, 82). For example, the measurements may be carried out with any suitable technique. For example, the measurements may be taken with ELISA, HTRF, BRDU incorporation (proliferation), electrochemiluminescence (ECL) or flow cytometry (e.g. FACS). In a particular embodiment, the measurements are carried out with an apoptosis or proliferation assay as described in the definition of "neutralisation" hereinabove. These techniques are well-known to those skilled in the art and are described elsewhere herein. In one embodiment, the assay is flow cytometry. In one embodiment, the assay is ELISA. In one embodiment, the assay is HTRF.

In one embodiment, the TRAIL-mediated apoptosis is measured by a proliferative assay (e.g. a SMC proliferation TRAIL mediated cytotoxicity assay) or any other functional assay as described above.

Concept 52. A multispecific (e.g. bispecific) antibody or fusion protein comprising an antagonist (e.g. an antibody or fragment thereof) as defined in any preceding concept.

Concept 52a. A dual binding antibody or fusion protein comprising an antagonist (e.g. an antibody or fragment thereof) as defined in any preceding concept.

A dual binding antibody has the meaning as set out above.

In one embodiment, the multispecific antibody is a bispecific antibody. In another embodiment, the bispecific antibody is as described hereinabove. In another embodiment, the bispecific antibody has a bispecific format is selected from DVD-Ig, mAb², FIT-Ig, mAb-dAb, dock and lock, SEEDbody, scDiabody-Fc, diabody-Fc, tandem scFv-Fc, Fab-scFv-Fc, Fab-scFv, intrabody, BiTE, diabody, DART, TandAb, scDiabody, scDiabody-CHs, Diabody-CH3, minibody, knobs-in-holes, knobs-in-holes with common light chain, knobs-in-holes with common light chain and charge pairs, charge pairs, charge pairs with common light chain, in particular mAb², knob-in-holes, knob-in-holes with common light chain, knobs-in-holes with common light chain and charge pairs and FIT-Ig, e.g. mAb² and FIT-Ig.

In a further embodiment, the bispecific format is selected from DVD-Ig, mAb², FIT-Ig, mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BITE, diabody, DART, TandAb, scDiabody, scDiabody-CH₃, Diabody-CH3, Triple body, Miniantibody, minibody, TriBi minibody, scFv-CH₃ KIH, scFv-CH-CL-scFv, F(ab')₂-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig and zybody.

In a further embodiment, the bispecific format is selected from DVD-Ig, FIT-Ig, mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BITE, diabody, DART, TandAb, scDiabody, scDiabody-CH₃, Diabody-CH₃, Triple body, Miniantibody, minibody, TriBi minibody, scFv-CH₃ KIH, scFv-CH-CL-scFv, F(ab')₂-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG (L,H)-Fv, IgG(H)-V, V(H)-IgG, IgG(L)-V, V(L)-IgG, KIH IgG-scFab, 2scFv-IgG, IgG-2scFv, scFv4-Ig and zybody, for example DVD-Ig, FIT-Ig, mAb-dAb, dock and lock, SEED-body, scDiabody-Fc, diabody-Fc, tandem scFv-Fc, Fab-scFv-Fc, Fab-scFv, intrabody, BITE, diabody, DART, TandAb, scDiabody, scDiabody-CH3, Diabody-CH3, minibody, knobs-in-holes, knobs-in-holes with common light chain, knobs-in-holes with common light chain and charge pairs, charge pairs, charge pairs with common light chain, in particular knob-in-holes, knob-in-holes with common light chain, knobs-in-holes with common light chain and charge pairs and FIT-Ig, e.g. FIT-Ig.

In another embodiment, the bispecific format is selected from DVD-Ig, mAb², mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BITE, diabody, DART, TandAb, scDiabody, scDiabody-CH₃, Diabody-CH₃, Triple body, Miniantibody, minibody, TriBi minibody, scFv-CH₃ KIH, scFv-CH-CL-scFv, F(ab')₂-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig and zybody, for example DVD-Ig, mAb², mAb-dAb, dock and lock, SEED-body, scDiabody-Fc, diabody-Fc, tandem scFv-Fc, Fab-scFv-Fc, Fab-scFv, intrabody, BITE, diabody, DART, TandAb, scDiabody, scDiabody-CH₃, Diabody-CH₃, minibody, knobs-in-holes, knobs-in-holes with common light chain, knobs-in-holes with common light chain and charge pairs, charge pairs, charge pairs with common light chain, in particular mAb², knob-in-holes, knobs-in-holes with common light chain and charge pairs, and knob-in-holes with common light chain, e.g. mAb².

In another embodiment, the bispecific format is selected from DVD-Ig, mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BITE, diabody, DART, TandAb, scDiabody, scDiabody-CH₃, Diabody-CH₃, Triple body, Miniantibody, minibody, TriBi minibody, scFv-CH₃ KIH, scFv-CH-CL-scFv, F(ab')₂-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig and zybody, for example DVD-Ig, mAb-dAb, dock and lock, SEEDbody, scDiabody-Fc, diabody-Fc, tandem scFv-Fc, Fab-scFv-Fc, Fab-scFv, intrabody, BITE, diabody, DART, TandAb, scDiabody, scDiabody-CH3, Diabody-CH3, minibody, knobs-in-holes, knobs-in-holes with common light chain, knobs-in-holes with common light chain and charge pairs, charge pairs, charge pairs with common light chain, in particular knob-in-holes, knobs-in-holes with common light chain and charge pairs, and knob-in-holes with common light chain.

In one embodiment, the multispecific (e.g. bispecific) antibody or fusion protein specifically binds to hOPG and another target antigen, e.g. another target antigen selected from TRAIL, or FAS.

Concept 53. An antagonist (e.g. an antibody or fragment thereof) as defined in any preceding concept for use in treating or preventing a hOPG-mediated disease or condition, e.g. selected from hypertension, cancer, bone-related disorders, fibrotic diseases and disorders, COPD, infectious diseases and autoimmune disorders; such as systemic hypertension, resistant hypertension, pulmonary hypertension (PH), pulmonary arterial hypertension (PAH) (e.g. idiopathic pulmonary arterial hypertension (IPAH), hereditary pulmonary arterial hypertension (hPAH) and/or associative pulmonary arterial hypertension (APAH)), prostate cancer, breast cancer, multiple myeloma, tumour-induced bone disease, kidney fibrosis, lung fibrosis and connective tissue fibrosis and diseases, COPD, malaria, HIV-associated cardiovascular disease, HIV-associated bone loss, persistent arthralgia following alphavirus infection, Paget's disease, osteoporosis (e.g. postmenopausal osteoporosis, glucocorticoid-induced osteoporosis, and senile osteoporosis), arthritis, rheumatoid arthritis, metabolic syndrome, atherosclerosis, diabetes, vascular calcification, metastatic bone disease, periodontal disease, cardiovascular disease, coronary artery disease, cerebrovascular disease and peripheral vascular disease, in particular hypertension such as pulmonary hypertension.

Concept 54. Use of an antagonist (e.g. an antibody or fragment thereof) as defined in any one of concepts 1 to 52 in the manufacture of a medicament for administration to a human for treating or preventing a hOPG-mediated disease or condition, e.g. selected from hypertension, cancer, bone-related disorders, fibrotic diseases and disorders, COPD, infectious diseases and autoimmune disorders; such as systemic hypertension, resistant hypertension, pulmonary hypertension (PH), pulmonary arterial hypertension (PAH) (e.g. idiopathic pulmonary arterial hypertension (IPAH), hereditary pulmonary arterial hypertension (hPAH) and/or associative pulmonary arterial hypertension (APAH)), prostate cancer, breast cancer, multiple myeloma, tumour-induced bone disease, kidney fibrosis, lung fibrosis and connective tissue fibrosis and diseases, COPD, malaria, HIV-associated cardiovascular disease, HIV-associated bone loss, persistent arthralgia following alphavirus infection, Paget's disease, osteoporosis (e.g. postmenopausal osteoporosis, glucocorticoid-induced osteoporosis, and senile osteoporosis), arthritis, rheumatoid arthritis, metabolic syndrome, atherosclerosis, diabetes, vascular calcification, metastatic bone disease, periodontal disease, cardiovascular disease, coronary artery disease, cerebrovascular disease and peripheral vascular disease, in particular hypertension such as pulmonary hypertension.

Concept 55. A method of treating or preventing a hOPG-mediated disease or condition, e.g. selected from hypertension, cancer, bone-related disorders, fibrotic diseases and disorders, COPD, infectious diseases, and autoimmune disorders; such as systemic hypertension, resistant hypertension, pulmonary hypertension (PH), pulmonary arterial hypertension (PAH) (e.g. idiopathic pulmonary arterial hypertension (IPAH), hereditary pulmonary arterial hypertension (hPAH) and/or associative pulmonary arterial hypertension (APAH)), prostate cancer, breast cancer, multiple myeloma, tumour-induced bone disease, kidney fibrosis, lung fibrosis and connective tissue fibrosis and diseases, COPD, malaria, HIV-associated cardiovascular disease, HIV-associated bone loss, persistent arthralgia following alphavirus infection, Paget's disease, osteoporosis (e.g. postmenopausal osteoporosis, glucocorticoid-induced osteoporosis, and senile osteoporosis), arthritis, rheumatoid arthritis, metabolic syndrome, atherosclerosis, diabetes, vascular calcification, metastatic bone disease, periodontal disease, cardiovascular disease, coronary artery disease, cerebrovascular disease and peripheral vascular disease, in particular hypertension such as pulmonary hypertension in a human, comprising administering to said human a therapeutically effective amount of an antagonist (e.g. an antibody or fragment thereof) as defined in any one of concepts 1 to 52, wherein the hOPG-mediated disease or condition is thereby treated or prevented.

In any of concepts 53 to 55, the hOPG-mediated disease may be any of those as described herein. In one embodiment, in any of concepts 53 to 55, the hOPG-mediated disease is a hypertension, such as systemic hypertension, resistant hypertension, pulmonary hypertension (PH), pulmonary arterial hypertension (PAH) (e.g. idiopathic pulmonary arterial hypertension (IPAH), hereditary pulmonary arterial hypertension (hPAH) and/or associative pulmonary arterial hypertension (APAH)).

In one embodiment, in any of concepts 53 to 55, the hOPG-mediated disease is a cancer, e.g. a malignant tumour, such as prostate cancer, breast cancer or multiple myeloma. For a discussion on the role of OPG in cancer, see "Role of osteoprotegerin (OPG) in cancer", Ingunn Holen & Claire M. Shipman, Clinical Science (2006), 110, 279-291.

In one embodiment, in any of concepts 53 to 55, the hOPG-mediated disease is a bone-related disorder, such as tumour-induced bone disease, Paget's disease or osteoporosis (e.g. postmenopausal osteoporosis, glucocorticoid-induced osteoporosis, and senile osteoporosis). For a discussion on the role of OPG in Paget's disease, see "Serum osteoprotegerin and its ligand in Paget's disease of bone: relationship to disease activity and effect of treatment with bisphosphonates" Alvarez, L et al., Arthritis Rheum., 2003, 48(3), 824-8.

In one embodiment, in any of concepts 53 to 55, the hOPG-mediated disease is a fibrotic disease, such as kidney fibrosis, lung fibrosis and connective tissue fibrosis and diseases.

In one embodiment, in any of concepts 53 to 55, the hOPG-mediated disease is COPD.

In one embodiment, in any of concepts 53 to 55, the hOPG-mediated disease is an infectious disease or a disease associated with an infection, such as malaria, HIV-associated cardiovascular disease, HIV-associated bone loss and persistent arthralgia following alphavirus infection. For a discussion on the role of OPG in these diseases see Weigiang Chen et al., "Arthritogenic alphaviruses: new insights into arthritis and bone pathology", Trends in Microbiology January 2015, Vol. 23, No. 1, p35-43; Weigiang Chen et al., "Arthritogenic alphaviral infection perturbs osteoblast function and triggers pathologic bone loss", PNAS, 2014, 111 (16), 6040-6045; and Niamh O'Regan, et al., "Marked elevation in plasma osteoprotegerin constitutes an early and consistent feature of cerebral malaria", Thrombosis and Haemostasis, 2016, 115(4), 773-780.

In one embodiment, in any of concepts 53 to 55, the hOPG-mediated disease does not include infectious diseases.

In one embodiment, in any of concepts 53 to 55, the hOPG-mediated disease is an autoimmune disorder, such as arthritis, rheumatoid arthritis, metabolic syndrome, atherosclerosis, diabetes, vascular calcification, metastatic bone disease, periodontal disease, cardiovascular disease, coronary artery disease, cerebrovascular disease or peripheral vascular disease. For a discussion of the role of OPG in various autoimmune diseases and bone-related disorders, see "Osteoprotegerin in Cardiometabolic Disorders", Pérez de Ciriza, C., et al., International Journal of Endocrinology, Volume 2015, Article ID 564934, 15 pages. For a discussion of the role of OPG in various diseases, including metastatic bone disease and periodontal disease, see "Osteoprotegerin: a link between osteoporosis and arterial calcification?", Hofbauer, L C & Schoppet, M, Lancet, 2001, 358(9278), 257-9. For a discussion on OPG expression in a number of diseases, see "Osteoprotegerin: a biomarker with many faces", Caidahl K, et al., Arterioscler. Thromb. Vasc. Biol., 2010, 30(9), 1684-6.

Concept 56. The antagonist (e.g. antibody or fragment thereof) according to concept 53, the use according to concept 54 or the method according to concept 54, wherein the hOPG-mediated disease or condition is cancer.

Concept 57. The antagonist (e.g. antibody or fragment thereof), use or the method according to concept 56, further comprising administering (e.g. to the human) a further therapy, for example a further therapeutic agent, optionally wherein the further therapeutic agent is independently selected from the group consisting of:
  a. immune checkpoint inhibitors (such as anti-PD-1 antibodies, anti-PD-L1 antibodies, anti-TIM-3 antibodies, anti-CTLA-4 antibodies, anti-TIGIT antibodies and anti-LAG-3 antibodies);
  b. immune stimulators (such as anti-OX40 antibodies, anti-GITR antibodies, anti-CD137 antibodies, anti-ICOS antibodies and anti-CD40 antibodies);
  c. chemokine receptor antagonists (such as CXCR4, CCR4 and CXCR2);

d. targeted kinase inhibitors (such as CSF-1R or VEGFR inhibitors);
e. angiogenesis inhibitors (such as anti-VEGF-A or Delta-like Ligand-4);
f. immune stimulating peptides or chemokines (such as CXCL9 or CXCL10);
g. cytokines (such as IL-15 and IL-21);
h. bispecific T-cell engagers (BiTEs) having at least one specificity against CD3 (e.g. CD3/CD19 BiTE);
i. other bi-specific molecules (for example IL-15-containing molecules targeted towards tumour associated antigens, for example Epidermal growth factor receptors such as EGFR, Her-2, New York Esophageal Cancer-1 (NY-ESO-1), GD2, EpCAM or Melanoma Associated Antigen-3 (MAGE-A3));
j. oncolytic viruses (such as HSV virus (optionally which secretes GMCSF), Newcastle disease virus and Vaccinia virus);
k. vaccination with tumour associated antigens (such as New York Esophageal Cancer-1 [NY-ESO-1], Melanoma Associated Antigen-3 [MAGE-3]);
l. cell-based therapies (such as chimeric Antigen Receptor-T cells (CAR-T) for example expressing anti-CD19, anti-EpCam or anti-mesothelin); and
m. adoptive transfer of tumour specific T-cells or LAK cells, or optionally wherein the further therapy is chemotherapy, radiotherapy and surgical removal of tumours.

Chemotherapeutic agents may any as described hereinabove, in particular agents that induce immunogenic cell death, for example platinum therapies, such as oxaliplatin. In one embodiment, the chemotherapy is a standard of care cytotoxic chemotherapy for the cancer being treated.

In this aspect, the bispecific molecules include "bispecific antibodies" and antibody fusion proteins, including those formats and molecules described in concepts 1, 52 and 52a.

The further therapeutic agents of this concept may be delivered by any method, which methods are well-known to those skilled in the art. For example, the further therapeutic agents may be delivered orally, systemically or locally (to the tumour environment). In one embodiment, the further therapeutic agent is delivered orally. In one embodiment, the further therapeutic agent is delivered systemically (e.g. intravenously). In one embodiment, the further therapeutic agent is delivered locally to the tumour environment.

Compositions and routes of administration are described in more detail hereinbelow.

Concept 58. The antagonist (e.g. antibody or fragment thereof) according to concept 53, the use according to concept 54 or the method according to concept 55, wherein the hOPG-mediated disease or condition is hypertension.

Concept 59. The antagonist (e.g. antibody or fragment thereof), use or the method according to concept 58, further comprising administering to the human a further therapy, for example a further therapeutic agent, optionally wherein the further therapeutic agent is independently selected from the group consisting of calcium channel blockers, diuretics, ACE inhibitors, angiotensin receptor blockers (ARBs), enthothelin receptor antagonists, prostacyclins, soluble guanalate cyclase agonists, phosphodiesterase inhibitors, alpha-adrenoceptor (α-adrenergic receptor) antagonists (α-blockers) and beta-adrenoceptor (β-adrenergic receptor) antagonists (β-blockers), or dual α-,β-blockers.

In one embodiment, the further therapeutic agent is a calcium channel blocker. In another embodiment, the calcium channel blocker is selected from a dihydropyridine calcium channel blocker, a phenylalkylamine calcium blocker, a benzothiazepine calcium channel blocker and a gabapentinoid calcium channel blocker. Examples of dihydropyridine calcium channel blockers include, but are not limited to Amlodipine (Norvasc), Aranidipine (Sapresta), Azelnidipine (Calblock), Barnidipine (HypoCa), Benidipine (Coniel), Cilnidipine (Atelec, Cinalong, Siscard), Clevidipine (Cleviprex), Isradipine (DynaCirc, Prescal), Efonidipine (Landel), Felodipine (Plendil), Lacidipine (Motens, Lacipil), Lercanidipine (Zanidip), Manidipine (Calslot, Madipine), Nicardipine (Cardene, Carden SR), Nifedipine (Procardia, Adalat), Nilvadipine (Nivadil), Nimodipine (Nimotop), Nisoldipine (Baymycard, Sular, Syscor), Nitrendipine (Cardif, Nitrepin, Baylotensin) and Pranidipine (Acalas). Examples of phenylalkylamine calcium channel blockers include, but are not limited to Verapamil (Calan, Isoptin), Gallopamil, Fendiline, Benzothiazepine and Diltiazem (Cardizem). Examples of gabapentinoid calcium channel blockers include, but are not limited to Gabapentin and Pregabalin. Other calcium channel blockers include, but are not limited to mibefradil, bepridil, Diltiazem, flunarizine and fluspirilene. Thus, in one embodiment, the calcium channel blocker is selected from Amlodipine (Norvasc), Aranidipine (Sapresta), Azelnidipine (Calblock), Barnidipine (HypoCa), Benidipine (Coniel), Cilnidipine (Atelec, Cinalong, Siscard), Clevidipine (Cleviprex), Isradipine (DynaCirc, Prescal), Efonidipine (Landel), Felodipine (Plendil), Lacidipine (Motens, Lacipil), Lercanidipine (Zanidip), Manidipine (Calslot, Madipine), Nicardipine (Cardene, Carden SR), Nifedipine (Procardia, Adalat), Nilvadipine (Nivadil), Nimodipine (Nimotop), Nisoldipine (Baymycard, Sular, Syscor), Nitrendipine (Cardif, Nitrepin, Baylotensin), Pranidipine (Acalas), Verapamil (Calan, Isoptin), Gallopamil, Fendiline, Benzothiazepine, Diltiazem (Cardizem), Gabapentin, Pregabalin, mibefradil, bepridil, flunarizine, Diltiazem and fluspirilene. In one embodiment, the calcium channel blocker is Nifedipine.

In one embodiment, the further therapeutic agent is a diuretic. In another embodiment, the diuretic is selected from a thiazide diuretic, thiazide-like diuretic, loop diuretic, a potassium diuretic or a combination thereof. Examples of thiazide diuretics include, but are not limited to, Hydrochlorothiazide (Hydrodiuril, Esodrex), Epitizide, Chlorothiazide (Diuril), Bendroflumethiazide, Hydroflumethiazide (Diucardin), Methyclothiazide and Polythiazide (Renese). Examples of thiazide-like diuretics include, but are not limited to Indapamide (Lozol), Chlorthalidone (Hygroton) and Metolazone (Zaroxolyn). Examples of Loop diuretics include, but are not limited to Bumetanide, Ethacrynic acid, Furosemide (Lasix) and Torsemide. Examples of potassium-sparing diuretics include, but are not limited to Spironolactone (Aldactone), Eplerenone, Triamterene and Potassium canrenoate.

A diuretic can also be selected from vasopressin V2 receptor (V2R) antagonists, Na—H exchanger antagonists, osmotic diuretics, xanthines and acidifying salts. Examples of V2R antagonists include, but are not limited to, Amphotericin B, Lithium citrate, Lithium, Tolvaptan, Conivaptan, Licivaptan, Mozavaptan and Satavaptan. An example of an Na—H exchanger antagonist is Dopamine. Examples of osmotic diuretics include, but are not limited to, Glucose and Mannitol. Examples of xanthines include, but are not limited to Caffeine, Theophylline and Theobromine. Examples of acidifying salts include, but are not limited to, $CaCl_2$ and $NH_4Cl$.

In one embodiment, the further therapeutic agent is an ACE inhibitor. In one embodiment the ACE inhibitor is selected from, but not limited to, Benazepril (Lotesin), Captopril (Capoten), Enalapril (Vasotec), Fosinopril (Monopril), Lisinopril (Zestoretic/Zestril), Moexipril, Quinapril (Accupril), Ramipril (Altace) and Perindopril (Coversyl, Coversum, Preterax, Aceon).

In another embodiment, the further therapeutic agent is an angiotensin receptor blocker (ARB). In one embodiment, the ARB is a tetrazole. In another embodiment, the ARB is selected from Candesartan (Atacand), Eprosartan (Teveten), Fimasartan, Irbesartan (Avapro), Losartan (Cozaar), Olmesartan, Telmisartan (Micardis) and Valsartan (Diovan).

In one embodiment, the further therapeutic agent is an endothelin receptor antagonist. In one embodiment, the endothelin receptor antagonist is selected from, but not limited to, Sitaxentan, Ambrisentan, Atrasentan, BQ-123, Zibotentan, Bosentan, Macitentan, Tezosentan, BQ-788 and A192621 and Edonentan.

In another embodiment, the further therapeutic agent is an endothelin receptor antagonist which is Bosentan. In Example 8 hereinbelow, it appears that the combination of Bosentan and Ky3 (15F11) show a statistically significant reduction in RVSP compared to monotherapies, i.e. a synergistic effect. Furthermore, there appears to be a reduction in both ePVRi and RVEa as compared to Bosentan alone.

In one embodiment, the further therapeutic agent is a prostacyclin (prostaglandin I2 ($PGI_2$)). In one embodiment, the prostacyclin is selected from, but not limited to, Epoprostenol (Veletri), Epoprostenol sodium (Flolan), Treprostinil (Remodulin) and Iloprost (Ventavis).

In one embodiment, the further therapeutic agent is a soluble guanylate cyclase agonist. In one embodiment, the soluble guanylate cyclase agonist is selected from, but not limited to, Cinaciguat and Riociguat.

In one embodiment, the further therapeutic agent is a phosphodiesterase inhibitor. In another embodiment, the phosphodiesterase inhibitor is selective for enzyme phosphodiesterase subtype PDE5 or a methylated xanthine (or a derivative thereof). In a further embodiment, the phosphodiesterase inhibitor is selected from, but not limited to, Sildenafil, Tadalafil, Vardenafil, Udenafil and Avanafil, Dipyridamole, Icariin, 4-methylpiperazine, Pyrazolo pyrimidin-7-1, Paraxanthine, aminophylline, pentoxifylline, theobromine, theophylline, Vinpocetine, erythro-9-(2-hydroxy-3-nonyl) adenine (EHNA), BAY 60-7550, Oxindole, 9-(6-Phenyl-2-oxohex-3-yl)-2-(3,4-dimethoxybenzyl)-purin-6-one (PDP), Inamrinone, milrinone, Enoximone, Anagrelide, Cilostazol, Pimobendan, Mesembrenone, Rolipram, Ibudilast, Piclamilast, Luteolin, Drotaverine, Roflumilast, Apremilast, Quinazoline and Papaverine.

In another embodiment, the further therapeutic agent is a phosphodiesterase inhibitor which is Sildenafil. In Example 8 hereinbelow, it appears that the combination of Sildenafil and Ky3 (15F11) show a reduction in ePVRi and RVEa compared to sildenafil alone.

In one embodiment, the further therapeutic agent is an alpha-adrenoceptor (α-adrenergic receptor) antagonist (α-blocker). In one embodiment, the α-adrenoceptor antagonist is selected from, but not limited to, Phentolamine, Phenoxybenzamine, Prazosin (Minipress), Terazosin (Hytrin), Doxazosin (Cardura) and Trimazosin.

In one embodiment, the further therapeutic agent is a beta-adrenoceptor (β-adrenergic receptor) antagonist (β-blocker). In one embodiment, the β-adrenoceptor antagonist is selected from, but not limited to, Carteolol, Carvedilol, Labetalol (Normodyne, Trandate), Nadolol (Cprgard), Penbutolol, Pindolol (Visken), Propranolol (Inderal), Timolol, Acebutolol (Sectral), Atenolol (Tenormin), Betaxolol, Bisoprolol, Esmolol, Metoprolol (Lopressor), Nebivolol, Bisoprolol and Sotalol.

In one embodiment, the further therapeutic agent is a dual α-,β-blocker. In one embodiment, the dual α-,β-blocker is selected from, but not limited to, labetalol (Normodyne, Trandate) and Carvedilol (Coreg).

Concept 59a. The antagonist (e.g. antibody or fragment thereof), use or the method according to concept 57 or concept 59, wherein the further therapeutic agent is administered sequentially or simultaneously with the anti-hOPG antagonist (e.g. antibody or fragment thereof).

Concept 60. A pharmaceutical composition comprising an antagonist (e.g. antibody of fragment thereof) as defined in any one of concepts 1 to 52 and a pharmaceutically acceptable excipient, diluent or carrier and optionally further comprising a further therapeutic agent independently selected from the group consisting of calcium channel blockers, diuretics, ACE inhibitors, angiotensin receptor blockers (ARBs), enthothelin receptor antagonists, prostacyclins, soluble guanalate cyclase and phosphodiesterase inhibitors.

Pharmaceutical formulations are well-known to those skilled in the art. In one embodiment, the antagonist (e.g. antibody or fragment thereof) is administered intravenously. In one embodiment, the antagonist (e.g. antibody or fragment thereof) is administered subcutaneously.

In an example, an antagonist (e.g. antibody or fragment thereof) as disclosed herein is contained in a medical container, e.g., a vial, syringe, IV container or an injection device (such as an intraocular or intravitreal injection device). In an example, the antagonist (e.g. antibody or fragment thereof) is in vitro, for example, in a sterile container.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilising agent and a local anesthetic such as lignocaine to ease pain at the site of the injection. Such compositions, however, may be administered by a route other than intravenous.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The further therapeutic agents of this concept may be delivered by any method, which methods are well-known to those skilled in the art. For example, the further therapeutic agents may be delivered orally, systemically or locally (to the tumour environment). In one embodiment, the further therapeutic agent is delivered orally. In one embodiment, the further therapeutic agent is delivered systemically (e.g. intravenously). In one embodiment, the further therapeutic agent is delivered locally to the tumour environment.

Concept 61. A pharmaceutical composition according to concept 60, or a kit comprising a pharmaceutical composition as defined in concept 60, wherein the composition is for treating and/or preventing a hOPG-mediated disease or condition, e.g. selected from hypertension, cancer, bone-related disorders, fibrotic diseases and disorders, COPD, infectious diseases and autoimmune disorders; such as systemic hypertension, resistant hypertension, pulmonary hypertension (PH), pulmonary arterial hypertension (PAH) (e.g. idiopathic pulmonary arterial hypertension (IPAH), hereditary pulmonary arterial hypertension (hPAH) and/or associative pulmonary arterial hypertension (APAH)), prostate cancer, breast cancer, multiple myeloma, tumour-induced bone disease, kidney fibrosis, lung fibrosis and connective tissue fibrosis and diseases, COPD, malaria, HIV-associated cardiovascular disease, HIV-associated bone loss, persistent arthralgia following alphavirus infection, Paget's disease, osteoporosis (e.g. postmenopausal osteoporosis, glucocorticoid-induced osteoporosis, and senile osteoporosis), arthritis, rheumatoid arthritis, metabolic syndrome, atherosclerosis, diabetes, vascular calcification, metastatic bone disease, periodontal disease, cardiovascular disease, coronary artery disease, cerebrovascular disease and peripheral vascular disease, in particular hypertension such as pulmonary hypertension.

Concept 62. A pharmaceutical composition according to concept 60 or concept 61 in combination with, or kit according to concept 61 comprising, a label or instructions for use to treat and/or prevent said disease or condition in a human; optionally wherein the label or instructions comprise a marketing authorisation number (e.g., an FDA or EMA authorisation number); optionally wherein the kit comprises an IV or injection device that comprises said antibody or fragment.

Concept 63. A method of modulating TRAIL/OPG and/or RANKL/OPG interaction in a patient, comprising administering an effective amount of an antagonist (e.g. an antibody or fragment thereof) as defined in any one of concepts 1 to 52 to said patient.

In one embodiment, the effective amount is a therapeutically and/or propylatically effective amount.

An another embodiment, the modulation of TRAIL/OPG and/or RANKL/OPG interaction treats, prevents, or reduces the risk of an OPG-mediated disease or condition in the patient. The OPG-mediated disease or condition is any of the diseases or conditions described elsewhere herein, in particular as in concepts 53 to 58 above. In this embodiment, the effective amount may be a therapeutically or prophylactically effective amount of the antagonist (e.g. antibody or fragment thereof), which is administered to the patient. Thus, the OPG-mediated disease or condition is treated or prevented, or the risk of the OPG-mediated disease or condition is reduced.

In another embodiment, there is provided a method of modulating RANKL/OPG interaction in a patient, comprising administering an effective amount of an antagonist (e.g. an antibody or fragment thereof) as defined in any one of concepts 1 to 52 to said patient. In another embodiment, the antagonist (e.g. antibody or fragment thereof) modulates RANKL/OPG interaction, but does not modulate TRAIL/OPG interaction. In another embodiment, the antagonist (e.g. antibody or fragment thereof) blocks RANKL/OPG interaction, but does not block TRAIL/OPG interaction. In another embodiment, the antagonist (e.g. antibody or fragment thereof) inhibits RANKL/OPG interaction, but does not inhibit TRAIL/OPG interaction. In another embodiment, the antagonist (e.g. antibody or fragment thereof) inhibits both RANKL/OPG interaction and TRAIL/OPG interaction.

Concept 64. A method of inhibiting OPG activity in a patient, comprising administering an effective amount of an antibody or fragment as defined in any one of concepts 1 to 52 to said patient.

In one embodiment, the antibody or fragment blocks or inhibits TRAIL binding to OPG. In one embodiment, the antibody or fragment blocks or inhibits RANKL binding to OPG.

Concept 65. A nucleic acid that encodes the CDRH3 of an antibody or fragment thereof as defined in any one of concepts 1 to 52.

In one embodiment, the nucleic acid is an isolated and purified nucleic acid.

Concept 66. A nucleic acid that encodes a $V_H$ domain and/or a $V_L$ domain of an antibody or fragment thereof as defined in any one of concepts 1 to 52.

The $V_H$ and $V_L$ domain nucleic acid sequences of the invention are provided in the sequence listing. In one embodiment, the nucleic acid sequence is at least 70% identical to the specified Seq ID No. In one embodiment, the nucleic acid sequence is at least 75% identical to the specified Seq ID No. In one embodiment, the nucleic acid sequence is at least 95% identical to the specified Seq ID No. In one embodiment, the nucleic acid sequence is at least 96% identical to the specified Seq ID No. In one embodiment, the nucleic acid sequence is at least 97% identical to the specified Seq ID No. In one embodiment, the nucleic acid sequence is at least 98% identical to the specified Seq ID No. In one embodiment, the nucleic acid sequence is at least 99% identical to the specified Seq ID No. In one embodiment, the nucleic acid sequence is at least 99.5% identical to the specified Seq ID No.

Concept 66a. The nucleic acid according to concept 65 comprising a nucleotide sequence that is at least 80% identical to the sequence of Seq ID No:13 and/or Seq ID No:23.

Concept 66b. A nucleic acid according to concept 65 comprising a nucleotide sequence that is at least 80% identical to the sequence of Seq ID No:33 and/or Seq ID No:43.

Concept 66c. A nucleic acid according to concept 65 comprising a nucleotide sequence that is at least 80% identical to the sequence of Seq ID No:53 and/or Seq ID No:63.

Concept 66d. A nucleic acid according to concept 65 comprising a nucleotide sequence that is at least 80% identical to the sequence of Seq ID No:73 and/or Seq ID No:83.

Concept 66e. A nucleic acid according to concept 65 comprising a nucleotide sequence that is at least 80% identical to the sequence of Seq ID No:93 and/or Seq ID No:103.

In one embodiment, the nucleic acid sequence is at least 70% identical to the specified Seq ID No. In one embodiment, the nucleic acid sequence is at least 75% identical to the specified Seq ID No. In one embodiment, the nucleic acid sequence is at least 95% identical to the specified Seq ID No. In one embodiment, the nucleic acid sequence is at least 96% identical to the specified Seq ID No. In one embodiment, the nucleic acid sequence is at least 97% identical to the specified Seq ID No. In one embodiment, the nucleic acid sequence is at least 98% identical to the specified Seq ID No. In one embodiment, the nucleic acid sequence is at least 99% identical to the specified Seq ID No. In one embodiment, the nucleic acid sequence is at least 99.5% identical to the specified Seq ID No.

Concept 67. The nucleic acid according to concept 66 comprising a nucleotide sequence that is at least 80% identical to the sequence of Seq ID NO: 53 and/or Seq ID NO: 63.

Concept 68. A nucleic acid that encodes a heavy chain or a light chain of an antibody or fragment thereof as defined in any one of concepts 1 to 52.

Concept 69. A vector comprising the nucleic acid as defined in any one of concepts 65 to 68; optionally wherein the vector is a CHO or HEK293 vector.

Concept 70. A host comprising the nucleic acid of any one of claims 65 to 68 or the vector as defined in concept 69.

Concept 71. A method of detecting OPG expression in a sample, comprising contacting the sample with an antagonist (e.g. antibody or fragment thereof) as defined in any one of concepts 1 to 52.

Concept 72. A method comprising contacting a biological sample with an antagonist (e.g. an antibody or fragment thereof) as defined in any one of concepts 1 to 52 to form a complex with OPG present in the sample and measuring the presence, absence or level of the complex in the biological sample.

Concept 73. The method according to concept 72, wherein the presence, absence and/or level of OPG expression is detected prior to treatment and a high level of surface expressed OPG is indicative of successful treatment.

Concept 74. The method according to concept 72, wherein the presence, absence and/or level of OPG expression is detected during treatment as an early response biomarker.

Concept 75. The method according to concept 72 or concept 73, wherein the presence, absence and/or level of OPG expression is detected during or after treatment to help determine one or more of: whether treatment has been successful, whether treatment should continue, and/or whether treatment should be modified.

Concept 76. The method according to any one of concepts 72 to 75, wherein therapy comprises treatment with an anti-OPG antagonist (e.g. an anti-OPG antibody or fragment thereof), optionally as defined in any one of concepts 1 to 52.

Concept 77. A method for monitoring therapy efficacy, the method comprising detecting expression of surface expressed hOPG in a patient prior to therapy, and during or after therapy, wherein an antagonist (e.g. an antibody or fragment thereof) as defined in any one of concepts 1 to 52 is used to detect expression of surface expressed hOPG.

Concept 78. The method according to concept 77, wherein surface expressed hOPG expression is detected in vivo.

Concept 79. The method according to concept 77, wherein surface expressed hOPG expression is detected in a tissue sample in vitro.

Concept 80. A method for identifying binding partners for OPG, the method comprising immunoprecipitating an intact protein complex comprising OPG using an antagonist (e.g. an antibody or fragment thereof) as defined in any one of concepts 1 to 52.

Concept 81. A method of diagnosing a disease in a human subject associated with altered hOPG expression comprising the steps of contacting a biological sample from the human subject with an antagonist (e.g. an antibody or fragment thereof) as defined in any one of concepts 1 to 52 to form a complex between the antibody and hOPG present in the sample; and detecting the amount of the complex.

4. Uses for Antibodies

Therapeutic

In one embodiment, the OPG specific antagonists (e.g. antibody or fragment thereof) described herein can be used for therapeutic modulation of the TRAIL/OPG and/or the RANKL/OPG pathway. In one embodiment, the OPG specific antagonist (e.g. antibody or fragment thereof) is as described in any concept herein.

In one embodiment, the antagonist (e.g. antibody or fragment thereof) specifically binds to OPG and thereby inhibits OPG activity. In another embodiment, the antagonist (e.g. antibody or fragment thereof) specifically binds to OPG and thereby inhibits binding of OPG to TRAIL. In another embodiment, the antagonist (e.g. antibody or fragment thereof) specifically binds to OPG and thereby inhibits binding of OPG to RANKL. In yet another embodiment, the antagonist (e.g. antibody or fragment thereof) blocks OPG induced signalling.

In yet another embodiment, the antagonist (e.g. antibody or fragment thereof) is capable of stimulating one or more of the following activities: circulating OPG, circulating RANKL, circulating TRAIL, RANKL-mediated apoptosis, TRAIL-mediated apoptosis, a circulating other ligand of OPG (such as a TNF superfamily member or a TNF-receptor superfamily member, e.g. as described above).

Still further embodiments include methods of treating a proliferative or invasion-related disease in a mammal by administering to the animal a therapeutically effective dose of an antagonist (e.g. antibody or fragment thereof). This may be achieved by enhancing RANKL-mediated apoptosis, and/or TRAIL-mediated apoptosis. In another embodiment, the antibodies or antigen binding fragments thereof can be used in a method for treating a mammal suffering from a disease selected from: pulmonary arterial hypertension (PAH), [which may be idiopathic (IPAH) or hereditary (hPAH), or may be in association with other diseases (APAH), e.g. connective tissue disease. PAH can also result from left heart disease, lung diseases (particularly Congestive Obstructive Disease [COPD] and pulmonary fibrosis), thrombo-embolism as well as may other multifactorial conditions such as portal hypertension, sickle cell disease and HIV], wherein the method includes administering to the mammal a therapeutically effective dose of an antagonist (e.g. antibody or fragment thereof).

Still further embodiments include methods of treating infectious diseases including malaria, HIV-associated cardiovascular disease, HIV-associated bone loss and persistent arthralgia following alphavirus infection.

Other Diseases

Examples of cancers that can be treated with the antibodies or fragments described herein include neoplastic diseases, and the metastasis associated with such neoplastic disease, such as, melanoma, uveal melanoma, skin cancer, small cell lung cancer, non-small cell lung cancer, salivary gland, glioma, hepatocellular (liver) carcinoma, gallbladder cancer, thyroid tumour, bone cancer, gastric (stomach) cancer, prostate cancer, breast cancer (including triple negative breast cancer), ovarian cancer, cervical cancer, uterine cancer, vulval cancer, endometrial cancer, testicular cancer, bladder cancer, lung cancer, glioblastoma, thyroid cancer, endometrial cancer, kidney cancer, colon cancer, colorectal cancer, pancreatic cancer, esophageal carcinoma, brain/CNS cancers, neuronal cancers, head and neck cancers (including but not limited to squamous cell carcinoma of the head and neck (SCCHN)), mesothelioma, sarcomas, biliary (cholangiocarcinoma), small bowel adenocarcinoma, pediatric malignancies, epidermoid carcinoma, sarcomas, cancer of the pleural/peritoneal membranes and leukaemia, including acute myeloid leukaemia, acute lymphoblastic leukaemia, and multiple myeloma.

The antagonist (e.g. antibody or fragment thereof) can be administered alone, or in combination with other antibodies or chemotherapeutic drugs, radiation therapy or therapeutic vaccines. In one embodiment, the antagonist (e.g. antibody or fragment thereof) is administered as an antibody-drug conjugate in which the antagonist (e.g. antibody or fragment thereof) is linked to a drug moiety such as a cytotoxic or cytostatic agent. The use of antibody-drug conjugates for the local delivery of cytotoxic or cytostatic agents in the treatment of cancer allows targeted delivery of the drug moiety to tumours, and intracellular accumulation therein, where systemic administration of unconjugated drug may result in unacceptable levels of toxicity. Drugs in antibody drug conjugates can include, but are not limited to, daunomycin, doxorubicin, methotrexate, and vindesine. Toxins can also be used in antibody-toxin conjugates, including, for example, bacterial toxins such as diphtheria toxin, plant toxins such as ricin, small molecule toxins such as geldanamycin. The toxins may effect their cytotoxic and cytostatic effects by mechanisms including tubulin binding, DNA binding, or topoisomerase.

Detection

In another embodiment, the antibodies or fragments can be used to detect the presence, absence and/or level of circulating OPG expression in a sample. Circulating OPG can be detected in vivo and/or in vitro and is useful in helping diagnose diseases or conditions that involve expression and/or overexpression of OPG.

In Vitro Diagnostic

In another embodiment, the OPG specific antibodies or fragments thereof can be used for the assessment of expression and localization of OPG in a biological sample from a patient. In one embodiment, the biological sample is a tissue sample and OPG expression is detected using known methods such as Flow cytometry, IHC in fresh tissue, IHC in FFPE tissue and/or IHC in frozen tissue. In other embodiments, the biological sample is blood, plasma or serum.

In one embodiment, the antagonist (e.g. antibody or fragment thereof) described herein is labeled with a detectable moiety, for example, a radiolabel, fluorescent label, enzymatic label chemiluminescent labeled or a biotinyl group. Radioisotopes or radionuclides may include $^{3}H$, $^{14}C$, $^{15}N$, $^{35}S$, $^{90}Y$, $^{99}Tc$, $^{115}In$, $^{125}I$, $^{131}I$, fluorescent labels may include rhodamine, lanthanide phosphors or FITC and enzymatic labels may include horseradish peroxidase, β-galactosidase, luciferase, alkaline phosphatase. Additional labels include, by way of illustration and not limitation: enzymes, such as glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase; dyes; additional fluorescent labels or fluorescers include, such as fluorescein and its derivatives, fluorochrome, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cisbio Assays); chemoluminescent labels or chemiluminescers, such as isoluminol, luminol and the dioxetanes; sensitisers; coenzymes; enzyme substrates; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of Pseudomonas exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

In Vivo Diagnostic

In one embodiment, the antagonist (e.g. antibody or fragment thereof) can be administered to a patient, wherein the antagonist (e.g. antibody or fragment thereof) is conjugated to a label. The presence of the label in the patient can be measured or observed, wherein a relatively high amount of the label may indicate a high risk of disease and a relatively low amount of the label may indicate a relatively low risk of the disease. In one embodiment, the label is a contrast agent, isotopic tag, radioactive label, or fluorescent marker, such as green fluorescent protein.

In one embodiment, the antagonist (e.g. antibody or fragment thereof) is used to monitor therapy that involves the use of other therapeutic agents, including, for example, chemotherapeutic agents or other antibodies that specifically bind OPG. In one embodiment, the antibody does not compete with the therapeutic OPG antibodies.

Guide Patient Selection

In one embodiment, detection of OPG expression can be used to guide patient selection. In one embodiment, the antibodies or fragments thereof can be used to assist in patient selection for therapeutic antibody treatment with an anti-OPG antibody, including, but not limited to anti-OPG antibodies disclosed in WO2015/036737 (University of Sheffield), WO2013/064810 (University of Sheffield), WO01/83560 (UAB Research Foundation), WO03/038043 (UAB Research Foundation), WO03/037913 (UAB Research Foundation), WO97/23614 (Amgen) and WO98/46751 (Amgen). In some cases, higher levels of OPG may be indicative of successful therapy, whereas lower levels may indicate a reduced likelihood of success. Preferential expression of splice variants and/or protein processing may produce unique protein mixture profiles which may impact a patient's response to treatment or may change following treatment. These profiles may help to identify patients and define patient subsets who should receive treatment, continue to receive treatment or who should receive an alternative treatment. In another embodiment, the antibodies or fragments thereof can be used for detection of OPG isoforms. Patient samples can include, for example, blood, plasma, serum, sputum, saliva, urine, CSF, tears, exhaled exogenous particle samples, cell supernatant, cell or tissue lysate or tissue samples.

In one embodiment, the antibodies or fragments thereof can be used to identify the presence, absence and/or level of OPG expression at baseline, i.e., before treatment.

In another embodiment, the OPG specific antibodies or fragments thereof can be used as an exclusion marker to suggest treatment with therapies that do not target OPG. In another embodiment, the OPG specific antibodies or fragments thereof can be used as a prognostic marker for life expectancy. In particular, OPG expression on tumours is linked to poor prognosis and life expectancy can be estimated based on historical data within tumour types.

Methods for detection of proteins are known, and include, for example, IHC, Flow cytometry, Western blotting and Mass Spectroscopy, Immunoprecipitation, aptamers, immuno-PCR, and protein array.

Guide Therapy

The antibodies can be used to guide therapy. For example, the antibodies or fragments thereof can be used to identify the presence, absence and/or level of OPG expression during or after treatment. In one embodiment, the antibodies or fragments thereof can be used as early response biomarkers to assist in patient management, drug approval and reimbursement. In another embodiment, the antibodies or fragments thereof can be used to identify the presence, absence and/or level of OPG expression to help guide therapy. For example, OPG expression can help determine whether the treatment is effective, and hence, whether or not treatment should be continued, or whether the dose should be adjusted (increased or decreased) and whether a combination regimen should be changed. For example, in one embodiment, the OPG specific antibodies or fragments thereof can be used for determining receptor occupancy of OPG on cells in a patient treated with anti-OPG therapy for dose setting (PK/PD). In particular, receptor occupancy can be used as a measure of target engagement or target coverage. Estimates of the amount or duration of target engagement needed to elicit a biological or clinical response could be used to determine if a patient has been dosed sufficiently or not. In particular, the antibodies can be used to assist in evaluating the relationship between, dose, exposure, receptor occupancy, pharmacodynamic response and clinical benefit.

Monitor Efficacy of Therapy

In another embodiment, the OPG specific antibodies or fragments thereof can be used for patient monitoring, to help evaluate whether a course of treatment is effective and whether or not treatment should be continued. For example, in one embodiment, the antibodies or fragments thereof can be used detect expression before a patient receives therapeutic treatment that targets OPG. In another embodiment, the antibodies or fragments thereof can be used to detect expression during therapy or after a patient has received therapeutic anti-OPG treatment. In another embodiment, the antibodies or fragments thereof can be used as an early response marker to assist in the determination as to whether or not a course of therapy is effective and should be continued or discontinued. In one embodiment, the expression of OPG is detected after washout, wherein the term "washout" refers to a period of time after which the administered drug has been eliminated from the body. In particular, expression of OPG may be detected after washout if the patient is treated with anti-OPG therapy that competes with the detection antibody. However, if the patient is treated with an antibody that does not compete with an anti-OPG antibody, detection can be performed without waiting for washout. In another embodiment, the detection antibody can bind to OPG but not compete with a therapeutic antibody that binds to OPG. In this situation, washout may not be necessary. The washout period can vary depending upon many factors, but is generally a period of at least about 1, 2, 3, 4, 5, or 6 weeks and up to about 1, 2, 3, 4, 5 or 6 months from the most recent chemotherapy or immunotherapy treatment. The antibodies or fragments thereof can be used to determine expression of OPG on biopsy samples (e.g. lung biopsy cells).

In one embodiment, labelled antibodies or fragments thereof can be used to identify a peripheral correlate to enable non-invasive assessment of pulmonary status pre-, during and post-treatment.

Methods for detection of proteins are known, and include, for example, IHC, flow cytometry, Western blotting and Mass Spectroscopy, immunoprecipitation, aptamers, immuno-PCR, and protein array.

Identify Protein Binding Partners for OPG

In another embodiment, antibodies or fragments thereof can be used as a capture reagent or detection reagent for examination of the protein binding partners of OPG protein species in the context of a protein "pull-down." A protein "pull down" refers to immunoprecipitation of intact protein complexes, such as antigen along with any proteins or ligands that are bound to it—also known as co-immunoprecipitation (Co-IP). Co-IP works by selecting an antibody that targets a known protein that is believed to be a member of a larger complex of proteins. By targeting the known member with an antibody it may become possible to pull the entire protein complex out of solution and thereby identify unknown members of the complex. Antibodies and fragments could improve knowledge of the interplay among accessory proteins and factors, which may determine a patient's propensity to respond to specific therapies or immunotherapy in general.

5. Pharmaceutical Compositions

Unless otherwise apparent from the context, the compositions for antibodies or fragments applies mutatis mutandis to the antagonists of the invention.

In one embodiment, there is provided a pharmaceutical composition comprising an effective amount of an antagonist (e.g. antibody or fragment thereof) and a pharmaceutically acceptable carrier. An effective amount of antibody to be employed therapeutically will depend, for example, upon the therapeutic objectives, the route of administration, and the condition of the patient. In one embodiment, the composition includes other excipients or stabilizers.

Pharmaceutically acceptable carriers are known and include carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as Ethylenediaminetetraacetic acid (EDTA); sugar alcohols such as mannitol or sorbitol; salt-forming counterions such as sodium; and/or nonionic surfactants such as TWEEN™, polyethylene glycol (PEG), and PLURONICS™.

The antibodies or fragments can be administered intravenously or through the nose, lung, for example, as a liquid or powder aerosol (lyophilized). The composition can also be administered parenterally or subcutaneously. When administered systemically, the composition should be sterile, pyrogen-free and in a physiologically acceptable solution having due regard for pH, isotonicity and stability. These conditions are known to those skilled in the art.

Methods of administering a prophylactic or therapeutic agent (e.g., an antibody as disclosed herein), or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, a prophylactic or therapeutic agent (e.g., an antibody as disclosed herein), or a pharmaceutical composition is administered intranasally, intramuscularly, intravenously, or subcutaneously. The prophylactic or therapeutic agents, or compositions may be administered by any convenient route, for example by infusion or bolus injection, by absorption through epithelial or mucocutaneous linings (e.g., oral mucosa, intranasal mucosa, rectal and intestinal mucosa, etc.) and may be administered together with other biologically active agents. Administration can be systemic or local. Each dose may or may not be administered by an identical route of administration. In one embodiment, an anti-OPG antagonist (e.g. antibody or fragment thereof) as disclosed herein may be administered via multiple routes of administration simultaneously or subsequently to other doses of the same or a different anti-OPG antagonist (e.g. antibody or fragment thereof) as disclosed herein.

Various delivery systems are known and can be used to administer a prophylactic or therapeutic agent (e.g., an antagonist (e.g. antibody or fragment thereof) as disclosed herein), including, but not limited to, encapsulation in liposomes, microparticles, microcapsules, recombinant cells capable of expressing the antibody, receptor-mediated endocytosis (see, e.g., Wu and Wu, J. Biol. Chem. 262:4429-4432 (1987)), construction of a nucleic acid as part of a retroviral or other vector, etc. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO92/19244, WO97/32572, WO97/44013, WO98/31346, and WO99/66903, each of which is incorporated herein by reference their entirety.

In a specific embodiment, it may be desirable to administer a prophylactic or therapeutic agent, or a pharmaceutical composition as described herein locally to the area in need of treatment. This may be achieved by, for example, local infusion, by topical administration (e.g., by intranasal spray), by injection, or by means of an implant, said implant being of a porous, non-porous, or gelatinous material, including membranes, such as silastic membranes, or fibres. When administering an anti-OPG antagonist (e.g. antibody or fragment thereof), care must be taken to use materials to which the antibody does not absorb.

6. Kits and Articles of Manufacture

Unless otherwise apparent from the context, the kits and articles of manufacture for antibodies or fragments applies mutatis mutandis to the antagonists of the invention.

In one embodiment, the invention provides a kit for detecting OPG in a biological sample. The kit can be used to screen for OPG-mediated diseases. In one embodiment, the kit includes an antagonist (e.g. antibody or fragment thereof) and a means for determining whether the antagonist (e.g. antibody or fragment thereof) is bound to OPG in a sample. In one embodiment, the antagonist (e.g. antibody or fragment thereof) is labelled. In another embodiment, the antagonist (e.g. antibody or fragment thereof) is an unlabelled primary antibody and the kit includes means for detecting the primary antibody. In one embodiment, the means for detecting includes a labelled secondary antibody that is an anti-immunoglobulin antibody. The antibody may be labelled with any suitable marker, including, for example, a fluorochrome, an enzyme, a radionuclide and a radiopaque material. Suitable antibodies and antigen binding fragments are described in detail above.

In one embodiment, a kit for detecting OPG is provided, wherein the kit includes an antagonist (e.g. antibody or fragment thereof) described herein. In one embodiment, the kit may also include instructions and one or more reagents for detecting OPG. In one embodiment, the kit includes an antagonist (e.g. antibody or fragment thereof), along with instructions for preparing a formalin-fixed paraffin-embedded (FFPE) tissue sample for IHC and/or one or more reagents for IHC. In one embodiment, the kit includes an antigen or antigen binding fragment described herein as a primary antibody and a secondary antibody that specifically binds thereto. In one embodiment, the kit includes a labeled antigen or antigen binding fragment described herein, wherein the label includes a fluorescent label such as fluoroscein or rhodamine or an enzymatic reporter such as horseradish peroxidase (HRP) or alkaline phosphatase (AP). In one embodiment, the kit includes a blocking reagent that includes at least about 1% and up to about 5%, or between about 2% and 3%, or about 2% cold water fish skin gelatin protein (CWF) in a buffer, such as phosphate buffered saline (PBS). In one embodiment, the kit includes buffer for antigen retrieval, such as a citrate buffer, for example sodium citrate, at a concentration of at least about 1, 2, 5, or 10 mM and up to about 10, 15 or 20 mM and at a pH between about 5.5 and 9, or a pH of about 6.

In another embodiment, a kit for treating diseases involving the expression of OPG is provided, wherein the kit includes an antagonist (e.g. antibody or fragment thereof) described herein and instructions to administer the antagonist (e.g. antibody or fragment thereof) to a subject in need of treatment. There is also provided a pharmaceutical or diagnostic pack or kit comprising one or more containers filled with one or more of the ingredients of the pharmaceutical compositions as disclosed herein, such as one or more anti-OPG antibodies or fragments provided herein. Optionally associated with such container(s) can be a notice in the form prescribed by a governmental agency regulating the manufacture, use or sale of pharmaceuticals or biological products, which notice reflects approval by the agency of manufacture, use or sale for human administration, e.g., an authorisation number.

In another embodiment, an article of manufacture that includes a container in which a composition containing an antagonist (e.g. antibody or fragment thereof) described herein and a package insert or label indicating that the composition can be used to treat diseases characterized by the expression or overexpression of OPG is provided. In one embodiment, there is provided a kit for treating and/or preventing a OPG-mediated disease or condition, the kit comprising an antagonist (e.g. antibody or fragment thereof) as disclosed herein in any embodiment or combination of embodiments (and optionally a further therapeutic agent as described elsewhere herein) optionally in combination with a label or instructions for use to treat and/or prevent said disease or condition in a human; optionally wherein the label or instructions comprise a marketing authorisation number (e.g., an FDA or EMA authorisation number); optionally wherein the kit comprises an IV or injection device that comprises the antagonist (e.g. antibody or fragment thereof). In another embodiment, the kit comprises an antagonist (e.g. antibody or fragment thereof) contained within a container or an IV bag. In another embodiment, the container or IV bag is a sterile container or a sterile IV bag. In another embodiment, the antagonist (e.g. antibody or fragment thereof) is formulated into a pharmaceutical composition contained within a (sterile) container or contained within a (sterile) IV bag. In a further embodiment, the kit further comprises instructions for use.

7. Examples

Example 1—Antigen Preparation, Immunization Procedures and Hybridoma Generation The following example provides a detailed description of the generation and identification of a panel of anti-human OPG monoclonal antibodies using the KyMouse™ system (see, e.g., WO2011/004192, WO2011/158009 and WO2013/061098). To this end, genetically engineered mice containing a large number of human immunoglobulin genes were immunized with recombinant human and rat OPG. Various immunisation regimens, including conventional intraperitoneal injections as well as a rapid immunisation at multiple sites (RIMMS) regimen were set up, boosting animals over several weeks (see detailed methods below). At the end of each regime, secondary lymphoid tissue such as the spleen, and in some cases, the lymph nodes were removed. Tissues were prepared into a single cell suspension and fused with SP2/0 myeloma cells to generate a stable hybridoma cell lines.

Materials and Methods a) Cloning and Expression of Recombinant Proteins

Human, rat and cyno OPG, as well as human TRAIL, were generated in house and used either for immunisations or to set up assays part of the screening cascade. RANKL was the only commercial recombinant protein used and sourced from R&D Systems (390-TN).

For the generation of recombinant proteins, synthetic DNA strings were cloned into appropriate mammalian expression vectors for transient expression in Expi293 and CHO cells. The sequence listing shows the sequences of antigens, where available, and affinity tags for purification/labelling (shown in bold and underlined), see Seq ID No:154, Seq ID No:156 and Seq ID No:159.

b) Immunisations

Genetically engineered HK and HL Kymouse™ strains, containing human immunoglobulin genes producing human kappa (HK) and lambda (HL) light chain antibodies (Lee et al., Nature Biotechnology, 32, 6-363, 2014) were immunized by various immunisation regimens for the generation of human anti-OPG antibodies. Summary of immunisation campaigns is detailed in Table 1.

Mice were immunised with recombinant human OPG-Fc (Seq ID No:154) alone or in combination with rat OPG-Fc (Seq ID No:156) using a modified sub-cutaneous immunisation procedure (RIMMS; modified after Kilpatrick et al., ("Rapid development of affinity matured monoclonal antibodies using RIMMS"; Hybridoma. 1997 August; 16(4): 381-9.) hereafter referred to as KM058). A second immunisation regime (hereafter referred to as KM059) using recombinant human OPG-Fc (Seq ID No:154) alone or in combination with rat OPG-Fc (Seq ID No:156) (co-administration or a regime alternating the delivery of both proteins) were used in a prime-rest-boost regime with rest intervals usually between 2 and 3 weeks. Serum prepared from terminal blood samples (KM058) or from serial bleeds (KM059) were analysed for the presence of anti-OPG antibodies by DELFIA® Time Resolved Fluorescence and used, where possible, to select mice for hybridoma fusions.

TABLE 1

Summary of immunisation regime for KM058 and KM059 immunisation campaigns

| Immunisation | Mice | Details | Adjuvant | Procedure |
|---|---|---|---|---|
| KM058 (RIMMS) | 3 mice | recombinant human OPG-Fc | Sigma Adjuvant with CpG | s.c. at multiple sites |
|  | 3 mice | co-administration of recombinant human and rat OPG-Fc |  |  |
| KM059 (Conventional) | 6 mice | recombinant human OPG-Fc | CFA for prime then IFA; CpG/alum adjuvant except final boost | Prime s.c.; Boost ip; Final boost iv |
|  | 6 mice | co-administration of recombinant human and rat OPG-Fc |  |  |
|  | 6 mice | alternated administation of recombinant human and rat OPG-Fc |  |  | c) Determining Serum Titres by DELFIA® Time-Resolved Fluorescence

All animals immunised following KM058 regime were selected for hybridoma fusions. Level of response was assessed by measuring titres of terminal bleeds and therefore data was merely informative. Titre levels following KM059 immunisation regime were determined using samples collected following three boosts with human and/or rat OPG recombinant proteins. Results obtained allowed to pick three best responders, from which spleen and lymph nodes were collected for hybridoma fusions.

Immune response in mouse serum samples was determined by DELFIA® Time-resolved fluorescence. Goat anti-mouse IgG capture antibody (Southern Biotech), prepared at 4 pg/mL in PBS, was added to high protein binding 96-well plates (Costar) (50 µL/well) and incubated for 1 hour at room temperature or overnight at 4° C. Excess IgG was removed by washing three times with PBS Tween (0.1% v/v) before wells were blocked with 1% w/v bovine serum albumin (BSA, Sigma) in PBS for 1 hour at room temperature. Following this blocking step, plates were washed again three times with PBS-Tween (0.1% v/v). Titrations of mouse serum samples and anti-OPG control antibody (MAB805, R&D Systems) for the generation of a standard control curve were prepared in dilution buffer (0.1% w/v BSA in PBS) and added to assay plates (50 µL/well). Immune response was determined by comparing response detected in samples collected from immunised mice to levels observed in pre-immunisation samples. Following 1 hour incubation at room temperature, plates were washed as detailed previously. 50 µL/well of biotinylated human OPG (R&D, 185-OS-025/CF), labelled in house using Sulfo-NHS-LC-Biotin (Thermo) was then added at 0.1 pg/ml to plates and incubated for 1 hour at room temperature. Unbound biotinylated human OPG was removed by washing with PBS-Tween (0.1% v/v), while the remaining biotinylated human OPG was detected by streptavidin-Europium (Perkin Elmer) diluted 1/10000 in DELFIA® Assay Buffer (Perkin Elmer). Following incubation for 1 hour at room temperature, plates were washed before the addition of 50 µL DELFIA® Enhancement Solution (Perkin Elmer). Plates were incubated for 5 minutes protected from light and read at 615 nm using appropriate settings for DELFIA® Time resolved fluorescence on an Envision plate reader (Perkin Elmer). Data was plotted onto Prism for analysis.

d) Murine Tissue Isolation and Preparation

Immunised animals were sacrificed three days following the final boost. Spleen and lymph nodes were excised and washed in 1×PBS. These tissues were subsequently prepared in buffer containing 1×PBS (Invitrogen) and 3% heat-inactivated FBS (Invitrogen). Splenocytes were homogenised by mashing the tissue through a 45 µm strainer (BD Falcon) and rinsing with 30 mL 3% FBS/PBS buffer before centrifugation at 700 g for 10 minutes at 4° C. To remove red blood cells, the pelleted splenocytes were resuspended in 4 mL Red Blood Cell Lysis Buffer (Sigma). After 4 minutes of incubation, the lysis reaction was stopped by addition of 3% FBS/1×PBS buffer. Cell clumps were filtered out with a 45 µm strainer. The remaining splenocytes were pelleted before further processing. Inguinal and axillary lymph nodes were also homogenised in the same manner as described above with splenocytes, but red blood cell lysis was not required. The homogenised lymph node cells were pelleted before further processing.

Processed cells from the same animal were combined ahead of IgG B cell enrichment and subjected to a positive selection method using the MACS® Separation system for the enrichment of IgG B cells. This protocol was adapted from the manufacturer's guidelines and was used for the simultaneous selection of IgG1 and IgG2a+b positive B cells. Briefly, the cell number was determined and the cells were resuspended in an appropriate volume of 3% FBS/PBS buffer. A mixture of anti-mouse IgG1 plus anti-mouse IgG2a+b MicroBeads (both by Miltenyi Biotec) were added to the cells and incubated for 15 minutes at 4° C. The cells/MicroBeads mixture was then applied to a pre-wetted LS column placed in a magnetic MACS Separator. IgG positive cells were collected by pelleting in the labelled, column-bound fraction. The enriched B-cells were then cultured overnight in a medium containing CpG at 2×10$^6$ cells/mL. This CpG medium consisted of Advance DMEM, 10% FBS, 1× Glutamax (Gibco), 1×PenStrep (Gibco), 2-mercaptoethanol (Sigma), and 25 pM CpG (Hokkaido System Science).

e) Hybridoma Fusions

After an overnight CpG culture, the B-cells were washed once in BSA fusion buffer (0.3 M D-Sorbitol, 0.11 mM calcium acetate hydrate, 0.5 mM magnesium acetate tetrahydrate and 0.1% BSA (v/w) (all Sigma), adjusted to pH 7.2). Washed cells were resuspended in a small volume of BSA fusion buffer and cell number determined. The myeloma cell line, SP2/0, were also washed and counted in the same manner. After the cell number of CpG stimulated B-cells and SP2/0 myeloma cells were determined, the two cell populations were mixed in a ratio of 3:1 (B cells: SP2/0). Electrofusion was carried out using a BTX ECM 2001 Electro Cell Manipulator (Harvard Apparatus). Fused hybridoma cells were incubated overnight in the recovery medium (Dulbecco's Modified Eagle's Medium (high glucose, no phenol red) supplemented with OPI (Sigma), 1× L-Glutamax, 20% FBS and 0.05 mM 2-mercaptoethanol). After an overnight incubation following electrofusion, hybridoma cells from each fusion were pelleted and resuspended in 10 mL Hybridoma Medium consisted of Advance DMEM, 1×L (Glutamax), 20% FBS, 1× PenStrep, 2-mercaptoethanol and 1× HT (Gibco). The 10 mL hybridoma cell suspension was added to 90 mL of Semi-Solid Medium (ClonaCell-HY Medium D, Stemcell Technologies) and mixed thoroughly before seeding into 10 cm petri-dishes at 10 mL per dish. The hybridoma cells were left in culture for 12 days at 37° C., 5% $CO_2$. Visible colonies were picked into 96-well plates and cultured for a further 2 to 3 days prior to screening.

Table 2 is a summary of hybridoma fusions.

TABLE 2

Summary of hybridoma fusions for KM058 and KM059

| Immunisation Campaign | Number of Mice | Processed samples | Number of fusions | Number of hybridoma screened |
|---|---|---|---|---|
| KM058 | 6 | Spleen and lymph nodes | 7 | 2424 |
| KM059 | 3 | Spleen | 4 | 822 |

Example 2—Hybridoma Supernatant Screening

The following example provides a detailed description of the screening cascade designed to identify anti-OPG antibodies, which are required to bind with high affinity to human OPG but also rat OPG to enable testing of clones in appropriate rat disease models. After generation of hybridoma clones, hybridoma supernatants were assessed in a sequential primary and secondary screen and appropriate hybridoma clones selected following confirmation of binding to human and rat OPG, affinity measurement and receptor neutralization profile (TRAIL and RANKL).

Materials and Methods a) Primary Screen: Binding to Recombinant Human and Rat OPG by HTRF Supernatants collected from hybridoma wells were screened for the ability of secreted antibodies to bind to human and rat OPG expressed as recombinant proteins by HTRF® (Homogeneous Time-Resolved Fluorescence, Cisbio). A total of four assays were set up for screening of KM058 supernatants using human OPG-Fc (Seq ID No:154), biotinylated human OPG-Fc (OPG-Fc having the amino acid sequence of Seq ID No:154) and rat OPG-Fc (Seq ID No:156). An irrelevant Fc protein was used to counter-screen and exclude Fc binders from the pool of identified hits. Clones taken forward to secondary screen were selected if above the cut-off defined for the assay and if showing the ability to bind to both human and rat OPG. Screening of KM059 supernatants was performed as a simplified version of the first screening campaign. Binding of antibodies in hybridoma supernatants was tested by HTRF binding to human OPG (805-OS-100/CF, R&D Systems) and rat OPG-Fc (Seq ID No:156). However, decision was made to progress not only the cross-reactive clones but all binders to human OPG to secondary screen.

Protocol details, namely the description of the recombinant protein used for each binding assay, are summarised in Table 3, as well as the % Effect used as cut-off criteria for hit selection.

TABLE 3

Summary of KM058 and KM059 primary screen

| Campaign | HTRF binding Assays | Working concentration | % Effectcut-off | Hits selected for secondary screen |
|---|---|---|---|---|
| KM058 | Human OPG-Fc | 5 nM | >20% | 154 |
|  | Biotinylated Human OPG-FC | 5 nM |  |  |
|  | Rat OPG-Fc | 16 nM |  |  |
|  | Irrelevant protein Fc tag | 16 nM | >50% |  |
|  | Controls (MAB805/Mouse IgG1) | 1.6 nM |  |  |
| KM059 | Biotinylated Human OPG (R&D) | 16 nM | >20% | 27 |
|  | Rat OPG-Fc | 16 nM |  |  |
|  | Controls (MAB805/Mouse IgG1) | 4.4 nM |  |  |

For each binding assay, 5 μL hybridoma supernatant were transferred to a white 384 well, low-volume, non-binding surface polystyrene plate (Greiner) and mixed with 5 μL of recombinant protein prepared in HTRF assay buffer (PBS (Sigma)+0.53 M KF (Sigma)+0.1% w/v BSA (Sigma)) at the concentrations detailed in Table 3.5 μL of antibody MAB805 (R&D Systems) were added to maximum binding control wells and mouse IgG1 isotype control (MAB5284, Sigma) to control wells to detect nonspecific binding. Both reagents were diluted in Hybridoma Maintenance Media (HMM) at concentrations detailed in summary table. Binding control curves were added on to a separate plate and set up using anti-OPG control antibody MAB805/Mouse IgG1 prepared at 120 nM working concentration in HMM and diluted 1:3, 11 dilution points. Detection solutions of HTRF binding assays using Fc tag proteins were set up using anti-human Fc D2 (Cisbio) whereas biotinylated proteins were detected by Streptavidin D2 (Cisbio). Both were diluted at 1/100 in HTRF assay buffer and combined with goat anti-mouse IgG (Southern Biotech) labelled with Europium cryptate (Cisbio) at 1/1000 in HTRF assay buffer. 10 μL of this mixture was added to assay plates, which were incubated protected from light for 1 hour at room temperature. Finally, plates were read using an EnVision plate reader (Perkin Elmer) for measurement of wells at 620 nm and 665 nm emission wavelengths. More details of the HTRF® assay technology can be found in Mathis (1995) Clinical Chemistry 41(9), 1391-1397. Data were analysed by calculating 665/620 ratio (Equation 1) and % Effect (Equation 2) for each sample.

Calculation of 665/620 ratio $$\text{ratio} = \frac{\text{well value at 665 nm}}{\text{well value at 620 nm}} \quad \text{Equation 1}$$

Calculation of percentage of effect $$\% \text{ of Effect} = \left(\frac{\text{sample well} - \text{non specific binding}}{\text{total binding} - \text{non specific binding}}\right) \times 100 \quad \text{Equation 2}$$

where values used were the 665/620 nm ratio (Equation 1) calculated for sample wells and controls as defined:

Non-specific binding=values from wells containing isotype control antibody

Total Binding=values from wells containing reference antibodyCriteria for hit selection were based on % Effect greater of equal to 20%. Hit selection to exclude Fc binders was based on % Effect greater of equal to 50%.

b) Secondary Screen: OPG/TRAIL and OPG RANKL HTRF Receptor Ligand Assays

Following primary screen, selected hybridoma clones were cultured for additional 3 days and supernatants collected for further characterisation. Confirmation of binding to human and rat OPG and additional data on binding to cyno OPG was obtained by SPR. KM058 primary hits were also tested in the OPG/TRAIL and OPG/RANKL HTRF inhibition assays and ranked % TRAIL specific binding. This data, together with affinity to human and rat OPG, were the criteria used to pick a sub-group of high affinity antibodies with a diverse inhibition profile for further characterisation as purified material. In the case of KM059 primary hits, all confirmed cross reactive clones were taken forward regardless of their inhibition profile (not tested for this particular screening campaign). Protocol details and criteria used for hit selection are detailed in Table 4.

TRAIL/OPG HTRF assay was prepared using 5 μL hybridoma supernatant transferred to a white 384 well, low-volume, non-binding surface polystyrene plate (Greiner) and mixed with 5 μL of 4 nM human OPG-Fc (Seq ID No:154) prepared in HTRF assay buffer (PBS (Sigma)+0.53 M KF (Sigma)+0.1% w/v BSA (Sigma)). 5 μL of TRAIL diluted to 16 nM in HTRF buffer assay buffer were then added to assay plates with the exception of control wells used to detect non-specific binding. Before adding the detection solution, plates were incubated for 30 minutes at room temperature to allow receptor-ligand interaction to occur. 10 μL of a solution composed of anti-human Fc D2 (Cisbio) and anti-Flag cryptate (Cisbio) at 1/100 in HTRF assay buffer was added to assay plates.

TABLE 4

Summary of KM058 and KM059 secondary screen

| Campaign | Assay | Details/Working concentration | Hit selection criteria | Hits |
|---|---|---|---|---|
| KM058 | HTRF OPG-Fc/TRAIL-Flag | 4 nM OPG-Fc 16 nM TRAIL-Flag | Hits ranked by % TRAIL binding and then sorted by affinity Panel of clones includes different TRAIL/RANKL neutralisation profiles | 36 |
|  | HTRF OPG-Fc/RANKL-647 | 20 nM OPG-Fc 55.6 nM RANKL (R&D) |  |  |
|  | SPR | Human OPG-Fc Rat OPG-Fc Cyno OPG-Fc |  |  |
| KM059 | SPR | Human OPG-Fc Rat OPG-Fc Cyno OPG-Fc | Indication of cross-reactivity by HTRF and/or SPR | 9 |

HTRF assay to identify antibodies able to inhibit OPG/RANKL interaction was set up following the same method but using 20 nM hOPG-Fc (Seq ID No:154) mixed with 55.6 nM 647-RANKL. Detection solution was prepared using anti-Fc cryptate (Cisbio) diluted at 1/100 in HTRF assay buffer.

Control curves were set up using anti-OPG antibody MAB805/Mouse IgG1 prepared at 120 nM working concentration in HMM and diluted 1:3, 11 dilution points.

Plates were incubated for 1 hour at room temperature and protected from light before measurement of wells at 620 nm and 665 nm emission wavelengths using an EnVision plate reader (Perkin Elmer). Data were analysed by calculating 665/620 ratio (Equation 1) and % Specific Binding (Equation 3) for each sample.

Percentage of % TRAIL and RANKL specific binding $$\% \text{ of specific binding} = \left(\frac{\text{sample well} - \text{non specific binding}}{\text{total binding} - \text{non specific binding}}\right) \times 100 \quad \text{Equation 3}$$

Where values used were the 665/620 nm ratio (Equation 1) calculated for sample wells and controls as defined: Total binding=5 µL OPG-Fc+5 µL TRAIL-Flag or 647-RANKL+5 µL HMM+5 µL detection reagents Non-specific binding=5 µL OPG-Fc+10 µL HMM+5 µL detection reagents c) Secondary Screen: Determination of Affinity by Surface Plasmon Resonance Affinity of secreted antibodies was assessed by testing hybridoma supernatants by Label-free surface plasmon resonance (SPR). This analysis was carried out on the ProteOn XPR36 (BioRad) array SPR machine. An anti-mouse IgG capture surface was created on a GLC biosensor chip using amine coupling of an anti-mouse IgG from GE Healthcare. Test antibodies were captured on this surface and human, rat and cyno OPG (in-house, Seq ID No:154, Seq ID No:156 and Seq ID No:159, respectively) were used as analyte. The assay was carried out at 25° C. using HBS-EP (Teknova H8022). Buffer alone was used to reference the binding sensorgrams. The data was analysed using the 1:1 model inherent to the ProteOn XPR36 analysis software.

Example 3—Characterisation of Secondary Hits as Purified Material

The following example describes confirmation assays performed to further characterise binding and inhibition profile of secondary hits using purified material from hybridoma supernatants. HTRF assays and details of protocols are listed in Table 5. Clones were tested in the HTRF® binding assay and SPR to exclude antibodies not binding to target or showing poor $K_D$s. Duplicated sequences were also excluded following sequence analysis to select a unique panel of antibodies. Full titration curves of each clone at known concentration were tested in the ligand/receptor assays, which resulted in the identification of antibodies able to: 1) inhibit OPG/TRAIL and/or OPG/RANKL (complete curves, reported $IC_{50}$ value); 2) partial inhibition of the interaction (% maximum specific binding); 3) no inhibition. However, this data was not used to exclude clones from the lead panel which was narrowed down exclusively based on performance in binding assays. Clone's ability to block interaction of anti-OPG antibodies to TRAIL was also tested in a cell based assay using HT1080 cells that are sensitive to TRAIL induced killing (section h).

TABLE 5

Summary of hits selected following confirmation assays

| Campaign | Assays |  | Protocol details (protein working concentrations) | Controls (MAB805/Mouse IgG1 working concentrations) | Selected clones |
|---|---|---|---|---|---|
| KM058 | HTRF Binding |  | Human OPG-Fc 5 nM | 1.6 nM | 18/35 |
|  |  |  | Human OPG-B (R&D) 40 nM | 13.2 nM |  |
|  |  |  | Rat OPG-Fc 16 nM | 1.6 nM |  |
|  | HTRF neutralisation |  | TRAIL-Flag 4 nM OPG-Fc 16 nM TRAIL-Flag | Titration from 120 nM |  |

TABLE 5-continued

Summary of hits selected following confirmation assays

| Campaign | Assays | Protocol details (protein working concentrations) | | Controls (MAB805/Mouse IgG1 working concentrations) | Selected clones |
|---|---|---|---|---|---|
| | | RANKL-647 | 20 nM OPG 55.6 nM RANKL | Titration from 120 nM | |
| KM059 | HTRF Binding | Human OPG-B | 16 nM | 4.4 nM | 7/8 |
| | | Rat OPG-Fc | 16 nM | 4.4 nM | |
| | HTRF neutralisation | TRAIL-Flag | 4 nM OPG-Fc 16 nM TRAIL-Flag | Titration from 120 nM | |
| | | RANKL-647 | 4 nM OPG 16 nM RANKL | Titration from 120 nM | |

Materials and Methods a) Purification of Antibodies from Hybridoma Supernatant

Protein G resin in a gravity-flow column was first washed with water, then IgG Elute (Pierce) and was then equilibrated with tissue culture grade PBS. Clarified hybridoma supernatant containing 10% v/v 10× tissue culture grade PBS was applied several times to the equilibrated protein G column. Resin was washed with tissue culture grade PBS to remove unbound material. Antibody was then eluted with IgG Elute (Pierce) and the eluted fraction was then neutralized with 100 mM final TRIS, at pH 8.0. The eluted fraction was then concentrated down to <1.5 mL by centrifugation in a 10 kDa cut-off centrifugal filter unit. Tissue culture grade PBS was then added and the sample was concentrated down again to <1.5 mL. Protein concentration was quantified at OD280 using the molar extinction coefficient inherent to the Nanodrop for IgG. Finally, sample was analysed on a SDS-PAGE to assess purity.

b) Confirmation of Binding Profile to Human and Rat OPG by HTRF

HTRF binding assays set up for screening were also used to confirm binding to human and rat OPG of purified material. Antibodies were diluted in HTRF buffer to a working concentration of 120 nM and sequentially diluted in a 1:3 dilution series to generate a 11-point curve. Protocol was followed as previously described in Example 2. Working concentrations of recombinant proteins and control antibodies were on occasions adjusted and are detailed in Table 5.

d) Confirmation of TRAIL and RANKL Inhibition Profile by HTRF

Similar to binding assays, TRAIL and RANKL HTRF assays set up for secondary screening were used to test purified molecules. Antibodies were prepared as detailed above for the generation of 11-point titration curves. % Specific TRAIL/RANKL binding (Equation 3) and generation of $IC_{50}$ values (Equation 4) were calculated. Protocols set up previously as detailed in Example 2 were followed with changes to working concentrations used detailed in Table 5.

Equation 4: Four Parameter Logistic Calculation $$Y = Bottom + (Top - Bottom)/(1 + 10^{((Log\ IC_{50} - X)*Hill\text{-}Slope)})$$

X = logarithm of concentration.
Y = specific binding (equation 3)
Top and Bottom = Plateaus in same units as Y (specific binding)

Log $IC_{50}$ in same units as X. Y starts at Bottom and goes to Top with a sigmoid shape. Specific binding decreases as X increases.

e) Determination of Affinity by Surface Plasmon Resonance

Methodology as described in Example 2, no deviations to protocol were introduced.

f) RNA Isolation from Hybridoma Cells

Total RNA was extracted from hybridoma cells using TRIzol™ Reagent (Invitrogen). The quantity and quality of the isolated RNA was analysed spectrophotometrically.

g) Antibody Variable Domain Recovery by RT-PCR

Selected clones were used to prepare total RNA, which was used in an RT-PCR reaction to recover the heavy and light chain V-regions. Murine IgG-specific reverse primers and human Ig-leader sequence-specific forward primer sets were used for the heavy chains. Murine kappa constant region specific reverse primers and human kappa-leader sequence specific forward primer sets were used for the kappa light chains. The RT-PCR products were separated by agarose gel electrophoresis with the DNA of the predicted size being gel purified and sequenced in the forward and reverse directions. Alternatively, the RT-PCR products were subcloned into a cloning vector and DNA of individual colonies submitted for sequencing.

h) HT1080 TRAIL-Dependent Killing Assay for Characterisation of Anti-OPG Antibodies This example describes a cell based assay that may be used for lead characterisation of anti-OPG antibodies, in particular clones that have the demonstrated ability to neutralise OPG interaction with TRAIL. An assay was set up using HT1080 cells (ATCC® CCL-121™), which undergo apoptosis and cell death if treated with TRAIL. When OPG is added to culture and following binding to TRAIL, cell death is inhibited. However, killing may be restored if an anti-OPG antibody, such as KY3 (15F11), is added to assay as depicted in FIG. 5.

Anti-OPG antibodies and isotype control were diluted 1:2 from 200 nM to generate a 7-points concentration curve. 25 µl of antibody titrations were then transferred to a 96-well plate and mixed with equal volume of OPG-Fc (SEQ ID No:154) prepared at 200 nM in MEM 1% FBS. Following a 30 minutes incubation, 25 µl TRAIL (SEQ ID No:4) at 4 nM and 25 µl HT1080 cells (ATCC® CCL-121™), re-suspended at $2 \times 10^5$ cells/ml in MEM 1% FBS, were added to the assay plates and incubated for 72 hours at 37° C., 5% $CO_2$. Cell Titer Glo Kit (Promega) was used to quantify the number of viable cells at the end-point of the experiment. Following the protocol recommended by the manufacturer, 100 μl of Cell Titer Glo buffer was added to assay plates, which were placed for 2 minutes on an orbital shaker to induce cell lysis. Plates were incubated at room temperature in the dark for 10 minutes and read in the EnVision for quantification of the luminescence signal, which is proportional to the amount of ATP and therefore dependent on the number of viable cells present in each well. Percentage of TRAIL induced killing of HT1080 was calculated as detailed in Equation 5.

Calculation of % TRAIL-induced killing $$\% \text{ killing} = 100 - \left(\left(\frac{\text{assay signal} - \text{maximum killing}}{\text{maximum killing inhibition} - \text{maximum killing}}\right) \times 100\right) \quad \text{Equation 5}$$

Maximum killing = signal of wells treated with TRAIL only
Maximum killing inhibition =
    signal of wells treated with TRAIL and OPG

Example 4—Selection of Final Lead Panel

This example describes the rational for lead selection of antibodies for in vivo studies. KM058 and KM059 confirmed hits (Table 5) were ranked accordingly with their apparent affinity to human OPG as measured by SPR. This ranking resulted in the selection of 9 top clones (Table 6), presenting sub nanomolar affinity to human OPG and equivalent binding $K_D$s to cyno OPG, with the exception of Ky1 (6D07). This panel of antibodies is also characterised by low nanomolar affinities to rat OPG which enables their in vivo testing in relevant rat PAH models.

TABLE 6

Selected clones ranked by apparent affinities against human OPG

| Lead panel | Campaign | Human $K_D$ (nM) | Rat $K_D$ (nM) | Cyno $K_D$ (nM) |
|---|---|---|---|---|
| Ky1 (6D07) | KM059 | 0.17 | 1.35 | 14.8 |
| Ky2 (8C10) | KM059 | 0.1 | 7.39 | CNROR[1] |
| Ky3 (15F11) | KM058 | CNROR[1] | 0.12 | CNROR[1] |
| Ky4 (16G05) | KM058 | 0.18 | 1.3 | 0.17 |
| Ky5 (15H06) | KM058 | 0.18 | 0.36 | CNROR[1] |
| 5A06 | KM058 | 0.23 | 2.7 | 0.24 |
| 25F06 | KM058 | 0.38 | 2.3 | 0.41 |
| 15B08 | KM058 | 0.4 | 2.4 | 0.59 |
| 10B07 | KM058 | 0.46 | 1.1 | 0.37 |

[1]CNROR: Cannot resolve off rate

Further narrowing down of antibodies listed in Table 7 was performed using the detailed characterisation of their inhibition profile, which resulted in grouping antibodies in one the four distinct inhibition profiles: 1) complete inhibition of OPG-TRAIL interaction, RANKL partial inhibitors; 2) inhibition of OPG-TRAIL interaction, no effect on the interaction with RANKL; 3) partial inhibition of OPG-TRAIL and OPG RANKL interactions; 4) inhibition of TRAIL/RANKL interaction.

TABLE 7

Selected clones organised by neutralisation data

| Lead Panel | Campaign | Neutralisation profile |
|---|---|---|
| Ky1 (6D07) | KM059 | 2 |
| Ky2 (8C10) | KM059 | 4 |
| Ky3 (15F11) | KM058 | 1 |
| Ky4 (16G05) | KM058 | 3 |
| Ky5 (15H06) | KM058 | 4 |
| 25F06 | KM058 | 1 |
| 5A06 | KM058 | 3 |
| 15B08 | KM058 | 4 |
| 10B07 | KM058 | 4 |

The best affinity clones from each category were selected for testing in vivo studies and these five antibodies are detailed in Table 8, reflecting the diversity of antibodies and inhibition profile present in the pool of screened KM058 and KM059 clones.

Materials and Methods a) SPR Binding

Affinity of secreted antibodies was assessed by testing hybridoma supernatants by Label-free surface plasmon resonance (SPR). This analysis was carried out on the ProteOn XPR36 (BioRad) array SPR machine. An anti-mouse IgG capture surface was created on a GLC biosensor chip using amine coupling of an anti-mouse IgG from GE Healthcare. Test antibodies were captured on this surface and human, rat and cyno OPG (in-house) was used as the analyte at 256 nM, 64 nM, 16 nM, 4 nM and 1 nM for Ky3 (15F11), Ky4 (16G05), 5A06, 25F06, 15B08 and 10B07 and at a single concentration of 100 nM for Ky1 (6D07) and Ky2 (8C10). The assay was carried out at 25° C. using HBS-EP (Teknova H8022). Buffer alone was used to reference the binding sensorgrams. The data was analysed using the 1:1 model inherent to the ProteOn XPR36 analysis software.

b) Epitope Coverage and Antibody Binning by ProteOn

The work was carried out on the ProteOn XPR36 array system (BioRad™). This system has a unique six by six flow cell matrix and allows the flowcells to be addressed in either a vertical or horizontal orientation. In this method, "Ligand Ab" refers to an antibody directly captured on the ProteOn biosensor chip, and "analyte", refers the antibody in solution that is passed over the captured surface. Anti-mouse IgG (GE Healthcare B-1008-38) was captured on a ProteOn GLC Biosensor chip (BioRad 176-5011) by primary amine coupling. "Ligand Abs" were captured on the anti-mouse surface in the vertical orientation. The capture surface was blocked using ⅟₅₀₀ dilution of mouse serum from terminal bleed of an irrelevant immunised mouse+50 ug/mL of recombinant mouse and human irrelevant antibody in the horizontal orientation. Human OPG-Fc (human IgG-Fc fusion, Seq ID No:154) was then captured by the "Ligand Ab" in the horizontal orientation. Then, a further injection of the "Ligand Ab" was passed over the complex to ensure that all sites on the dimeric OPG were saturated with the Ligand antibody. Next, the first competing "analyte" antibody was passed over the "Ligand Ab"-OPG complex and the sensorgram monitored. If no binding was seen, then the antibodies shared a similar epitope, and the analyte antibody was prevented from binding to hOPG. If binding did occur, then the analyte Abs could still bind the ligand antibody-saturated hOPG, and therefore the epitope was sufficiently different to allow binding to OPG without competing with the ligand antibody. Binding was defined as a response greater than 200 RU's.

Since there will always be some background binding due incomplete blocking of the capture surface and/or incomplete blocking of available OPG molecules, the binding sensorgrams were double referenced using an irrelevant antibody surface. The assay was run using HBS-EP and at 25° C. The antibodies were examined in both orientations, so that every antibody tested was both as a ligand and as an analyte.

The five final antibodies ((Ky1 (6D07), Ky2 (8C10), Ky3 (15F11), Ky4 (16G05) and Ky5 (15H06)) showed different profiles for OPG/TRAIL and OPG/RANKL inhibition, suggesting that the likely binding epitope on the OPG molecule differ between the five antibodies.

and respiratory rate were recorded continuously throughout the study. Anaesthesia was induced and maintained using isoflurane. Echocardiography was performed and analysed as previously described in Hameed et al., "Inhibition of tumor necrosis factor-related apoptosis-inducing ligand (TRAIL) reverses experimental pulmonary hypertension", J. Exp. Med., 209:1919-1935, 2012. Following echocardiography and under isoflurane induced anaesthesia, left and right ventricular catheterisation was performed using a closed chest method via the right internal carotid artery and right external jugular vein as described in Hameed et al., 2012 supra and in Rothman et al., "MicroRNA-140-5p and SMURF1 regulate pulmonary arterial hypertension" J. Clin.

TABLE 8

Selected clones for in vivo study

| Antibody ID | $K_D$ (Human OPG) [nM] | $K_D$ (Rat OPG) [nM] | $K_D$ (Cyno OPG) [nM] | OPG-TRAIL inhibition | OPG-RANKL inhibition |
|---|---|---|---|---|---|
| Ky1 (6D07) | 0.17 | 1.35 | 14.8 | Inhibition % Max Specific binding 4.8% | No inhibition |
| Ky2 (8C10) | 0.1 | 7.39 | CNROR[2] | Inhibition % Max Specific binding = 20.1% | Inhibition % Max Specific binding = 47.1% |
| Ky3 (15F11) | CNROR[2] | 0.12 | CNROR[2] | Complete inhibition $IC_{50}$ 1.4 nM | Partial inhibition % Max Specific binding 27.1% |
| Ky4 (16G05) | 0.18 | 1.3 | 0.166 | Partial inhibition % Max Specific binding 50.7% | Partial inhibition % Max Specific binding 65.1% |
| Ky5 (15H06) | 0.18 | 0.36 | CNROR[2] | Inhibition % Max Specific binding 55.8% | Inhibition % Max Specific binding 86.6% | a - Gene segment and mutation characteristics of lead antibodies

| Antibody ID | IGH V gene | IGH D gene | IGH J gene | CDRH3 length | Non-germline CDRH3 Amino acid | Mutations outside CDRH3 Nucleic acid | Mutations outside CDRH3 Amino acid | IGL V gene | IGL J gene | CDRL3 length | Non-germline CDRL3 Amino acid | Mutations outside CDRL3 Nucleic acid | Mutations outside CDRL3 Amino acid |
|---|---|---|---|---|---|---|---|---|---|---|---|---|---|
| KY1 (6D07) | IGH V1-18*01 | IGH D1-26*01 | IGH J5*02 | 10 | 3 | 3 | 1 | IGκ V1-17*01 | IGκ J3*01 | 9 | 0 | 2 | 2 |
| KY2 (8C10) | IGH V3-9*01 | IGH D3-9*01 | IGH J4*02 | 16 | 4 | 7 | 6 | IGκ V1D-39*01 | IGκ J1*01 | 11 | 3 | 6 | 4 |
| KY3 (15F11) | IGH V3-13*01 | IGH D3-10*01 | IGH J4*02 | 20 | 7 | 5 | 5 | IGκ V1D-33*01 | IGκ J3*01 | 8 | 0 | 0 | 0 |
| KY4 (16G05) | IGH V3-9*01 | IGH D3-22*01 | IGH J4*02 | 16 | 3 | 3 | 3 | IGκ V1D-39*01 | IGκ J4*01 | 9 | 1 | 4 | 3 |
| KY5 (15H06) | IGH V3-15*01 | IGH D3-22*01 | IGH J3*02 | 13 | 7 | 5 | 1 | IGκ V1D-12*02 | IGκ J4*01 | 9 | 1 | 4 | 4 |

[2]CNROR: Cannot resolve off rate

Example 5—Monoclonal Human Anti-Human OPG Attenuates Development of Monocrotaline Induced PAH in Rats Antibodies (Ky1 (6D07), Ky2 (8C10), Ky3 (15F11) and Ky4 (16G05)) were tested for their ability to attenuate the development of monocrotaline induced PAH.

Materials and Methods a) Cardiac Catheterisation

Operators were blinded to treatment groups through the collection and analysis of phenotype data. Echocardiography was performed using the Vevo 770 system (VisualSonics, Toronto, Canada) using either the RMV707B (mice) or RMV710B (rat) scan head. Rectal temperature, heart rate Invest 126(7):2495-1508, 2016. Briefly, methods were carried out substantially as described: ultra-miniature pressure-volume SPR-838 2F catheter (LV) and SPR-847 1.4F catheter (RV; Millar Instruments Inc.) coupled to a Millar MPVS 300 and a PowerLab 8/30 data acquisition system (AD Instruments) and Chart v7 software (AD Instruments) are utilised to collect data. Pressure volume analysis is performed using PVAN v2.3 (Millar Instruments Inc). The animals were then humanely killed under anaesthesia and tissues harvested as previously described in Hameed et al., 2012 & Rothman et al., 2016 infra. Estimated pulmonary vascular resistance (ePVRi) is calculated by estimating mean pulmonary artery pressure (EmPAP) from the right ventricular systolic pressure (RVSP) by adapting the equation from Chemla et al., New formula for predicting mean pulmonary artery pressure (mPAP) using systolic pulmonary artery pressure. Chest. 126:1313-1317 2004 and substituting the systolic pulmonary artery pressure for RVSP to give [EmPAP=(0.61×RVSP)+2 mm Hg]. EmPAP was then substitute for mPAP in the pulmonary vascular resistance index (PVRi) equation described by McMurtry et al., Gene therapy targeting survivin selectively induces pulmonary vascular apoptosis and reverses pulmonary arterial hypertension. J. Clin. Invest. 115:1479-1491 2005; mPAP-left ventricular end-diastolic pressure [LVEDP]/cardiac index).

b) Right Ventricular Hypertrophy

Right ventricular hypertrophy (RVH) was measured by calculating the ratio of the right ventricular free wall over left ventricle plus septum.

c) Immunohistochemistry

Immediately after harvest, the right lung was tied off and removed for biochemical analysis and the left lung was perfusion fixed via the trachea with 10% (v/v) Formalin buffered saline by inflation to 20 cm of $H_2O$. The lungs were then processed into paraffin blocks for sectioning. Paraffin embedded sections (5 µm) of lung were histologically stained for Alcian Blue Elastin van Gieson (ABEVG), immunohistochemically stained for α-smooth muscle actin (α-SMA (1:150), M0851, Dako, Cambridgeshire, UK), von Willebrand Factor (vWF (1:300), A0082 Dako) and OPG (1:50) ab73400, Abcam). To assess proliferation, slides were stained with a mouse anti-human proliferating cell nuclear antigen antibody (PCNA (1:125), M0879, Dako). A secondary biotinylated anti-mouse antibody (1:200) was added before an Avidin Biotin enzyme Complex (Vectastain® Kit, Vector Laboratories, US) and apoptotic nuclei were detected with a TdT-mediated dUTP nick-end labeling (TUNEL) assay using a colorimetric DNA fragmentation detection kit (fragEL™, QIA33, Calbiochem®, Merck Biosciences, UK) as previously outlined in Hameed et al., 2012, infra. Briefly, methods were carried out substantially as described: the TUNEL assay uses a colorimetric DNA fragmentation detection kit, which is performed according to the manufacturer's instruction and is counterstained with methyl green. Apoptotic cells are defined using 3, 3'-diaminobenzidine (DAB) stain.

d) Quantification of Pulmonary Vascular Remodelling

Pulmonary vascular remodelling was quantified by assessing the degree of muscularisation and the percentage of affected pulmonary arteries and arterioles as previously described in Hameed et al., 2012, infra. Briefly, methods were carried out substantially as described: this is assessed in three groups based on vessel size: small pulmonary arterioles with a diameter <50 µm, medium pulmonary arteries with a range in diameter from 51 to 100 µm, and large pulmonary arteries with a diameter >100 µm. Standard immunohistochemical techniques are applied as previously described by Hameed et al., 2012 & Rothman et al., 2016 infra.

e) Measurement of PK and OPG Plasma Levels a. IgG4 Assay for PK

Rat serum samples were diluted 1:200 and assayed using the IgG4 ELISA (Cayman Technologies CAY500920) as per manufacturers instruction. Plate is read using the Varioskan colorimetric plate reader and results calculated from a standard curve from each assay plate analysed.

b. Rat OPG

25 µL neat rat serum was assayed for OPG (Merck Millipore RBN1MAG-31K) as per manufacturer's instructions and analysed using Luminex 200 bead assay plate reader.

f) Quantification of Bone Structure by microCT

Femora were scanned on a Skyscan microCT scanner (1172a, Bruker, Belgium) at 50 kV and 200 µA using a 0.5 mm aluminium filter and a detection pixel size of 4.3 µm. Images were captured every 0.7° through 180° rotation and 2× averaging of each bone. Scanned images were reconstructed using Skyscan NRecon software (v. 1.6.8.0) and datasets analysed using Skyscan CT analysis software (v. 1.13.2.1). Trabecular bone was measured over a 1 $mm^3$ volume, 0.2 mm from the growth plate. Trabecular bone volume as a proportion of tissue volume (BV/TV, %), trabecular thickness (Tb. Th, mm), trabecular number (Tb. N, mm-1), and trabecular structure model index (SMI) were assessed in this area. Cortical bone was measured over a 1 $mm^3$ volume, 1 mm from the growth plate, and cortical bone volume (C.BV, $mm^3$) assessed in this area.

g) Statistics

Statistical analysis was performed using two-way ANOVA or one-way ANOVA followed by Sidak's multiple comparisons test or Bonferroni's multiple comparisons test. When there were only two groups, unpaired t-test was used. $P<0.05$ was deemed statistically significant (Prism 7.0a for Macintosh, Graphpad Software).

h) Protocol Example 5:

Monoclonal human anti-human OPG attenuates development of monocrotaline induced PAH in rats
  a. Rat; Sprague Dawley; TEKLAD Global 18% Protein Rodent Diet/Yorkshire tap water
  b. Starting body weights 200-220 g
  c. Standard housing, 3-4 per cage, i.e. not IVC (individually ventilated cages) housing in animal facility
  d. Baseline echocardiography: rats are anesthetized with isoflurane and the following parameters are recorded:
    i. PA AT
    ii. PA-ET
    iii. PA Vti
    iv. CO=cardiac output, (mL/min)
    v. Ao VTi
    vi. RVID=right ventricle, inner diameter, (mm)
    vii. RVFWT=right ventricle, free wall, thickness, (mm)
    viii. LVID=left ventricle, inner diameter, (mm)
    ix. LVFWT=left ventricle, free wall, thickness, (mm)
  e. Weigh rats immediately prior to injection (ideally ~210-240 g) and inject 60 mg/kg monocrotaline (~0.5 mL) subcutaneously into the left flank of each rat
  f. Time line for experiment—3 wks (3 wks Room Air)
  g. Rats are assigned to treatment groups by equally distributing body weights across groups
  h. Weekly i.p injection of the anti-hOPG antibody(s) will be administered. Body weights and dosing volumes to be recorded
  i. Blood is collected and serum prepared at day 0, day 7 & day 14 during the study, and day 21 at harvest
  j. Rats are weighed routinely
  k. At week 3, rats are anesthetized with isoflurane, echocardiography was performed recording: PA AT, PA-ET, PA VTi, CO, Ao VTi, RVID RVFWT, LVID, LVFWT
  l. Left ventricular pressure volume analysis was performed. Rats were anesthetized, a Millar SPR-838 2F catheter was inserted into the right internal carotid artery and parameters were recorded. The artery was tied off after measurements
  m. Right ventricular pressure volume analysis was performed. A Millar SPR-847 2F catheter was inserted into the right external jugular vein and parameters were recorded n. Blood is collected from cardiac puncture (see below)
o. Heart and lungs are removed (see below)
p. Data and or/analysis taken
   i. Body weight, atria, RV, LV weights, tibia length
   ii. Echo and PV loop hemodynamics
   iii. RVH and lung histology (see below)
q. Blinding of study endpoints:
   i. RV, atria, LV in 10% neutral buffered formalin (see below)
   ii. Lung portion frozen or in RNALater (see below)
2. Groups
1. Normal control; no monocrotaline, normoxia (n=4)
2. Disease control; 60 mg/kg monocrotaline, normoxia; (n=8)
3. Ky1 (6D07); 3 mg/kg monocrotaline, normoxia, (n=8)
4. Ky2 (8C10); 3 mg/kg monocrotaline, normoxia, (n=8)
5. Ky3 (15F11); 3 mg/kg monocrotaline, normoxia, (n=8)
6. Ky4 (16G05); 3 mg/kg monocrotaline, normoxia, (n=8)
7. human IgG4-PE isotype control; 3 mg/kg monocrotaline, normoxia, (n=8)
8. Positive control monocrotaline, normoxia, AF 459 (pump); (n=7)
n=67 animals total
3. Preparation of Monocrotaline
a. Prepare monocrotaline (C2401, Sigma-Aldrich) for injection by dissolving 500 mg in 1.5 mL of 1 M HCl. Crush lumps with spatula and vortex for 30-40 minutes. Add sterile $H_2O$ to 12.5 mL and adjust to pH 7.0 with NaOH prior to making up to final volume of 25 mL with sterile $H_2O$. Mix thoroughly to give a final stock concentration of 60 mg/mL
4. Procedures during study
a. Body weight
   i. Body weight was recorded twice weekly, daily if end value percentage weight loss values were encountered
b. Dosing of the anti-OPG antibody at 3 mg/kg i.p is at D7 D14 & D21 of the study
c. Blood collection from i.v tail venipuncture for serum was prior to the antibody dosing
5. End of study
a. PV Loop Measurements
   i. Prepare Chart file for each animal. Refine the calibration using the pre-set outputs on the MPVS300 and set the baseline saline pressure to −1 mmHg
   ii. Induce (rapid induction 5%) or maintain anaesthesia (2-3%) with isoflurane delivered with air (~2 L/min)
   iii. If not already prepared from echocardiography, depilate the neck from midline to right foreleg using Veet™
   iv. Ensure adequate anaesthesia for surgery by establishing the lack of pedal response
   v. Make a small incision with scissors in the midline of the neck just under the 'chin'. Carefully separate skin from the neck down to the top of the rib cage and cut the skin from chin to ribs
b. Left Ventricle
   i. Retract the skin to expose the neck.
   ii. Blunt dissect through the tissue layers until you can see the muscle around the trachea
   iii. Gently separate the muscle layer by pulling from the mid-point to the left and right with forceps held in each hand. Pull muscle apart to reveal trachea
   iv. Identify the right internal carotid artery between the trachea and the layer of muscle on the right hand side, and free from connective tissue by blunt dissection
   v. Gently lift the carotid artery with forceps and free from the nerve
   vi. Apply a proximal sling of suture to the artery and tie off. Secure suture to nose cone applying some tension
   vii. Apply a distal sling and tie loosely and use needle clips to 'weight' and apply tension distally
   viii. Ensure the volume channel is connected to the SPR-838 catheter
   ix. Start recording on Chart Software and ensure saline pressure reading is set between 0 and −1 mmHg
   x. Use a bent needle or perform an arteriotomy to introduce the SPR-838 catheter into the lumen of the carotid artery
   xi. Advance the catheter down the carotid past the distal sling, through the aortic arch and into the LV
   xii. Carefully advance the catheter to the apex of the LV and then pull back slightly
   xiii. Leave catheter in place for 1 minute or until a stable signal is recorded
   xiv. Pull the catheter back through the LVOT into the aorta and leave catheter in place until a stable Aortic pressure is recorded
   xv. Stop recording on Chart and carefully remove catheter
   xvi. Tie off distal sling and trim off excess suture
c. Right Ventricle
   i. From the midline incision, carefully cut towards the foreleg at ~45° C.
   ii. Blunt dissect down to find the right external jugular vein, and free from surrounding connective tissue and nerve
   iii. Apply a proximal sling of suture to the vein and tie off. Secure suture to nose cone applying some tension
   iv. Apply a distal sling and tie loosely and use needle clips to 'weight' and apply tension distally
   v. Switch the volume connector from the SPR-838 to SPR-847 catheter
   vi. Start recording on Chart Software and ensure saline pressure reading is set between 0 and −1 mmHg
   vii. Use a bent needle to introduce the SPR-847 catheter into the lumen of the jugular vein
   viii. Advance the catheter down the jugular past the distal sling, through the right atria and into the RV
   ix. Carefully advance the catheter to the apex of the RV and then pull back slightly
   x. Leave catheter in place for 1 minute or until a stable signal is recorded
   xi. Carefully remove catheter and tie off distal suture
d. Blood and Tissue Harvest
   i. Under anaesthesia perform cardiac puncture to collect blood for RNA, Tempus tube; plasma, Sodium Citrate; serum, plain gel
   ii. Following exsanguination, the rats were humanely killed under anaesthesia by cervical dislocation
   iii. Peel back chest skin to expose the chest
   iv. Pierce the diaphragm to allow air to enter and make lungs collapse
   v. Cut along the sternum and open chest up to allow access to the cavity, remove ribs carefully
   vi. Cut down above liver to sever the aorta
   vii. Inject 10-20 mL PBS into Right ventricle to wash out lungs and heart
   viii. Turn animal around; positioning for the next step
   ix. Find sheath around trachea and pull apart cut end of trachea away at base of mouth x. Lift the trachea freeing lungs and heart from connective tissue with blunt dissection without damage to the lung tissue
xi. Cut free along the spinal cord to free heart and lungs
xii. From the bottom pull up oesophagus and extend above the trachea
xiii. Left lung—single lobe
xiv. Right lung—Multi lobed
xv. Tie off right lung at right bronchus with double knot
xvi. Pull knot tight and cut off right lung below the suture
  1. Store half in Liquid Nitrogen
  2. Store half in 500 μL RNA later (Life technologies AM7020)
e. Place loose double knot around the formalin tube
f. Cut off the oesophagus and top of the trachea
g. Place the trachea over the formalin cannula and knot over the join and tie off
h. Open the drip to inflate the lung
i. Pull off the cannula and tighten the knot
j. Tidy off any fat on the heart
k. Place in a falcon tube and add more formalin (10%) to cover the tissue
  1. Lung
    a. The left lobe was fully immersed in 10% NBF, processed, embedded sections cut and staining for pulmonary vascular remodeling
      i. ABEVG (Alcian Blue Elastin Van-Gieson); Alcain dye stains mucopollysaccharides; van geison stains collagen and connective tissue
      ii. vWF; endothelial cell marker
      iii. SMA; smooth muscle
    b. Part of the right lobe was placed in RNALater
  2. Heart
    a. The heart was isolated and cleared of any connective tissue. The atria, RV and LV were isolated and weighed as a measure of model-induced weight changes Results Weekly delivery of 3 mg/kg antibody or human IgG4-PE control resulted in expected levels of circulating plasma antibody (FIG. 1a). Analysis of the complete dataset identified Ky3 (15F11) antibody as having a significant attenuation on markers of PAH including RVSP (FIG. 1b), RVH (FIG. 1c) and ePVRi (FIG. 1d). There was no significant effect of any antibody treatment on left ventricular end-systolic pressure (LVESP) (FIG. 1e). Immunohistochemical analysis of the lung demonstrated a significant reduction in the media/CSA area of all pulmonary arteries and arterioles (FIG. 1f & FIG. 1i) and in particular both the thickness (FIG. 1g & FIG. 1i) and percentage of thickened sub-50 μm vessels in rats treated with the Ky3 (15F11) antibody (FIG. 1h & FIG. 1i). Interestingly rats treated with Ky3 resulted in a significant increase in serum levels of OPG (FIG. 1J), possibly due to retention of antibody bound OPG in the circulation rather than allowing access to the vessel wall.

Example 6—Antibody Ky3 (15F11) was Tested Prophylactically in a Rat Model with Severe Established PAH, Sugen Hypoxia (SuHx)

Figure 2:
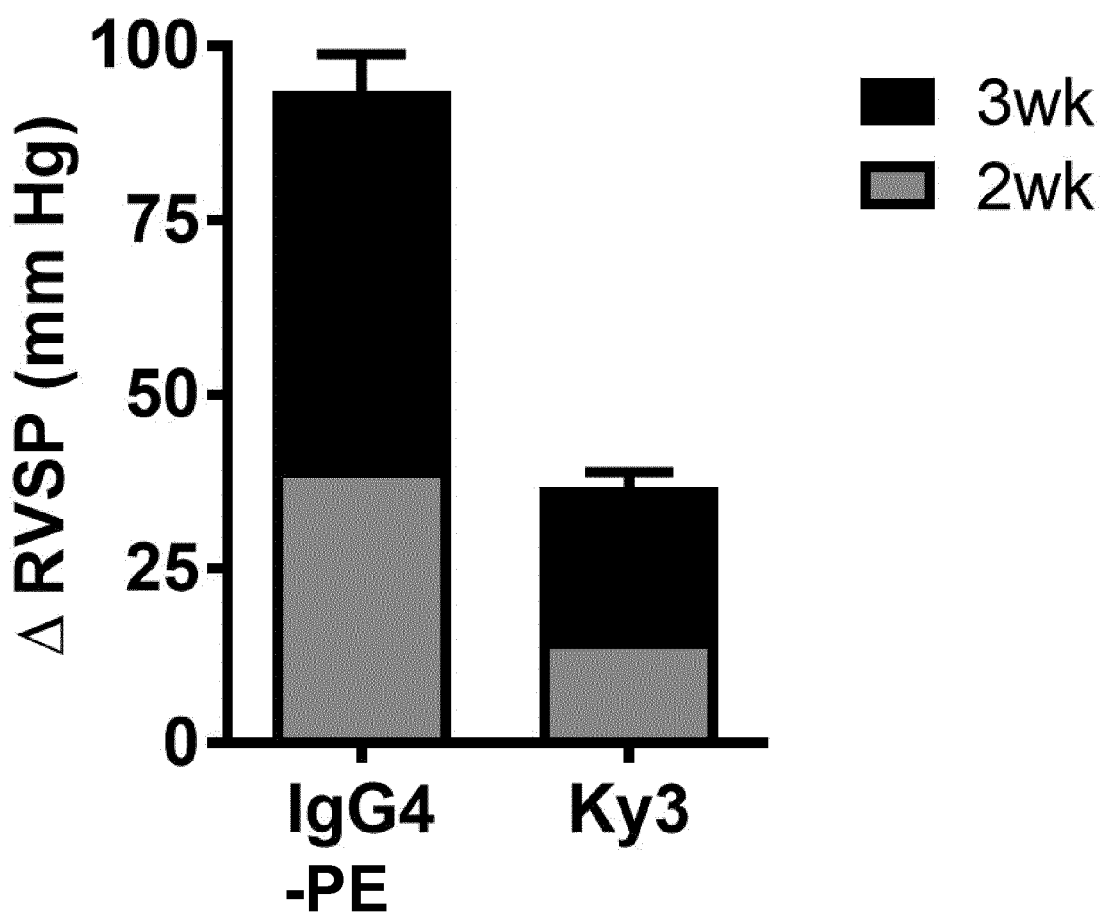
FIG. 2: Antibody Ky3 (15F11) was tested prophylactically in a rat model with severe established Sugen Hypoxia (SuHx) PAH.

Materials and Methods
Protocol
1. Antibody Ky3 (15F11) was tested prophylactically in a rat model with severe established PAH, Sugen Hypoxia (SuHx)
  a. Rat; Wistar; TEKLAD Global 18% Protein Rodent Diet/Yorkshire tap water
  b. Starting body weights 200-220 g
  c. Standard housing, 3-4 per cage, i.e. not IVC (individually ventilated cages) housing in animal facility
  d. Placement of DSI HD telemetry device via abdominal trans diaphragm procedure. Placing a transducer via the Right Ventricle into the Pulmonary Artery to collect continuous pressure readings. Also placing a transducer into the abdominal aorta to collect continuous pressure readings
  e. Rats are weighed and injected with 20 mg/kg SU5416, s/c in the left flank
  f. Time line for experiment—3 wks
  g. Hypobaric (18000 ft), Duffau (Bespoke Chambers manufactured in France—based on Design for Actelion Pharmaceuticals Ltd, Switzerland)
  h. Rats are assigned to treatment groups by equally distributing body weights across groups
  i. Weekly i.p injection of the anti-OPG antibody(s) will be administered. Body weights and dosing volumes to be recorded
  j. Blood is collected and serum prepared at day 0, day 7 & day 14 during the study
  k. Rats are weighed T=0 and weekly during treatments
  l. Telemetry pressure readings were performed at days 14 and 21
  m. Blood was collected from cardiac puncture (see below)
  n. Heart and lungs are removed (see below)
  o. Data and or/analysis taken
    i. Body weight, atria, RV, LV weights, tibia
    ii. RV and aortic blood pressures
    iii. RVH and lung histology (see below)
  p. Blinding of study endpoints
    i. RV, atria, LV in 10% neutral buffered formalin (see below)
    ii. Lung portion frozen or in RNALater (see below)
2. Groups
  a. Disease control; 20 mg/kg SU5416, normoxia; (n=1)
  b. Ky3 (15F11); 3 mg/kg. 20 mg/kg SU5416, normoxia, (n=3)
  c. Human IgG4-PE isotype control; 3 mg/kg. 20 mg/kg SU5416, normoxia, (n=3)
  n=7 animals total
3. Preparation of Sugen
  a. Preparation of SU5416 at 2 mg/mL (wt/vol) CMC
    i. Subcutaneous injection of 20 mg/kg of SU5416 in right flank e.g. for a rat of 200 g: 4 mg/animal=0.4 mL/rat.
4. Procedures during study
  a. Body weight
    i. Body weight was recorded twice weekly, daily if end value percentage weight loss values were encountered
  b. Dosing of the anti-OPG antibody at 3 mg/kg i.p is at D0, D7 & D14 of the study
  c. Blood collection from i.v tail venipuncture for serum was prior to the antibody dosing
5. Blood and Tissue Harvest
  i. Under anaesthesia, perform cardiac puncture to collect blood for RNA, Tempus tube; plasma, Sodium Citrate; serum, plain gel.
  ii. Following exsanguination, the rats were humanely killed under anaesthesia by cervical dislocation
  iii. Peel back chest skin to expose the chest iv. Pierce the diaphragm to allow air to enter and make lungs collapse
v. Cut along the sternum and open chest up to allow access to the cavity, remove ribs carefully
vi. Cut down above liver to sever the aorta
vii. Inject 10-20 mL PBS into Right ventricle to wash out lungs and heart
viii. Turn animal around; positioning for the next step
ix. Find sheath around trachea and pull apart cut end of trachea away at base of mouth
x. Lift the trachea freeing lungs and heart from connective tissue with blunt dissection without damage to the lung tissue
xi. Cut free along the spinal cord to free heart and lungs
xii. From the bottom pull up oesophagus and extend above the trachea
  1. Left lung—single lobe
  2. Right lung—Multi lobed
xiii. Tie off right lung at right bronchus with double knot
xiv. Pull knot tight and cut off right lung below the suture
  1. Store half in Liquid Nitrogen
  2. Store half in 500 µL RNA later (Life technologies AM7020)
xv. Place loose double knot around the formalin tube
xvi. Cut off the oesophagus and top of the trachea
xvii. Place the trachea over the formalin cannula and knot over the join and tie off
xviii. Open the drip to inflate the lung
xix. Pull off the cannula and tighten the knot
xx. Tidy off any fat on the heart
xxi. Place in a falcon tube and add more formalin (10%) to cover the tissue
  1. Lung
    a. The left lobe was fully immersed in 10% NBF, processed, embedded sections cut and staining for pulmonary vascular remodeling
      i. ABEVG (Alcian Blue Elastin Van-Gieson); Alcain dye stains mucopollysaccharides; van geison stains collagen and connective tissue
      ii. vWF; endothelial cell marker
      iii. SMA; smooth muscle
    b. Part of the right lobe was placed in RNALater
  2. Heart
    a. The heart was isolated and cleared of any connective tissue. The atria, RV and LV were isolated and weighed as a measure of model-induced weight changes Results RVSP was measured at week 2 and week 3 (FIG. 2a). Weekly delivery of 3 mg/kg Ky3 (15F11) antibody resulted in an attenuation of the increase in RVSP from wk 0 to wk 2, and wk 0 to wk 3 compared to IgG4-PE control (FIG. 2a).

Example 7—the Therapeutic Treatment Efficacy of Anti-OPG mAbs in the Sprague Dawley Rat Monocrotaline Model of Pulmonary Arterial Hypertension Antibody Ky3 (15F11) was tested therapeutically in a rat model with severe PAH induced by monocrotaline.

Materials and Methods

Protocols

Figure 3A:
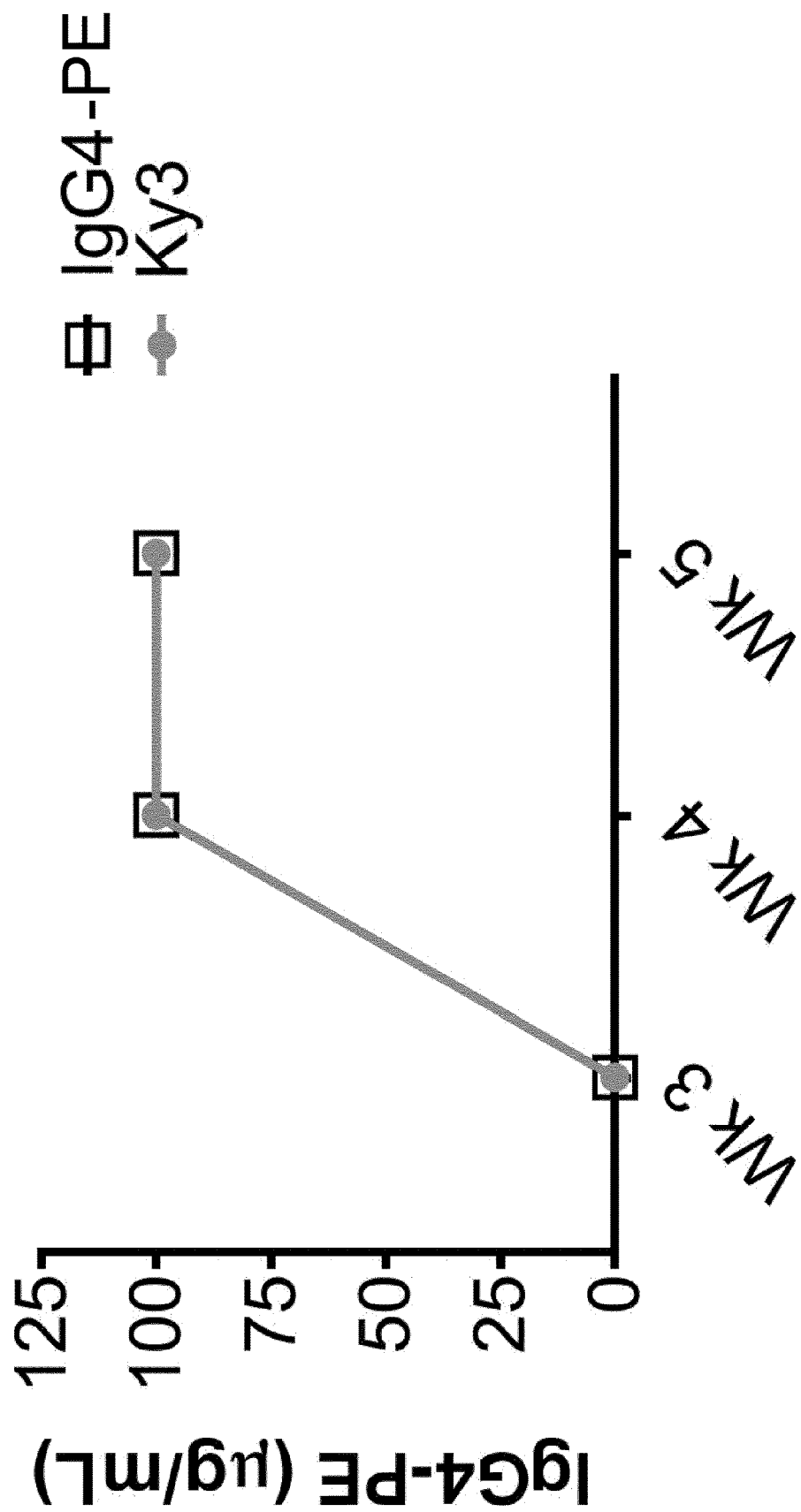
(FIG. 3a) Plasma concentrations of antibodies (Ky3 (15F11) and control human IgG4-PE). Bar graphs show (FIG. 3b) Pulmonary Artery Acceleration Time (PA AT), (FIG. 3c) cardiac output (CO), (FIG. 3d) right ventricular systolic pressure (RVSP), (FIG. 3e) right ventricular arterial elastance (RV Ea), (FIG. 3f) right ventricular hypertrophy (RVH), (FIG. 3g) estimated pulmonary vascular resistance (ePVRi), (FIG. 3h) left ventricular end-systolic pressure (LVESP). Bar graphs (FIG. 3i) show the relative percentage of muscularised small pulmonary arteries and arterioles in <50 μm vessels and (FIG. 3j) 51-100 μm vessels. Bars represent mean+/−SEM, dots represent individual animals. (Ctrl n=8, SuHx n=6, IgG4-PE n=8, Ky3 (15F11) n=7 animals per group), *=p<0.05, =p<0.01, *=p<0.001 compared to IgG4-PE treated rats.
Figure 3B:
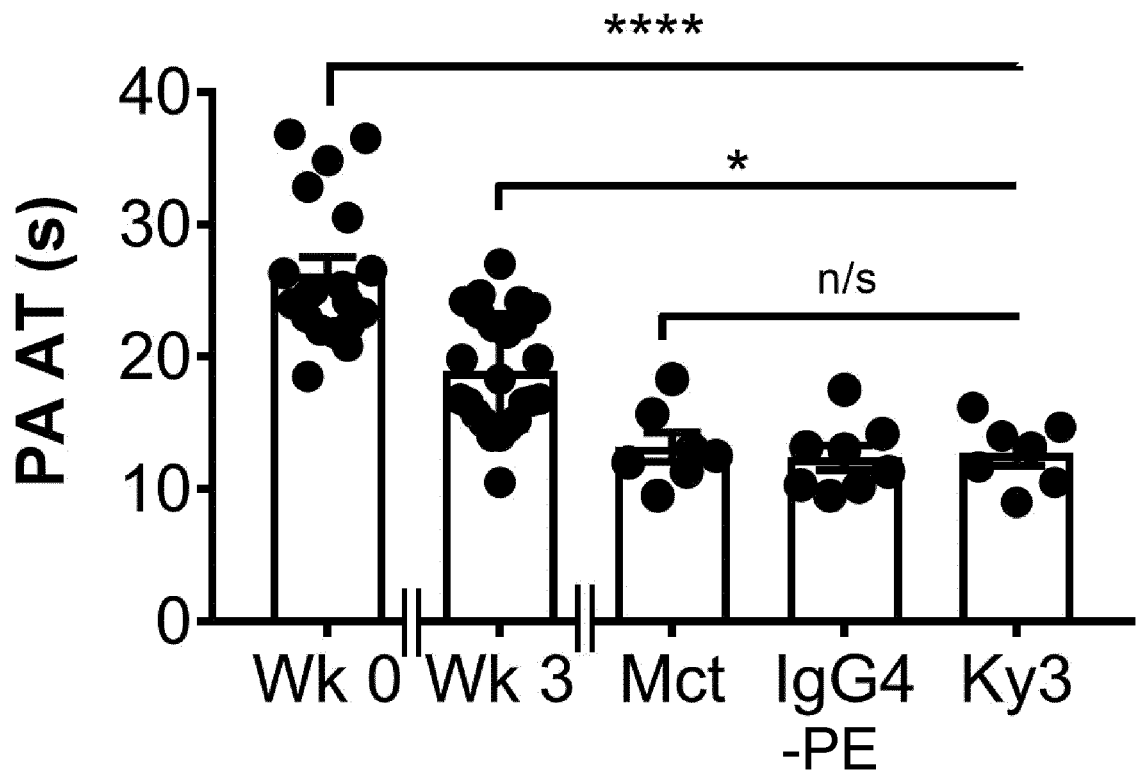
FIG. 3: Therapeutic delivery of monoclonal human anti-human OPG to rats with severe PAH induced by monocrotaline.
Figure 3C:
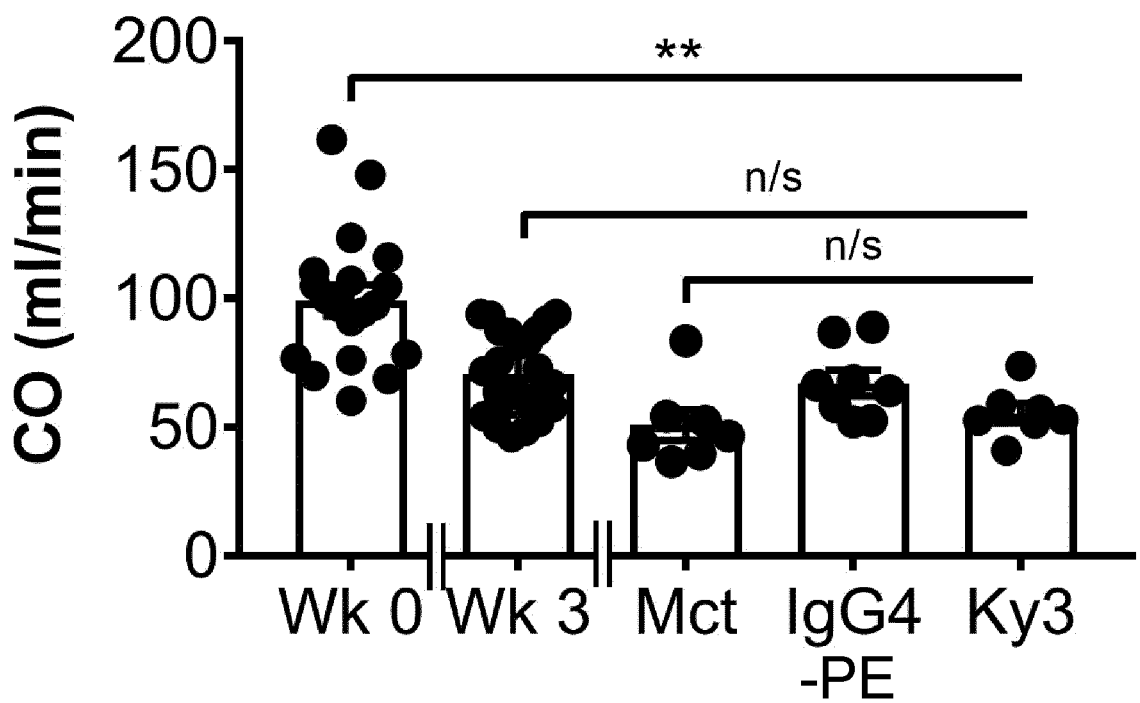
Figure 3D:
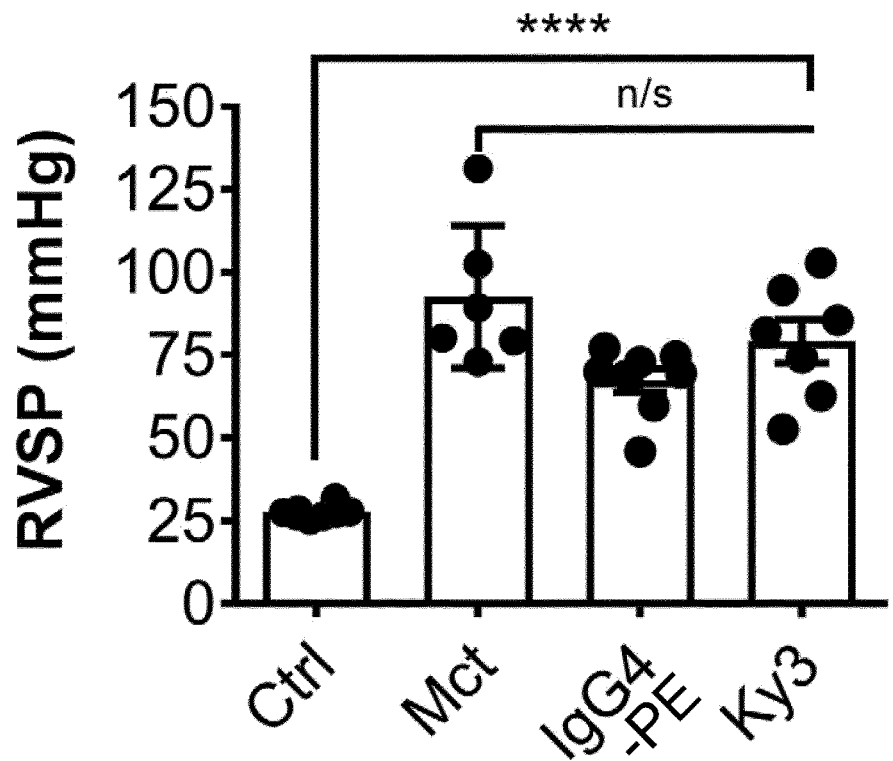
Figure 3E:
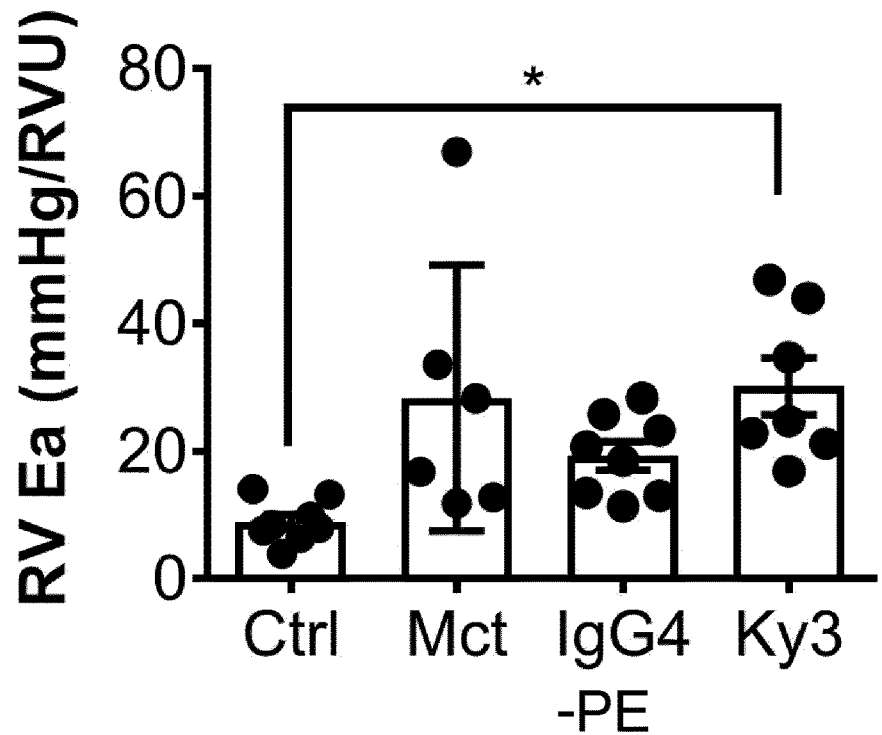
Figure 3F:
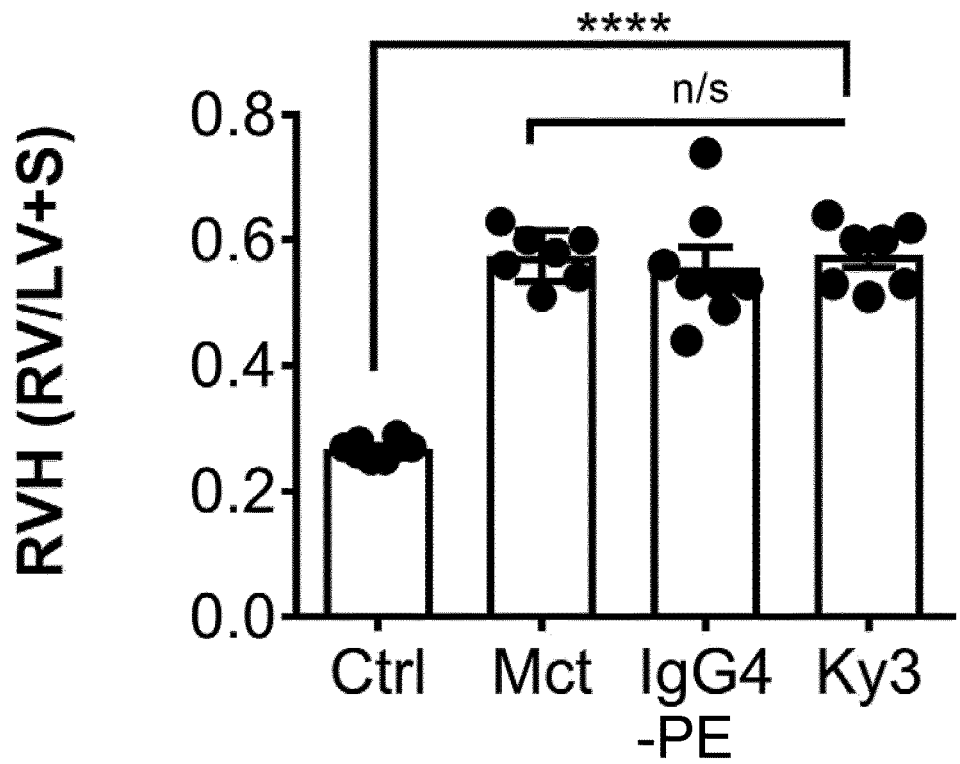
Figure 3G:
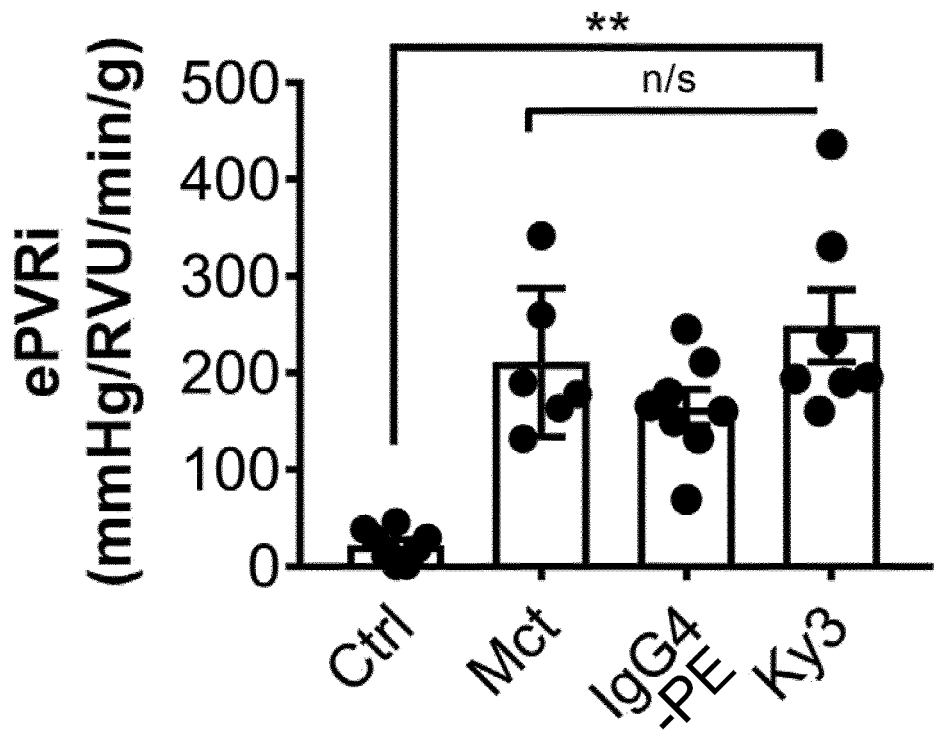
Figure 3H:
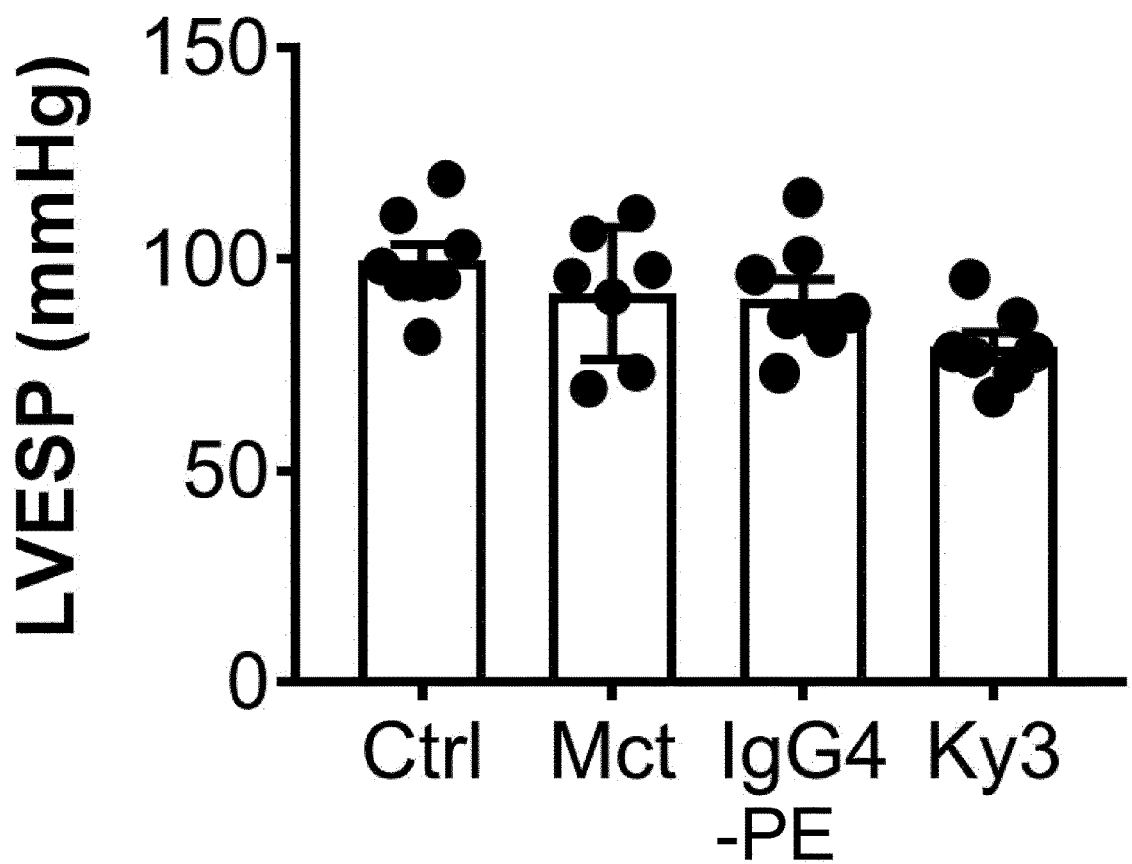
Figure 3I:
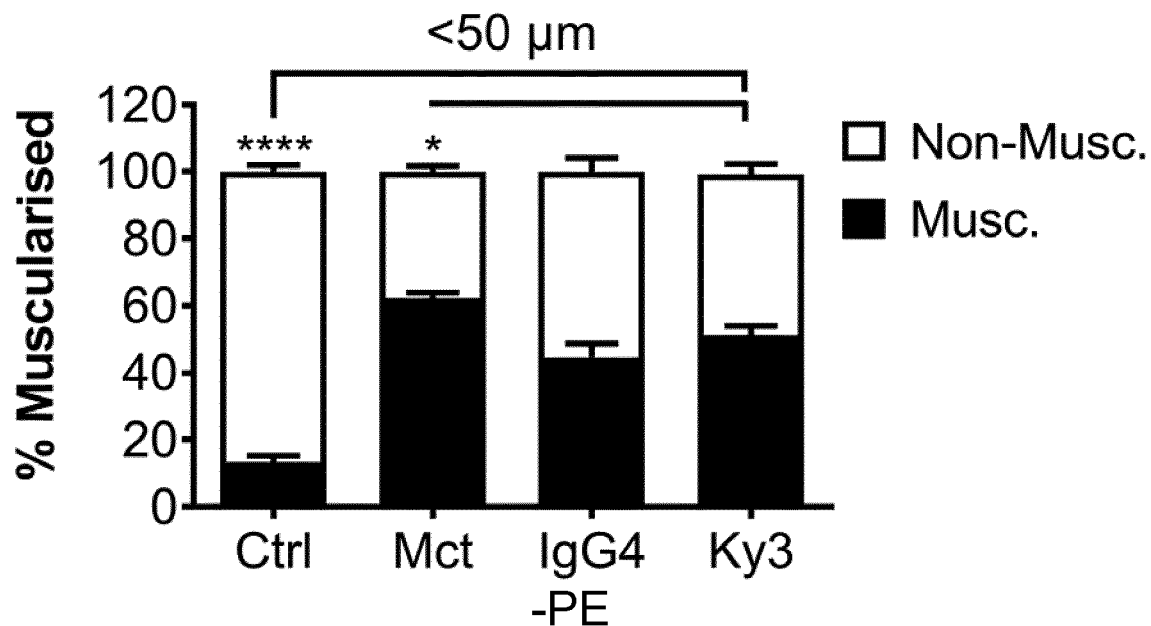
Figure 3J:
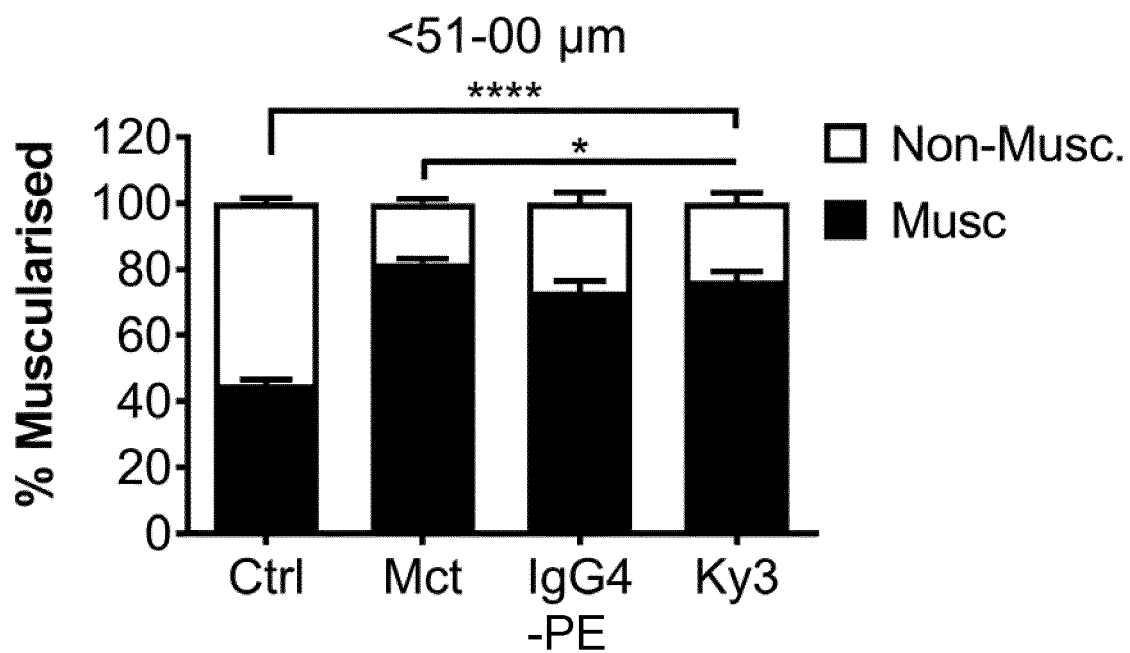

1. The therapeutic treatment efficacy of anti-OPG mAbs in the Sprague Dawley rat Monocrotaline model of Pulmonary Arterial Hypertension
  a. Rat; Sprague Dawley; TEKLAD Global 18% Protein Rodent Diet/Yorkshire tap water
  b. Starting body weights 200-220 g
  c. Standard housing, 3-4 per cage, i.e. not IVC (individually ventilated cages) housing in animal facility
  d. Baseline echocardiography: rats are anesthetized with isoflurane and the following parameters are recorded:
    i. PA AT
    ii. PA-ET
    iii. PA Vti
    iv. CO=cardiac output, (mL/min)
    v. Ao VTi
    vi. RVID=right ventricle, inner diameter, (mm)
    vii. RVFWT=right ventricle, free wall, thickness, (mm)
    viii. LVID=left ventricle, inner diameter, (mm)
    ix. LVFWT=left ventricle, free wall, thickness, (mm)
  e. Weigh rats immediately prior to injection (ideally ~210-240 g) and inject 60 mg/kg monocrotaline (~0.5 mL) subcutaneously into the left flank of each rat
  f. Time line for experiment—5 wks (3 wk disease progression/2 wks Treatment)
  g. Rats are assigned to treatment groups by equally distributing body weights across groups
  h. Weekly i.p injection of the anti-OPG antibody(s) will be administered. Body weights and dosing volumes to be recorded
  i. Blood is collected and serum prepared at Week 3, 4 & 5 during the study
  j. Rats are weighed routinely
  k. At week 5, rats are anesthetized with isoflurane, echocardiography was performed recording: PA AT, PA-ET, PA VTi, CO, Ao VTi, RVID RVFWT, LVID, LVFWT
  l. Left ventricular pressure volume analysis was performed. Rats were anesthetized, a Millar SPR-838 2F catheter was inserted into the right internal carotid artery and parameters were recorded. The artery was tied off after measurements
  m. Right ventricular pressure volume analysis was performed. A Millar SPR-847 2F catheter was inserted into the right external jugular vein and parameters were recorded
  n. Blood is collected from cardiac puncture (see below)
  o. Heart and lungs are removed (see below)
  p. Data and or/analysis taken
    i. Body weight, atria, RV, LV weights, tibia length
    ii. echo and PV loop hemodynamics
    iii. RVH and lung histology (see below)
  q. Blinding of study endpoints
    i. RV, atria, LV in 10% neutral buffered formalin (see below)
    ii. Lung portion frozen or in RNALater (see below)
2. Groups
  a. Normal control; no monocrotaline; (n=8)
  b. Disease control; 60 mg/kg monocrotaline; (n=8)
  c. Ky3 (15F11); 3 mg/kg monocrotaline, (n=8)
  d. Human IgG4-PE isotype control; 3 mg/kg monocrotaline, (n=8)
  n=40 animals total
3. Preparation of monocrotaline
  a. Prepare monocrotaline (C2401, Sigma-Aldrich) for injection by dissolving 500 mg in 1.5 mL of 1 M HCL. Crush lumps with spatula and vortex for 30-40 minutes. Add sterile $H_2O$ to 12.5 mL and adjust to pH 7.0 with NaOH prior to making up to final volume of 25 mL with sterile $H_2O$. Mix thoroughly to give a final stock concentration of 60 mg/mL 4. Procedures during study
   a. Body weight
      i. Body weight was recorded twice weekly, daily if end value percentage weight loss values were encountered
   b. Dosing of the anti-OPG antibody at 3 mg/kg i.p is at D21 & D28 of the study.
   c. Blood collection from i.v tail venipuncture for serum was prior to the antibody dosing
5. End of study
   a. PV Loop Measurements
      i. Prepare Chart file for each animal using the PVAN Template file. Refine the calibration using the pre-set outputs on the MPVS300 and set the baseline saline pressure to −1 mmHg
      ii. Induce (rapid induction 5%) or maintain anaesthesia (2-3%) with isoflorane delivered with air (~2 L/min)
      iii. If not already prepared from echocardiography, depilate the neck from midline to right foreleg using Veet
      iv. Ensure adequate anaesthesia for surgery by establishing the lack of pedal response
      v. Make a small incision with scissors in the midline of the neck just under the 'chin'. Carefully separate skin from the neck down to the top of the rib cage and cut the skin from chin to ribs
   b. Left Ventricle
      i. Retract the skin to expose the neck
      ii. Blunt dissect through the tissue layers until you can see the muscle around the trachea
      iii. Gently separate the muscle layer by pulling from the mid-point to the left and right with forceps held in each hand. Pull muscle apart to reveal trachea
      iv. Identify the right internal carotid artery between the trachea and the layer of muscle on the right hand side, and free from connective tissue by blunt dissection
      v. Gently lift the carotid artery with forceps and free from the nerve
      vi. Apply a proximal sling of suture to the artery and tie off. Secure suture to nose cone applying some tension
      vii. Apply a distal sling and tie loosely and use needle clips to 'weight' and apply tension distally
      viii. Ensure the volume channel is connected to the SPR-838 catheter ix. Start recording on Chart Software and ensure saline pressure reading is set between 0 and −1 mmHg
      x. Use a bent needle or perform an arteriotomy to introduce the SPR-838 catheter into the lumen of the carotid artery
      xi. Advance the catheter down the carotid past the distal sling, through the aortic arch and into the LV
      xii. Carefully advance the catheter to the apex of the LV and then pull back slightly
      xiii. Leave catheter in place for 1 minute or until a stable signal is recorded
      xiv. Pull the catheter back through the LVOT into the aorta and leave catheter in place until a stable Aortic pressure is recorded
      xv. Stop recording on Chart and carefully remove catheter
      xvi. Tie off distal sling and trim off excess suture
   c. Right Ventricle
      i. From the midline incision, carefully cut towards the foreleg at ~45°
      ii. Blunt dissect down to find the right external jugular vein, and free from surrounding connective tissue and nerve
      iii. Apply a proximal sling of suture to the vein and tie off. Secure suture to nose cone applying some tension
      iv. Apply a distal sling and tie loosely and use needle clips to 'weight' and apply tension distally
      v. Switch the volume connector from the SPR-838 to SPR-847 catheter
      vi. Start recording on Chart Software and ensure saline pressure reading is set between 0 and −1 mmHg
      vii. Use a bent needle to introduce the SPR-847 catheter into the lumen of the jugular vein
      viii. Advance the catheter down the jugular past the distal sling, through the right atria and into the RV
      ix. Carefully advance the catheter to the apex of the RV and then pull back slightly
      x. Leave catheter in place for 1 minute or until a stable signal is recorded
      xi. Carefully remove catheter and tie off distal suture
   d. Blood and Tissue Harvest
      i. Under anaesthesia, perform cardiac puncture to collect blood for RNA, Tempus tube; plasma, Sodium Citrate; serum, plain gel
      ii. Following exsanguination, the rats were humanely killed under anaesthesia by cervical dislocation
      iii. Peel back chest skin to expose the chest
      iv. Pierce the diaphragm to allow air to enter and make lungs collapse
      v. Cut along the sternum and open chest up to allow access to the cavity, remove ribs carefully
      vi. Cut down above liver to sever the aorta
      vii. Inject 10-20 mL PBS into Right ventricle to wash out lungs and heart
      viii. Turn animal around; positioning for the next step
      ix. Find sheath around trachea and pull apart cut end of trachea away at base of mouth
      x. Lift the trachea freeing lungs and heart from connective tissue with blunt dissection without damage to the lung tissue
      xi. Cut free along the spinal cord to free heart and lungs
      xii. From the bottom pull up oesophagus and extend above the trachea
         1. Left lung—single lobe
         2. Right lung—Multi lobed
      xiii. Tie off right lung at right bronchus with double knot
      xiv. Pull knot tight and cut off right lung below the suture
         1. Store half in Liquid Nitrogen
         2. Store half in 500 µL RNA later (Life technologies AM7020)
      xv. Place loose double knot around the formalin tube
      xvi. Cut off the oesophagus and top of the trachea
      xvii. Place the trachea over the formalin cannula and knot over the join and tie off
      xviii. Open the drip to inflate the lung
      xix. Pull off the cannula and tighten the knot
      xx. Tidy off any fat on the heart
      xxi. Place in a falcon tube and add more formalin (10%) to cover the tissue
         1. Lung
            a. The left lobe was fully immersed in 10% NBF, processed, embedded sections cut and staining for pulmonary vascular remodeling.

i. ABEVG (Alcian Blue Elastin Van-Gieson); Alcain dye stains mucopollysaccharides; van geison stains collagen and connective tissue
  ii. vWF; endothelial cell marker
  iii. SMA; smooth muscle
  b. Part of the right lobe was placed in RNALater
2. Heart
  a. The heart was isolated and cleared of any connective tissue. The atria, RV and LV were isolated and weighed as a measure of model-induced weight changes Results Sustained levels of Ky3 (15F11) and human IgG4-PE were maintained throughout the study (FIG. 3a). There was no significant treatment effect in the monocrotaline model (as quantified by Pulmonary artery acceleration time (PA AT) (FIG. 3b), CO (FIG. 3c), RVSP (FIG. 3d), RV Ea (FIG. 3e), RVH (FIG. 3f), ePVRi (FIG. 3g), LVESP (FIG. 3h) and percentage of muscularised pulmonary arterioles (FIGS. 3i and 3j)). We propose this was due to the already particularly severe phenotype.

Example 8—the Therapeutic Treatment Efficacy of Novel Human OPG mAbs in the Wistar Rat SuHx Model of Pulmonary Arterial Hypertension Antibody Ky3 (15F11) was tested therapeutically alone and in combination with Sildenafil Citrate or Bosentan in a rat model with severe established PAH, SuHx.

Materials and Methods

PAH was induced in male Wistar (Charles River, UK) rats of 200-220 g by a single subcutaneous injection of Sugen5416 (SU5416, Tocris, UK) at 20 mg/kg followed by housing in hypobaric chambers at an equivalent of 18000 feet (equivalent to 10.8% O2) for 3 weeks, followed by normobaric pressures for remaining 6 weeks to allow the progression of pulmonary vascular remodelling. Rats were then randomised into groups to receive either Ky3 (15F11) or human IgG4-PE isotype control antibody from week 6 of the study. As both a comparator to existing therapies, and to test efficacy in combination with existing therapies, a subset of rats were treated with Sildenafil Citrate (50 mg/kg/day) or Bosentan (60 mg/kg/day) in chow alone or in combination with Ky3 (15F11) from week 6. Therapeutic treatments with Ky3 (15F11) or human IgG4-PE isotype control were performed (3 mg/kg, i.p.) at weeks 6, 7 and 8 weeks with sacrifice at week 9. Antibodies were delivered by intraperitoneal injection. Sildenafil and Bosentan were administered orally by food. Right Ventricular Hypertrophy, Immunohistochemistry, Quantification of pulmonary vascular remodelling and statistics are performed as outlined in Example 5.

Protocol

1. The therapeutic treatment efficacy of novel human OPG mAbs in the Wistar Rat SuHx Model of Pulmonary Arterial Hypertension
  a. Rat; Wistar Crl:WI; TEKLAD Global 18% Protein Rodent Diet/Yorkshire tap water
  b. Starting body weights 200-220 g
  c. Standard housing, 3-4 per cage, i.e. not IVC (individually ventilated cages) housing in animal facility
  d. Time line for experiment—9 wks (3 wk Hypobaric/3 wks Room Air/3 wks Room Air+Treatment)—Hypobaric (18000 ft), Duffau (Bespoke Chambers)
  e. Baseline echocardiography: rats are anesthetized with isoflurane and the following parameters are recorded:
    i. PA AT
    ii. PA-ET
    iii. PA Vti
    iv. CO=cardiac output, (mL/min)
    v. Ao VTi
    vi. RVID=right ventricle, inner diameter, (mm)
    vii. RVFWT=right ventricle, free wall, thickness, (mm)
    viii. LVID=left ventricle, inner diameter, (mm)
    ix. LVFWT=left ventricle, free wall, thickness, (mm)
  f. Preparation of carboxyl methylcellulose sodium (CMC) vehicle for Sugen 5416
    i) carboxyl methylcellulose sodium 0.9% (wt/vol) NaCl, 0.4% (vol/vol) polysorbate, 0.9% (vol/vol) benzyl alcohol in deionized water
      i. Preparation of SU5416 at 2 mg/mL (wt/vol) CMC
      ii. Subcutaneous injection of 20 mg/kg of SU5416 in right leg
  g. Rats are placed in hypobaric chamber for 3 weeks, then returned to normobaric conditions for a further 3 weeks
  h. At week 6, rats are anesthetized with isoflurane, echocardiography was performed recording: PA AT, PA-ET, PA VTi, CO, Ao VTi, RVID RVFWT, LVID, LVFWT
  i. Rats are assigned to treatment groups by equally distributing body weights across groups and assigned regular chow, Sildenafil chow or Bosentan chow
  j. Weekly i.p injection of the Kymab antibody(s) will be administered. Body weights and dosing volumes to be recorded
  k. Blood is collected and serum prepared at week 6, 7 & 8 during the study, and at harvest
  l. Rats are weighed routinely
  m. At week 9, rats are anesthetized with isoflurane, echocardiography was performed recording: PA AT, PA-ET, PA VTi, CO, Ao VTi, RVID RVFWT, LVID, LVFWT
    Left ventricular pressure volume analysis was performed. Rats were anesthetized, a Millar SPR-838 2F catheter was inserted into the right internal carotid artery and parameters were recorded:
      i) LVeSP=left ventricle end-systolic pressure (mm Hg)
      ii) LVeDP=left ventricle end-Diastolic pressure (mm Hg)
      iii) LVeSV=left ventricle end-systolic Volume (RVU)
      iv) LVeDV=left ventricle end-diastolic Volume (RVU)
    The artery was tied off after measurements
  n. Right ventricular pressure volume analysis was performed. A Millar SPR-847 2F catheter was inserted into the right external jugular vein and parameters were recorded:
    i) RVeSP=right ventricle end-systolic pressure (mm Hg)
    ii) RVeDP=right ventricle end-Diastolic pressure (mm Hg)
    iii) RVeSV=right ventricle end-systolic Volume (RVU)

iv) RVeDV=right ventricle end-diastolic Volume (RVU)
v) RVEa=right ventricle arterial elastance
The vein was tied off after measurements
o. Blood is collected from cardiac puncture (see below)
p. Heart and lungs are removed (see below)
q. Data and or/analysis taken
  i. Body weight, atria, RV, LV weights, tibia length
  ii. echo and PV loop hemodynamics
  iii. RVH and lung histology (see below)
r. Blinding of study endpoints
  i. RV, atria, LV in 10% neutral buffered formalin (see below)
  ii. Lung portion frozen or in RNALater (see below)
2. Groups
Batch 1:
  a. Normal control; no hypobaric chamber, no Sugen 5416; (n=4)
  b. Disease control—Sugen5416+Hypoxia (SuHx); (n=4)
  c. SuHx+Ky3 (15F11); 3 mg/kg, (n=8)
  d. SuHx+Human IgG4-PE isotype control 3 mg/kg (n=8)
  n=24 animals total
Batch 2:
  a. Normal control; no hypobaric chamber, no Sugen 5416; (n=4)
  b. Disease control—Sugen5416+Hypoxia (SuHx); (n=4)
  c. SuHx+Ky3 (15F11); 3 mg/kg, (n=8)
  d. SuHx+Human IgG4-PE isotype control 3 mg/kg (n=8)
  e. SuHx+Sildenafil; 50 mg/kg/day (n=8)
  f. SuHx+Sildenafil+Ky3 (n=8)
  n=40 animals total
Batch 3:
  a. Normal control; no hypobaric chamber, no Sugen 5416; (n=4)
  b. Disease control—Sugen5416+Hypoxia (SuHx); (n=4)
  c. SuHx+Ky3 (15F11); 3 mg/kg, (n=8)
  d. SuHx+Human IgG4-PE isotype control 3 mg/kg (n=8)
  e. SuHx+Bosentan; 60 mg/kg/day (n=8)
  f. SuHx+Bosentan+Ky3 (n=8)
  n=40 animals total
3. Procedures during study
  a. Body weight
    i. Body weight was recorded twice weekly, daily if end value percentage weight loss values were encountered
  b. Dosing of the anti-OPG antibody at 3 mg/kg i.p is at D42, D49 & D56 of the study. Dosing of Sildenfil was at 50 mg/kg/day by food from D42 of the study. Dosing of Bosentan was at 50 mg/kg/day by food from D42 of the study
  c. Blood collection from i.v tail venipuncture for serum was prior to the antibody dosing at Day 42, 49 & 56
4. End of study
  a. PV Loop Measurements
    i. Prepare Chart file for each animal. Refine the calibration using the pre-set outputs on the MPVS300 and set the baseline saline pressure to −1 mmHg
    ii. Induce (rapid induction 5%) or maintain anaesthesia (2-3%) with isoflorane delivered with air (~2 L/min)
    iii. If not already prepared from echocardiography, depilate the neck from midline to right foreleg using Veet
    iv. Ensure adequate anaesthesia for surgery by establishing the lack of pedal response
    v. Make a small incision with scissors in the midline of the neck just under the 'chin'. Carefully separate skin from the neck down to the top of the rib cage and cut the skin from chin to ribs
  b. Left Ventricle
    i. Retract the skin to expose the neck
    ii. Blunt dissect through the tissue layers until you can see the muscle around the trachea
    iii. Gently separate the muscle layer by pulling from the mid-point to the left and right with forceps held in each hand. Pull muscle apart to reveal trachea
    iv. Identify the right internal carotid artery between the trachea and the layer of muscle on the right hand side, and free from connective tissue by blunt dissection
    v. Gently lift the carotid artery with forceps and free from the nerve—this will 'release' the artery and it will be much more elastic
    vi. Apply a proximal sling of suture to the artery and tie off. Secure suture to nose cone applying some tension
    vii. Apply a distal sling and tie loosely and use needle clips to 'weight' and apply tension distally
    viii. Ensure the volume channel is connected to the SPR-838 catheter
    ix. Start recording on Chart Software and ensure saline pressure reading is set between 0 and −1 mmHg
    x. Use a bent needle or perform an arteriotomy to introduce the SPR-838 catheter into the lumen of the carotid artery
    xi. Advance the catheter down the carotid past the distal sling, through the aortic arch and into the LV
    xii. Carefully advance the catheter to the apex of the LV and then pull back slightly
    xiii. Leave catheter in place for 1 minute or until a stable signal is recorded
    xiv. Pull the catheter back through the LVOT into the aorta and leave catheter in place until a stable Aortic pressure is recorded. Mark as "Aorta"
    xv. Stop recording on Chart and carefully remove catheter
    xvi. Tie off distal sling and trim off excess suture
  c. Right Ventricle
    i. From the midline incision, carefully cut towards the foreleg at ~45° C.
    ii. Blunt dissect down to find the right external jugular vein, and free from surrounding connective tissue and nerve
    iii. Apply a proximal sling of suture to the vein and tie off. Secure suture to nose cone applying some tension
    iv. Apply a distal sling and tie loosely (to allow catheter to slide through) and use needle clips to 'weight' and apply tension distally
    v. Switch the volume connector from the SPR-838 to SPR-847 catheter
    vi. Start recording on Chart Software and ensure saline pressure reading is set between 0 and −1 mmHg vii. Use a bent needle to introduce the SPR-847 catheter into the lumen of the jugular vein
viii. Advance the catheter down the jugular past the distal sling, through the right atria and into the RV—obvious change in diastolic pressure trace
ix. Carefully advance the catheter to the apex of the RV and then pull back slightly
x. Leave catheter in place for 1 minute or until a stable signal is recorded
xi. Carefully remove catheter and tie off distal suture d. Blood and Tissue Harvest
   i. Under anaesthesia, perform cardiac puncture to collect blood for RNA, Tempus tube; plasma, Sodium Citrate; serum, plain gel
   ii. Following exsanguination, the rats were humanely killed under anaesthesia by cervical dislocation
   iii. Peel back chest skin to expose the chest
   iv. Pierce the diaphragm to allow air to enter and make lungs collapse
   v. Cut along the sternum and open chest up to allow access to the cavity, remove ribs carefully
   vi. Cut down above liver to sever the aorta
   vii. Inject 10-20 mL PBS into Right ventricle to wash out lungs and heart
   viii. Turn animal around; positioning for the next step
   ix. Find sheath around trachea and pull apart cut end of trachea away at base of mouth
   x. Lift the trachea freeing lungs and heart from connective tissue with blunt dissection without damage to the lung tissue
   xi. Cut free along the spinal cord to free heart and lungs
   xii. From the bottom pull up oesophagus and extend above the trachea
      1. Left lung—single lobe
      2. Right lung—Multi lobed
   xiii. Tie off right lung at right bronchus with double knot
   xiv. Pull knot tight and cut off right lung below the suture
      1. Store half in Liquid Nitrogen
      2. Store half in 500 μL RNA later (Life technologies AM7020)
   xv. Place loose double knot around the formalin tube
   xvi. Cut off the oesophagus and top of the trachea
   xvii. Place the trachea over the formalin cannula and knot over the join and tie off
   xviii. Open the drip to inflate the lung
   xix. Pull off the cannula and tighten the knot
   xx. Tidy off any fat on the heart
   xxi. Place in a falcon tube and add more formalin (10%) to cover the tissue
      1. Lung
         a. The left lobe was fully immersed in 10% NBF, processed, embedded sections cut and staining for pulmonary vascular remodeling
            i. ABEVG (Alcian Blue Elastin Van-Gieson); Alcain dye stains mucopollysaccharides; van geison stains collagen and connective tissue
            ii. vWF; endothelial cell marker
            iii. SMA; smooth muscle
         b. Part of the right lobe was placed in RNALater
      2. Heart
         a. The heart was isolated and cleared of any connective tissue. The atria, RV and LV were isolated and weighed as a measure of model-induced weight changes Results Data from batches 1-3 were pooled together for analysis. There was a significant attenuation of disease in the SuHx model with Ky3 (15F11) alone, and further attenuation in combination with Bosentan (Bos) (60 mg/kg/day) compared to Bos, or Ky3 (15F11) alone. Sustained levels of Ky3 (15F11) and human IgG4-PE were maintained throughout the study in all treated groups (FIG. 4a). By ANOVA there was no significant effect of any treatment on PA AT (FIG. 4b), or CO (FIG. 4c) as measure by non-invasive echocardiography. There was however a significant decrease in RVSP with Ky3 (15F11) treatment compared to IgG4-PE, Sildenafil (Sil) and Bos compared to SuHx (FIG. 4d). Furthermore, there was a significant further reduction in RVSP when treated with Ky3 (15F11) and Bos in combination compared to Ky3 (15F11) and Bos alone (FIG. 4d). RV arterial elastance (RV Ea) was significantly reduced only in animals receiving treatment with Ky3 (15F11), either alone or in combination with Sil or Bos (FIG. 4e). RVH was significantly reduced in Sildenfil and Ky3 (15F11) plus Bos treated animals (FIG. 4f), and ePVRi was significantly reduced only in animals receiving treatment with Ky3 (15F11), either alone or in combination with Sil or Bos (FIG. 4g). These data strongly indicate a beneficial therapeutic effect on pulmonary hypertension with no significant detrimental effect of any treatment on LVESP (FIG. 4h). Immunohistochemical analysis of the lung demonstrated that these hemodynamic changes were associated with a reduction in both the media/CSA and percentage of muscularised pulmonary arterioles sub-50 μm in diameter only in rats treated with Ky3 (15F11) alone, or in combination (FIG. 4i, FIG. 4j & FIGS. 4k & 4k-1—NB only 2/8 Bos and 2/8 Ky3+Bos rat have been analysed at this time). This was also associated is a reduction in PCNA positive cells within the remodeled pulmonary arterioles (FIGS. 4k & 4k-1). Serum OPG levels were elevated in all groups compared to control rats at D42 prior to treatment commencement (FIG. 4l). Rats receiving Ky3 (15F11) either alone or in combination (FIG. 4l). Plasma levels of OPG were significantly elevated in all SuHx rats compared to controls at week 6 (FIG. 4l). Consistent with previous data in Mct treated rats (FIG. 14), rats treated with Ky3 (15F11) displayed a significant increase in circulating OPG from week 7 through to week 9 compared to other groups (FIG. 4). To assess any potential detrimental side-effect of anti-OPG treatment on bone turnover microCT studies were performed on the tibia. Treatment with Ky3 (15F11) had no significant effect on bone volume (FIG. 4) or trabecular thickness (FIG. 4) compared to IgG4-PE treated rats however there was a small but significant decrease in trabecular number (FIG. 4o) in IgG4-PE treated rats compared to Ky3 (15F11), however Ky3 (15F11) treated rats were not significantly different compared to control or SuHx rats.

INCORPORATION BY REFERENCE

All references cited herein, including patents, patent applications, papers, text books and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and Examples detail certain preferred embodiments of the invention. It will be appreciated, however, that the invention may be practiced in many ways and the invention should be construed in accordance with the appended claims and any equivalents thereof.

It will be understood that particular configurations, aspects, examples, clauses and embodiments described herein are shown by way of illustration and not as limitations of the invention. Any part of this disclosure may be read in combination with any other part of the disclosure, unless otherwise apparent from the context.

SEQUENCE LISTING

| Seq ID No: | Description | Sequence |
|---|---|---|
| 1 | Human OPG NCBI Reference Sequence: NP_002537.3 signal peptide sequence (usually cleaved upon expression) is underlined. | MNNLLCCALVFLDISIKWTTQETFPPKYLHYDEETSHQLLCDKCPPGTYLKQHCTAKWKTVCAPCPDHYYTDSWHTSD ECLYCSPVCKELQYVKQECNRTHNRVCECKEGRYLEIEFCLKHRSCPPGFGVVQAGTPERNTVCKRCPDGFFSNETSS KAPCRKHTNCSVFGLLLTQKGNATHDNICSGNSESTQKCGIDVTLCEEAFFRFAVPTKFTPNWLSVLVDNLPGTIMAE SVERIKRQHSSQEQTFQLLKLWKHQNKDQDIVKKIIQDIDLCENSVQRHIGHANLTFEQLRSLMESLPGKKVGAEDIE KTIKACKPSDQILKLLSLWRIKNGDQDTLKGLMHALKHSKTYHFPKTVTQSLKKTIRFLHSFTMYKLYQKLFLEMIGN QVQSVKISCL |
| 2 | Cyno OPG NCBI GenBank number: EHH64388.1 signal peptide sequence (usually cleaved upon expression) is underlined. | MSARAAETHRSARPAAASKRLRPPGTTMNKLLCCALVFLDISIKWTTQETFPPKYLHYDQETSHQLLCDKCPPGTYL KQHCTAKRKTVCAPCPDHYYTDSWHTSDECLYCSPVCKELQYVKQECNRTHNRVCECKEGRYLEIEFCLKHRSCPPGF GVVQAGTPERNTVCKRCPDGFFSNETSSKAPCRKHTNCSVFGLLLTQKGNATHDNICSGNSESTQKCGIDVTLCEEAF FRFAVPTKFTPNWLSVLVDNLPGTKVNAESVERIKRRHSSQEQTFQLLKLWKHQNKDQDIVKKIIQDIDLCENSVQRH IGHANLTFEQLRSLMESLPGKKVGAEDIEKTTIKACKPSDQIIKLLSLWRIKNGDQDTLKGLMHALKHSKTYHFPKWT QSLKKTIRFLHSFTMYKLYQKLFLEMIGNQVQSVKISCL |
| 3 | Rat OPG NCBI Reference Sequence: NP_037002.1 signal peptide sequence (usually cleaved upon expression) is underlined. | MNKWLCCALLVFLDIIEWTTQETFPPKYLHYDPETGRQLLCDKCAPGTYLKQHCTVRRKTLCVPCDYSYTDSWHTSD ECVYCSPVCKELQTVKQECNRTHNRVCECEEGRYLELEFCLKHRSCPPGLGVLQAGTPERNTVCKRCPDGFFSGETS KAPCRKHTNCSSLGLLLIQKGNATHDNVCSGNREATQNCGIDVTLCEEAFFRAVPTKIIPNWLSVLVDSLPGTIMAE SVERIKRHSSQEQTFQLLKLWKHQNRDQEMVKKIIQDIDLCESSVQRHIGHANLTFEQLRILMESLPGKKISPDEIE RTRKTCKPSEQLLKLLSLWRIKNGDQDTLKGLMYALKHLKAYHFPKTVTHSLRKTIRFLHSFTMYRLYQKLFLEMIGN QVQSVKISCL |
| 4 | Human TRAIL NCBI Reference Sequence: NP_003801.1 signal peptide sequence (usually cleaved upon expression) is underlined. | MAMMEVQGGPSLGQTCVLIVIFTVLLQSLCVAVTYVYFTNELKQMQDKYSKSGIACFLKEDDSYWDPNDEESMNSPCW QVKWQLRQLVRKMILRTSEETISTVQEKQQNISPLVRERGPQRVAAHITGTRGRSNTLSSPNSKNEBALGRKINSWES SRSGHSFLSNLHLRNGELVIHEKGFYYTYSQTYFRFQEIKENTKNDKQMVQYIYKYTSYPDPILLMKSARNSCWSKD AEYGLYSIYQGGIFELKENDRIFVSVTNEHLIDMDHEASFFGAFLVG |
| 5 | Human RANKL NCBI GenBank number: AAB86811.1 Cytoplasmic domain is highlighted in italics, helical domain is underlined and the extracellular domain is highlighted in bold. | MRRASRDYTKYLRGSEEMGGGPGAPHEGPLHAPPPPAPHQPPAASRMFVALLGLGLGQVVCSVALFFYFRAQMDPNR ISEDGTHCIYRIRLHENADFQDTTLESQDTKLIPDSCRRIKQAFQGAVQKELQHIVGSQHIRAEKAMVDGSWLDLAK RSKLEAQPFAHLTINATDIPSGSHKVSLSSWTHDRGWAKISNMTFSNGKLIVNQDGFYYLYANICFRHHETSGDLATE YLQLMVTVTKTSIKIPSSHTLMKGGSTKYWSGNSEFHFYSINVGGFFKLRSGEEISIEVSNPSLLDPPDQDATYFGAFK VRDID |
| 6 | Amino acid sequence of CDRH1 of Ky1 (6D07) using IMGT | GYTFTSYG |
| 7 | Amino acid sequence of CDRH2 of Ky1 (6D07) using IMGT | ISAYNGNT |
| 8 | Amino acid sequence of CDRH3 of Ky1 (6D07) using IMGT | ARGGSGRYYP |
| 9 | Amino acid sequence of CDRH1 of Ky1 (6D07) using Kabat | SYGIS |
| 10 | Amino acid sequence of CDRH2 of Ky1 (6D07) using Kabat | WISAYNGNTNYKQKLQG |

-continued

SEQUENCE LISTING

| Seq ID No: | Description | Sequence |
|---|---|---|
| 11 | Amino acid sequence of CDRH3 of Ky1 (6D07) using Kabat | GGSGRYYP |
| 12 | Amino acid sequence of V$_H$ of Ky1 (6D07) | QVQLVQSGAEVKKPGASVKVSCKASGYTFTSYGISWVRQAPGQGLEWMGWISAYNGNTNYKQLQGRVTMTDTSTST AYMELRSLRSDDTAVYYCARGGSGRYYPWGQGTLVTVSS |
| 13 | Nucleic acid sequence of V$_H$ of Ky1 (6D07) | CAGGTTCAGCTGGTGCAGTCTGGAGCTGAGGTGAAGAAGCCTGGGGCCTCAGTGAAGGTCTCCTGCAAGGCTTCTGGT TACACCTTTACCAGCTATGGTATCAGCTGGGTGCGACAGGCCCCTGGACAAGGGCTTGAGTGGATGGGATGGATCAGT GCTTACAATGGTAACACAAACTATAAACAGAAGCTCCAGGGCAGAGTCACCATGACCGACACATCCACGAGCACA GCCTACATGGAGCTGAGGAGCCTGAGATCTGACGACGCCGTGTATTACTGTGCCAGAGGAGGGGCAGTGGGAGGTAC TATCCCTGGGGCCAGGGAACCCTGGTCACCGTCTCCTCA |
| 14 | Amino acid sequence of Ky1 (6D07) heavy chain | QVQLVQSGAEVKKPGASVKVSCKASGYTFTSYGISWVRQAPGQGLEWMGWISAYNGNTNYKQLQGRVTMTDTSTST AYMELRSLRSDDTAVYYCARGGSGRYYPWGQGTLVTVSSASTKGPSVFPLAPCSRSTSESTAALGCLVKDYFPEPVTV SWNSGALTSGVHTFPAVLQSSGLYSLSSVVTVPSSSLGTKTYTCNVDHKPSNTKVDKRVESKYGPPCPPCPAPEFEGG PSVFLFPPKPKDTLMISRTPEVTCVVVDVSQEDPEVQFNWYVDGVEVHNAKTKPREEQFNSTYRVVSVLTVLHQDWLN GKEYKCKVSNKGLPSSIEKTISKAKGQPREPQVYTLPPSQEEMTKNQVSLTCLVKGFYPSDIAVEWESNGQPENNYKT TPPVLDSDGSFFLYSRLTVDKSRWQEGNVFSCSVMHEALHNHYTQKSLSLSLGK |
| 15 | Nucleic acid sequence of Ky1 (6D07) heavy chain | CAGGTGCAGCTGGTGCAGTCTGGCGCCGAAGTGAAGAAACCTGGCGCTCCGTGAAGGTGTCTCCTGCAAGGCCTCCGGC TACACCTTTACCAGCTACGGCATCTCTTGGGTGCGACAGGCTCCTGGACAGGGCCTGGAATGGATGGGCTGGATCTCC GCCTACAACGGCAACACCAACTACAAGCAGAAACTGCAGGGCAGAGTCACCATGACCGACACCTCCACCAGCACC GCCTACATGGAACTGCGTCCCTGAGATCTGACGACGCCGTGTACTACTGTGCCAGAGGCGGCTCCGGCCGGTAC TATCCTTGGGGACAGGGCACCCTCGAGTCACCGTCTCCTCAGCCTCCACCAAGGGACCCAGCGTGTTCCCTCTGGCCCCT TGCTCCAGATCTACCTCCGAGTCTACCGCCGGCTCTGGCTGCACACCTTCCCGTGCCACCTTGAGGTGCTGGTCACAGCCTG TCCTCCGTGCTGGCAGGCAGTCTGGGCACCAAGACCTACACCTGCAACGTGGACCACAAGCCCTCCAAC ACCAAGGTGGACAAGCGGGTGGAATCTAAGTACGGCCCTCCGTGCCCACCCTGTCCCAGCCCTGAATTGAGGGGGA CCCTCTGTTTCTGTTCCCCAAGCCCGAGGGACAGGTCAGTTCAATTGGTACGTGGACGGCGTGGAGTCACAACGCCAAGAC AAGCCTAGAGAGGAACAGTTCAACTCCACCTACCGGGTGTCCTCGTGCTGACCGTGCTGCACCAGGATTGGCTGAAC GGCAAAGTACAAGTGCAAGGTGTCCAACAAGGCCCTGCCCAGCTCCATCGAGAAAACCATCTCCAAGGCCAAGGC CAGCCCCCGGAACCCAGGTGTACACCCTGCCCTCCCAGGAAGAGATGACCAAGAACCAGGTGTCCCTGACCTGT CTCGTGAAAGGCTTCTACCCCTCCGACATCGCCGTGGAATGGAGTCCAACGGCCAGCCTGAAAACTACAAGAAC ACCCCCCCTGTGCTGGACTCCGACGGCTCCTTCTTCCTGTACTCCCGCCTGACCGTGGACAAGTCCAGGATGGCAGGAA GGCAAGCGGTGTTCTCCTGCTCCGTGATGCACGAGGCCCTGCACAACCACTACACCCAGAAGTCCTGCCCTGTCTCTG GGAAAG |
| 16 | Amino acid sequence of CDRL1 of Ky1 (6D07) using IMGT | QGIRND |
| 17 | Amino acid sequence of CDRL2 of Ky1 (6D07) using IMGT | DAS |
| 18 | Amino acid sequence of CDRL3 of Ky1 (6D07) using IMGT | LQHNSYPPT |

-continued

SEQUENCE LISTING

| Seq ID No: | Description | Sequence |
|---|---|---|
| 19 | Ky1 (6D07)-CDRL1 (Kabat) Amino acid sequence of CDRL1 of Ky1 (6D07) using Kabat | RASQGIRNDLG |
| 20 | Ky1 (6D07)-CDRL2 (Kabat) Amino acid sequence of CDRL2 of Ky1 (6D07) using Kabat | DASSLQS |
| 21 | Ky1 (6D07)-CDRL3 (Kabat) Amino acid sequence of CDRL3 of Ky1 (6D07) using Kabat | LQHNSYPFT |
| 22 | Ky1 (6D07)-Light chain variable region Amino acid sequence of V<sub>L</sub> of Ky1 (6D07) | DIQMTQSPSSLSASVGDRVTITCRASQGIRNDLGVVYQQIPGKAPKRLIYDASSLQSGVPSRFSGSGSGTEFTLTISS LQPEDFATYYCLQHNSYPFTFGPGTKVDIK |
| 23 | Ky1 (6D07)-Light chain variable region Nucleic acid sequence of V<sub>L</sub> of Ky1 (6D07) | GACATCCAGATGACCCAGTCTCCATCCTCCCTGTCTGCATCTGTAGGAGACAGAGTCACCATCACTTGCCGGCAAGT CAGGGCATTAGAAATGATTTAGGCTGGTATCAGCAGATACCAGGGAAAGCCCCTAAGCGCCTGATCTATGATGCATCC AGTTTGCAAAGTGGGGTCCCATCAAGGTTCAGCGGCAGTGGATCTGGGACAGAATTCACTCTCACAATCAGCAGCCTG CAGCCTGAAGATTTTGCAACTTATTACTGTCTACAGCATAATAGTTACCCATTCACTTTCGGCCCTGGGACCAAAGTG GATATCAAA |
| 24 | Ky1 (6D07)-full light chain sequence Amino acid sequence of Ky1 (6D07) light chain | DIQMTQSPSSLSASVGDRVTITCRASQGIRNDLGWYQQIPGKAPKRLIYDASSLQSGVPSRPSGSGSGTEFTLTISSL QPEDFATYYCLQHNSYPFTFGPGTKVDIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKSFNRGEC |
| 25 | Ky1 (6D07)-full light chain sequence Nucleic acid sequence of Ky1 (6D07) light chain | GACATCCAGATGACCCAGTCTCCTTCCGTGTCTGCTTCCGTGGGCGACAGAGTGACCATCACTTGTAGAGCCTCC CAGGGCATCCGGAACGACCTGGGCTGGTATCAGCAGATCCCTGGCAAGGCCCCCAAGCGCCTGATCTACGATGCCAGC TCTCTGCAGTCCGGCGTGCCCTCCAGATTCTCCGGCTCTGGCACAGAATTCACCCTGACCATCAGCTCCCTG CAGCCCGAGGACTTCGCCACCTACTACTGCCTGCAGCACAACTCCTACCCTTTCACCTTCGGCCAGAGTGACCAAGGTG GACATCAAGAGAACCGTGGCCGCTCCCTCCGTGTTCATCTTCCCACCCTCTGACGAGCAGCTGAAGTCGGCACCGCT TCTGTCGTGTGCCTGCTGAACAACTTTTACCCCCGCGAGGCCAAGGTGCAGTGGAAAGTGGATAACGCCCTGCAGAGC GGCAACTCCCAGGAATCCGTGACGAGCAGGACTCCAAGGACAGCACCTACTCCCTGTCCTCCACCCTGACCCTGTCC AAGGCCGACTACGAGAAGCACAAGGTGTACGCCTGCGAAGTGACCCACCAGGGCCTGTCTAGCCCTGTGACCAAGTCT TTCAACCGGGGCGAGTGC |
| 26 | Ky2 (8C10)-CDRH1 (IMGT) Amino acid sequence of CDRH1 of Ky2 (8C10) using IMGT | GFTFDDYA |
| 27 | Ky2 (8C10)-CDRH2 (IMGT) Amino acid sequence of CDRH2 of Ky2 (8C10) using IMGT | ISWNSGRI |
| 28 | Ky2 (8C10)-CDRH3 (IMGT) Amino acid sequence of CDRH3 of Ky2 (8C10) using IMGT | AKDGFYDILTGSFFDY |
| 29 | Ky2 (8C10)-CDRH1 (Kabat) Amino acid sequence of CDRH1 of Ky2 (8C10) using Kabat | DYAMH |
| 30 | Ky2 (8C10)-CDRH2 (Kabat) Amino acid sequence of CDRH2 of Ky2 (8C10) using Kabat | SISWNSGRIDYADSVKG |
| 31 | Ky2 (8C10)-CDRH3 (Kabat) Amino acid sequence of CDRH3 of Ky2 (8C10) using Kabat | DGFYDILTGSFFDY |

-continued

SEQUENCE LISTING

| Seq ID No: | Description | Sequence |
|---|---|---|
| 32 | Ky2 (8C10)-Heavy chain variable region | EVQLVESGGGLVQPGRSLRLSCAASGFTFDDYAMHWVRQGPGKGLEWVSSISWNSGRIDYADSVKGRFTISRDNAKN SLYLQMNRLRAEDTALYYCAKDGFYDILTGSFFDYWGQGILVTVSS |
| 33 | Ky2 (8C10)-Heavy chain variable region | GAAGTGCAGCTGGTGGAGTCTGGGGAGGCTTGGTACAGCCTGGGGAGGTCCCTGAGACTCTCCTGTGCAGCCTCTGG AATTCACCTTTGATGATTATGCCATGCACTGGGTCCGCCAAGTCCCAGGGAAGGGCCTGGAGTGGGTCTCAAGTATTA GTTGGAATAGCGGTAGGATAGACTATGCGGACTCTGTGAAGGGCCGATTCACCATCTCCAGAGACAACGCCAAGAAC TCCCTGTATCTGCAAATGAACAGTCTGAGAGCTGAGGACACGGCTGTATATTACTGTGCAAAAGATGGATTTTACGA TATTTTGACTGGCTCCTTTTTGACTACTGGGGCCAGGGAATCCTGGTCACCGTCTCCTCA |
| 34 | Ky2 (8C10)-full heavy chain sequence (mutations from germline are shown in small letters) | EVQLVESGGGLVQPGRSLRLSCAASGFTFDDYAMHWVRQGPGKGLEWVSSISWNSGRIDYADSVKGRFTISRDNAKN SLYLQMNRLRAEDTALYYCAKDGFYDILTGSFFDYWGQGILVTVSSASTKGPSVFPLAPCSRSTSESTAALGCLVKD YFPEPVTVSWNSGALTSGVHTFPAVLQSSGLYSLSSVVTVPSSSLGTKTYTCNVDHKPSNTKVDKRVESKYGPPCPP CPAPEFEGGPSVFLFPPKPKDTLMISRTPEVTCVVVDVSQEDPEVQFNWYVDGVEVHNAKTKPREEQFNSTYRVVSV LtVLHQDWLNGkEYKCKVSNKGLPSSIEKTISKAKGQPREPQVYTLPPSQEEMTKNQVSLTCLVKGFYPSDIAVEWE SNGQPENNYKTTPPVLDSDGSFFLYSRLIVDKSRWQEGNVFSCSVMHEALHNHYTQKSLSLSLGK |
| 35 | Ky2 (8C10)-full heavy chain sequence | GAAGTGCAGCTGGTGGAATCTGGCGGCGGACTCTGGCGCAGCCTGGCAGATCCCTGAGACTCTCTTGTGCCGCTCCGG CTTCACCTTTGACGACTACGCTATGCACTGGGTGCGACAGGAGCCTGGCAAGGGCCTGGAATGGGTGTCTCCATCT CCTGGAACAGCCGGCCGGATCGACTACGCCGACTCCGTTGAAGGCCGGTTCACCATCTCCCGGGACAACGCCAAGAAC TCCCTGTACCTGCAGATGAACAGCCTGCGGGCCGAGGATACCGCCCTGTACTACTGTGCCAAGGACGGCTTCTACGA TATCCTGACCGGCTCCTTCTTCGACTACTGGGGCCAGATCACCCTCGAGTCTACCGCCGTCTTCTGTCCTCCGTGAAGGAC CCTCCGTGTTCTCCCGAGCCCGTGACAGTGCTTCGACCTGCCCCTGCTCGGCTGCACACCTTTCCAGCTGTGCT GCATCCTCGTGCCCTCCGTACCTCCCCTGCCCTGCCCCCAGCTCTCTGGGCACCCTCTGGCACCTACCCTGAAGCCCCCT GTAACGTGGACCACAAGCCCTCGAATTGAGGGCGGACCCCGTGGTGGTGGATGTGTCCCAGGAAGATCCCGAGGTGC AGTTCAATTGGTACGTGG ACGGCGTGGTGCACATGCCAAGACCAAGCCAAGACCAAGCCAAGCCAGCCAAGCCCCCCTACCGGGTGGTGTCCGTG CTGACCGTGCTGCATCAGGACTGGCTGAACGGCAAGGAATACAAGTGCAAGGTCTCCAACAAGGACCTGCCCAGCTC CATCGAAAAGACCATCTCCAAGGCCAAGGGCCAGCCCCGAGAACCAGCAGTTCACCCTGCCCCTGTCTCAAGAGAAG ATGACCAAGACACAGGTGTCCCTGACCTGTCTGGTGAAGGGCTTCTACCCCTCCGATATCGCCGTGGAATGGGAG AGCAACGGCCAGCCCGAGAACACCTACAAGACAACCCCCCCTGTCTGACCCCTGGATCGCCTCCTTTTTCCTGTACTC TCGCCTGACCGTGGACAAGTCCCGGTGGCAGGAAGGCAACGTGTTCTCCTGCAGCGTGATGCACGAGGCCCTGCACA ACCACTACACCCAGAAGTCCCTGTCCCTGTCTCTGGGAAAG |
| 36 | Ky2 (8C10)-CDRL1 (IMGT) | QSISSY |
| 37 | Ky2 (8C10)-CDRL2 (IMGT) | GAS |
| 38 | Ky2 (8C10)-CDRL3 (IMGT) | QQSYSAPPEVVT |
| 39 | Ky2 (8C10)-CDRL1 (Kabat) | RASQSISSYLN |
| 40 | Ky2 (8C10)-CDRL2 (Kabat) | GASSLQSG |

-continued

SEQUENCE LISTING

| Seq ID No: | Description | Sequence |
|---|---|---|
| 41 | Ky2 (8C10)-CDRL3 (Kabat) | QQSYSAPPEVT |
| 42 | Ky2 (8C10)-Light chain variable region | DIQMTQSPSSLSASVGDRVTITCRASQSISSYLNWYHQEPGKAPNLLIYGASSLQSGVPSRFSGSGSGTDFTLTISS LQPEDFATYYCQQSYSAPPEWTFGQGTWEIK |
| 43 | Ky2 (8C10)-Light chain variable region | GACATCCAGATGACCCAGTCTCCATCCTCCCTGTCTGCATCTGTAGGAGACAGAGTCACCATCACTTGCCGGCAAG TCAGAGTATTAGCAGCTTATTAAATTGGTATCACCAGGAACCAGGGAAAGCCCCTAACCTCCTGATCTATGGTGCAT CAGTTTGCAAAGTGGGTCCCATCCAGGTTCAGTGGCAGTGGATCTGGGACAGATTTCACTCTCACCATCAGCAGT CTGCAACCTGAAGATTTTGCAACTTACTACTGTCAACAGAGTTACAGTGCCCCTCCGGAGTGGACGTTCGGCCAAGG GACCAAGGTGGAAATCAAA |
| 44 | Ky2 (8C10)-full light chain sequence | DIQMTQSPSSLSASVGDRVTITCRASQSISSYLNVVYHQEPGKAPNLLIYGASSLQSGVPSRFSGSGSGTDFTLTIS SLQPEDFATYYCQQSYSAPPEVVTFGQGTWEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGLSSPVTKSFNRGEC |
| 45 | Ky2 (8C10)-full light chain sequence | GACATCCAGATGACCCAGTCTCCCCTCCAGCCTGTCTGCTTCCGTGGCGACAGAGTGACCATCACTTGTCGGGCCTC CAGTCCATCTCTCCTACCTGAACTGGTATCACCAGAAACCCGGACAAGGCCCCAACCTGCTGATCTACGGCGCTTT CAGTCTGCAGTCCGGCGTGCCCTCTAGATTCTCCGGCTCTGGCTCTGGCACCGACTTTACCCTGACCATCAGCTCC CTGCAGCCCGAGGACTTCGCCACCTACTACTGCCAGCAGTCCTACTCCGTGTTCATCTTCCGACGAGCAGTTGGCCAGG CACCAAGGTGGAAATCAAGCGGACCGTGGCCGCTCCAGTCTTCATCTTCCCCCCGAGGCCAAGGTCAGTGGAACAAC TTCTACCCCCGCGAGCCAAGGTGCAGTGGAAGGTGGACAAC GCCCTGCAGAGCGGCAACTCCCAGGAATCCGTGACAGAGCAGGACTCCAAGGACAGCACCTACTCCCTGTCCTCCAC CCTGACCCTGTCCAAGGCCGACTACGAGAAGCACAAGGTGTACGCCTGCGAAGTGACCCACCAGGGCCTGTCTAGCC CCGTGACCAAGTCTTTCAACCGGGGCGAGTGC |
| 46 | Ky3 (15F11)-CDRH1 (IMGT) | GFTFGRYD |
| 47 | Ky3 (15F11)-CDRH2 (IMGT) | IGTAGDT |
| 48 | Ky3 (15F11)-CDRH3 (IMGT) | ARARPYYDSGSYYHAPFDY |
| 49 | Ky3 (15F11)-CDRH1 (Kabat) | RYDMN |
| 50 | Ky3 (15F11)-CDRH2 (Kabat) | AIGTAGDTYYPGSVKG |
| 51 | Ky3 (15F11)-CDRH3 (Kabat) | ARPYYDSGSYYHAPFDY |
| 52 | Ky3 (15F11)-Heavy chain variable region | EVQLVESGGGLVQPGGSLRLSCAASGFTFGRYDMNWVRQTTGKGLEWVSAIGTAGDTYYPGSVKGRFTISRENAKNS LYLQMNSLRPGDTAVYYCARARPYYDSGSYYHAPFDYWGQGTLVTVSS |

| Seq ID No: | Description | Sequence |
|---|---|---|
| 53 | Ky3 (15F11)-Heavy chain variable region | Nucleic acid sequence of V_H of Ky3 (15F11) | GAGGTGCAGCTGGTGGAGTCTGGGGGAGGCTTGGTACAGCCTGGGGGGTCCCTGAGACTCTCCTGTGCAGCCTCTGGATTCACCTTCGGTAGTTACGACATGAACTGGGTCCGCCAAACTACAGGAAAGGTCTGGAGTGGTCTCAGTATTGGTATGCTGGTGACACATACTATCCAGGCTCCGTGAAGGGCCGATTCACCATCTCCAGAGAAAATGCCAAGAACTCCTTGTATCTTCAAATGAACAGCCTGAGACCCGAGGACACGGCTGTGTATTACTGTGCAAGAGACCAAGGCCGTATTACTATGATTCGGGGAGTTATTATCACGCCCCTTTGACTACTGGGGCCAGGGAACCCTGGTCACCGTCTCCTCA |
| 54 | Ky3 (15F11)-full heavy chain sequence | Amino acid sequence of Ky3 (15F11) heavy chain | EVQLVESGGGLVQPGGSLRLSCAASGFTFGRYDMNWVRQTTGKGLEVVSAIGTAGDTYYPGSVKGRFTISRENAKNSLYLQMNSLRPGDTAVYYCARAPYYYDSGSYYHAPFDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFEGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLVTDKSRWQEGNVFSCSVMHEALHNHYTQKSLSLSLGK |
| 55 | Ky3 (15F11)-full heavy chain sequence | Nucleic acid sequence of Ky3 (15F11) heavy chain | GAAGTGCAGCTGGTGGAATCTGGCGGCGGACTGGTGCAGCCTGGCGGATCTCTGAGACTCTCTTGTGCCGCCTCCGGCTTCACCTTCGGCAGATACGACATGAACTGGGTGCGACAGACCACCGGAAAGGGCCTTGGAATGGGTGTCCGCTATCGGCACCGCTGGCGACACCTACTACCCTGGCTCTGTGAAGGGCCGGTTCACCATCTCCAGAGAGAACGCCAAGAACTCCCTGTACCTGCAGATGAACAGCCTGCGGCCTGGCGATACCGCCGTGTACTACTGCGCTAGGGCCCCCTACTACTACGATAGCGGCTCTTACTACCACGCCCCCTTTGACTACTGGGGCCAGGGCACCCTGGTCACCGTGTCTAGCGCCTCTACCAAGGGCCCATCCGTGTTCCCTCTGGCCCCTTGCTCCAGGTCTACCAGCGAGTCTACAGCCGCTCTGGGATGCCTGGTGAAGGACTACTTCCCCGAGCCCGTGACAGTGTCTTGGAACTCTGGAGCCCTGACCAGCGGAGTGCACACCTTCCCAGCCGTGCTCCAGAGCTCCGGACTGTACTCCCTGAGCAGCGTGGTGACCGTGCCCTCCAGCAGCCTGGGCACCAAGACCTACACCTGTAACGTGGACCACAAGCCCAGCAACACCAAAGTGGACAAGAGAGTGGAATCTAAGTACGGCCCTCCCTGCCCCCCTTGTCCTGCCCCTGAATTTGAGGGCGGACCTTCCGTGTTCCTGTTCCCCCCAAAGCCCAAGGACACCCTGATGATCTCCCGGACCCCCGAAGTGACCTGCGTGGTGGTGGATGTGTCCCAGGAAGATCCCGAGGTGCAGTTCAATTGGTACGTGGACGGCGTGGAAGTGCACAATGCCAAGACCAAGCCTAGAGAGGAACAGTTCAACTCCACCTACCGGGTGGTGTCCGTGCTGACCGTGCTGCATCAGGACTGGCTGAACGGCAAAGAGTACAAGTGCAAGGTGTCCAACAAGGGCCTGCCCAGCTCCATCGAAAAGACCATCAGCAAGGCCAAGGGCCAGCCTCGCGAGCCCCAGGTGTACACACTGCCTCCAAGCCAGGAAGAGATGACCAAGAACCAGGTGTCCCTGACCTGTCTGGTGAAAGGCTTCTACCCCTCCGATATCGCCGTGGAATGGGAGAGCAACGGCCAGCCCGAGAACAACTACAAGACCACCCCCCCTGTGCTGGACTCCGACGGCTCCTTCTTCCTGTACTCCCGGCTGGTGACCGACAAGTCCCGGTGGCAGGAAGGCAACGTGTTCTCCTGCAGCGTGATGCACGAGGCCCTGCACAACCACTACACCCAGAAGTCCCTGTCCCTGTCTCTGGGAAAG |
| 56 | Ky3 (15F11)-CDRL1 (IMGT) | Amino acid sequence of CDRL1 of Ky3 (15F11) using IMGT | QDISNY |
| 57 | Ky3 (15F11)-CDRL2 (IMGT) | Amino acid sequence of CDRL2 of Ky3 (15F11) using IMGT | DAS |
| 58 | Ky3 (15F11)-CDRL3 (IMGT) | Amino acid sequence of CDRL3 of Ky3 (15F11) using IMGT | QQYDNLFT |
| 59 | Ky3 (15F11)-CDRL1 (Kabat) | Amino acid sequence of CDRL1 of Ky3 (15F11) using Kabat | QASQDISNYLN |
| 60 | Ky3 (15F11)-CDRL2 (Kabat) | Amino acid sequence of CDRL2 of Ky3 (15F11) using Kabat | DASNLET |
| 61 | Ky3 (15F11)-CDRL3 (Kabat) | Amino acid sequence of CDRL3 of Ky3 (15F11) using Kabat | QQYDNLFT |

-continued

SEQUENCE LISTING

| Seq ID No: | Description | Sequence |
|---|---|---|
| 62 | Amino acid sequence of V_L of Ky3 (15F11) Ky3 (15F11)-Light chain variable region | DIQMTQSPSSLSASVGDRVTITCQASQDISNYLNWYQQKPGKAPKLLIYDASNLETGVPSRFSGSGSGTDFTFTISS LQPEDIATYYCQQYDNLFTFGPGTKVDIK |
| 63 | Nucleic acid sequence of V_L of Ky3 (15F11) Ky3 (15F11)-Light chain variable region | GACATCCAGATGACCCAGTCTCCATCCTCCCTGTCTGCATCTGTAGGAGACAGAGTCACCATCACTTGCCAGGCGAG TCAGGACATTAGCAACTATTTAAATTGGTATCAGCAGAAACCAGGGAAAGCCCCTAAGCTCCTGATCTACGATGCAT CCAATTTGGAAACAGGGGTCCCATCAAGGTTCAGTGGAAGTGGATCTGGGACAGATTTCACTTTCACCATCAGCAGC CTGCAGCCTGAAGATATTGCAACATATTACTGTCAACAGTATGATAATCTATTCACTTTCGGCCCTGGGACCAAAGT GGATATCAAA |
| 64 | Amino acid sequence of Ky3 (15F11)-full light chain sequence | DIQMTQSPSSLSASVGDRVTITCQASQDISNYLNWYQQKPGKAPKLLIYDASNLETGVPSRFSGSGSGTDFTFTISS LQPEDIATYYCQQYDNLFTFGPGTKVDIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKSFNRGEC |
| 65 | Nucleic acid sequence of Ky3 (15F11)-full light chain sequence | GACATCCAGATGACCCAGTCTCCATCCTCCCTGTCTGCATCTGTAGGCGACAGAGTGACCATCACCTGTCAGGCCTC CAGGACATCTCCAACTACTGAACTGGTATCAGCAGAAGCCCGGCAAGGCCCCTAAGCTGCTGATCTACGACGCCT CCAACCTGGAAACCGGCGTGCCCTCCAGATTCTCCGGCTCTGGCAGCGGCACAGACTTCACCTTCACCATCAGCTCC CTGCAGCCCGAGGATATCGCCACCTACTACTGCCAGCAGTACGACAACCTGTTCACCTTCGGCCCTGGCACCAAGGT GGACATCAAGAGAACCGTGGCCGCTCCAGTCTTCATCTTCCCACCCTCCGACGAGCAGCTGAAGTCCGGCACCG CTTCTGTCGTGTGCCTGCTGAATAACTTCTACCCCCGCGAGGCCAAGGTGCAGTGGAAAGTGGATAACGCCCTGCAG TCCGGCAACTCCCAGGAATCCGTGACCGAGCAGGACTCCAAGGACAGCACCTACTCCCTGTCCTCCACCCTGACCCT GTCCAAGGCCGACTACGAGAAGCACAAGGTGTACGCCTGCGAAGTGACCCACCAGGGCCTGTCTAGCCCCGTGACCA AGTCTTTCAACCGGGGCGAGTGC |
| 66 | Amino acid sequence of CDRH1 of Ky4 (16G05) using IMGT | GFTFDDYA |
| 67 | Amino acid sequence of CDRH2 of Ky4 (16G05) using IMGT | ISWNSGSI |
| 68 | Amino acid sequence of CDRH3 of Ky4 (16G05) using IMGT | AKDYYYDSSAYVLFDY |
| 69 | Amino acid sequence of CDRH1 of Ky4 (16G05) using Kabat | DYAMH |
| 70 | Amino acid sequence of CDRH2 of Ky4 (16G05) using Kabat | GISWNSGSIDYADSVKG |
| 71 | Amino acid sequence of CDRH3 of Ky4 (16G05) using Kabat | DYYYDSSAYVLFDY |
| 72 | Amino acid sequence of V_H of Ky4 (16G05) Ky4 (16G05)-Heavy chain variable region | EVQLVESGGGLVQPGRSLRLSCAVSGFTFDDYAMHWVRQPPGKGLEWVSGISWNSGSIDYADSVKGRFTISRDNAKN SLYLQMNSLRAEDTALYYCAKDYYYDSSAYVLFDYWGQGTLVTVSS |
| 73 | Nucleic acid sequence of V_H of Ky4 (16G05) Ky4 (16G05)-Heavy chain variable region | GAAGTGCAGCTTGTGGAGTCTGGGGGAGGCTTGGTACAGCCTGGCAGGTCCCTGAGACTCTCCTGTGCAGTCTCTGG ATTCACCTTTGATGATTATGCCATGCACTGGGTCCGGCAACTCCAGGAAGGGCCTGGAGTGGGTCTCAGGTATTA GTTGGAATAGTGGTAGCATAGACTATGCGGACTCTGTGAAGGGCCGATTCACCATCTCCAACACGCCAAGAACTCC GAGACAACGCCAAGAACTCCCTGTATCTGCAAATGAACAGTCTGAGAGCTGAGGACACGGCTGTGTATTATTGTGCAAAAGATTATTACTATGA TAGTAGTGCTTATGTCCTTTTGACTACTGGGGCCAGGGAACCCTGGTCACCGTCTCCTCA |

| Seq ID No: | Description | Sequence |
|---|---|---|
| 74 | Ky4 (16G05)-full heavy chain sequence | Amino acid sequence of Ky4 (16G05) heavy chain | EVQLVESGGGLVQPGRSLRLSCAVSGFTFDDYAMHWVRQPPGKGLEWVSGISWNSGSIDYADSVKGRFTISRDNAKN SLYLQMNSLRAEDTALYYCAKDYYYDSSAYVLFDYWGQGTLVTVSSASTKGPSVFPLAPCSRSTSESTAALGCLVKD YFPEPVTVSWNSGALTSGVHTFPAVLQSSGLYSLSSVVTVPSSSLGTKTYTCNVDHKPSNTKVDKRVESKYGPPCPP CPAPEFEGGPSVFLFPPKPKDTLMISRTPEVTCVVVDVSQEDPEVQFNWYVDGVEVHNAKTKPREEQFNSTYRVSV LIVLHQDWLNGKEYKCKVSNKGLPSSIEKTISKAKGQPREPQVYTLPPSQEEMTKNQVSLTCLVKGFYPSDIAVEWE SNGQPENNYKTTPPVLDSDGSFFLYSRLTVDKSRWQEGNVFSCSVMHEALHNHYTQKSLSLSLGK |
| 75 | Ky4 (16G05)-full heavy chain sequence | Nucleic acid sequence of Ky4 (16G05) heavy chain | GAAGTGCAGCTGGTGGAATCTGGCGGCGGACTGGTGCAGCCTGGCAGATCCCTGAGACTCCTGTCCTGTCCGG CTTCACCTTCGACGACTACGCCATGCACTGGGTGCGACAGCCTCCAGGCAAGGGCCTGGAATGGGTGTCCGGCATCT CCTGGAACTCCGGCTCCATCGATTACGCCGACTCCGTGAAGGGCCGGTTCACCATCTCCCGGGACAACGCCAAGAAC TCCCTGTACCTGCAGATGAACAGCCTGCGGGCCGAGGACACCGCCCTGTACTACTGCGCCAAGGACTACTACTACGA CTCCTCCGCCTACGTCCTGTTCGACTACTGGGGCCAGGGCACCCTGGTCACCGTGTCCTCTGCCAGCACCAAGGGCC CCTCCGTGTTCCCCCTGGCCCCTTGCTCCAGATCCACCTCTGAATCTACCGCCGCTCTGGGCTGCCTGGTCAAGGAT TACTTCCCCGAGCCCGTGACAGTGTCTTGGAACTCTGGCGCTCTGACCTCTGGCGTGCACACCTTCCAGTGTGCT GCAGTCCTGCAGTCCTCCGTGGTCACCGTGCCCTCCAGCTCTCTGGGCACCAAGACCTACACCT GTAACGTGGACCACAAGCCCTCCAACACCAAGGTGGACAAGAGAGTGGAATCTAAGTACGGCCCTCCTTGCCCCCCT TGTCCTGCCCCTGAATTTGAGGGCGGACCCTCTGTGTTTCTGTTCCCCCCAAAGCCCAAGGACACCCTGATGATCTC CCGGACCCCCGAAGTGCACATGCCTGGTGGTGGATGTGTCCCAGGAAGATCCCGAGGTGCAGTTCAATTGGTACGTG ACGGCGTGGAAGTGCACAACGCCAAGACCAAGCCTAGAGAGGAACAGTTCAACTCCACCTACCGGGTGTCCGTG CTGACCGTGCTGCATCAGGACTGGCTGAACGGCAAGGAGTACAAGTGCAAAGTGTCCAACAAGGCTCTGCCTGCCCC CATCGAAAAGACCATCTCCAAGGCCAAGGGCCAGCCCCGAGACCCCCAGGTGTACCTCACCCCCTCCCAGGAGGAGA TGATGACCAAGAACCAGGTGTCCCTGACCTGCCTGGTCAAGGGCTTCTACCCCTCCGACATCGCCGTGGAATGGGAG AGCAACGGCCAGCCCGAGAACAACTACAAGACCACCCCCCCTGTCCTGGACTCCGACGGCTCCTTCTTTCTGTACTC TCGCCTGACCGTGGACAAGTCCCGGTGGCAGGAAGGCAACGTCTTCTCCTGCAGCGTGATGCACGAGGCCCTGCACA ACCACTACACCCAGAAGTCCCTGTCCCTGTCTCTGGGAAAG |
| 76 | Ky4 (16G05)-CDRL1 (IMGT) | Amino acid sequence of CDRL1 of Ky4 (16G05) using IMGT | QSISSY |
| 77 | Ky4 (16G05)-CDRL2 (IMGT) | Amino acid sequence of CDRL2 of Ky4 (16G05) using IMGT | GAS |
| 78 | Ky4 (16G05)-CDRL3 (IMGT) | Amino acid sequence of CDRL3 of Ky4 (16G05) using IMGT | QQSFSTPLT |
| 79 | Ky4 (16G05)-CDRL1 (Kabat) | Amino acid sequence of CDRL1 of Ky4 (16G05) using Kabat | RASQSISSYLN |
| 80 | Ky4 (16G05)-CDRL2 (Kabat) | Amino acid sequence of CDRL2 of Ky4 (16G05) using Kabat | GASSLQS |
| 81 | Ky4 (16G05)-CDRL3 (Kabat) | Amino acid sequence of CDRL3 of Ky4 (16G05) using Kabat | QQSFSTPLT |
| 82 | Ky4 (16G05)-Light chain variable region | Amino acid sequence of VL of Ky4 (16G05) | DIQMTQSPSSLSASVGDRVIITCRASQSISSYLNWYQQKPGKAPELLIYGASSLQSGVPSRFSGSGSGTDFTLTISS LQPEDFATYYCQQSFSTPLTFGGGTKVEIK |

| Seq ID No: | Description | Sequence |
|---|---|---|
| 83 | Ky4 (16G05)-Light chain variable region | Nucleic acid sequence of VL of Ky4 (16G05) | GACATCCAGATGACCCAGTCTCCATCTCCCTGTCTGCATCTGTAGGAGACAGAGTCATCATCACTTGCCGGCAAG TCAGAGCATTAGCAGCTATTTAAATTGGTATCAACAGAAACCAGGGAAAGCCCCTGAGTCCTGATCTATGGTGCAT CCAGTTTGCAAAGTGGGGTCCCATCAAGGTTCAGTGGCAGTGGATCTGGGACAGATTTCACTCTCACCATCAGCAGT CTGCAACCTGAAGATTTTGCAACTTACTGTCAACAGAGTTTCAGTAGTCCCGCTCACTTTCGGCGGAGGGACCAA GGTGGAGATCAAA |
| 84 | Ky4 (16G05)-full light chain sequence | Amino acid sequence of Ky4 (16G05) light chain | DIQMTQSPSSLSASVGDRVIITCRASQSISSYLNWYQQKPGKAPELLIYGASSLQSGVPSRFSGSGSGTDFTLTISS LQPEDFATYYCQQSFSTPLTFGGGTKVEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPVTKSFNRGEC |
| 85 | Ky4 (16G05)-full light chain sequence | Nucleic acid sequence of Ky4 (16G05) light chain | GACATCCAGATGACCCAGTCTCCATCTCCCTGTCTGCTTCCGTGGGCGACAGAGTGATCATCACTTGTAGAGCCTC CCAGTCCATCTCCTCCTACCTGAACTGGTATCAGCAGAAGCCCGGCAAGGCCCCTGAGCTGCTGATCTATGGCGCTT CCAGTCTGCAGTCCGGCGTCCCGTCCAGATTCTCCGGCTCTGGCTCCGGCACCGACTTTACCCTGACCATCAGCTCC CTGCAGCCCGAGGACTTCGCCACCTACTGCCAGCAGTCTTTCTCCACCCCCCTGACCTTTGGCGGAGGCACCAA GGTGGAAATCAAGCGGACCGTGGCCGCTCCCTCTGTATTCATCTTCCCACCCTCCGATGAGCAGCTGAAGTCCGGA CCGCTTCTGTGTGCCTGCTGAACAACTTCTACCCCCGCGAGGCCAAGGTCCAGTGGAAGGTGGACAACGGTGAC CCCTGCGCAGGCCGACTACGAGAAGCACAAGGTGTACGCCTGCGAAGTGACCCACCAGGGCCTGTCTAGCCCCGTGA CCAAGTCTTTCAACCGGGCGAGTGC |
| 86 | Ky5 (15H06)-CDRH1 (IMGT) | Amino acid sequence of CDRH1 of Ky5 (15H06) using IMGT | GFTFSNAW |
| 87 | Ky5 (15H06)-CDRH2 (IMGT) | Amino acid sequence of CDRH2 of Ky5 (15H06) using IMGT | IKSKTDGTT |
| 88 | Ky5 (15H06)-CDRH3 (IMGT) | Amino acid sequence of CDRH3 of Ky5 (15H06) using IMGT | TTDGAYYPAAFDI |
| 89 | Ky5 (15H06)-CDRH1 (Kabat) | Amino acid sequence of CDRH1 of Ky5 (15H06) using Kabat | NAWMS |
| 90 | Ky5 (15H06)-CDRH2 (Kabat) | Amino acid sequence of CDRH2 of Ky5 (15H06) using Kabat | RIKSKTDGGTTDYAAPVKG |
| 91 | Ky5 (15H06)-CDRH3 (Kabat) | Amino acid sequence of CDRH3 of Ky5 (15H06) using Kabat | DGAYYPAAFDI |
| 92 | Ky5 (15H06)-Heavy chain variable region | Amino acid sequence of V_H of Ky5 (15H06) | EVQLVESGGGLVKPGGSLRLSCAASGFTFSNAWMSWVRQAPGKGLEVVVGRIKSKTDGGTTDYAAPVKGRFTISRDD SKNTLYLQMNSLKTEDTAVYYCTTDGAYYPAAFDIWGQGTMVSVSS |
| 93 | Ky5 (15H06)-Heavy chain variable region | Nucleic acid sequence of V_H of Ky5 (15H06) | GAGGTGCAGCTGGTGGAGTCTGGGGGAGGCTTGGTAAAGCCTGGGGGGTCCCTTAGACTCTCCTGTGCAGCTTCTGG ATTCACTTTTAGTAACGCCTGATGAGTTGGGTCCGCCAGGCTCCAGGGAAGGGGCTGGAGTGGGTTGCCGTATTA AAGCAAAACTGATGGTGGGACAACAGACTACGCTGCACCCGTGAAAGGCCGATTCACCATCTCAAGAGATGATTCA AAAAACACGCTGTATCTGCAAATGAACAGCCTGAAAACCGAGGACACGCCGTGTATTACTGTACCACAGATGGGGC TTACTATCCCGCTGCGATATCTGGGGTCAAGGGACAATGGTCAGCGTCTCTTCA |

| Seq ID No: | Description | Sequence |
|---|---|---|
| 94 | Ky5 (15H06)-full heavy chain sequence | Amino acid sequence of Ky5 (15H06) heavy chain | EVQLVESGGGLVKPGGSLRLSCAASGFTFSNAWMSWVRQAPGKGLEVVVGRIKSKTDGGTTDYAAPVKGRFTISRDDSKNTLYLQMNSLKTEDTAVYYCTTDGAYYPAAFDIWGQGTMVSVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFEGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 95 | Ky5 (15H06)-full heavy chain sequence | Nucleic acid sequence of Ky5 (15H06) heavy chain | GAAGTGCAGCTGGTGGAATCTGGCGGCGGACTCGTGAAGCCTGGAGGCTCTCTGAGACTGTCTTGTGCCGCCTCCGGCTTCACCTTCTCCAACGCTGATGAGCTGGGTGCGACAGGCTCCTGGCAAGGGCCTGGAATGGGTGGACGGATCAAGTCCAAGACCGACGGCGGCACCACCGACTACGCTGCCCCTGTGAAGGGCCGGTTCACCATCTCCGGAGACGACTCCAAGAACACCCTGTACCTGCAGATGAACTCCCTGAAAACCGAGGACGCCGTGTACTACTGTACCACCGATGGCGCCTACTACCCGCGCCTTCGATATCGGGGCCAGGGCACAATGGTGTCCGTGTCCTCCGCTTCTACCAAGGGCCCTCTGTGTTTCCTCGGCCTTCCTGGCCGTGTCCTGGAACTCTGGCGTGCACACCTTCCCAGCTGTCCTGCAGCTCCTCGGGCTGTACTCCCTGAGCCTGTGACCGTGCCCTCCGTGGTGACCGTGCCCTCCAGCTCTGGGCACCCAGACCTACACCTGCAACGTGGACCACAAGCCCTCCAACACCAAGGTGGACAAGAGAGTGGAATCTAAGTACGGCCCTCCCTGCCCCCTGTCCTGCCCCCTGAATTTGAGGGCGACCTCCGTCTTCCTGTTCCCCAAGAAGATCCCGAGGTGCAGTTCAATTGGTACGTGGACGGACCCCTGAAGTGCACAACGCCAAGCGTGCTGTCCGTGCTGGATGTGTCCAGGAAGATCCCGAGGTGCAGTTCAATTGGTACGTGGACGGAGTGGAGGTGCATAATGCCAAGACTACAAGACCTACCGTGTCTCCAACAGGAAGCTTCAACCTCCACCTACCGGGTGTCTGTGCTGACCGTGCTGCACCAGGACTGGCTGAATGGCAAGGAGTACAAGTGCAAGGTCTCCAACAAAGGCCTCCCAAGCGCCCTGAATATGCCTGCCTGCTCCCCAGCATCGAAAAGACCATCTCCAAGGCCAAGGGCCAGCCCAGAGAGCCTCAGGTGTACACCCTGCCCCCTGGAATCCAAGCCTCCAGGTCCAGGTCTGACCAAGAACCAGGTGTCCCTGACCTGTCTGGTTAAGGGCTTCTACCCTGACCTGTGGAGGAATGGAGTCCAACGGCCAGCCTGAGAACAACTACAAGACCACCCCTCCTGTGCTGGACTCCGACGGCTCCTTCTTTCTGTACTCTCGCCTGACAGTCGATAAGTCCCGGTGGCAGGAAGGCAACGTCTTCTCCTGCAGCGTGATGCACGAGGCCCTGCACAACCACTACACCCAGAAGTCCCTGTCTCTGTCTCTGGGAAAG |
| 96 | Ky5 (15H06)-CDRL1 (IMGT) | Amino acid sequence of CDRL1 of Ky5 (15H06) using IMGT | QGISSW |
| 97 | Ky5 (15H06)-CDRL2 (IMGT) | Amino acid sequence of CDRL2 of Ky5 (15H06) using IMGT | MS |
| 98 | Ky5 (15H06)-CDRL3 (IMGT) | Amino acid sequence of CDRL3 of Ky5 (15H06) using IMGT | QQSNSFPLT |
| 99 | Ky5 (15H06)-CDRL1 (Kabat) | Amino acid sequence of CDRL1 of Ky5 (15H06) using Kabat | RASQGISSWLA |
| 100 | Ky5 (15H06)-CDRL2 (Kabat) | Amino acid sequence of CDRL2 of Ky5 (15H06) using Kabat | AASSLHS |
| 101 | Ky5 (15H06)-CDRL3 (Kabat) | Amino acid sequence of CDRL3 of Ky5 (15H06) using Kabat | QQSNSFPLT |
| 102 | Ky5 (15H06)-Light chain variable region | Aminoacid sequence of V_L of Ky5 (15H06) | AIQMTQSPSSVSASVGDRVTITCRASQGISSWLAWYQQKPGKAPKLLIYAASSLHSGVPSRFSGSGSETDFTLTISSLHPEDFATYYCQQSNSFPLTFGGGTKVEIK |

SEQUENCE LISTING -continued

| Seq ID No: | Description | Sequence |
|---|---|---|
| 103 | Ky5 (15H06)-Light chain variable region | Nucleic acid sequence of V<sub>L</sub> of Ky5<br>GCCATCCAGATGACCCAGTCTCCATCTTCCGTGTCTGCATCTGTAGGAGACAGAGTCACCATCACTTGTCGGGCGAG<br>TCAGGGTATTAGCCTGGTTAGCCTGGTATCAGCAGAAACCAGGGAAAGCCCCTAAGCTCCTGATCTATGCTGCAT<br>CCAGTTTGCACAGTGGGGTCCCATCAAGGTTCAGCGGCAGTGGATCTGGGACAGATTTCACTCTCACCATCAGCAGC<br>CTGCACCCTGAAGATTTTGCAACTTACTATTGTCAACAGTCTAACAGTTTCCCGCTCACTTTCGGCGGAGGGACCAA<br>GGTGGAGATCAAA |
| 104 | Ky5 (15H06)-full light chain sequence | Amino acid sequence of Ky5 light chain<br>AIQMTQSPSSVSASVGDRVTITCRASQGISSWLAWYQQKPGKAPKLLIYAASSLHSGVPSRFSGSGSGTDFTLTISS<br>LHPEDFATYYCQQSNSFPLTFGGGTKVEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPVTKSFNRGEC |
| 105 | Ky5 (15H06)-full light chain | Nucleic acid sequence of Ky5 light chain<br>GCCATCCAGATGACCCAGTCCCTCCCTCCGTGTCTGCTCTGTAGGGCGACAGAGTGACCATCACTTGTCGGGCCTC<br>CCAGGGCATCTCTTCTTGGCTGGCCTGGTATCAGCAGAAGCCCGGCAAGGCCCCAAGCTGCTGATCTACGCGCCT<br>CCTCTCTGCACTCTGGGCGTGCCCTCTAGATTCTCCGGCTCCGGCAGCGGGACAGACTTTTACCCTGACCATCTCCAGC<br>CTGCACCCCGAGACTTCGCCACTTACTACTGCCAGCAGTCCAATTCTTTCCGACCTTCGGCGGAGGCCACCAA<br>GGTGGAAATCAAGCGGACCGTGGCCGCTCCCTCTGAACACTTCATCTTCCCCCGCCTCTGATGAGCAGTTGAAGTCCGGA<br>CCGCTTCTGTGTGCTGCTGAACAACTTCTACCCCCGGGAGGCCAAGGTGCAGTGGAAGGTGGACAACGCCCTG<br>CAGTCCGGCAACTCCAGGAATCCGTGACCGAGCAGGACTCCAAGGACAGCACCTACTCCCTGTCCTCCACCCTGAC<br>CCTGTCCAAGGCCGACTACGAGAAGCACAAGGTGTACGCCTGCGAAGTGACCCACCAGGGCCTGTCTAGCCCCGTGA<br>CCAAGTCTTTCAACCGGGGCGAGTGC |
| 106 | Human IgG4 heavy chain constant region #1 | IGHC4*01 Heavy Chain Constant Region Nucleotide Sequence<br>gcttccaccaagggcccatccgtcttccccctggcgccctgctccaggagcacctccgagagcacagcggccctggg<br>ctgcctggtcaaggactacttccccgaaccggtgacggtgtcgtggaactcaggcgccctgaccagcggcgtgcaca<br>ccttcccggctgtcctacagtcctcaggactctactccctcagcagcgtggtgaccgtgccctccagcagcttgggc<br>acgaagacctacacctgcaacgtagatcacaagcccagcaacaccaaggtggacaagagagttgagtccaaatatgg<br>tccccatgcccatcatgcccagcacctgagttcctggggggaccatcagtcttcctgttccccccaaaacccaagg<br>acactctcatgatctcccggacccctgaggtcacgtgcgtggtggtggacgtgagccaggaagaccccgaggtccag<br>ttcaactggtacgtggatggcgtggaggtgcataatgccaagacaaagccgcgggaggagcagttcaacagcacgta<br>ccgtgtggtcagcgtcctcaccgtcctgcaccaggactggctgaacggcaaggagtacaagtgcaaggtctccaaca<br>aaggcctcccgtcctccatcgagaaaaccatctccaaagccaaagggcagccccgagaaccacaggtgtacaccctg<br>cccccatcccaggaggagatgaccaagaaccaggtcagcctgacctgcctggtcaaaggcttctaccccagcgacat<br>cgccgtggagtgggagagcaatgggcagccggagaacaactacaagaccacgcctcccgtgctggactccgacggct<br>ccttcttcctctacagcaggctaaccgtggacaagagcaggtggcaggaggggaatgtcttctcatgctccgtgatg<br>catgaggctctgcacaaccactacacagagctctggggtaaa |
| 107 | Human IgG4 heavy chain constant region #2 | IGHC4*02 Heavy Chain Constant Region Amino Acid Sequence<br>ASTKGPSVFPLAPCSRSTSESTAALGCLVKDYFPEPVTVSWNSGALTSGVHTFPAVLQSSGLYSLSSVVTVPSSSLG<br>TKTYTCNVDHKPSNTKVDKRVESKYGPPCPSCPAPEFLGGPSVFLFPPKPKDTLMISRTPEVTCVVVDVSQEDPEVQ<br>FNWYVDGVEVHNAKTKPREEQFNSTYRVVSVLTVLHQDWLNGKEYKCKVSNKGLPSSIEKTISKAKGQPREPQVYTL<br>PPSQEEMTKNQVSLTCLVKGFYPSDIAVEWESNGQPENNYKTTPPVLDSDGSFFLYSRLTVDKSRWQEGNVFSVSVM<br>HEALHNHYTQKSLSLSGK |
| 108 | Human IgG4 heavy chain constant region #2 | IGHC4*02 Heavy Chain Constant Region Nucleotide Sequence<br>gcttccaccaagggcccatccgtcttccccctggcgccctgctccaggagcacctccgagagcacagcggccctggg<br>ctgcctggtcaaggactacttccccgaaccggtgacggtgtcgtggaactcaggcgccctgaccagcggcgtgcaca<br>ccttcccggctgtcctacagtcctcaggactctactccctcagcagcgtggtgaccgtgccctccagcagcttgggc<br>acgaagacctacacctgcaacgtagatcacaagcccagcaacaccaaggtggacaagagagttgagtccaaatatgg<br>tccccatgcccaccatgcccagcacctgagttcctggggggaccatcagtcttcctgttccccccaaaacccaagg<br>acactctcatgatctcccggacccctgaggtcacgtgcgtggtggtggacgtgagccaggaagaccccgaggtccag<br>ttcaactggtacgtggatggcgtggaggtgcataatgccaagacaaagccgcgggaggagcagttcaacagcacgta<br>ccgtgtggtcagcgtcctcaccgtcctgcaccaggactggctgaacggcaaggagtacaagtgcaaggtctccaaca<br>aaggcctcccgtcctccatcgagaaaaccatctccaaagccaaagggcagccccgagagccacaggtgtacaccctg<br>cccccatcccaggaggagatgaccaagaaccaggtcagcctgacctgcctggtcaaaggcttctaccccagcgacat |

| Seq ID No: | Description | Sequence |
|---|---|---|
| 109 | Heavy Chain Constant Region Amino Acid Sequence | cgccggtggagtggaagcaatgggcagccggagaacaatacaagaccaagctctccgtgctgactcagcggct<br>ccttctccctacacgaggctaacctggacaagagccaggagggaatgcttctcatgctctcgtgtaaa<br>catgaggctctgcacaaccactacacgcagaagagcctctccctgtctctgggtaaa<br>ASTKGPSVFPLAPSCRSTSESTAALGCLVKDYFPEPVTVSWNSGALTSGVHTFPAVLQSSGLYSLSSVVTVPSSSLG<br>TKTYTCNVDHKPSNTKVDKRVESKYGPPCPSCPAPEFLGGPSVFLFPPKPKDTLMISRTPEVTCVVVDVSQEDPEVQ<br>FNWYVDGVEVHNAKTKPREEQFNSTYRVVSVLTVVHQDWLNGKEYKCKVSNKGLPSSIEKTISKAKGQPREPQVYTL<br>PPSQEEMTKNQVSLTCLVKGFYPSDIAVEWESNGQPENNYKTTPPVLDSDGSFFLYSRLTVDKSRWQEGNVFSCSVM<br>HEALHNHYTQKSLSLSLGK |
| 110 | IGHC4*03 Human IgG4 heavy chain constant region #3 | gctccaccaagggcccatccgtcttccccctggcgccctgctccaggagcacctccgagagcacagcggccctgg<br>ctgcctgtcaaggactactccctacacgaggcagatgacaccaggcgccccagcaggtgtgcaca<br>cctccgcgctcactgcctacagcctcaggagctgacctgctgcaatgaaggagagcgcaggtgagtcccaaataatgg<br>acgaagacctacacctgcaacgtagatccacccaaggtgacaaccaacccaaaaccaaaggtgagaaatatgg<br>tccccatgccatcaatgcccatgtccgcccgaggtctgcgtgcacgtgcgtggtcgaggagacagggccaggtccag<br>acctcccatgatctccggacccctgaggtcacgtgcgtggtggtggacgtgagcacggaagaccccgaggtccag<br>ttcaactggtactgtggacggcgtggagtgcataatgccaagacaaagccgcgggaggagcagttcaacagcacgta<br>ccgtgtgtcagtgctcaccgtcctgcaccaggactggctgaacggcaaggagtacaagtgcaaggtctccaaca<br>aaggcctcccgtcccatcgagaaaaccatctccaaagccaaaggcaggcccccgagaaccacaggtgtaccccta<br>cccccatcccgggaggagatgaccaagaaccaggtcagcctgacctgcctggtcaaaggcttctacccagcgacat<br>cgccgtggagtgggagagcaatgggcagccggagaacaactacaagaccacgcctcccgtgctggactcgcagacggct<br>ccttctctctacagcaggctaaccgtggacaagagcaggtggcaggagggaatgtcttctcatgctccgtgatg<br>catgaggctctgcacaaccactacacgcagaagagcctctccctgtctctgggtaaa<br>ASTKGPSVFPLAPCSRSTSESTAALCLVKDYFPEPVTVSWNSGALTSGVHTFPAVLQSSGLYSLSSVVTVPSSSLGT<br>KTYTCNVDHKPSNTKVDKRVESKYGPPCPSCPAPEFLGGPSVFLFPPKPKDTLMISRTPEVTCVVVDVSQEDPEVQF<br>NWYVDGVEVHNAKTKPREEQFNSTYRVVSVLTVLHQDWLNGKEYKCKVSNKGLPSSIEKTISKAKGQPREPQVYTLP<br>PSQEEMTKNQVSLTCLVKGFYPSDIAVEWESNGQPENNYKTTPPVLDSDGSFFLYSKLTVDKSRWQEGNVFSCSVMH<br>EALHNHYTQKSLSLSLGK |
| 111 | Heavy Chain Constant Region Amino Acid Sequence | |
| 112 | Heavy Chain Constant Region Nucleotide Sequence-Synthetic Version A | gctccaccaagggcccatccgtcttccccctggcgccctgctccaggagcacctccgagagcacctgagcgccctggg<br>ctgcctgtcaaggactactccctgcctcagtcctcaggactccaccgccgtgaactcaggcgtgtgacctgccctgagcagctggcc<br>cctcccggctgtcctcacactgcgtctcaggactactcctcctcagcacacaaaggtgacactcacctgacccagcagtggctggc<br>acgaagacctacacctgcaacgtagacacaaggtgacaaccaaggtgacaaggaggagtgactctcctcgttccccaccaaggt<br>tccccccatgccatcagtgccatgtccgcccgaattgaggggggacactgaggtccactgcgtggtggtggatgtgagccaagt<br>acacttcatgatctccgtactgtggatggcggtggaggtgcataatgccaagacaaagccgcggaggagtacaacagcactacgta<br>ttcaactggtactgtgtcagtgctcaccgtcctgcaccaggactggctgaatggcaaggagtacaagtgcaaggtctccaaca<br>ccgtgtgtcagtgctcatcgatcgagaaaaccatctccaaagccaaagggcagcccagagccacaggtgtacaccctg<br>aaggcctcccgtcccctgatcgagaaaaccatctccaaagccaaagggcagcccagagccacaggtgtacaccctg<br>ccccatccccgggaggagatgaccaagaaccaggtcagcctgacctgcctggtcaaaggcttctacccagcgacat<br>cgccgtggagtgggagagcaatggcagccggagaacaactacaagaccacgcctcccgtgctgactcgcagacggat<br>ccttctcctctacagcaggctaaccgtggacaagagcaggtggcaggagggaatgtcttctcatgctctcgtgatg<br>catgaggctctgcacaaccactacacacagaagagcctctccctgtctctgggtaaa |
| 113 | IgG4 heavy chain constant region-IgG4-PE Heavy Chain Constant Region Amino Acid Sequence-Encoded by Synthetic Version A, B & C | ASTKGPSVFPLAPCSRSTSESTAALGCLVKDYFPEPVTVSWNSGALTSGVHTFPAVLQSSGLYSLSSVVTVPSSSLG<br>TKTYTCNVDHKPSNTKVDKRVESKYGPPCPPCPAPEFEGGPSVFLFPPKPKDTLMISRTPEVTCVVVDVSQEDPEVQVYTL<br>FNWYVDGVEVHNAKTKPREEQFNSTYRVVSVLTVLHQDWLNGKEYKCKVSNKGLPSSIEKTISKAKGQPREPQVYTL<br>PPSQEEMTKNQVSLTCLVKGFYPSDIAVEWESNGQPENNYKTTPPVLDSDGSFFLYSRLTVDKSRWQEGNVFSCSVM<br>HEALHNHYTQKSLSLSLGK |

SEQUENCE LISTING

| Seq ID No: | Description | Sequence |
|---|---|---|
| 114 | IgG4 heavy chain constant region | Heavy Chain Constant Region Nucleotide Sequence-Synthetic Version B<br><br>gctccaccaaggactagtgtgtccctctgccctcttccagtccacaagcgagtccacgtgcctcgg ctgtctggtgaagactacttcccgagccgtgaccgtctcctgaataccggaggcctgctgtgcaca cattcccggctgcagagcagcagcgactgtatagcctggaactgatggacagtggtgcagcagcagt accaaaactacaccctgccctcttcgaacgtgacccacaccaagtgatgacaaggtgtacaaccacg cccctcgcctgcctcctcgtccctgacaccgagtgacctgtgtcgtgactctgagggagccctgggtgtgtcccccaaaccaagg acacctgatctccggacacccgagttgactgtgtgtgtgacctcagccaggagcaggtgcagg ttcaactggtatgtgagcgtggagcgtgccagtccatcagaagaccatcagcaagtgcccgacctct gtgacctgcaaaatgcgcgctgaacaatgccaaaccaagctgtccctgaccctgtgctggttgtcaaca aggactgtccatccagcatcagagaccatccagcagtgcagctttgaaggacacgaggagcccatgttctaccctgtatacctg cgccgtaggatggaggcaatgtgccagccagccagcagaacaattacaaaacaaccctccgtgctgataccgctgctgatggcagtccctccggtgtctccctgtgctctgatg cacgaggccctgcacaataccaccagagcctcccctgtccctgggcaag |
| 115 | IgG4 heavy chain constant region | Heavy Chain Constant Region Nucleotide Sequence-Synthetic Version C<br><br>gcagcaccaagggcccttcctgtgttccctggcccctgcagcagccacctcgaatccacagctgcccgctggg ctgtctggtgaagactacttccccgaaccagtgaccgtgtcgtgagactctgagcatcggggtaccac acctttcctgcctgtcagtcctgacctgtacggtggactcaacgggtgagagacaagtca caccaagacctcacctgtaacggtcctgcctccgtggacaccaagtggacaacaagtcctgacaacgagcccagtgatccacaagggcttcctgttcctcctaagcca aggaccctctgatgactccagccaaccacacccagtgggggtacagcagctgttgctggtgcaggaccctgagtc cagtcaactggtatgtcgatgctgaccgtgctgcatccaggaccctgtgaggtcacaacgcaagcagcaagtcaactccac ctacagggtggtcagcgtgctgaccgtgctcatcaggactcctcaagctaaggccccagcccagcagcagcagcagtccagcagcaaggtgcagctggtgtacacc tgcccgtggggtgagagagccagcatccaaggtgaaccagcaggtgagccctcctgcctccgacacc catcgccctccagctcagaaatatataagacaaccaggatgcagtagttcaagtgagaaagccgaagttcagctgctcgacg gatcctcctttgtactccaggctgcaccggctgacctgatgaagtgatgagaaacgtgcagatccagcatcaacaggactggcagtttcagtgctcctgctgtgcacgtg atgcacgaggccctgcacaatactaccacacagagcctctcccgttgcctggagaag |
| 116 | IgG4 heavy chain constant region-inactivated | Heavy Chain Constant Region Nucleotide Sequence<br><br>gctccaccaaggccccatcctgcttccccgaacagtgcctctccaggaggagcaggccctggg ctgcctggtcaaggactacttcccgaagccaccagtgtcggtgaactcaggcgccctgaccagcggtgcaca cttcccagctgtcctacagtctcctcaggactctactcctcagcacctgaccgtgccctgcagcagcttggc acgaagactacacctgcaacctgaccctagatcagaaaggtgacaaccacaagggccgatggaggtgactgaagaggttgagtcaaatatgg tccgcccctatccacatgccagcgcctgcgtgggggaccacagtcagtctcctgttccccaaaccaagg acactctcatgatctccggacccctgaggtcacgtcgtgtgtgtgacgtgaccatgccgacacacacgagtga ttcaactggtacgtggacggcgtggaggtgcataatgccaagacaaagccggcagggaggagcagttcaacagcactgttcaacaa cctgtggtcggtgctgaccgtcctgcaccaggactggctgaacgcaaggagtacaagtgcaaggtctccaacaaa ggcctcccagtccctcgatcgataccatctccaaagccaaagggcagccccgagaaccacaggtgtacaccctg cccccatccgggaggatgaatgagcaatggagcagcagaaccaagggacacagagaccagtgagaagaccagaaggcagcagcagctttacacccctg cgcctgagtgggagagcaatgggcagccggagaaaacaactacaagaccacgcctcccgtgctggactccgacggat cttcttcctctacgccagcaagctcaccgtggacaagagcaggtggcagcaggggaatgtcttctcatgctccgtgatg catgaggtgctccacacaccaactacaagaaggagcctctcctgtctccgggtaaa |
| 117 | IgG4 heavy chain constant region-inactivated | Heavy Chain Constant Region Amino Acid Sequence (inactivating mutations from human WT IgG4 shown in bold)<br><br>ASTKGPSVFPLAPSCRSTSESTAALGCLVKDYFPEPVTVSWNSGALTSGVHTFPAVLQSSGLYSLSSVVTVPSSSLG TKTYTCNVDHKPSNTKVDKRVESKYGPPCPSCPAPPVAGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQPREPQVYTL PPSQEEMTKNQVSLTCLVKGFYPSDIAVEWESNGQPENNYKTTPPVLDSDGSFFLYSRLTVDKSRWQEGNVFSCSVM HEALHNHYTQKSLSLSLGK |

SEQUENCE LISTING (continued)

| Seq ID No: | | Description | Sequence |
|---|---|---|---|
| 118 | Human WT IgG1 constant region | WT human IgG1 amino acid sequence | ASTKGPSVFPLAPSSKSTSGGTAALGCLVKDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVLDSDGSFFLYSKLTVDKSRWQQGNVFSC SVMHEALHNHYTQKSLSLSPGK |
| 119 | IgG1 | WT human IgG1 nucleic acid sequence | GCCAGCACCAAGGGCCCCTCTGTGTTCCCTCTGGCCCCTTGCAGCAAGTCCACCTCTGGCGGAACAGCCGCTCTGG CTGCCTGCGTGAAGGACTACTTCCCCGAGCCTGTGACCGTGTCCTGGAACTCTGGCGCTCTGACCAGCGGAGTGCACA CCTTCCCTGCTGTGCTGCAGTCCTCCGGCCTGTACTCCCTGTCCAGCGTCGTGACCGTGCCTTCCAGTCTCTGGGC ACCCAGACCTACATCTGCAACGTGAACCACAAGCCCTCTAACACCAAGGTGGACAAGAAGGTGGAACCCAAGTCCTG CGACAAGACCCACACCTGTCCCCCTTGCCCAGCCCCTGAAGTGCTGGGCGGACCTTCCGTGTTCCTGTTCCCCCCAA AGCCCAAGGACACCCTGATGATCTCCCGGACCCCTGAAGTGACATGCGTGGTGGTGGATGTGTCCCACGAGGACCCT GAAGTGAAGTTCAATTGGTACGTGGACGGCGTGGAAGTGCACAACGCCAAGACCAAGCCTAGAGAGGAACAGTACAA CTCCACCTACCGGGTGGTGTCCGTGCTGACCGTGCTGCACCAGGATTGGCTGAACGGCAAGGAGTACAAGTGCAAGG TGTCCAACAAGGCCCTGCCTGCCCCCATCGAGAAGACCATCTCCAAGGCCAAGGGCCAGCCCCGGGAACCCCAGGTG TACACACTGCCCCCTAGCAGGGACGAGCTGACCAAGAACCAGGTGTCCCTGACCTGTCTGGTGAAAGGCTTCTACCC CTCCGATATCGCCGTGGAATGGGAGTCCAACGGCCAGCCTGAGAACAACTACAAGACCACACCCCCTGTGCTGGACT CCGACGGCTCATTCTTCCTGTACAGCAAGCTGACAGTGGACAAGTCCCGGTGGCAGCAGGGCAACGTCTTCTCCTGC TCCGTGATGCACGAGGCCCTGCACAACCACTACACCCAGAAGTCCCTGTCCCTGAGCCCCGGCAAGTGATGA |
| 120 | Disabled Human IgG1 heavy chain constant region | Heavy Chain Constant Region Nucleotide Sequence | gcctccaccaagggcccatcggtcttccccctggcacctcctccaagagcacctctgggggcacagcggccctggg ctgcctggtcaaggactacttccccgaaccggtgacggtgtcgtggaactcaggcgctctgaccagcggcgtgcaca ccttccccggctgtcctacagtcctcaggactctactccctcagcagcgtggtgaccgtgccctccagcagttggc tgaccagacctacatctgcaacgtgaatcacaagcccagcaacaccaaggtggacaagaaagttgagcccaaatcttg tgacaaaactcacacatgcccaccgtgcccagcacctgaactcctggggggaccgtcagtcttcctcttccccccaa aacccaaggacaccctcatgatctcccggacccctgaggtcacatgcgtggtggtggacgtgagccacgaagaccct gaggtcaagttcaactggtacgtggacggcgtggaggtgcataatgccaagacaaagccgcgggaggagcagtacaa tctccacaaagccctcccagcccccatcgagaaaaccatctccaaagccaaagggcagccccgagaaccacaggtg tacaccctgcccccatcccgggatgagctgaccaagaaccaggtcagcctgacctgcctggtcaaaggcttctatcc cagcgacatcgccgtggagtgggagagcaatgggcagccggagaacaactacaagaccacgcctcccgtgctggact ccgacggctccttcttcctctatagcaagctcaccgtggacaagagcaggtggcagcaggggaacgtcttctcatgc tccgtgatgcatgaggctctgcacaaccactacacgcagaagagcctctccctgtctccgggtaaa |
| 121 | | Heavy Chain Constant Region Amino Acid Sequence | ASTKGPSVFPLAPSSKSTSGGTAAGLCVKDYFPEPVTVSWNSGALTSVHTFPAVLQSSGLYLSSVVTVPSSSLGT QTYICNVNHKPSNTKVDKKVEPKSCDKTHTCPPCPAPELAGAPSVFLFPPKPKDTLMISRTPEVTCVVVDVSHEDPE VKFNWYVDGVEVHNAKTKPREEQYNSTYRVVSVLTVLHQDWLNGKEYKCKVSNKALPAPIEKTISKAKGQPREPQVY TLPPSRDELTKNQVSLTCLVKGFYPSDIAVEWESNGQEPNNYKTTPPVLDSDGSFFLYSKLTVDKSRWQQGNVFSCS VMHEALHNHYTQKSLSLSPQK |
| 122 | Human Cκ constant region | Cκ Light Chain Constant Region Nucleotide Sequence | cgtacggtggccgctcccctcctgtctcatcttcccacctcgacagcagcgtgaagtccggacctgcttctgtcgt gttcctgttgaacaacttctacccccgaggccaaggccaggtgcagtggaaggtggacaacgccctgcagtccggcaacc caggaaatgctgaccgagcaggacagcaaggacagcacctactccctcagcagcaccctgaccctgtccaaggccg actacgagaagcacaaggtgtacgcctgcgaagtgacccaccagggcctgtcatgctagccccgtgaccaagtcttcaac cggggcagtgt |
| 123 | IGKC*01 | Cκ Light Chain Constant Region Amino Acid Sequence | RTVAAPSVFIFPPSDEQLKSGTASVVCLLNNFYPREAKVQWKVDNALQSGNSQESVTEQDSKDSTYSLSSTLTLSKAD YEKHKVYACEVTHQGLSSPVTKSFNRGEC |

SEQUENCE LISTING - continued

| Seq ID No: | | | Description | Sequence |
|---|---|---|---|---|
| 124 | Human Cκ constant region | IGKC*02 | Cκ Light Chain Constant Region Nucleotide Sequence | cgaactggctgcaccatctgtctcatcttcccgccattctgatgagcagttgaaatctggaactgcctcttgtt gtgcctctgaataacttctatcccagagaggccaaagtacagtggaaggtggataacgcctccaatcgggtaact cccaggagagtgtcacagagtcaggacagcaaggacagcacctacagcctcagcagcaccctgacgctgagcaaagca gactacgagaaacacaaagtctacgcctgcgaagtcacccatcagggcctgagctcgcccgtcacaaagagcttcaa cagggagagtgt |
| 125 | | | Cκ Light Chain Constant Region Amino Acid Sequence | RTVAAPSVFIFPPSDEQLKSGTASVVCLLNNFYPREAKVQWKVDNALQSGNSQESVTEQDSKDSTYSLSSTLTLSKA DYEKHKVYACEVTHQGLSSPVTKSFNRGEC |
| 126 | Human Cκ constant region | IGKC*03 | Cκ Light Chain Constant Region Nucleotide Sequence | cgaactggctgcaccatctgtcttcatctcccgagagcagttgaaatctggaactgctcttgttgt gtgcctctgatgagcagttgaaatctggaactgcctcccatcgggtaact cccaggagagtgtcacagagtcaggacagcaaggacagcacctacagcctcagcagcaccctgacgctgagcaaagca gactacgagaaacacaaagtctacgcctgcgaagtcacccatcagggcctgagctcgcccgtcacaaagagcttcaa cagggagagtgt |
| 127 | | | Cκ Light Chain Constant Region Amino Acid Sequence | RTVAAPSVFIFPPSDEQLKSGTASVVCLLNNFYPREAKVQRKVDNALQSGNSQESVTEQESKDSTYSLSSTLTLSKA DYEKHKVYACEVTHQGLSSPVTKSFNRGEC |
| 128 | Human Cκ constant region | IGKC*04 | Cκ Light Chain Constant Region Nucleotide Sequence | cgaactggctgcaccatctgtcttcatctcccgagagcagttgaaatctggaactgcctcttgtgt gtgcctctgaataacttctatcccagagaggccaaagtacagtggaaggtggataacgcctccaatcgggtaact cccaggagagtgtcacagagtcaggacagcaaggacagcacctacagcctcagcagcaccctgacgctgagcaaagca gactacgagaaacacaaagtctacgcctgcgaagtcacccatcagggcctgagctcgcccgtcacaaagagcttcaa cagggagagtgt |
| 129 | | | Cκ Light Chain Constant Region Amino Acid Sequence | RTVAAPSVFIFPPSKEQLKSGTASVVCLLNNFYPREAKVQWKVDNALQSGNSQESVTEQDSKDSTYSLSSTLTLSKA DYEKHKLYACEVTHQGLSSPVTKSFNRGEC |
| 130 | Human Cκ constant region | IGKC*05 | Cκ Light Chain Constant Region Nucleotide Sequence | cgaactggctgcaccatctgtcttcatctcccgccattctgatgagcagttgaaatctggaactgcctcttgtgt gtgcctctgaataacttctatcccagagaggccaaagtacagtggaaggtggataacgcctccaatcgggtaact cccaggagagtcacagagtcaggacagcagcaggactctcagcaacctacgccctgagctctcagctcacccgtgagcaaagca gactacgagaaacacaaagtctacgcctgcgaagtcacccatcagggcctgagctcgcccgtcacaaagagcttcaa cagggagagtgc |
| 131 | | | Cκ Light Chain Constant Region Amino Acid Sequence | RTVAAPSVFIFPPSDEQLKSGTASVVCLLNNFYPREAKVQWKVDNALQSGNSQESVTEQDSKDSTYSLSNTLTLSKA DYEKHKVYACEVTHQGLSSPVTKSFNRGEC |
| 132 | Human Cλ constant region | IGLC1*01 | Cλ Light Chain Constant Region Nucleotide Sequence | cccaaggcccaaccccacgtcactctgttcccgccctcctctgaggagctccaagccaacaaggccacagtgtg tctgatcagtgacttctacccgggagctgtgacagtggtgcagtggaaggcagatggcagccccgtcaaggcggagtgg agacgaccaaacctccaaacagagaccaacaacaaagtacggggccagcagctacctgagcctgacgcccgactgg aagtcccacaagagctacagctgccaggtcacgcatgaagggagcaccgtggagactaccaaacaagagccccacaaat tca |
| 133 | | | Cλ Light Chain Constant Region Amino Acid Sequence | PKANPTVTLFPPSSEELQANKATLVCLISDFYPGAVTVASWKADGSPVKAGVETTKPSKQSNNKYAASSYLSLTPEQ WKSHRSYSCQVTHEGSTVEKTVAPTECS |
| 134 | Human Cλ constant region | IGLC1*02 | Cλ Light Chain Constant Region Nucleotide Sequence-Version A | ggtcagcccaaggctgccccctgactcactcgttcactctgttcccgccctcttgaggagctccaagccaacata gtgtgtctgatcagtgacttctacccgggagctgtgacagtggtgcagtggaaggcagatggcagccccgtcaaggcggg agtggagaccaccaaaccctccaaacagagcaacaacaagtacgcggccagcagctacctgagcctgacgccgcagc agtggaagtcccacaagagctacagctgccaggtcacgcatgaagggagcaccgtggagaagacagtggcccctacaca gaatgttca |
| 135 | | | Cλ Light Chain Constant Region Amino Acid Sequence-Encoded by version A & B | GQPKANPTVTLFPPSSEELQANKATLVCLISDFYPGAVTVAWKADGSPVKAGVETTKPSKQSNNKYAASSYLSLTP EQWKSHRSYSCQVTHEGSTVEKTVAPTECS ggtcagcccaaggctgccccactgtcactcttcactctgttcccgccctcctctgaggagctccaagccaacact |

| Seq ID No: | Description | Sequence |
|---|---|---|
| 136 | | agtgtctgatcagtgacttctaccggaggagctgacagtggcctgaaggcagcagtgaagcccgtcaaggcgg<br>agtggaagaccaacaaacctccaagcagagctgcctgaaggccagcagcctgacctgaggagacgagccgag<br>cagtgaagtcccacagaagctacagtgccaggtcacgtcatgcgccaaggcagcagcctgaggagaagacagtggccctac<br>agaatgtca |
| 137 | IGLC2*01<br>Cλ Light Chain Constant Region<br>Nucleotide Sequence-Version A | ggccagcctaaggccgtcctcttctgtgaccctctgttccccatcctccagcgacagtggcctgaaggcagaactgcaggctaacaaggccaccct<br>cgtgtgcctgatcagcgacttctaccctggcgccgtgacagtcgcctggcctgaaggcctgtatagctctctgtgaaggccg<br>gctgaaaccacacacccctccaagcagtccaacaacacaaatcgccaagtcacgtcatgcgccaaggcagcagcctgacccctgac<br>cctgagcagtgaagtcccaagtcctacaagtgccaagtcacgcatgaagggagcaccgtgacagtggagaagacagtggccctac<br>ctcctaccgagtgctcc |
| 138 | Cλ Light Chain Constant Region<br>Nucleotide Sequence-Version B | ggccagcctaaggctgtccctcccagctacttcctctgttctctccctcccagcgagagcgacagtggcctgaaggcctcaacaaggccaccct<br>cgtgtgcctgatcagcgacttctaccctggcgctgtgactgtgacaggcgtgaaagcgagctgcaagccgccgtcaagcg<br>gctggagacacacacacccccagctccaacaacacagtcacgcgccaaggcagcagcctgacccctgac<br>cagtgaagtcccaagtcctacaagtgccaagtcacgccgaggctcaccgtggaaaagaccgtcgccccac<br>cgagtgctcc |
| 139 | Cλ Light Chain Constant Region<br>Amino Acid Sequence-Encoded by version A & B | GQPKAAPSVTLFPPSSEELQANKATLVCLISDFYPGAVTVAWKADSSPVKAGVETTTPSKQSNNKYAASSYLSLTPE<br>QWKSHRSYSCQVTHEGSTVEKTVAPTECS |
| 140 | IGLC2*02<br>Cλ Light Chain Constant Region<br>Nucleotide Sequence | ggtcagcccaaggctgcccctccgtcactctgttccccctctgagagcttcaagccaacaagccacact<br>ggtgtgtctcataagtgacttctaccggaggagctgacagtggcctgaaggcagatagcagccccgtcaaggcgg<br>agtggaagaccaacacacccccaaacagctaagatgccaagtcacgcggccagcagctatcgagcctgacgctgag<br>gagtggaagtcccaagtcacgcaagtgccaggtcacgcatgaggagcaccgtgacagtggagaagacagtggccctac<br>agaatgtca |
| 141 | Cλ Light Chain Constant Region<br>Amino Acid Sequence | GQPKAAPSVTLFPPSSEELQANKATLVCLISDFYPGAVTVAWKDADSSPVKAGVETTTPSKQSNNKYAASSYLSLTP<br>EQWKSHRSYSCQVTHEGSTVEKTVAPTECS |
| 142 | IGLC3*01<br>Cλ Light Chain Constant Region<br>Nucleotide Sequence | cccaaggctgccccctcggtcactctgttccaccctctgagagcttcaagccaacaagccacccgcaaggggttg<br>tctcataagtgacttctaccggaggagctgacagtgcctgaaggcagatcagccccgtcaaggcgggtg<br>agaccaacaccacaacccccaaacagctaagatgccaggtcacgcggccagcagctactgagcctgacgctgag<br>aagtcccaagtcacgcaagtgccaggtcacgcatgaaggagcaccgtgacagttgccctacgacagtg<br>ttca |
| 143 | Cλ Light Chain Constant Region<br>Amino Acid Sequence | PKAAPSVTLFPPSSEELQANKATLVCLISDFYPGAVTVAWKDADSSPVKAGVETTTPSKQSNNKYAASSYLSLTPEQW<br>KSHKSYSCQVTHEGSTVEKTVAPTECS |
| 144 | Cλ Light Chain Constant Region<br>Nucleotide Sequence | ggtcagcccaaggctgcccctccgtcactctgttccccaccctctgagagcttcaagccaacaagccacact<br>ggtgtgtctcataagtgacttctcaccgggagctgacagtgcctgaaggcagatagcagccccgtcaaggcgg<br>ggtggaagaccaacacacccccaaagctacagtgccaggtcacgcggccagcagctaccctgagcctgacgctgag<br>cagtggaagtcccaagtcacgcatgaaggagcaccgtgacagtggagaagacagtggccctac<br>ggaatgtca |
| 145 | Cλ Light Chain Constant Region<br>Amino Acid Sequence | GQPKAAPSVTLFPPSSEELQANKATLVCLISDFYPGPVTVAWKDADSSPVKAGVETTTPSKQSNNKYAASSYLSLTP<br>EQWKSHKSYSCQVTHEGSTVEKTVAPTECS |
| 146 | IGLC3*03<br>Cλ Light Chain Constant Region<br>Nucleotide Sequence | ggtcagcccaaggctgccccctcggtcactctgttccaccctctgaggagcttcaagccaacaaggccacact<br>ggtgtgtctcataagtgacttctcaccggggagctgacagtgcctgaaggcagatagcagccccgtcaaggcgg<br>gagtggaagaccaacacacccccaaaagctacaacaagtcacgcggccagcagctacctgagcctgacgctgag<br>cagtggaagtcccaagtcacgcatgaaggagcaccgtgacagtggagaagacagtggccctac<br>agaatgtca |

SEQUENCE LISTING -continued

| Seq ID No: | Description | Sequence |
|---|---|---|
| 147 | Human Cλ constant region | GQPKAAPSVTLFPPSSEELQANKATLVLISDFYPGAVTVAWKADSSPVKAGVETTTPSKQSNNKYAASSYLSLTPEQ WKSHKSYSCQVTHEGSTVEKTVAPTECS |
| 148 | Human Cλ constant region IGLC3*04 Cλ Light Chain Constant Region Nucleotide Sequence | ggtcagcccaaggctgcccccctcggtcactctgttcccgccctcctgaggagcttcaagccaacaaggccacact ggtgtgtctcataagtgacttctacccgggagccgtgacagtggcctggaaggcagatagcagccccgtcaaggcgg gagtggagaccaccacaccctccaaacaaagcaacaacaagtacgcggccagcagctacctgagcctgacgcctgag cagtggaagtcccacagaagctacagctgccaggtcacgcatgaagggagcaccgtggagaagacagtggcccctac agaatgttca |
| 149 | Cλ Light Chain Constant Region Amino Acid Sequence | GQPKAAPSVTLFPPSSEELQANKATLVCLISDFYPGAVTVAWKADSSPVKAGVETTTPSKQSNNKYAASSYLSLTPE QWKSHRSYSCQVTHEGSTVEKTVAPTECS |
| 150 | Human Cλ constant region IGLC6*01 Cλ Light Chain Constant Region Nucleotide Sequence | ggtcagcccaaggctgcccatgctgcccccctcggtcactctgttcccaccctcctgaggagcttcaagccaacact ggtgtgcctgataagtgacttctacccgggagctgtgacagtggcctggaaggcagatggcagccccgtcaacacg gagtggagaccaccacaccctccaaacaaagcaacaacaagtacgcggccagcagctacctgagcctgacgcctgag cagtggaagtcccacagaagctcccagctgccaggtcacgcacgaagggagcaccgtggagaagacagtggcccctgc agaatgttca |
| 151 | Cλ Light Chain Constant Region Amino Acid Sequence | GQPKAAPSVTLFPPSSEELQANKATLVCLISDFYPGAVKVAWKADGSPVNTGVETTTPSKQSNNKYAASSYLSLTP EQWKSHRSYSCQVTHEGSTVEKTVAPECS |
| 152 | Human Cλ constant region IGLC7*01 And *02 Cλ Light Chain Constant Region Nucleotide Sequence | ggtcagcccaaggctgcccccctcggtcactctgttcccaccctcctgaggagcttcaagccaacaaggccacact ggtgtgtctcgtaagtgacttctacccgggagccgtgacagtggccagtaaggcagagtcagccccgtcaaggtgg gagtggagaccaccaaacccctccaaacaaagcaacaacaagtcccggtcacgcacgaagggagcaccgtggagaagacagtggcccctgc agaatgtct |
| 153 | Cλ Light Chain Constant Region Amino Acid Sequence | GQPKAAPSVTLFPPSSEELQANKATLVCLVSDFYPGAVTVAWKADGSPVKVGVETTKPSKQSNNKYAASSYLSLTPE QWKSHRSYSCRVTHEGSTVEKTVAPAECS |
| 154 | Human OPG-Fc Amino acid sequence. signal peptide sequence (usually cleaved upon expression) is underlined, polypeptide linker is underlined and in italics, Fc tag is shown in italics. | MGWSCIILFLVATATGVHSETPPKYLHYDEETSHQLLCDKCPPGTYLKQHCTAKWTVCAPCPDHYYTDSWHTSDE CLYCSPVCKELQTVKQECNRTHNRVCECKEGRYLKTVCAPCPDHYYTDSWHTSDECLYCSPVCKELQVKQECNRTH NRVCECKEGRYLEIEFCLKHRSCPPGFGVVQAGTPERNTVCKRCPDGFFSNETSSKAPCRKHTNCSVFGLLLTQKGN ATHDNICSGNSESTQKCGIDVTLCEEAFFRRAVPTKFTPNWLSVLVLNLPGTKVNAESCERIKRQHSSQEQTFQLLK LWKHQNKDQDIVKKIIQDIDLCENSVQRHIGHANLTFEQLRCLMESLPGKKVGAEDIEKTIKACKPSDQILKLLSLW RIKNGDQDTLKGLMHALKSKTYHPFKTVTQSLKKTIRFLHSFTMYKLYQKLFLEMIGNQVQSVKISCLIEGMDEP KSCDKTHTCPPCPAPELLGGPSVFLFPPKPKDTLMISRTPEVTCVVVDVSHEDPEVKFNWYVDGVEVHNAKTKPREE QINSTYRVVSVLTVLHQDWLNGKEYKCKVSNKALPAPIEKTISKAKGQPREPQVYTLPPSRDELTKNQVSLTCLVKG FYPSDIAVEWESNGQPENNYKTTPPVLDSDGSFFLYSKLTVDKSRWQQGNVFSCSVMHEALHNHYTQKSLSLSP |
| 155 | Human OPH-His Amino acid sequence. signal peptide sequence (usually cleaved upon expression) is underlined, polypeptide linker is underlined, polyhistidine tag is shown in italics. | MGWSCIILFLVATATGVHSETPPKYLHYDEETSHQLLCDKCPPGTYLKQHCTAKWTVCAPCPDHYYTDSWHTSDE CLYCSPVCKELQTVKQECNRTHNRVCECKEGRYLEIEFCLKHRSCPPGFVVQAGTPERNTVCKRCPDGFFSNETSS KAPCRKHTNCSVFGLLLTQKGNATHDNICSGNSESTQKCGIDVTLCEEAFFRRAVPTKFTPNWLSVLVDNLPGTKVN AESVERIKRQHSSQEQTFQLLKLWKHQNKDQDIVKKIIQDIDLCENSVQRHIGHANLTFEQLRSLMESLPGKKVGAE DIEKTIKACKPSDQILKLLSLWRIKNGDQDTLKGLMHALKHSKTYHPFKTVTQSLKKTIRFLHSFTMYKLYQKLFLE MIGNQVQSVKISCLHHHHHH |
| 156 | Rat OPG-Fc Amino acid sequence. signal peptide sequence (usually cleaved upon expression) is underlined, polypeptide linker is underlined and in italics, Fc tag | MGWSCIILFLVATATGVHSETPPKYLHYDPETGRQLLCDKCAPGTYLKQHCTVRRKTLCVPCPDYSYTDSWHTSDE CVVCSPVCKELQTVKQECNRTHNRVCECEEGRYLELEPCLKHRSCPPGLGVLQAGTPERNTVCKRCPDGFFSGETS KAPCRKHTNCSSLGLLLIQKGNATHDNVCSGNREATQNCGIDVTLCEEAFFRFAVPTKIIPNWLSVLVDSKPGTKVN AESVERIKRRHSSQEQTFQLLKLWKHQNRDQEMVKKIIQDIDLCESSVQRIHGHANLTEQLRILMESLPGKKISPD EIERTRKTCKPSEQLLKLLSLWRIKNGQDTLKGLMVALKHLKAYHPFKTVTHSLRKTIRFLHSFTMYRLYQKLFLE |

-continued

SEQUENCE LISTING

| Seq ID No: | Description | Sequence |
|---|---|---|
| | is shown in italics. | MIGNQVQSVKISCLLEGRMDEPKSCDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSNKALPAPIEKTISKAKGQPREPQVY<br>TLPPSRDELTKNQVSLTCLVKGFYPSDIAVEWESNGQPENNYKTTPPVLDSDGSFFLYSKLTVDKSRWQQGNVFSCS<br>VMHEALHNHYTQKSLSLSP |
| 157 | Rat OPG-His<br>Amino acid sequence.<br>Signal peptide sequence (usually<br>cleaved upon expression) is<br>underlined, polyhistidine tag is<br>shown in italics. | HGWSCIILFLVATATGVHSETFPPKYLHYDPETGRQLLCDKKEAFRRAVPTKIIPNWLSVLVDSLPGTKVN<br>CVYCSPVCKELQTVKQECNRTHNRVCECEEGRYLELEFCLKHRSCPPGLGVLQAGTPERNTVCKRCPDGFFSGETSS<br>KAPCRKHTNCSSLGLLLQKGNATHDNVCSGNREATQNCGIDVTLCEEAFRRAVPTKIIPNWLSVLVDSLPGTKVN<br>AESVERIKRRHSSQEQTFQLLKLWKHQNRDQEMVKKIIQDIDLCESSVQRHIGHANLTTEQLRILMESLPGKKISPD<br>EIERTRKTCKPSEQLLKLLSLWRIKNGDQDTLKGLMYALKHLKAYHPKTVTHSLRKTIRFLHSFTMYRLQKLFLEM<br>IGNQVQSVKISCLHHHHHH |
| 158 | Cyno OPG-His<br>Signal peptide sequence (usually<br>cleaved upon expression) is<br>underlined, polyhistidine tag is<br>shown in italics. | MGWSCIILFLVATATGVHSETFPPKYLHYDQETSHQLLCDKCPPGTYLKQHCTAKRKTVCAPCPDHYYTDSWHTSDE<br>CLYCSPVCKELQVVKQECNRTHNRVCECKEGRYLEIEFCLKHRSCPPGFGVVQAGTPERNTVCKRCPDGFFSNETSS<br>KAPCRKHTNCSVFGLLLTQKGNATHDNICSGNSESTQKCGIDVTLVEEAFRRAVPTKFTPNWLSVLDLNPGTKVNA<br>ESVERIKRRHSSQEQTFQLLLMKHQNRDQDIVKKIIQDIDLCENSVQRHIGHANLTFEQLRSLMESLPGKKVGAED<br>IEKTTKACKPSDQILKLLSLWRIKNGDQDTLKGLMHALKHSKTYHPFKTVTQSLKKTIRFLHSFTMYKLYQKLFLEM<br>IGNQVQSVKISCLHHHHHH |
| 159 | Cyno OPG-Fc<br>Amino acid sequence.<br>Signal peptide sequence (usually<br>cleaved upon expression) is<br>underlined and in italics, Fc tag<br>is shown in italics. | MGWSCIILFLVATATGVHSETFPPKYLHYDQETSHQLLCDKCPPGTYLKQHCTAKRKTVCAPCPDHYYTDSWHTSDE<br>CLYCSPVCKELQVVKQECNRTHNRVCECKEGRYLEIEFCLKHRSCPPGFGVVQAGTPERNTVCKRCPDGFFSNETSS<br>KAPCRKHTNCSVFGLLLTQKGNATHDNICSGNSESTQKCGIDVTLCEEAFRRAVPTKFTPNWLSVLVDNLPGTKVN<br>AESVERIRKRRHSSQEQTFQLLKLWKHQNKDQDIVKKIIQDIDLCENSVQRHIGHANLTFEQLRSLMESLPGKKVGA<br>EDIEKTTKACKPSDQILKLLSLWRIKNGDQDTLKGLMHALHSKTYHPFKTVTQSLKKTIRFLHSFTMYKLYQKLFL<br>EMIGNQVQSVKISCLLIERGRMDEPKSCDKTHTCPPCPAPELLGGPSVFLFPPKPKDTLMISRTPEVTCVVVDVSHED<br>PEVKFNWYVDGVEVHNAKTKPREEQYNSTYRVVSVLTVLHQDWLNGKEYKCKVSNAKLPAPIEKTISKAKGQPREPQ<br>VYTLPPSRDELTKNQVSLTCLVKGFYPSDIAVEWESNGQPENNYKTTPPVLDSDGSFFLYSKLTVDKSRWQQGNVFS<br>CSVMHEALHNHYTQKSLSLSP |
| 160 | FLAG-isoleucine<br>zipper- $(G_3S)_3$ -Human<br>TRAIL<br>Amino acid sequence.<br>Signal peptide sequence (usually<br>cleaved upon expression) is<br>underlined, FLAG tag is underlined<br>and in italics, the isoleucine<br>zipper is in italics and the<br>$(G_3S)_3$ linker is in bold. | MGWSCIILFLVATATGVHSDYKDDDDKRMKQIEDKIEEILSKIYHIENEIARIKKLIGERGGGSGGGSGGGSTSEET<br>ISTVQEKQQNISPLVRERGPQRVAAHITGTRGRSNTLSSPNSKNEKALGRKINSWESSRSGHSFLSNLHLRNGELVI<br>HEKGFYYIYSQTYFRFQEEIKENTKNDKQMVQYIYKYTSYPDPILLMKSARNSCWSKDAEYGLYSIYQGGIFELKEN<br>DIRFVSVTNEHLIDMDHEASFFGAFLVG |
| 161 | Human RANKL<br>Amino acids 64 to 245 of full-<br>length human RANKL (NCBI<br>GenBank number: AAC51762) | QSOHIRAEKAMVDGSWLDLAKRSKLEAQPFAHLTINATDIPSGSHKVSLSSWVHDRGWGKISNMTFSNGKLIVNQDG<br>FYYLYANICFRHHETSGDLATEYLQLMVYVTKTSIKIPSSHTLMKGGSTKYWSGNSEFHFYSINVGGFFKLRSGEEI<br>SIEVSNPSLLDDPQDATYFGAFKVRDID |
| 162 | Human Cλ IGLC7*03<br>constant<br>region<br>Cλ Light Chain Constant Region<br>Nucleotide Sequence | CAGCCCAAGGCTGCCCCCTCGGTCACTCTGTTCCCACCCTCCTCTGAGGAGCTTCAAGCCAACAAGGCCACACTGGT<br>GTGTCTCGTAAGTGACTTCAACCCGGGAGCCGTGACAGTGGCCTGGAAGGCAGATGCAGCCCGTCAAGGTGGGAG<br>TGGAGACCACCAAACCCTCCAAACAACAAGTACGCGGCCAGCAGCTACCTGAGCCTGACGCCTGAGCAG<br>TGGAAGTCCCACAGAAGTACAGCTGCCGGGTCACGCATGAAGGGAGCCCTGAAGACAGTGCCCCTGCAGA<br>ATGCTCT |
| 163 | Cλ Light Chain Constant Region<br>Amino Acid Sequence | QPKAAPSVTLFPPSSEELQANKATLVCLVSDFNPGAVTVAWKADGSPVKVGVETTKPSKQSNNKYAASSYLSLTPEQ<br>WKSHRSYSCRVTHEGSTVEKTVAPAECS |

The invention claimed is:

1. An antibody or an antigen-binding fragment thereof that specifically binds to human osteoprotegerin (hOPG), and inhibits the interaction of hOPG with human receptor activator of NF$_K$B ligand (hRANKL), comprising a heavy chain variable (V$_H$) region and a light chain variable (V$_L$) region, comprising:
  (a) the CDRH1 amino acid sequence of SEQ ID NO: 46 or SEQ ID NO: 49, the CDRH2 amino acid sequence of SEQ ID NO: 47 or SEQ ID NO: 50, the CDRH3 sequence of SEQ ID NO: 48 or SEQ ID NO: 51; and
  (b) the CDRL1 sequence of SEQ ID NO: 56 or SEQ ID NO: 59, the CDRL2 sequence of SEQ ID NO: 57 or SEQ ID NO: 60, and the CDRL3 sequence of SEQ ID NO: 58 or SEQ ID NO: 61.

2. The antibody or antigen-binding fragment thereof of claim 1, comprising a heavy chain constant region comprising the amino acid sequence of SEQ ID NO: 107, SEQ ID NO: 109, SEQ ID NO: 111, SEQ ID NO: 113, SEQ ID NO: 117, SEQ ID NO: 118, or SEQ ID NO: 121.

3. The antibody or antigen-binding fragment thereof of claim 1, comprising a light chain constant region comprising the amino acid sequence of SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, or SEQ ID NO: 163.

4. A pharmaceutical composition comprising the antibody or antigen-binding fragment thereof of claim 1 and a pharmaceutically acceptable carrier.

5. The pharmaceutical composition of claim 4, further comprising a further therapeutic agent.

6. The pharmaceutical composition of claim 5, wherein the further therapeutic agent is selected from the group consisting of calcium channel blockers, diuretics, ACE inhibitors, angiotensin receptor blockers (ARBs), endothelin receptor antagonists, prostacyclins, soluble guanalate cyclase agonists, phosphodiesterase inhibitors, alpha-adrenoceptor antagonists (α-blockers), beta-adrenoceptor antagonists (β-blockers), and dual α-, β-blockers.

7. A multispecific antibody or fusion protein comprising the antibody or antigen-binding fragment thereof of claim 1.

8. An antibody or an antigen-binding fragment thereof that specifically binds to human osteoprotegerin (hOPG), and inhibits the interaction of hOPG with human receptor activator of NF$_K$B ligand (hRANKL), comprising a heavy chain variable (V$_H$) region and a light chain variable (V$_L$) region, the antibody or antigen-binding fragment thereof comprising the V$_H$ region amino acid sequence of SEQ ID NO: 52 and the V$_L$ region amino acid sequence of SEQ ID NO: 62.

9. A pharmaceutical composition comprising the antibody or antigen-binding fragment thereof of claim 8 and a pharmaceutically acceptable carrier.

10. The pharmaceutical composition of claim 9, further comprising a further therapeutic agent.

11. The pharmaceutical composition of claim 10, wherein the further therapeutic agent is selected from the group consisting of calcium channel blockers, diuretics, ACE inhibitors, angiotensin receptor blockers (ARBs), endothelin receptor antagonists, prostacyclins, soluble guanalate cyclase agonists, phosphodiesterase inhibitors, alpha-adrenoceptor antagonists (α-blockers), beta-adrenoceptor antagonists (β-blockers), and dual α-, β-blockers.

12. A multispecific antibody or fusion protein comprising the antibody or antigen-binding fragment thereof of claim 8.

13. An antibody that specifically binds to human osteoprotegerin (hOPG), and inhibits the interaction of hOPG with human receptor activator of NF$_K$B ligand (hRANKL), the antibody or antigen-binding fragment thereof comprising a full-length heavy chain comprising the amino acid sequence of SEQ ID NO: 54 and a full-length light chain comprising the amino acid sequence of SEQ ID NO: 64.

14. A pharmaceutical composition comprising the antibody or antigen-binding fragment thereof of claim 13 and a pharmaceutically acceptable carrier.

15. The pharmaceutical composition of claim 14, further comprising a further therapeutic agent.

16. The pharmaceutical composition of claim 15, wherein the further therapeutic agent is selected from the group consisting of calcium channel blockers, diuretics, ACE inhibitors, angiotensin receptor blockers (ARBs), endothelin receptor antagonists, prostacyclins, soluble guanalate cyclase agonists, phosphodiesterase inhibitors, alpha-adrenoceptor antagonists (α-blockers), beta-adrenoceptor antagonists (β-blockers), and dual α-, β-blockers.

17. A multispecific antibody or fusion protein comprising the antibody of claim 13.

* * * * *

SEQUENCE LISTING

<160> NUMBER OF SEQ ID NOS: 163

<210> SEQ ID NO 1
<211> LENGTH: 401
<212> TYPE: PRT
<213> ORGANISM: Homo sapiens

<400> SEQUENCE: 1

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
        355                 360                 365

```
Ile Arg Phe Leu His Ser Phe Thr Met Tyr Lys Leu Tyr Gln Lys Leu
        370                 375                 380

Phe Leu Glu Met Ile Gly Asn Gln Val Gln Ser Val Lys Ile Ser Cys
385                 390                 395                 400

Leu

<210> SEQ ID NO 2
<211> LENGTH: 428
<212> TYPE: PRT
<213> ORGANISM: Cynomolgus

<400> SEQUENCE: 2

Met Ser Ala Arg Ala Ala Glu Thr His Arg Ser Ala Arg Pro Ala Ala
1               5                   10                  15

Ala Ser Lys Arg Leu Arg Phe Pro Gly Thr Thr Met Asn Lys Leu Leu
            20                  25                  30

Cys Cys Ala Leu Val Phe Leu Asp Ile Ser Ile Lys Trp Thr Thr Gln
        35                  40                  45

Glu Thr Phe Pro Pro Lys Tyr Leu His Tyr Asp Gln Glu Thr Ser His
    50                  55                  60

Gln Leu Leu Cys Asp Lys Cys Pro Pro Gly Thr Tyr Leu Lys Gln His
65                  70                  75                  80

Cys Thr Ala Lys Arg Lys Thr Val Cys Ala Pro Cys Pro Asp His Tyr
                85                  90                  95

Tyr Thr Asp Ser Trp His Thr Ser Asp Glu Cys Leu Tyr Cys Ser Pro
            100                 105                 110

Val Cys Lys Glu Leu Gln Tyr Val Lys Gln Glu Cys Asn Arg Thr His
        115                 120                 125

Asn Arg Val Cys Glu Cys Lys Glu Gly Arg Tyr Leu Glu Ile Glu Phe
130                 135                 140

Cys Leu Lys His Arg Ser Cys Pro Pro Gly Phe Gly Val Val Gln Ala
145                 150                 155                 160

Gly Thr Pro Glu Arg Asn Thr Val Cys Lys Arg Cys Pro Asp Gly Phe
                165                 170                 175

Phe Ser Asn Glu Thr Ser Ser Lys Ala Pro Cys Arg Lys His Thr Asn
            180                 185                 190

Cys Ser Val Phe Gly Leu Leu Leu Thr Gln Lys Gly Asn Ala Thr His
        195                 200                 205

Asp Asn Ile Cys Ser Gly Asn Ser Glu Ser Thr Gln Lys Cys Gly Ile
210                 215                 220

Asp Val Thr Leu Cys Glu Glu Ala Phe Phe Arg Phe Ala Val Pro Thr
225                 230                 235                 240

Lys Phe Thr Pro Asn Trp Leu Ser Val Leu Val Asp Asn Leu Pro Gly
                245                 250                 255

Thr Lys Val Asn Ala Glu Ser Val Glu Arg Ile Lys Arg Arg His Ser
            260                 265                 270

Ser Gln Glu Gln Thr Phe Gln Leu Leu Lys Leu Trp Lys His Gln Asn
        275                 280                 285

Lys Asp Gln Asp Ile Val Lys Lys Ile Ile Gln Asp Ile Asp Leu Cys
290                 295                 300

Glu Asn Ser Val Gln Arg His Ile Gly His Ala Asn Leu Thr Phe Glu
305                 310                 315                 320

Gln Leu Arg Ser Leu Met Glu Ser Leu Pro Gly Lys Lys Val Gly Ala
                325                 330                 335
```

```
Glu Asp Ile Glu Lys Thr Thr Lys Ala Cys Lys Pro Ser Asp Gln Ile
                340                 345                 350

Leu Lys Leu Leu Ser Leu Trp Arg Ile Lys Asn Gly Asp Gln Asp Thr
            355                 360                 365

Leu Lys Gly Leu Met His Ala Leu Lys His Ser Lys Thr Tyr His Phe
        370                 375                 380

Pro Lys Thr Val Thr Gln Ser Leu Lys Lys Thr Ile Arg Phe Leu His
385                 390                 395                 400

Ser Phe Thr Met Tyr Lys Leu Tyr Gln Lys Leu Phe Leu Glu Met Ile
                405                 410                 415

Gly Asn Gln Val Gln Ser Val Lys Ile Ser Cys Leu
            420                 425

<210> SEQ ID NO 3
<211> LENGTH: 401
<212> TYPE: PRT
<213> ORGANISM: Rattus rattus

<400> SEQUENCE: 3

Met Asn Lys Trp Leu Cys Cys Ala Leu Leu Val Phe Leu Asp Ile Ile
1               5                   10                  15

Glu Trp Thr Thr Gln Glu Thr Phe Pro Pro Lys Tyr Leu His Tyr Asp
                20                  25                  30

Pro Glu Thr Gly Arg Gln Leu Leu Cys Asp Lys Cys Ala Pro Gly Thr
            35                  40                  45

Tyr Leu Lys Gln His Cys Thr Val Arg Arg Lys Thr Leu Cys Val Pro
        50                  55                  60

Cys Pro Asp Tyr Ser Tyr Thr Asp Ser Trp His Thr Ser Asp Glu Cys
65              70                  75                  80

Val Tyr Cys Ser Pro Val Cys Lys Glu Leu Gln Thr Val Lys Gln Glu
                85                  90                  95

Cys Asn Arg Thr His Asn Arg Val Cys Glu Cys Glu Glu Gly Arg Tyr
                100                 105                 110

Leu Glu Leu Glu Phe Cys Leu Lys His Arg Ser Cys Pro Pro Gly Leu
            115                 120                 125

Gly Val Leu Gln Ala Gly Thr Pro Glu Arg Asn Thr Val Cys Lys Arg
        130                 135                 140

Cys Pro Asp Gly Phe Phe Ser Gly Glu Thr Ser Ser Lys Ala Pro Cys
145                 150                 155                 160

Arg Lys His Thr Asn Cys Ser Ser Leu Gly Leu Leu Ile Gln Lys
                165                 170                 175

Gly Asn Ala Thr His Asp Asn Val Cys Ser Gly Asn Arg Glu Ala Thr
                180                 185                 190

Gln Asn Cys Gly Ile Asp Val Thr Leu Cys Glu Glu Ala Phe Phe Arg
            195                 200                 205

Phe Ala Val Pro Thr Lys Ile Ile Pro Asn Trp Leu Ser Val Leu Val
        210                 215                 220

Asp Ser Leu Pro Gly Thr Lys Val Asn Ala Glu Ser Val Glu Arg Ile
225                 230                 235                 240

Lys Arg Arg His Ser Ser Gln Glu Gln Thr Phe Gln Leu Leu Lys Leu
                245                 250                 255

Trp Lys His Gln Asn Arg Asp Gln Glu Met Val Lys Lys Ile Ile Gln
                260                 265                 270

Asp Ile Asp Leu Cys Glu Ser Ser Val Gln Arg His Ile Gly His Ala
            275                 280                 285
```

```
Asn Leu Thr Thr Glu Gln Leu Arg Ile Leu Met Glu Ser Leu Pro Gly
        290                 295                 300

Lys Lys Ile Ser Pro Asp Glu Ile Glu Arg Thr Arg Lys Thr Cys Lys
305                 310                 315                 320

Pro Ser Glu Gln Leu Leu Lys Leu Leu Ser Leu Trp Arg Ile Lys Asn
                325                 330                 335

Gly Asp Gln Asp Thr Leu Lys Gly Leu Met Tyr Ala Leu Lys His Leu
            340                 345                 350

Lys Ala Tyr His Phe Pro Lys Thr Val Thr His Ser Leu Arg Lys Thr
        355                 360                 365

Ile Arg Phe Leu His Ser Phe Thr Met Tyr Arg Leu Tyr Gln Lys Leu
    370                 375                 380

Phe Leu Glu Met Ile Gly Asn Gln Val Gln Ser Val Lys Ile Ser Cys
385                 390                 395                 400

Leu

<210> SEQ ID NO 4
<211> LENGTH: 281
<212> TYPE: PRT
<213> ORGANISM: Homo sapiens

<400> SEQUENCE: 4

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255
```

Phe Val Ser Val Thr Asn Glu His Leu Ile Asp Met Asp His Glu Ala
                260                 265                 270

Ser Phe Phe Gly Ala Phe Leu Val Gly
        275                 280

<210> SEQ ID NO 5
<211> LENGTH: 317
<212> TYPE: PRT
<213> ORGANISM: Homo sapiens

<400> SEQUENCE: 5

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
    130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
    290                 295                 300

Ala Thr Tyr Phe Gly Ala Phe Lys Val Arg Asp Ile Asp
305                 310                 315

<210> SEQ ID NO 6
<211> LENGTH: 8
<212> TYPE: PRT

```
<213> ORGANISM: Artificial Sequence
<220> FEATURE:
<223> OTHER INFORMATION: Amino acid sequence of CDRH1 of Ky1 (6D07)
      using IMGT

<400> SEQUENCE: 6

Gly Tyr Thr Phe Thr Ser Tyr Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Amino acid sequence of CDRH2 of Ky1 (6D07)
      using IMGT

<400> SEQUENCE: 7

Ile Ser Ala Tyr Asn Gly Asn Thr
1               5

<210> SEQ ID NO 8
<211> LENGTH: 10
<212> TYPE: PRT
<213> ORGANISM: Artificial Sequence
<220> FEATURE:
<223> OTHER INFORMATION: Amino acid sequence of CDRH3 of Ky1 (6D07)
      using IMGT

<400> SEQUENCE: 8

Ala Arg Gly Gly Ser Gly Arg Tyr Tyr Pro
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Amino acid sequence of CDRH1 of Ky1 (6D07)
      using Kabat

<400> SEQUENCE: 9

Ser Tyr Gly Ile Ser
1               5

<210> SEQ ID NO 10
<211> LENGTH: 17
<212> TYPE: PRT
<213> ORGANISM: Artificial Sequence
<220> FEATURE:
<223> OTHER INFORMATION: Amino acid sequence of CDRH2 of Ky1 (6D07)
      using Kabat

<400> SEQUENCE: 10

Trp Ile Ser Ala Tyr Asn Gly Asn Thr Asn Tyr Lys Gln Lys Leu Gln
1               5                   10                  15

Gly

<210> SEQ ID NO 11
<211> LENGTH: 8
<212> TYPE: PRT
<213> ORGANISM: Artificial Sequence
<220> FEATURE:
<223> OTHER INFORMATION: Amino acid sequence of CDRH3 of Ky1 (6D07)
      using Kabat

<400> SEQUENCE: 11
```

```
Gly Gly Ser Gly Arg Tyr Tyr Pro
1               5
```

<210> SEQ ID NO 12
<211> LENGTH: 117
<212> TYPE: PRT
<213> ORGANISM: Artificial Sequence
<220> FEATURE:
<223> OTHER INFORMATION: Amino acid sequence of VH of Ky1 (6D07)

<400> SEQUENCE: 12

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Lys Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Ser Gly Arg Tyr Tyr Pro Trp Gly Gln Gly Thr Leu
            100                 105                 110

Val Thr Val Ser Ser
        115
```

<210> SEQ ID NO 13
<211> LENGTH: 351
<212> TYPE: DNA
<213> ORGANISM: Artificial Sequence
<220> FEATURE:
<223> OTHER INFORMATION: Nucleic acid sequence of VH of Ky1 (6D07)

<400> SEQUENCE: 13

```
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag gcttgagtg gatgggatgg atcagtgctt acaatggtaa cacaaactat      180
aaacagaagc tccagggcag agtcaccatg accacagaca catccacgag cacagcctac     240
atggagctga ggagcctgag atctgacgac acggccgtgt attactgtgc gagagggggc     300
agtgggaggt actatccctg gggccaggga accctggtca ccgtctcctc a              351
```

<210> SEQ ID NO 14
<211> LENGTH: 444
<212> TYPE: PRT
<213> ORGANISM: Artificial Sequence
<220> FEATURE:
<223> OTHER INFORMATION: Amino acid sequence of Ky1 (6D07) heavy chain

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Lys Gln Lys Leu
```

```
            50                  55                  60
Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Gly Ser Gly Arg Tyr Tyr Pro Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 15
<211> LENGTH: 1332
<212> TYPE: DNA
<213> ORGANISM: Artificial Sequence
```

```
<220> FEATURE:
<223> OTHER INFORMATION: Nucleic acid sequence of Ky1 (6D07) heavy chain

<400> SEQUENCE: 15
caggtgcagc tggtgcagtc tggcgccgaa gtgaagaaac ctggcgcctc cgtgaaggtg      60
tcctgcaagg cctccggcta cacctttacc agctacggca tctcctgggt gcgacaggct     120
cctggacagg gcctggaatg gatgggctgg atctccgcct acaacggcaa caccaactac     180
aagcagaaac tgcagggcag agtgaccatg accaccgaca cctccaccag caccgcctac     240
atggaactgc ggtccctgag atccgacgac accgccgtgt actactgtgc cagaggcggc     300
tccggccggt actatccttg gggacagggc accctcgtga ccgtgtcctc tgcttctacc     360
aagggcccct ccgtgttccc tctggcccct gctccagat ccacctccga gtctaccgcc     420
gctctgggct gcctcgtgaa ggactacttc cccgagcccg tgacagtgtc ttggaactct     480
ggcgccctga cctctggcgt gcacaccttc cctgctgtgc tgcagtcctc cggcctgtac     540
agcctgtcct ccgtcgtgac tgtgccctcc agctctctgg caccaagac ctacacctgt     600
aacgtggacc acaagccctc caacaccaag gtggacaagc gggtggaatc taagtacggc     660
cctccctgcc ctccttgccc agcccctgaa tttgagggcg accctctgt gtttctgttc     720
cccccaaagc ccaaggacac cctgatgatc tcccggaccc ccgaagtgac ctgcgtggtg     780
gtggatgtgt cccaggaaga tcccgaggtg cagttcaatt ggtacgtgga cggcgtggaa     840
gtgcacaacg ccaagaccaa gcctagagag gaacagttca actccaccta ccgggtggtg     900
tccgtgctga ccgtgctgca ccaggattgg ctgaacggca agagtacaa gtgcaaggtg     960
tccaacaagg gcctgcccag ctccatcgaa aagaccatct ccaaggccaa gggccagccc    1020
cgggaacccc aggtgtacac actgcctcca agccaggaag atgaccaa gaaccaggtg    1080
tccctgacct gtctcgtgaa aggcttctac ccctccgata tcgccgtgga atgggagtcc    1140
aacggccagc ctgagaacaa ttacaagacc accccccctg tgctggactc cgacggctcc    1200
ttctttctgt actcccgcct gaccgtggac aagtccagat ggcaggaagg caacgtgttc    1260
tcctgcagcg tgatgcacga ggccctgcac aaccactaca cccagaagtc cctgtccctg    1320
tctctgggaa ag                                                        1332

<210> SEQ ID NO 16
<211> LENGTH: 6
<212> TYPE: PRT
<213> ORGANISM: Artificial Sequence
<220> FEATURE:
<223> OTHER INFORMATION: Amino acid sequence of CDRL1 of Ky1 (6D07)
      using IMGT

<400> SEQUENCE: 16

Gln Gly Ile Arg Asn Asp
1               5

<210> SEQ ID NO 17
<211> LENGTH: 3
<212> TYPE: PRT
<213> ORGANISM: Artificial Sequence
<220> FEATURE:
<223> OTHER INFORMATION: Amino acid sequence of CDRL2 of Ky1 (6D07)
      using IMGT

<400> SEQUENCE: 17

Asp Ala Ser
1
```

```
<210> SEQ ID NO 18
<211> LENGTH: 9
<212> TYPE: PRT
<213> ORGANISM: Artificial Sequence
<220> FEATURE:
<223> OTHER INFORMATION: Amino acid sequence of CDRL3 of Ky1 (6D07)
      using IMGT

<400> SEQUENCE: 18

Leu Gln His Asn Ser Tyr Pro Phe Thr
1               5

<210> SEQ ID NO 19
<211> LENGTH: 11
<212> TYPE: PRT
<213> ORGANISM: Artificial Sequence
<220> FEATURE:
<223> OTHER INFORMATION: Amino acid sequence of CDRL1 of Ky1 (6D07)
      using Kabat

<400> SEQUENCE: 19

Arg Ala Ser Gln Gly Ile Arg Asn Asp Leu Gly
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Amino acid sequence of CDRL2 of Ky1 (6D07)
      using Kabat

<400> SEQUENCE: 20

Asp Ala Ser Ser Leu Gln Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Amino acid sequence of CDRL3 of Ky1 (6D07)
      using Kabat

<400> SEQUENCE: 21

Leu Gln His Asn Ser Tyr Pro Phe Thr
1               5

<210> SEQ ID NO 22
<211> LENGTH: 107
<212> TYPE: PRT
<213> ORGANISM: Artificial Sequence
<220> FEATURE:
<223> OTHER INFORMATION: Amino acid sequence of VL of Ky1 (6D07)

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Ile Pro Gly Lys Ala Pro Lys Arg Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
```

```
                65                  70                  75                  80
Glu Asp Phe Ala Thr Tyr Tyr Cys Leu Gln His Asn Ser Tyr Pro Phe
                    85                  90                  95

Thr Phe Gly Pro Gly Thr Lys Val Asp Ile Lys
            100                 105

<210> SEQ ID NO 23
<211> LENGTH: 321
<212> TYPE: DNA
<213> ORGANISM: Artificial Sequence
<220> FEATURE:
<223> OTHER INFORMATION: Nucleic acid sequence of VL of Ky1 (6D07)

<400> SEQUENCE: 23
gacatccaga tgacccagtc tccatcctcc ctgtctgcat ctgtaggaga cagagtcacc      60
atcacttgcc gggcaagtca gggcattaga aatgatttag gctggtatca gcagatacca    120
gggaaagccc ctaagcgcct gatctatgat gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccattcac tttcggccct    300
gggaccaaag tggatatcaa a                                              321

<210> SEQ ID NO 24
<211> LENGTH: 214
<212> TYPE: PRT
<213> ORGANISM: Artificial Sequence
<220> FEATURE:
<223> OTHER INFORMATION: Amino acid sequence of Ky1 (6D07) light chain

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Ile Pro Gly Lys Ala Pro Lys Arg Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 25
<211> LENGTH: 642
<212> TYPE: DNA
<213> ORGANISM: Artificial Sequence
<220> FEATURE:
<223> OTHER INFORMATION: Nucleic acid sequence of Ky1 (6D07) light chain

<400> SEQUENCE: 25

```
gacatccaga tgacccagtc ccctccagc ctgtctgctt ccgtgggcga cagagtgacc      60
atcacctgta gagcctccca gggcatccgg aacgacctgg gctggtatca gcagatccct    120
ggcaaggccc ccaagcggct gatctacgat gccagctctc tgcagtccgg cgtgccctcc    180
agattctccg gctctggctc tggcaccgag tttacccctga ccatcagctc cctgcagccc    240
gaggacttcg ccacctacta ctgcctgcag cacaactcct acccctttcac cttcggccct    300
ggcaccaagg tggacatcaa gaaaccgtg gccgctccct ccgtgttcat cttcccacct    360
tccgacgagc agctgaagtc cggcaccgct tctgtcgtgt gcctgctgaa caacttttac    420
ccccgcgagg ccaaggtgca gtggaaagtg gataacgccc tgcagagcgg caactcccag    480
gaatccgtga ccgagcagga ctccaaggac agcacctact ccctgtcctc caccctgacc    540
ctgtccaagg ccgactacga gaagcacaag gtgtacgccc gcgaagtgac ccaccagggc    600
ctgtctagcc ccgtgaccaa gtctttcaac cgggggcgagt gc                      642
```

<210> SEQ ID NO 26
<211> LENGTH: 8
<212> TYPE: PRT
<213> ORGANISM: Artificial Sequence
<220> FEATURE:
<223> OTHER INFORMATION: Amino acid sequence of CDRH1 of Ky2 (8C10)
      using IMGT

<400> SEQUENCE: 26

Gly Phe Thr Phe Asp Asp Tyr Ala
1               5

<210> SEQ ID NO 27
<211> LENGTH: 8
<212> TYPE: PRT
<213> ORGANISM: Artificial Sequence
<220> FEATURE:
<223> OTHER INFORMATION: Amino acid sequence of CDRH2 of Ky2 (8C10)
      using IMGT

<400> SEQUENCE: 27

Ile Ser Trp Asn Ser Gly Arg Ile
1               5

<210> SEQ ID NO 28
<211> LENGTH: 16
<212> TYPE: PRT
<213> ORGANISM: Artificial Sequence
<220> FEATURE:
<223> OTHER INFORMATION: Amino acid sequence of CDRH3 of Ky2 (8C10)
      using IMGT

<400> SEQUENCE: 28

Ala Lys Asp Gly Phe Tyr Asp Ile Leu Thr Gly Ser Phe Phe Asp Tyr
1               5                   10                  15

<210> SEQ ID NO 29

```
<211> LENGTH: 5
<212> TYPE: PRT
<213> ORGANISM: Artificial Sequence
<220> FEATURE:
<223> OTHER INFORMATION: Amino acid sequence of CDRH1 of Ky2 (8C10)
      using Kabat

<400> SEQUENCE: 29

Asp Tyr Ala Met His
1               5

<210> SEQ ID NO 30
<211> LENGTH: 17
<212> TYPE: PRT
<213> ORGANISM: Artificial Sequence
<220> FEATURE:
<223> OTHER INFORMATION: Amino acid sequence of CDRH2 of Ky2 (8C10)
      using Kabat

<400> SEQUENCE: 30

Ser Ile Ser Trp Asn Ser Gly Arg Ile Asp Tyr Ala Asp Ser Val Lys
1               5                   10                  15

Gly

<210> SEQ ID NO 31
<211> LENGTH: 14
<212> TYPE: PRT
<213> ORGANISM: Artificial Sequence
<220> FEATURE:
<223> OTHER INFORMATION: Amino acid sequence of CDRH3 of Ky2 (8C10)
      using Kabat

<400> SEQUENCE: 31

Asp Gly Phe Tyr Asp Ile Leu Thr Gly Ser Phe Phe Asp Tyr
1               5                   10

<210> SEQ ID NO 32
<211> LENGTH: 123
<212> TYPE: PRT
<213> ORGANISM: Artificial Sequence
<220> FEATURE:
<223> OTHER INFORMATION: Amino acid sequence of VH of Ky2 (8C10)

<400> SEQUENCE: 32

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Gly Pro Gly Lys Gly Leu Glu Trp Val
            35                  40                  45

Ser Ser Ile Ser Trp Asn Ser Gly Arg Ile Asp Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Arg Leu Arg Ala Glu Asp Thr Ala Leu Tyr Tyr Cys
                85                  90                  95

Ala Lys Asp Gly Phe Tyr Asp Ile Leu Thr Gly Ser Phe Phe Asp Tyr
            100                 105                 110

Trp Gly Gln Gly Ile Leu Val Thr Val Ser Ser
        115                 120

<210> SEQ ID NO 33
<211> LENGTH: 369
```

```
<212> TYPE: DNA
<213> ORGANISM: Artificial Sequence
<220> FEATURE:
<223> OTHER INFORMATION: Nucleic acid sequence of VH of Ky2 (8C10)

<400> SEQUENCE: 33
gaagtgcagc tggtggagtc tgggggaggc ttggtacagc ctggcaggtc cctgagactc      60
tcctgtgcag cctctggatt cacctttgat gattatgcca tgcactgggt ccggcaaggt     120
ccagggaagg gcctggagtg ggtctcaagt attagttgga atagcggtag gatagactat     180
gcggactctg tgaagggccg attcaccatc tccagagaca acgccaagaa ctccctgtat     240
ctgcaaatga accgtctgag agctgaggac acggccttgt attactgtgc aaaagatgga     300 tttttacgata ttttgactgg ctccttcttt gactactggg gccagggaat cctggtcacc     360
gtctcctca                                                              369

<210> SEQ ID NO 34
<211> LENGTH: 450
<212> TYPE: PRT
<213> ORGANISM: Artificial Sequence
<220> FEATURE:
<223> OTHER INFORMATION: Amino acid sequence of Ky2 (8C10) heavy chain

<400> SEQUENCE: 34

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Gly Pro Gly Lys Gly Leu Glu Trp Val
        35                  40                  45

Ser Ser Ile Ser Trp Asn Ser Gly Arg Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Arg Leu Arg Ala Glu Asp Thr Ala Leu Tyr Tyr Cys
                85                  90                  95

Ala Lys Asp Gly Phe Tyr Asp Ile Leu Thr Gly Ser Phe Phe Asp Tyr
            100                 105                 110

Trp Gly Gln Gly Ile Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 35
<211> LENGTH: 1350
<212> TYPE: DNA
<213> ORGANISM: Artificial Sequence
<220> FEATURE:
<223> OTHER INFORMATION: Nucleic acid sequence of Ky2 (8C10) heavy chain

<400> SEQUENCE: 35
gaagtgcagc tggtggaatc tggcggcgga ctggtgcagc ctggcagatc cctgagactg      60
tcttgtgccg cctccggctt cacctttcgac gactacgcta tgcactgggt gcgacaggga    120
cctggcaagg gcctggaatg ggtgtcctcc atctcctgga cagcggccg atcgactac       180 gccgactccg tgaagggccg gttcaccatc tcccgggaca cgccaagaa ctccctgtac      240 ctgcagatga accggctgcg ggccgaggat accgccctgt actactgtgc caaggacggc    300
ttctacgata tcctgaccgg ctccttcttc gactactggg gccagggcat cctcgtgacc    360
gtgtcctctg cttccaccaa gggcccctcc gtgtttcctc tggccccttg ctccagatcc    420
acctccgagt ctaccgccgc tctgggctgc ctcgtgaagg actacttccc cgagcccgtg    480
acagtgtctt ggaactctgg cgccctgacc tctggcgtgc acacctttcc agctgtgctg    540
cagtcctccg gcctgtactc cctgtcctcc gtcgtgactg tgccctccag ctctctgggc    600
accaagacct acacctgtaa cgtggaccac aagcccctcca acaccaaggt ggacaagaga    660
gtggaatcta agtacggccc tcccgccccc cttgtcctg cccctgaatt tgagggcgga    720
ccttctgtgt ttctgttccc cccaaagccc aaggacaccc tgatgatctc ccggaccccc    780
gaagtgacct gcgtggtggt ggatgtgtcc caggaagatc ccgaggtgca gttcaattgg    840
tacgtggacg gcgtggaagt gcacaatgcc aagaccaagc ctagagagga acagttcaac    900
```

```
tccacctacc gggtggtgtc cgtgctgacc gtgctgcatc aggactggct gaacggcaaa      960
gagtacaagt gcaaggtgtc caacaaggga ctgcccagct ccatcgaaaa gaccatctcc     1020
aaggccaagg ccagccccg ggaacccag gtgtacacac tgcctccaag ccaggaagag      1080
atgaccaaga accaggtgtc cctgacctgt ctcgtgaaag gcttctaccc ctccgatatc     1140
gccgtggaat gggagagcaa cggccagccc gagaacaact acaagaccac cccccctgtg    1200
ctggactccg acggctcctt tttcctgtac tctcgcctga ccgtggacaa gtccggtgg     1260 caggaaggca acgtgttctc ctgcagcgtg atgcacgagg ccctgcacaa ccactacacc    1320
cagaagtccc tgtccctgtc tctgggaaag                                      1350
```

```
<210> SEQ ID NO 36
<211> LENGTH: 6
<212> TYPE: PRT
<213> ORGANISM: Artificial Sequence
<220> FEATURE:
<223> OTHER INFORMATION: Amino acid sequence of CDRL1 of Ky2 (8C10)
      using IMGT

<400> SEQUENCE: 36

Gln Ser Ile Ser Ser Tyr
1               5

<210> SEQ ID NO 37
<211> LENGTH: 3
<212> TYPE: PRT
<213> ORGANISM: Artificial Sequence
<220> FEATURE:
<223> OTHER INFORMATION: Amino acid sequence of CDRL2 of Ky2 (8C10)
      using IMGT

<400> SEQUENCE: 37

Gly Ala Ser
1

<210> SEQ ID NO 38
<211> LENGTH: 11
<212> TYPE: PRT
<213> ORGANISM: Artificial Sequence
<220> FEATURE:
<223> OTHER INFORMATION: Amino acid sequence of CDRL3 of Ky2 (8C10)
      using IMGT

<400> SEQUENCE: 38

Gln Gln Ser Tyr Ser Ala Pro Pro Glu Trp Thr
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Amino acid sequence of CDRL1 of Ky2 (8C10)
      using Kabat

<400> SEQUENCE: 39

Arg Ala Ser Gln Ser Ile Ser Ser Tyr Leu Asn
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Amino acid sequence of CDRL2 of Ky2 (8C10)
``` using Kabat

<400> SEQUENCE: 40

Gly Ala Ser Ser Leu Gln Ser Gly
1               5

<210> SEQ ID NO 41
<211> LENGTH: 11
<212> TYPE: PRT
<213> ORGANISM: Artificial Sequence
<220> FEATURE:
<223> OTHER INFORMATION: Amino acid sequence of CDRL3 of Ky2 (8C10) using Kabat

<400> SEQUENCE: 41

Gln Gln Ser Tyr Ser Ala Pro Pro Glu Trp Thr
1               5                   10

<210> SEQ ID NO 42
<211> LENGTH: 109
<212> TYPE: PRT
<213> ORGANISM: Artificial Sequence
<220> FEATURE:
<223> OTHER INFORMATION: Amino acid sequence of VL of Ky2 (8C10)

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr His Gln Glu Pro Gly Lys Ala Pro Asn Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Pro
                85                  90                  95

Glu Trp Thr Phe Gly Gln Gly Thr Lys Val Glu Ile Lys
            100                 105

<210> SEQ ID NO 43
<211> LENGTH: 327
<212> TYPE: DNA
<213> ORGANISM: Artificial Sequence
<220> FEATURE:
<223> OTHER INFORMATION: Nucleic acid sequence of VL of Ky2 (8C10)

<400> SEQUENCE: 43
gacatccaga tgacccagtc tccatcctcc ctgtctgcat ctgtaggaga cagagtcacc      60
atcacttgcc gggcaagtca gagtattagc agctatttaa attggtatca ccaggaacca     120
gggaaagccc ctaacctcct gatctatggt gcatccagtt tgcaaagtgg ggtcccatcc     180
aggttcagtg gcagtggatc tgggacagat tcactctca ccatcagcag tctgcaacct      240
gaagattttg caacttacta ctgtcaacag agttacagtg cccctccgga gtggacgttc     300
ggccaaggga ccaaggtgga aatcaaa                                         327

<210> SEQ ID NO 44
<211> LENGTH: 216
<212> TYPE: PRT
<213> ORGANISM: Artificial Sequence

```
<220> FEATURE:
<223> OTHER INFORMATION: Amino acid sequence of Ky2 (8C10) light chain

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr His Gln Glu Pro Gly Lys Ala Pro Asn Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Pro
                85                  90                  95

Glu Trp Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 45
<211> LENGTH: 648
<212> TYPE: DNA
<213> ORGANISM: Artificial Sequence
<220> FEATURE:
<223> OTHER INFORMATION: Nucleic acid sequence of Ky2 (8C10) light chain

<400> SEQUENCE: 45
gacatccaga tgacccagtc cccctccagc ctgtctgctt ccgtgggcga cagagtgacc      60
atcacctgtc gggcctccca gtccatctcc tcctacctga actggtatca ccaggaaccc     120
ggcaaggccc ccaacctgct gatctacggc gcttccagtc tgcagtccgg cgtgccctct     180
agattctccg gctctggctc tggcaccgac tttaccctga ccatcagctc cctgcagccc     240
gaggacttcg ccacctacta ctgccagcag tcctactccg cccctcccga gtggacattt     300
ggccagggca ccaaggtgga aatcaagcgg accgtggccg ctcccctccgt gttcatcttc     360 ccaccttccg acgagcagct gaagtccggc accgcttctg tcgtgtgcct gctgaacaac     420
ttctaccccc gcgaggccaa ggtgcagtgg aaggtggaca cgccctgca gagcggcaac      480 tcccaggaat ccgtgaccga gcaggactcc aaggacagca cctactccct gtcctccacc     540
ctgaccctgt ccaaggccga ctacgagaag cacaaggtgt acgcctgcga agtgacccac     600
cagggcctgt ctagccccgt gaccaagtct ttcaaccggg gcgagtgc               648
```

```
<210> SEQ ID NO 46
<211> LENGTH: 8
<212> TYPE: PRT
<213> ORGANISM: Artificial Sequence
<220> FEATURE:
<223> OTHER INFORMATION: Amino acid sequence of CDRH1 of Ky3 (15F11)
      using IMGT

<400> SEQUENCE: 46

Gly Phe Thr Phe Gly Arg Tyr Asp
1               5

<210> SEQ ID NO 47
<211> LENGTH: 7
<212> TYPE: PRT
<213> ORGANISM: Artificial Sequence
<220> FEATURE:
<223> OTHER INFORMATION: Amino acid sequence of CDRH2 of Ky3 (15F11)
      using IMGT

<400> SEQUENCE: 47

Ile Gly Thr Ala Gly Asp Thr
1               5

<210> SEQ ID NO 48
<211> LENGTH: 20
<212> TYPE: PRT
<213> ORGANISM: Artificial Sequence
<220> FEATURE:
<223> OTHER INFORMATION: Amino acid sequence of CDRH3 of Ky3 (15F11)
      using IMGT

<400> SEQUENCE: 48

Ala Arg Ala Arg Pro Tyr Tyr Tyr Asp Ser Gly Ser Tyr Tyr His Ala
1               5                   10                  15

Pro Phe Asp Tyr
            20

<210> SEQ ID NO 49
<211> LENGTH: 5
<212> TYPE: PRT
<213> ORGANISM: Artificial Sequence
<220> FEATURE:
<223> OTHER INFORMATION: Amino acid sequence of CDRH1 of Ky3 (15F11)
      using Kabat

<400> SEQUENCE: 49

Arg Tyr Asp Met Asn
1               5

<210> SEQ ID NO 50
<211> LENGTH: 16
<212> TYPE: PRT
<213> ORGANISM: Artificial Sequence
<220> FEATURE:
<223> OTHER INFORMATION: Amino acid sequence of CDRH2 of Ky3 (15F11)
      using Kabat

<400> SEQUENCE: 50

Ala Ile Gly Thr Ala Gly Asp Thr Tyr Tyr Pro Gly Ser Val Lys Gly
1               5                   10                  15

<210> SEQ ID NO 51
<211> LENGTH: 18
<212> TYPE: PRT
<213> ORGANISM: Artificial Sequence
<220> FEATURE:
```

<223> OTHER INFORMATION: Amino acid sequence of CDRH3 of Ky3 (15F11)
using Kabat

<400> SEQUENCE: 51

Ala Arg Pro Tyr Tyr Tyr Asp Ser Gly Ser Tyr Tyr His Ala Pro Phe
1               5                   10                  15

Asp Tyr

<210> SEQ ID NO 52
<211> LENGTH: 126
<212> TYPE: PRT
<213> ORGANISM: Artificial Sequence
<220> FEATURE:
<223> OTHER INFORMATION: Amino acid sequence of VH of Ky3 (15F11)

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Arg Tyr
            20                  25                  30

Asp Met Asn Trp Val Arg Gln Thr Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Pro Gly Asp Thr Ala Val Tyr Tyr Cys Ala
                85                  90                  95

Arg Ala Arg Pro Tyr Tyr Tyr Asp Ser Gly Ser Tyr Tyr His Ala Pro
            100                 105                 110

Phe Asp Tyr Trp Gly Gln Gly Thr Leu Val Thr Val Ser Ser
        115                 120                 125

<210> SEQ ID NO 53
<211> LENGTH: 378
<212> TYPE: DNA
<213> ORGANISM: Artificial Sequence
<220> FEATURE:
<223> OTHER INFORMATION: Nucleic acid sequence of VH of Ky3 (15F11)

<400> SEQUENCE: 53
gaggtgcagc tggtggagtc tgggggaggc ttggtacagc ctggggggtc cctgagactc       60
tcctgtgcag cctctggatt caccttcggt aggtacgaca tgaactgggt ccgccaaact      120
acaggaaaag gtctggagtg gtctcagct attggtactg ctggtgacac atactatcca      180
ggctccgtga agggccgatt caccatctcc agagaaaatg ccaagaactc cttgtatctt      240
caaatgaaca gcctgagacc cggggacacg gctgtgtatt actgtgcaag agcaaggccg      300
tattactatg attcggggag ttattatcac gccccctttg actactgggg ccagggaacc      360
ctggtcaccg tctcctca                                                   378

<210> SEQ ID NO 54
<211> LENGTH: 453
<212> TYPE: PRT
<213> ORGANISM: Artificial Sequence
<220> FEATURE:
<223> OTHER INFORMATION: Amino acid sequence of Ky3 (15F11) heavy chain

<400> SEQUENCE: 54

Glu Val Gln Leu Val Glu Ser Gly Gly Gly Leu Val Gln Pro Gly Gly

```
                1               5                    10                   15
        Ser Leu Arg Leu Ser Cys Ala Ala Ser Gly Phe Thr Phe Gly Arg Tyr
                        20                  25                  30

Asp Met Asn Trp Val Arg Gln Thr Thr Gly Lys Gly Leu Glu Trp Val
                        35                  40                  45

Ser Ala Ile Gly Thr Ala Gly Asp Thr Tyr Tyr Pro Gly Ser Val Lys
                        50                  55                  60

Gly Arg Phe Thr Ile Ser Arg Glu Asn Ala Lys Asn Ser Leu Tyr Leu
        65                  70                  75                  80

Gln Met Asn Ser Leu Arg Pro Gly Asp Thr Ala Val Tyr Tyr Cys Ala
                        85                  90                  95

Arg Ala Arg Pro Tyr Tyr Tyr Asp Ser Gly Ser Tyr Tyr His Ala Pro
                        100                 105                 110

Phe Asp Tyr Trp Gly Gln Gly Thr Leu Val Thr Val Ser Ser Ala Ser
                        115                 120                 125

Thr Lys Gly Pro Ser Val Phe Pro Leu Ala Pro Cys Ser Arg Ser Thr
                        130                 135                 140

Ser Glu Ser Thr Ala Ala Leu Gly Cys Leu Val Lys Asp Tyr Phe Pro
        145                 150                 155                 160

Glu Pro Val Thr Val Ser Trp Asn Ser Gly Ala Leu Thr Ser Gly Val
                        165                 170                 175

His Thr Phe Pro Ala Val Leu Gln Ser Ser Gly Leu Tyr Ser Leu Ser
                        180                 185                 190

Ser Val Val Thr Val Pro Ser Ser Ser Leu Gly Thr Lys Thr Tyr Thr
                        195                 200                 205

Cys Asn Val Asp His Lys Pro Ser Asn Thr Lys Val Asp Lys Arg Val
        210                 215                 220

Glu Ser Lys Tyr Gly Pro Pro Cys Pro Pro Cys Pro Ala Pro Glu Phe
        225                 230                 235                 240

Glu Gly Gly Pro Ser Val Phe Leu Phe Pro Pro Lys Pro Lys Asp Thr
                        245                 250                 255

Leu Met Ile Ser Arg Thr Pro Glu Val Thr Cys Val Val Val Asp Val
                        260                 265                 270

Ser Gln Glu Asp Pro Glu Val Gln Phe Asn Trp Tyr Val Asp Gly Val
                        275                 280                 285

Glu Val His Asn Ala Lys Thr Lys Pro Arg Glu Glu Gln Phe Asn Ser
                        290                 295                 300

Thr Tyr Arg Val Val Ser Val Leu Thr Val Leu His Gln Asp Trp Leu
        305                 310                 315                 320

Asn Gly Lys Glu Tyr Lys Cys Lys Val Ser Asn Lys Gly Leu Pro Ser
                        325                 330                 335

Ser Ile Glu Lys Thr Ile Ser Lys Ala Lys Gly Gln Pro Arg Glu Pro
                        340                 345                 350

Gln Val Tyr Thr Leu Pro Pro Ser Gln Glu Glu Met Thr Lys Asn Gln
                        355                 360                 365

Val Ser Leu Thr Cys Leu Val Lys Gly Phe Tyr Pro Ser Asp Ile Ala
                        370                 375                 380

Val Glu Trp Glu Ser Asn Gly Gln Pro Glu Asn Asn Tyr Lys Thr Thr
        385                 390                 395                 400

Pro Pro Val Leu Asp Ser Asp Gly Ser Phe Phe Leu Tyr Ser Arg Leu
                        405                 410                 415

Thr Val Asp Lys Ser Arg Trp Gln Glu Gly Asn Val Phe Ser Cys Ser
                        420                 425                 430
```

Val Met His Glu Ala Leu His Asn His Tyr Thr Gln Lys Ser Leu Ser
    435                 440                 445

Leu Ser Leu Gly Lys
    450

<210> SEQ ID NO 55
<211> LENGTH: 1359
<212> TYPE: DNA
<213> ORGANISM: Artificial Sequence
<220> FEATURE:
<223> OTHER INFORMATION: Nucleic acid sequence of Ky3 (15F11) heavy
      chain

<400> SEQUENCE: 55

| | | | | | | |
|---|---|---|---|---|---|---|
| gaagtgcagc | tggtggaatc | tgcggcgga | ctggtgcagc | ctggcggatc | tctgagactg | 60 |
| tcttgtgccg | cctccggctt | caccttcggc | agatacgaca | tgaactgggt | gcgacagacc | 120 |
| accggaaagg | gcctggaatg | ggtgtccgct | atcggcaccg | ctggcgacac | ctactaccct | 180 |
| ggctctgtga | agggccggtt | caccatctcc | agagagaacc | caagaactc | cctgtacctg | 240 |
| cagatgaaca | gcctgcggcc | tggcgatacc | gccgtgtact | actgtgccag | agcccggcct | 300 |
| tactactacg | actccggctc | ctactaccac | gcccccttcg | attattgggg | ccagggcacc | 360 |
| ctcgtgaccg | tgtcctctgc | ttctaccaag | ggcccctccg | tgttccctct | ggccccttgc | 420 |
| tccagatcca | cctccgagtc | taccgccgct | ctgggctgcc | tcgtgaagga | ctacttcccc | 480 |
| gagcccgtga | cagtgtcttg | gaactctggc | gccctgacct | ctggcgtgca | cacctttcca | 540 |
| gctgtgctgc | agtcctccgg | cctgtactcc | ctgtcctccg | tcgtgactgt | gccctccagc | 600 |
| tctctgggca | ccaagaccta | cacctgtaac | gtggaccaca | agccctccaa | caccaaggtg | 660 |
| gacaagagag | tggaatctaa | gtacggcccc | ccctgccccc | cttgtcctgc | ccctgaattt | 720 |
| gagggcggac | cctctgtgtt | tctgttcccc | ccaaagccca | aggacaccct | gatgatctcc | 780 |
| cggacccccg | aagtgacctg | cgtggtggtg | gatgtgtccc | aggaagatcc | cgaggtgcag | 840 |
| ttcaattggt | acgtggacgg | cgtggaagtg | cacaatgcca | agaccaagcc | tagagaggaa | 900 |
| cagttcaact | ccacctaccg | ggtggtgtcc | gtgctgaccg | tgctgcatca | ggactggctg | 960 |
| aacggcaaag | agtacaagtg | caaggtgtcc | aacaagggcc | tgcccagctc | catcgaaaag | 1020 |
| accatcagca | aggccaaggg | ccagccccgg | gaacccagg | tgtacacact | gcctccaagc | 1080 |
| caggaagaga | tgaccaagaa | ccaggtgtcc | ctgacctgtc | tcgtgaaagg | cttctacccc | 1140 |
| tccgatatcg | ccgtggaatg | ggagagcaac | ggccagcccg | agaacaacta | caagaccacc | 1200 |
| cccctgtgc | tggactccga | cggctccttc | tttctgtact | ctcgcctgac | cgtggacaag | 1260 |
| tcccggtggc | aggaaggcaa | cgtgttctcc | tgcagcgtga | tgcacgaggc | cctgcacaac | 1320 |
| cactacaccc | agaagtccct | gtccctgtct | ctgggaaag | | | 1359 |

<210> SEQ ID NO 56
<211> LENGTH: 6
<212> TYPE: PRT
<213> ORGANISM: Artificial Sequence
<220> FEATURE:
<223> OTHER INFORMATION: Amino acid sequence of CDRL1 of Ky3 (15F11)
      using IMGT

<400> SEQUENCE: 56

Gln Asp Ile Ser Asn Tyr
1               5

<210> SEQ ID NO 57
<211> LENGTH: 3
<212> TYPE: PRT
<213> ORGANISM: Artificial Sequence
<220> FEATURE:
<223> OTHER INFORMATION: Amino acid sequence of CDRL2 of Ky3 (15F11)
      using IMGT

<400> SEQUENCE: 57

Asp Ala Ser
1

<210> SEQ ID NO 58
<211> LENGTH: 8
<212> TYPE: PRT
<213> ORGANISM: Artificial Sequence
<220> FEATURE:
<223> OTHER INFORMATION: Amino acid sequence of CDRL3 of Ky3 (15F11)
      using IMGT

<400> SEQUENCE: 58

Gln Gln Tyr Asp Asn Leu Phe Thr
1               5

<210> SEQ ID NO 59
<211> LENGTH: 11
<212> TYPE: PRT
<213> ORGANISM: Artificial Sequence
<220> FEATURE:
<223> OTHER INFORMATION: Amino acid sequence of CDRL1 of Ky3 (15F11)
      using Kabat

<400> SEQUENCE: 59

Gln Ala Ser Gln Asp Ile Ser Asn Tyr Leu Asn
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Amino acid sequence of CDRL2 of Ky3 (15F11)
      using Kabat

<400> SEQUENCE: 60

Asp Ala Ser Asn Leu Glu Thr
1               5

<210> SEQ ID NO 61
<211> LENGTH: 8
<212> TYPE: PRT
<213> ORGANISM: Artificial Sequence
<220> FEATURE:
<223> OTHER INFORMATION: Amino acid sequence of CDRL3 of Ky3 (15F11)
      using Kabat

<400> SEQUENCE: 61

Gln Gln Tyr Asp Asn Leu Phe Thr
1               5

<210> SEQ ID NO 62
<211> LENGTH: 106
<212> TYPE: PRT
<213> ORGANISM: Artificial Sequence
<220> FEATURE:
<223> OTHER INFORMATION: Amino acid sequence of VL of Ky3 (15F11)

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Phe Thr
                85                  90                  95

Phe Gly Pro Gly Thr Lys Val Asp Ile Lys
            100                 105

<210> SEQ ID NO 63
<211> LENGTH: 318
<212> TYPE: DNA
<213> ORGANISM: Artificial Sequence
<220> FEATURE:
<223> OTHER INFORMATION: Nucleic acid sequence of VL of Ky3 (15F11)

<400> SEQUENCE: 63
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagtg gaagtggatc tgggacagat tttactttca ccatcagcag cctgcagcct     240
gaagatattg caacatatta ctgtcaacag tatgataatc tattcacttt cggccctggg     300
accaaagtgg atatcaaa                                                   318

<210> SEQ ID NO 64
<211> LENGTH: 213
<212> TYPE: PRT
<213> ORGANISM: Artificial Sequence
<220> FEATURE:
<223> OTHER INFORMATION: Amino acid sequence of Ky3 (15F11) light chain

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Phe Thr
                85                  90                  95

Phe Gly Pro Gly Thr Lys Val Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 65
<211> LENGTH: 639
<212> TYPE: DNA
<213> ORGANISM: Artificial Sequence
<220> FEATURE:
<223> OTHER INFORMATION: Nucleic acid sequence of Ky3 (15F11) light
      chain

<400> SEQUENCE: 65
gacatccaga tgacccagtc ccctccagc ctgtctgctt ccgtgggcga cagagtgacc      60
atcacctgtc aggcctccca ggacatctcc aactacctga actggtatca gcagaagccc     120
ggcaaggccc ccaagctgct gatctacgac gcctccaacc tggaaaccgg cgtgccctcc     180
agattctccg gctctggctc tggcaccgac tttaccttca ccatcagctc cctgcagccc     240
gaggatatcg ccacctacta ctgccagcag tacgacaacc tgttcacctt cggccctggc     300
accaaggtgg acatcaagag aaccgtggcc gctccctccg tgttcatctt cccaccttcc     360
gacgagcagc tgaagtccgg caccgcttct gtcgtgtgcc tgctgaacaa cttctacccc     420
cgcgaggcca aggtgcagtg gaaagtggat aacgccctgc agtccggcaa ctcccaggaa     480
tccgtgaccg agcaggactc caaggacagc acctactccc tgtcctccac cctgaccctg     540
tccaaggccg actacgagaa gcacaaggtg tacgcctgcg aagtgaccca ccagggcctg     600
tctagccccg tgaccaagtc tttcaaccgg ggcgagtgc                            639

<210> SEQ ID NO 66
<211> LENGTH: 8
<212> TYPE: PRT
<213> ORGANISM: Artificial Sequence
<220> FEATURE:
<223> OTHER INFORMATION: Amino acid sequence of CDRH1 of Ky4 (16G05)
      using IMGT

<400> SEQUENCE: 66

Gly Phe Thr Phe Asp Asp Tyr Ala
1               5

<210> SEQ ID NO 67
<211> LENGTH: 8
<212> TYPE: PRT
<213> ORGANISM: Artificial Sequence
<220> FEATURE:
<223> OTHER INFORMATION: Amino acid sequence of CDRH2 of Ky4 (16G05)
      using IMGT

<400> SEQUENCE: 67

Ile Ser Trp Asn Ser Gly Ser Ile
1               5

<210> SEQ ID NO 68

```
<211> LENGTH: 16
<212> TYPE: PRT
<213> ORGANISM: Artificial Sequence
<220> FEATURE:
<223> OTHER INFORMATION: Amino acid sequence of CDRH3 of Ky4 (16G05)
      using IMGT

<400> SEQUENCE: 68

Ala Lys Asp Tyr Tyr Tyr Asp Ser Ser Ala Tyr Val Leu Phe Asp Tyr
1               5                   10                  15

<210> SEQ ID NO 69
<211> LENGTH: 5
<212> TYPE: PRT
<213> ORGANISM: Artificial Sequence
<220> FEATURE:
<223> OTHER INFORMATION: Amino acid sequence of CDRH1 of Ky4 (16G05)
      using Kabat

<400> SEQUENCE: 69

Asp Tyr Ala Met His
1               5

<210> SEQ ID NO 70
<211> LENGTH: 17
<212> TYPE: PRT
<213> ORGANISM: Artificial Sequence
<220> FEATURE:
<223> OTHER INFORMATION: Amino acid sequence of CDRH2 of Ky4 (16G05)
      using Kabat

<400> SEQUENCE: 70

Gly Ile Ser Trp Asn Ser Gly Ser Ile Asp Tyr Ala Asp Ser Val Lys
1               5                   10                  15

Gly

<210> SEQ ID NO 71
<211> LENGTH: 14
<212> TYPE: PRT
<213> ORGANISM: Artificial Sequence
<220> FEATURE:
<223> OTHER INFORMATION: Amino acid sequence of CDRH3 of Ky4 (16G05)
      using Kabat

<400> SEQUENCE: 71

Asp Tyr Tyr Tyr Asp Ser Ser Ala Tyr Val Leu Phe Asp Tyr
1               5                   10

<210> SEQ ID NO 72
<211> LENGTH: 123
<212> TYPE: PRT
<213> ORGANISM: Artificial Sequence
<220> FEATURE:
<223> OTHER INFORMATION: Amino acid sequence of VH of Ky4 (16G05)

<400> SEQUENCE: 72

Glu Val Gln Leu Val Glu Ser Gly Gly Gly Leu Val Gln Pro Gly Arg
1               5                   10                  15

Ser Leu Arg Leu Ser Cys Ala Val Ser Gly Phe Thr Phe Asp Asp Tyr
                20                  25                  30

Ala Met His Trp Val Arg Gln Pro Pro Gly Lys Gly Leu Glu Trp Val
            35                  40                  45

Ser Gly Ile Ser Trp Asn Ser Gly Ser Ile Asp Tyr Ala Asp Ser Val
        50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Leu Tyr Tyr Cys
                    85                  90                  95

Ala Lys Asp Tyr Tyr Tyr Asp Ser Ser Ala Tyr Val Leu Phe Asp Tyr
                    100                 105                 110

Trp Gly Gln Gly Thr Leu Val Thr Val Ser Ser
        115                 120
```

<210> SEQ ID NO 73
<211> LENGTH: 369
<212> TYPE: DNA
<213> ORGANISM: Artificial Sequence
<220> FEATURE:
<223> OTHER INFORMATION: Nucleic acid sequence of VH of Ky4 (16G05)

<400> SEQUENCE: 73

```
gaagtgcagc tggtggagtc tgggggaggc ttggtacagc ctggcaggtc cctgagactc      60
tcctgtgcag tctctggatt cacctttgat gattatgcca tgcactgggt ccggcaacct     120
ccagggaagg gcctggagtg ggtctcaggt attagttgga atagtggtag catagactat     180
gcggactctg tgaagggccg attcaccatc tccagagaca acgccaagaa ctccctgtat     240
ctgcaaatga acagtctgag agctgaggac acggccttgt attactgtgc aaaagattat     300
tactatgata gtagtgctta tgtcctcttt gactactggg ccagggaac  cctggtcacc     360 gtctcctca                                                             369
```

<210> SEQ ID NO 74
<211> LENGTH: 450
<212> TYPE: PRT
<213> ORGANISM: Artificial Sequence
<220> FEATURE:
<223> OTHER INFORMATION: Amino acid sequence of Ky4 (16G05) heavy chain

<400> SEQUENCE: 74

```
Glu Val Gln Leu Val Glu Ser Gly Gly Gly Leu Val Gln Pro Gly Arg
1               5                   10                  15

Ser Leu Arg Leu Ser Cys Ala Val Ser Gly Phe Thr Phe Asp Asp Tyr
            20                  25                  30

Ala Met His Trp Val Arg Gln Pro Gly Lys Gly Leu Glu Trp Val
        35                  40                  45

Ser Gly Ile Ser Trp Asn Ser Gly Ser Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Tyr Tyr Tyr Asp Ser Ser Ala Tyr Val Leu Phe Asp Tyr
                    100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

```
                 180                 185                 190
Thr Val Pro Ser Ser Leu Gly Thr Lys Thr Tyr Thr Cys Asn Val
            195                 200                 205
Asp His Lys Pro Ser Asn Thr Lys Val Asp Lys Arg Val Glu Ser Lys
        210                 215                 220
Tyr Gly Pro Pro Cys Pro Cys Pro Ala Pro Glu Phe Glu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser Gln Glu
            260                 265                 270
Asp Pro Glu Val Gln Phe Asn Trp Tyr Val Asp Gly Val Glu Val His
        275                 280                 285
Asn Ala Lys Thr Lys Pro Arg Glu Glu Gln Phe Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Gln Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
            420                 425                 430
Glu Ala Leu His Asn His Tyr Thr Gln Lys Ser Leu Ser Leu Ser Leu
        435                 440                 445
Gly Lys
    450

<210> SEQ ID NO 75
<211> LENGTH: 1350
<212> TYPE: DNA
<213> ORGANISM: Artificial Sequence
<220> FEATURE:
<223> OTHER INFORMATION: Nucleic acid sequence of Ky4 (16G05) heavy
      chain

<400> SEQUENCE: 75
gaagtgcagc tggtggaatc tggcggcgga ctggtgcagc ctggcagatc cctgagactg      60
tcctgtgccg tgtccggctt caccttcgac gactacgcca tgcactgggt gcgacagcct     120
ccaggcaagg gcctggaatg ggtgtccggc atctcctgga actccggctc catcgattac     180
gccgactccg tgaagggccg gttcaccatc tcccgggaca cgccaagaa ctccctgtac     240 ctgcagatga acagcctgcg ggccgaggac accgccctgt actactgcgc caaggactac     300
tactacgact cctccgccta cgtgctgttc gactactggg gccagggcac cctcgtgacc     360
gtgtcctctg cttctaccaa gggcccctcc gtgttcccct ggccccttg ctccagatcc      420 acctccgagt ctaccgccgc tctgggctgc ctcgtgaagg attacttccc cgagcccgtg     480
```

```
acagtgtctt ggaactctgg cgccctgacc tctggcgtgc acacctttcc agctgtgctg      540
cagtcctccg gcctgtactc cctgtcctcc gtcgtgactg tgccctccag ctctctgggc      600
accaagacct acacctgtaa cgtggaccac aagccctcca acaccaaggt ggacaagaga      660
gtggaatcta agtacggccc tccctgcccc ccttgtcctg cccctgaatt tgagggcgga      720
ccctctgtgt ttctgttccc cccaaagccc aaggacaccc tgatgatctc ccggaccccc      780
gaagtgacct gcgtggtggt ggatgtgtcc caggaagatc ccgaggtgca gttcaattgg      840
tacgtggacg gcgtggaagt gcacaatgcc aagaccaagc tagagagga  acagttcaac      900 tccacctacc gggtggtgtc cgtgctgacc gtgctgcatc aggactggct gaacggcaaa      960
gagtacaagt gcaaggtgtc caacaaggga ctgccttcca gcatcgaaaa gaccatctcc     1020
aaggccaagg gccagccccg ggaacccag  gtgtacacac tgcctccaag ccaggaagag     1080
atgaccaaga accaggtgtc cctgacctgt ctcgtgaaag gcttctaccc ctccgatatc     1140
gccgtggaat gggagagcaa cggccagccc gagaacaact acaagaccac ccccctgtg      1200 ctggactccg acggctcctt ctttctgtac tctcgcctga ccgtggacaa gtcccggtgg     1260
caggaaggca acgtgttctc ctgcagcgtg atgcacgagg ccctgcacaa ccactacacc     1320
cagaagtccc tgtccctgtc tctgggaaag                                      1350
```

<210> SEQ ID NO 76
<211> LENGTH: 6
<212> TYPE: PRT
<213> ORGANISM: Artificial Sequence
<220> FEATURE:
<223> OTHER INFORMATION: Amino acid sequence of CDRL1 of Ky4 (16G05)
     using IMGT

<400> SEQUENCE: 76

Gln Ser Ile Ser Ser Tyr
1               5

<210> SEQ ID NO 77
<211> LENGTH: 3
<212> TYPE: PRT
<213> ORGANISM: Artificial Sequence
<220> FEATURE:
<223> OTHER INFORMATION: Amino acid sequence of CDRL2 of Ky4 (16G05)
     using IMGT

<400> SEQUENCE: 77

Gly Ala Ser
1

<210> SEQ ID NO 78
<211> LENGTH: 9
<212> TYPE: PRT
<213> ORGANISM: Artificial Sequence
<220> FEATURE:
<223> OTHER INFORMATION: Amino acid sequence of CDRL3 of Ky4 (16G05)
     using IMGT

<400> SEQUENCE: 78

Gln Gln Ser Phe Ser Thr Pro Leu Thr
1               5

<210> SEQ ID NO 79
<211> LENGTH: 11
<212> TYPE: PRT
<213> ORGANISM: Artificial Sequence
<220> FEATURE:

<223> OTHER INFORMATION: Amino acid sequence of CDRL1 of Ky4 (16G05)
      using Kabat

<400> SEQUENCE: 79

Arg Ala Ser Gln Ser Ile Ser Ser Tyr Leu Asn
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Amino acid sequence of CDRL2 of Ky4 (16G05)
      using Kabat

<400> SEQUENCE: 80

Gly Ala Ser Ser Leu Gln Ser
1               5

<210> SEQ ID NO 81
<211> LENGTH: 9
<212> TYPE: PRT
<213> ORGANISM: Artificial Sequence
<220> FEATURE:
<223> OTHER INFORMATION: Amino acid sequence of CDRL3 of Ky4 (16G05)
      using Kabat

<400> SEQUENCE: 81

Gln Gln Ser Phe Ser Thr Pro Leu Thr
1               5

<210> SEQ ID NO 82
<211> LENGTH: 107
<212> TYPE: PRT
<213> ORGANISM: Artificial Sequence
<220> FEATURE:
<223> OTHER INFORMATION: Amino acid sequence of VL of Ky4 (16G05)

<400> SEQUENCE: 82

Asp Ile Gln Met Thr Gln Ser Pro Ser Ser Leu Ser Ala Ser Val Gly
1               5                   10                  15

Asp Arg Val Ile Ile Thr Cys Arg Ala Ser Gln Ser Ile Ser Ser Tyr
            20                  25                  30

Leu Asn Trp Tyr Gln Gln Lys Pro Gly Lys Ala Pro Glu Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Thr Pro Leu
                85                  90                  95

Thr Phe Gly Gly Gly Thr Lys Val Glu Ile Lys
            100                 105

<210> SEQ ID NO 83
<211> LENGTH: 321
<212> TYPE: DNA
<213> ORGANISM: Artificial Sequence
<220> FEATURE:
<223> OTHER INFORMATION: Nucleic acid sequence of VL of Ky4 (16G05)

<400> SEQUENCE: 83
gacatccaga tgacccagtc tccatcctcc ctgtctgcat ctgtaggaga cagagtcatc    60

```
atcacttgcc gggcaagtca gagcattagc agctatttaa attggtatca acagaaacca    120
gggaaagccc ctgagctcct gatctatggt gcatccagtt tgcaaagtgg ggtcccatca    180
aggttcagtg gcagtggatc tgggacagat ttcactctca ccatcagcag tctgcaacct    240
gaagattttg caacttacta ctgtcaacag agtttcagta ccccgctcac tttcggcgga    300
gggaccaagg tggagatcaa a                                              321
```

<210> SEQ ID NO 84
<211> LENGTH: 214
<212> TYPE: PRT
<213> ORGANISM: Artificial Sequence
<220> FEATURE:
<223> OTHER INFORMATION: Amino acid sequence of Ky4 (16G05) light chain

<400> SEQUENCE: 84

```
Asp Ile Gln Met Thr Gln Ser Pro Ser Ser Leu Ser Ala Ser Val Gly
1               5                   10                  15

Asp Arg Val Ile Ile Thr Cys Arg Ala Ser Gln Ser Ile Ser Ser Tyr
            20                  25                  30

Leu Asn Trp Tyr Gln Gln Lys Pro Gly Lys Ala Pro Glu Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 85
<211> LENGTH: 642
<212> TYPE: DNA
<213> ORGANISM: Artificial Sequence
<220> FEATURE:
<223> OTHER INFORMATION: Nucleic acid sequence of Ky4 (16G05) light
      chain

<400> SEQUENCE: 85

```
gacatccaga tgacccagtc cccctccagc ctgtctgctt ccgtgggcga cagagtgatc    60
atcacctgta gagcctccca gtccatctcc tcctacctga actggtatca gcagaagccc    120
ggcaaggccc ccgagctgct gatctatggc gcttccagtc tgcagtccgg cgtgccctct    180
```

-continued

```
agattctccg gctctggctc tggcaccgac tttaccctga ccatcagctc cctgcagccc    240
gaggacttcg ccacctacta ctgccagcag tccttctcca cccccctgac ctttggcgga    300
ggcaccaagg tggaaatcaa gcggaccgtg gccgctccct ccgtgttcat cttcccacct    360
tccgacgagc agctgaagtc cggcaccgct tctgtcgtgt gcctgctgaa caacttctac    420
ccccgcgagg ccaaggtgca gtggaaggtg acaacgccc tgcagagcgg caactcccag    480
gaatccgtga ccgagcagga ctccaaggac agcacctact ccctgtcctc caccctgacc    540
ctgtccaagg ccgactacga aagcacaag gtgtacgcct gcgaagtgac ccaccagggc    600
ctgtctagcc ccgtgaccaa gtctttcaac cggggcgagt gc                      642
```

```
<210> SEQ ID NO 86
<211> LENGTH: 8
<212> TYPE: PRT
<213> ORGANISM: Artificial Sequence
<220> FEATURE:
<223> OTHER INFORMATION: Amino acid sequence of CDRH1 of Ky5 (15H06)
      using IMGT

<400> SEQUENCE: 86

Gly Phe Thr Phe Ser Asn Ala Trp
1               5

<210> SEQ ID NO 87
<211> LENGTH: 10
<212> TYPE: PRT
<213> ORGANISM: Artificial Sequence
<220> FEATURE:
<223> OTHER INFORMATION: Amino acid sequence of CDRH2 of Ky5 (15H06)
      using IMGT

<400> SEQUENCE: 87

Ile Lys Ser Lys Thr Asp Gly Gly Thr Thr
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Amino acid sequence of CDRH3 of Ky5 (15H06)
      using IMGT

<400> SEQUENCE: 88

Thr Thr Asp Gly Ala Tyr Tyr Pro Ala Ala Phe Asp Ile
1               5                   10

<210> SEQ ID NO 89
<211> LENGTH: 5
<212> TYPE: PRT
<213> ORGANISM: Artificial Sequence
<220> FEATURE:
<223> OTHER INFORMATION: Amino acid sequence of CDRH1 of Ky5 (15H06)
      using Kabat

<400> SEQUENCE: 89

Asn Ala Trp Met Ser
1               5

<210> SEQ ID NO 90
<211> LENGTH: 19
<212> TYPE: PRT
<213> ORGANISM: Artificial Sequence
<220> FEATURE:
<223> OTHER INFORMATION: Amino acid sequence of CDRH2 of Ky5 (15H06)
``` using Kabat

<400> SEQUENCE: 90

Arg Ile Lys Ser Lys Thr Asp Gly Gly Thr Thr Asp Tyr Ala Ala Pro
1               5                   10                  15
Val Lys Gly

<210> SEQ ID NO 91
<211> LENGTH: 11
<212> TYPE: PRT
<213> ORGANISM: Artificial Sequence
<220> FEATURE:
<223> OTHER INFORMATION: Amino acid sequence of CDRH3 of Ky5 (15H06)
      using Kabat

<400> SEQUENCE: 91

Asp Gly Ala Tyr Tyr Pro Ala Ala Phe Asp Ile
1               5                   10

<210> SEQ ID NO 92
<211> LENGTH: 122
<212> TYPE: PRT
<213> ORGANISM: Artificial Sequence
<220> FEATURE:
<223> OTHER INFORMATION: Amino acid sequence of VH of Ky5 (15H06)

<400> SEQUENCE: 92

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gly Ala Tyr Tyr Pro Ala Ala Phe Asp Ile Trp
            100                 105                 110

Gly Gln Gly Thr Met Val Ser Val Ser Ser
        115                 120

<210> SEQ ID NO 93
<211> LENGTH: 366
<212> TYPE: DNA
<213> ORGANISM: Artificial Sequence
<220> FEATURE:
<223> OTHER INFORMATION: Nucleic acid sequence of VH of Ky5 (15H06)

<400> SEQUENCE: 93
gaggtgcagc tggtggagtc tgggggaggc ttggtaaagc ctggggggtc ccttagactc      60
tcctgtgcag cttctggatt cactttagt aacgcctgga tgagttgggt ccgccaggct     120
ccagggaagg gctggagtg gttggccgt attaaaagca aaactgatgg tgggacaaca      180
gactacgctg cacccgtgaa aggcagattc accatctcaa gagatgattc aaaaaacacg     240
ctgtatctgc aaatgaacag cctgaaaacc gaggacacag ccgtgtatta ctgtaccaca     300 gatgggctt actatcccgc tgcttttgat atctggggtc aagggacaat ggtcagcgtc     360
tcttca                                                                366

<210> SEQ ID NO 94
<211> LENGTH: 449
<212> TYPE: PRT
<213> ORGANISM: Artificial Sequence
<220> FEATURE:
<223> OTHER INFORMATION: Amino acid sequence of Ky5 (15H06) heavy chain

<400> SEQUENCE: 94

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gly Ala Tyr Tyr Pro Ala Ala Phe Asp Ile Trp
            100                 105                 110

Gly Gln Gly Thr Met Val Ser Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr

```
                355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
                435                 440                 445

Lys

<210> SEQ ID NO 95
<211> LENGTH: 1347
<212> TYPE: DNA
<213> ORGANISM: Artificial Sequence
<220> FEATURE:
<223> OTHER INFORMATION: Nucleic acid sequence of Ky5 (15H06) heavy
      chain

<400> SEQUENCE: 95
gaagtgcagc tggtggaatc tggcggcgga ctcgtgaagc ctggcggctc tctgagactg     60
tcttgtgccg cctccggctt caccttctcc aacgcctgga tgagctgggt gcgacaggct    120
cctggcaagg gcctggaatg ggtgggacgg atcaagtcca agaccgacgg cggcaccacc    180
gactatgctg cccctgtgaa gggccggttc accatctctc gggacgactc caagaacacc    240
ctgtacctgc agatgaactc cctgaaaacc gaggacaccg ccgtgtacta ctgtaccacc    300
gatggcgcct actaccctgc cgccttcgat atcggggcc agggcacaat ggtgtccgtg    360
tcctccgctt ccaccaaggg ccctctgtg tttcctctgg cccttgctc ccggtccacc     420
tccgaatcta cagccgctct gggctgcctc gtgaaggact acttcccga gcctgtgacc    480
gtgtcctgga actctggcgc tctgacctct ggcgtgcaca ccttccctgc tgtgctgcag    540
tctagcggcc tgtactccct gtcctccgtc gtgaccgtgc cttccagctc tctgggcacc    600
aagacctaca cctgtaacgt ggaccacaag ccctccaaca ccaaggtgga caagagagtg    660
gaatctaagt acggccctcc ctgccccct tgtcctgccc ctgaatttga gggcggaccc     720
tccgtgtttc tgttcccccc aaagcctaag acaccctga tgatctcccg gacccccgaa     780
gtgacctgcg tggtggtgga tgtgtcccag gaagatcccg aggtgcagtt caattggtac    840
gtggacggcg tggaagtgca caacgccaag accaagccta gaggaaca gttcaactcc      900
acctaccggg tggtgtctgt gctgaccgtg ctgcaccagg actggctgaa cggcaaagag    960
tacaagtgca aggtgtccaa caagggactg ccctccagca tcgaaaagac catctccaag   1020
gccagggcc agccccggga accccaggtg tacacactgc ctccaagcca ggaagagatg    1080
accaagaacc aggtgtccct gacctgtctc gtgaaaggct ctaccccctc cgatatcgcc   1140
gtggaatggg agtccaacgg ccagcctgag aacaactaca agaccacccc cctgtgctg    1200
gactccgacg gctccttctt tctgtactct cgcctgaccg tggacaagtc ccggtggcag   1260
gaaggcaacg tgttctcctg cagcgtgatg cacgaggccc tgcacaacca ctacacccag   1320
aagtccctgt ccctgtctct gggaaag                                        1347

<210> SEQ ID NO 96
<211> LENGTH: 6
```

```
<212> TYPE: PRT
<213> ORGANISM: Artificial Sequence
<220> FEATURE:
<223> OTHER INFORMATION: Amino acid sequence of CDRL1 of Ky5 (15H06)
      using IMGT

<400> SEQUENCE: 96

Gln Gly Ile Ser Ser Trp
1               5

<210> SEQ ID NO 97
<211> LENGTH: 3
<212> TYPE: PRT
<213> ORGANISM: Artificial Sequence
<220> FEATURE:
<223> OTHER INFORMATION: Amino acid sequence of CDRL2 of Ky5 (15H06)
      using IMGT

<400> SEQUENCE: 97

Ala Ala Ser
1

<210> SEQ ID NO 98
<211> LENGTH: 9
<212> TYPE: PRT
<213> ORGANISM: Artificial Sequence
<220> FEATURE:
<223> OTHER INFORMATION: Amino acid sequence of CDRL3 of Ky5 (15H06)
      using IMGT

<400> SEQUENCE: 98

Gln Gln Ser Asn Ser Phe Pro Leu Thr
1               5

<210> SEQ ID NO 99
<211> LENGTH: 11
<212> TYPE: PRT
<213> ORGANISM: Artificial Sequence
<220> FEATURE:
<223> OTHER INFORMATION: Amino acid sequence of CDRL1 of Ky5 (15H06)
      using Kabat

<400> SEQUENCE: 99

Arg Ala Ser Gln Gly Ile Ser Ser Trp Leu Ala
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Amino acid sequence of CDRL2 of Ky5 (15H06)
      using Kabat

<400> SEQUENCE: 100

Ala Ala Ser Ser Leu His Ser
1               5

<210> SEQ ID NO 101
<211> LENGTH: 9
<212> TYPE: PRT
<213> ORGANISM: Artificial Sequence
<220> FEATURE:
<223> OTHER INFORMATION: Amino acid sequence of CDRL3 of Ky5 (15H06)
      using Kabat

<400> SEQUENCE: 101

Gln Gln Ser Asn Ser Phe Pro Leu Thr
```

<210> SEQ ID NO 102
<211> LENGTH: 107
<212> TYPE: PRT
<213> ORGANISM: Artificial Sequence
<220> FEATURE:
<223> OTHER INFORMATION: Amino acid sequence of VL of Ky5 (15H06)

<400> SEQUENCE: 102

Ala Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Glu Thr Asp Phe Thr Leu Thr Ile Ser Ser Leu His Pro
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys
            100                 105

<210> SEQ ID NO 103
<211> LENGTH: 321
<212> TYPE: DNA
<213> ORGANISM: Artificial Sequence
<220> FEATURE:
<223> OTHER INFORMATION: Nucleic acid sequence of VL of Ky5 (15H06)

<400> SEQUENCE: 103
gccatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcacagtgg ggtcccatca     180
aggttcagcg gcagtggatc tgagacagat ttcactctca ccatcagcag cctgcaccct     240
gaagattttg caacttacta ttgtcaacag tctaacagtt tcccgctcac tttcggcgga     300
gggaccaagg tggagatcaa a                                               321

<210> SEQ ID NO 104
<211> LENGTH: 214
<212> TYPE: PRT
<213> ORGANISM: Artificial Sequence
<220> FEATURE:
<223> OTHER INFORMATION: Amino acid sequence of Ky5 (15H06) light chain

<400> SEQUENCE: 104

Ala Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Glu Thr Asp Phe Thr Leu Thr Ile Ser Ser Leu His Pro
65                  70                  75                  80

```
Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 105
<211> LENGTH: 642
<212> TYPE: DNA
<213> ORGANISM: Artificial Sequence
<220> FEATURE:
<223> OTHER INFORMATION: Nucleic acid sequence of Ky5 (15H06) light chain

<400> SEQUENCE: 105

```
gccatccaga tgacccagtc cccctcctcc gtgtctgctt ccgtgggcga cagagtgacc      60
atcacctgtc gggcctccca gggcatctct tcttggctgg cctggtatca gcagaagccc     120
ggcaaggccc ccaagctgct gatctacgcc gcctcctctc tgcactctgg cgtgccctct     180
agattctccg gctccggcag cgagacagac tttaccctga ccatctccag cctgcacccc     240
gaggacttcg ccacctacta ctgccagcag tccaactcct tcccactgac cttcggcgga     300
ggcaccaagg tggaaatcaa gcggaccgtg gccgctccct ccgtgttcat cttcccacct     360
tccgacgagc agctgaagtc cggcaccgct tctgtcgtgt gcctgctgaa caacttctac     420
ccccgcgagg ccaaggtgca gtggaaggtg gacaacgccc tgcagtccgg caactcccag     480
gaatccgtga ccgagcagga ctccaaggac agcacctact ccctgtcctc caccctgacc     540
ctgtccaagg ccgactacga gaagcacaag gtgtacgcct gcgaagtgac ccaccagggc     600
ctgtctagcc ccgtgaccaa gtctttcaac cggggcgagt gc                        642
```

<210> SEQ ID NO 106
<211> LENGTH: 981
<212> TYPE: DNA
<213> ORGANISM: Homo sapiens

<400> SEQUENCE: 106

```
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
```

```
aaatatggtc cccatgccc atcatgccca gcacctgagt tcctgggggg accatcagtc    360
ttcctgttcc ccccaaaacc caaggacact ctcatgatct cccggacccc tgaggtcacg    420
tgcgtggtgg tggacgtgag ccaggaagac cccgaggtcc agttcaactg gtacgtggat    480
ggcgtggagt gcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtcc tccatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggctcct tcttcctcta cagcaggcta accgtggaca agagcaggtg gcaggagggg    900
aatgtcttct catgctccgt gatgcatgag gctctgcaca accactacac acagaagagc    960
ctctccctgt ctctgggtaa a                                              981
```

<210> SEQ ID NO 107
<211> LENGTH: 327
<212> TYPE: PRT
<213> ORGANISM: Homo sapiens

<400> SEQUENCE: 107

```
Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 108
<211> LENGTH: 981
<212> TYPE: DNA
<213> ORGANISM: Homo sapiens

<400> SEQUENCE: 108

```
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc cccgtgccc atcatgccca gcacctgagt tcctgggggg accatcagtc     360
ttcctgttcc cccaaaaccc aaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcgtgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtggaca agagcaggtg gcaggagggg     900
aatgtcttct catgctccgt gatgcatgag gctctgcaca accactacac gcagaagagc     960
ctctccctgt ctctgggtaa a                                               981
```

<210> SEQ ID NO 109
<211> LENGTH: 327
<212> TYPE: PRT
<213> ORGANISM: Homo sapiens

<400> SEQUENCE: 109

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr

```
                 65                  70                  75                  80
Tyr Thr Cys Asn Val Asp His Lys Pro Ser Asn Thr Lys Val Asp Lys
                     85                  90                  95

Arg Val Glu Ser Lys Tyr Gly Pro Pro Cys Pro Ser Cys Pro Ala Pro
                    100                 105                 110

Glu Phe Leu Gly Gly Pro Ser Val Phe Leu Phe Pro Pro Lys Pro Lys
                    115                 120                 125

Asp Thr Leu Met Ile Ser Arg Thr Pro Glu Val Thr Cys Val Val Val
                    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                    165                 170                 175

Asn Ser Thr Tyr Arg Val Val Ser Val Leu Thr Val Val His Gln Asp
                    180                 185                 190

Trp Leu Asn Gly Lys Glu Tyr Lys Cys Lys Val Ser Asn Lys Gly Leu
                    195                 200                 205

Pro Ser Ser Ile Glu Lys Thr Ile Ser Lys Ala Lys Gly Gln Pro Arg
                    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                    245                 250                 255

Ile Ala Val Glu Trp Glu Ser Asn Gly Gln Pro Glu Asn Asn Tyr Lys
                    260                 265                 270

Thr Thr Pro Pro Val Leu Asp Ser Asp Gly Ser Phe Phe Leu Tyr Ser
                    275                 280                 285

Arg Leu Thr Val Asp Lys Ser Arg Trp Gln Glu Gly Asn Val Phe Ser
                    290                 295                 300

Cys Ser Val Met His Glu Ala Leu His Asn His Tyr Thr Gln Lys Ser
305                 310                 315                 320

Leu Ser Leu Ser Leu Gly Lys
                    325

<210> SEQ ID NO 110
<211> LENGTH: 981
<212> TYPE: DNA
<213> ORGANISM: Homo sapiens

<400> SEQUENCE: 110
gcttccacca agggcccatc cgtcttcccc ctggcgccct gctccaggag cacctccgag     60
agcacagccg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacgaagacc    240
tacacctgca acgtagatca caagcccagc aacaccaagg tggacaagag agttgagtcc    300
aaatatggtc ccccatgccc atcatgccca gcacctgagt tcctgggggg accatcagtc    360
ttcctgttcc ccccaaaacc caaggacact ctcatgatct cccggacccc tgaggtcacg    420
tgcgtggtgg tggacgtgag ccaggaagac cccgaggtcc agttcaactg gtacgtggat    480
ggcgtggagg tgcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtcc tccatcgaga aaaccatctc caaagccaaa    660
```

```
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggctcct tcttcctcta cagcaagctc accgtggaca gagcaggtg gcaggagggg    900 aacgtcttct catgctccgt gatgcatgag gctctgcaca accactacac gcagaagagc    960 ctctcccctgt ctctgggtaa a                                            981
```

<210> SEQ ID NO 111
<211> LENGTH: 327
<212> TYPE: PRT
<213> ORGANISM: Homo sapiens

<400> SEQUENCE: 111

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
```

Leu Ser Leu Ser Leu Gly Lys
305             310             315             320
            325

<210> SEQ ID NO 112
<211> LENGTH: 981
<212> TYPE: DNA
<213> ORGANISM: Artificial Sequence
<220> FEATURE:
<223> OTHER INFORMATION: IgG4 heavy chain constant region ?IgG4-PE

<400> SEQUENCE: 112

| | | | | |
|---|---|---|---|---|
| gcctccacca | agggcccatc | cgtcttcccc | ctggcgccct | gctccaggag cacctccgag | 60 |
| agcacggccg | ccctgggctg | cctggtcaag | gactacttcc | ccgaaccagt gacggtgtcg | 120 |
| tggaactcag | gcgccctgac | cagcggcgtg | cacaccttcc | cggctgtcct acagtcctca | 180 |
| ggactctact | ccctcagcag | cgtggtgacc | gtgccctcca | gcagcttggg cacgaagacc | 240 |
| tacacctgca | acgtagatca | caagcccagc | aacaccaagg | tggacaagag agttgagtcc | 300 |
| aaatatggtc | ccccatgccc | accatgccca | gcgcctgaat | tgagggggg accatcagtc | 360 |
| ttcctgttcc | ccccaaaacc | caaggacact | ctcatgatct | cccggacccc tgaggtcacg | 420 |
| tgcgtggtgg | tggacgtgag | ccaggaagac | cccgaggtcc | agttcaactg gtacgtggat | 480 |
| ggcgtggagg | tgcataatgc | caagacaaag | ccgcgggagg | agcagttcaa cagcacgtac | 540 |
| cgtgtggtca | gcgtcctcac | cgtcctgcac | caggactggc | tgaacggcaa ggagtacaag | 600 |
| tgcaaggtct | ccaacaaagg | cctcccgtca | tcgatcgaga | aaaccatctc caaagccaaa | 660 |
| gggcagcccc | gagagccaca | ggtgtacacc | ctgcccccat | cccaggagga gatgaccaag | 720 |
| aaccaggtca | gcctgacctg | cctggtcaaa | ggcttctacc | ccagcgacat cgccgtggag | 780 |
| tgggagagca | atgggcagcc | ggagaacaac | tacaagacca | cgcctcccgt gctggactcc | 840 |
| gacggatcct | tcttcctcta | cagcaggcta | accgtggaca | agagcaggtg gcaggagggg | 900 |
| aatgtcttct | catgctccgt | gatgcatgag | gctctgcaca | accactacac acagaagagc | 960 |
| ctctccctgt | ctctgggtaa | a | | | 981 |

<210> SEQ ID NO 113
<211> LENGTH: 327
<212> TYPE: PRT
<213> ORGANISM: Artificial Sequence
<220> FEATURE:
<223> OTHER INFORMATION: IgG4 heavy chain constant region ?IgG4-PE

<400> SEQUENCE: 113

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

```
Glu Phe Glu Gly Gly Pro Ser Val Phe Leu Phe Pro Pro Lys
    115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 114
<211> LENGTH: 981
<212> TYPE: DNA
<213> ORGANISM: Artificial Sequence
<220> FEATURE:
<223> OTHER INFORMATION: IgG4 heavy chain constant region ?IgG4-PE

<400> SEQUENCE: 114

```
gcctccacca agggacctag cgtgttccct ctcgcccct gttccaggtc cacaagcgag      60
tccaccgctg ccctcggctg tctggtgaaa gactacttc ccgagcccgt gaccgtctcc     120
tggaatagcg gagccctgac ctccggcgtg cacacattc cgccgtgct gcagagcagc     180
ggactgtata gcctgagcag cgtggtgacc gtgcccagct ccagcctcgg caccaaaacc    240
tacacctgca acgtggacca caagccctcc aacaccaagg tggacaagcg ggtggagagc    300
aagtacggcc ccccttgccc tccttgtcct gcccctgagt tcgagggagg accctccgtg    360
ttcctgtttc cccccaaacc caaggacacc ctgatgatct cccggacacc cgaggtgacc    420
tgtgtggtcg tggacgtcag ccaggaggac cccgaggtgc agttcaactg gtatgtggac    480
ggcgtggagg tgcacaatgc aaaaccaag cccaggagg agcagttcaa ttccacctac    540
agggtggtga gcgtgctgac cgtcctgcat caggattggc tgaacggcaa ggagtacaag    600
tgcaaggtgt ccaacaaggg actgcccagc tccatcgaga agaccatcag caaggctaag    660
ggccagccga gggagccca ggtgtatacc ctgcctccta gccaggaaga gatgaccaag    720
aaccaagtgt ccctgacctg cctggtgaag ggattctacc cctccgacat cgccgtggag    780
```

```
tgggagagca atggccagcc cgagaacaac tacaaaacaa cccctcccgt gctcgatagc    840
gacggcagct tctttctcta cagccggctg acagtggaca agagcaggtg gcaggagggc    900
aacgtgttct cctgttccgt gatgcacgag gccctgcaca atcactacac ccagaagagc    960 ctctcccctgt ccctgggcaa g                                              981
```

```
<210> SEQ ID NO 115
<211> LENGTH: 981
<212> TYPE: DNA
<213> ORGANISM: Artificial Sequence
<220> FEATURE:
<223> OTHER INFORMATION: IgG4 heavy chain constant region ?IgG4-PE

<400> SEQUENCE: 115
gccagcacca agggcccttc cgtgttcccc ctggcccctt gcagcaggag cacctccgaa     60
tccacagctg ccctgggctg tctggtgaag gactactttc ccgagcccgt gaccgtgagc    120
tggaacagcg gcgctctgac atccggcgtc cacacctttc ctgccgtcct gcagtcctcc    180
ggcctctact ccctgtcctc cgtggtgacc gtgcctagct cctccctcgg caccaagacc    240
tacacctgta acgtggacca caaaccctcc aacaccaagg tggacaaacg ggtcgagagc    300
aagtacggcc ctcccctgccc tccttgtcct gcccccgagt tcgaaggcgg acccagcgtg    360
ttcctgttcc ctcctaagcc caaggacacc ctcatgatca gccggacacc cgaggtgacc    420
tgcgtggtgg tggatgtgag ccaggaggac cctgaggtcc agttcaactg gtatgtggat    480
ggcgtggagg tgcacaacgc caagacaaag ccccgggaag agcagttcaa ctccacctac    540
agggtggtca gcgtgctgac cgtgctgcat caggactggc tgaacggcaa ggagtacaag    600
tgcaaggtca gcaataaggg actgcccagc agcatcgaga agaccatctc caaggctaaa    660
ggccagcccc gggaacctca ggtgtacacc ctgcctccca gccaggagga gatgaccaag    720
aaccaggtga gcctgacctg cctggtgaag ggattctacc cttccgacat cgccgtggag    780
tgggagtcca acggccagcc cgagaacaat tataagacca cccctcccgt cctcgacagc    840
gacggatcct tctttctgta ctccaggctg accgtggata agtccaggtg gcaggaaggc    900
aacgtgttca gctgctccgt gatgcacgag gccctgcaca atcactacac ccagaagtcc    960
ctgagcctgt ccctgggaaa g                                              981
```

```
<210> SEQ ID NO 116
<211> LENGTH: 981
<212> TYPE: DNA
<213> ORGANISM: Artificial Sequence
<220> FEATURE:
<223> OTHER INFORMATION: IGHC4*03 - Inactivated Heavy Chain Constant
      Region Nucleotide Sequence

<400> SEQUENCE: 116
gcctccacca agggcccatc cgtcttcccc ctggcgccct gctccaggag cacctccgag     60
agcacggccg ccctgggctg cctggtcaag gactacttcc ccgaaccagt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacgaagacc    240
tacacctgca acgtagatca caagcccagc aacaccaagg tggacaagag agttgagtcc    300
aaatatggtc cccatgccc accatgccca gcgcctccag ttgcgggggg accatcagtc    360
ttcctgttcc cccaaaaacc caaggacact ctcatgatct cccggacccc tgaggtcacg    420
tgcgtggtgg tggacgtgag ccaggaagac cccgaggtcc agttcaactg gtacgtggat    480
```

```
ggcgtggagg tgcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtca tcgatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggatcct tcttcctcta cagcaggcta accgtggaca agagcaggtg gcaggagggg    900
aatgtcttct catgctccgt gatgcatgag gctctgcaca accactacac acagaagagc    960
ctctccctgt ctctgggtaa a                                              981
```

<210> SEQ ID NO 117
<211> LENGTH: 327
<212> TYPE: PRT
<213> ORGANISM: Artificial Sequence
<220> FEATURE:
<223> OTHER INFORMATION: IGHC4*03 - Heavy Chain Constant Region Amino
      Acid Sequence with inactivating mutations

<400> SEQUENCE: 117

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 118
<211> LENGTH: 330
<212> TYPE: PRT
<213> ORGANISM: Homo sapiens

<400> SEQUENCE: 118

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

```
                305                 310                 315                 320
           Gln Lys Ser Leu Ser Leu Ser Pro Gly Lys
                           325                 330

<210> SEQ ID NO 119
<211> LENGTH: 996
<212> TYPE: DNA
<213> ORGANISM: Homo sapiens

<400> SEQUENCE: 119
gccagcacca agggcccctc tgtgttccct ctggcccctt ccagcaagtc cacctctggc      60
ggaacagccg ctctgggctg cctcgtgaag gactacttcc ccgagcctgt gaccgtgtcc     120
tggaactctg gcgctctgac cagcggagtg cacaccttcc ctgctgtgct gcagtcctcc     180
ggcctgtact ccctgtcctc cgtcgtgacc gtgccttcca gctctctggg cacccagacc     240
tacatctgca acgtgaacca caagccctcc aacaccaagg tggacaagaa ggtggaaccc     300
aagtcctgcg acaagaccca cacctgtccc cttgtcctg ccctgaact gctgggcgga      360 ccttccgtgt tcctgttccc cccaaagccc aaggacaccc tgatgatctc ccggacccc      420 gaagtgacct gcgtggtggt ggatgtgtcc cacgaggacc ctgaagtgaa gttcaattgg     480
tacgtggacg gcgtggaagt gcacaacgcc aagaccaagc ctagagagga acagtacaac     540
tccacctacc gggtggtgtc cgtgctgacc gtgctgcacc aggattggct gaacggcaaa     600
gagtacaagt gcaaggtgtc caacaaggcc ctgcctgccc ccatcgaaaa gaccatctcc     660
aaggccaagg gccagccccg gaacccccag gtgtacacac tgcccccctag cagggacgag     720 ctgaccaaga accaggtgtc cctgacctgt ctcgtgaaag gcttctaccc ctccgatatc     780
gccgtggaat gggagtccaa cggccagcct gagaacaact acaagaccac ccccctgtg     840 ctggactccg acggctcatt cttcctgtac agcaagctga cagtggacaa gtcccggtgg    900
cagcagggca acgtgttctc ctgctccgtg atgcacgagg ccctgcacaa ccactacacc     960
cagaagtccc tgtccctgag ccccggcaag tgatga                              996

<210> SEQ ID NO 120
<211> LENGTH: 990
<212> TYPE: DNA
<213> ORGANISM: Homo sapiens

<400> SEQUENCE: 120
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agtggagccc     300
aaatcttgtg acaaaactca cacatgccca ccgtgcccag cacctgaact cgcggggca      360 ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
```

```
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990
```

<210> SEQ ID NO 121
<211> LENGTH: 330
<212> TYPE: PRT
<213> ORGANISM: Homo sapiens

<400> SEQUENCE: 121

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
           100                 105                 110

Pro Ala Pro Glu Leu Ala Gly Ala Pro Ser Val Phe Leu Phe Pro Pro
       115                 120                 125

Lys Pro Lys Asp Thr Leu Met Ile Ser Arg Thr Pro Glu Val Thr Cys
   130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
               165                 170                 175

Glu Gln Tyr Asn Ser Thr Tyr Arg Val Val Ser Val Leu Thr Val Leu
           180                 185                 190

His Gln Asp Trp Leu Asn Gly Lys Glu Tyr Lys Cys Lys Val Ser Asn
       195                 200                 205

Lys Ala Leu Pro Ala Pro Ile Glu Lys Thr Ile Ser Lys Ala Lys Gly
   210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
               245                 250                 255

Pro Ser Asp Ile Ala Val Glu Trp Glu Ser Asn Gly Gln Pro Glu Asn
           260                 265                 270

Asn Tyr Lys Thr Thr Pro Pro Val Leu Asp Ser Asp Gly Ser Phe Phe
       275                 280                 285

Leu Tyr Ser Lys Leu Thr Val Asp Lys Ser Arg Trp Gln Gln Gly Asn
   290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
               325                 330
```

```
              325                 330
```

<210> SEQ ID NO 122
<211> LENGTH: 321
<212> TYPE: DNA
<213> ORGANISM: Homo sapiens

<400> SEQUENCE: 122

```
cgtacggtgg ccgctccctc cgtgttcatc ttcccacctt ccgacgagca gctgaagtcc    60
ggcaccgctt ctgtcgtgtg cctgctgaac aacttctacc ccgcgaggc caaggtgcag    120 tggaaggtgg acaacgccct gcagtccggc aactcccagg aatccgtgac cgagcaggac    180
tccaaggaca gcacctactc cctgtcctcc accctgaccc tgtccaaggc cgactacgag    240
aagcacaagg tgtacgcctg cgaagtgacc caccagggcc tgtctagccc cgtgaccaag    300
tctttcaacc ggggcgagtg t                                              321
```

<210> SEQ ID NO 123
<211> LENGTH: 107
<212> TYPE: PRT
<213> ORGANISM: Homo sapiens

<400> SEQUENCE: 123

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 124
<211> LENGTH: 321
<212> TYPE: DNA
<213> ORGANISM: Homo sapiens

<400> SEQUENCE: 124

```
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag    120
tggaaggtgg ataacgccct ccaatcgggt aactcccagg agagtgtcac agagcaggag    180
agcaaggaca gcacctacag cctcagcagc accctgacgc tgagcaaagc agactacgag    240
aaacacaaag tctacgccgg cgaagtcacc catcagggcc tgagctcgcc cgtcacaaag    300
agcttcaaca ggggagagtg t                                              321
```

<210> SEQ ID NO 125
<211> LENGTH: 107
<212> TYPE: PRT
<213> ORGANISM: Homo sapiens

<400> SEQUENCE: 125

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                85                  90                  95

Pro Val Thr Lys Ser Phe Asn Arg Gly Glu Cys
                100                 105
```

```
<210> SEQ ID NO 126
<211> LENGTH: 321
<212> TYPE: DNA
<213> ORGANISM: Homo sapiens

<400> SEQUENCE: 126
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
cggaaggtgg ataacgccct ccaatcgggt aactcccagg agagtgtcac agagcaggag     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321
```

```
<210> SEQ ID NO 127
<211> LENGTH: 107
<212> TYPE: PRT
<213> ORGANISM: Homo sapiens

<400> SEQUENCE: 127

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Arg Lys Val Asp Asn Ala Leu Gln
        35                  40                  45

Ser Gly Asn Ser Gln Glu Ser Val Thr Glu Gln Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```

```
<210> SEQ ID NO 128
<211> LENGTH: 321
<212> TYPE: DNA
<213> ORGANISM: Homo sapiens

<400> SEQUENCE: 128
cgaactgtgg ctgcaccatc tgtcttcatc ttcccgccat ctgatgagca gttgaaatct      60
```

```
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaac tctacgcctg cgaagtcacc catcagggcc tgagctcgcc cgtcacaaag    300
agcttcaaca ggggagagtg t                                              321
```

<210> SEQ ID NO 129
<211> LENGTH: 107
<212> TYPE: PRT
<213> ORGANISM: Homo sapiens

<400> SEQUENCE: 129

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 130
<211> LENGTH: 321
<212> TYPE: DNA
<213> ORGANISM: Homo sapiens

<400> SEQUENCE: 130

```
cgaactgtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcaac accctgacgc tgagcaaagc agactacgag    240
aaacacaaag tctacgcctg cgaagtcacc catcagggcc tgagctcgcc cgtcacaaag    300
agcttcaaca ggggagagtg c                                              321
```

<210> SEQ ID NO 131
<211> LENGTH: 107
<212> TYPE: PRT
<213> ORGANISM: Homo sapiens

<400> SEQUENCE: 131

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

```
Thr Tyr Ser Leu Ser Asn Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 132
<211> LENGTH: 312
<212> TYPE: DNA
<213> ORGANISM: Homo sapiens

<400> SEQUENCE: 132

```
cccaaggcca accccacggt cactctgttc ccgccctcct ctgaggagct ccaagccaac    60
aaggccacac tagtgtgtct gatcagtgac ttctacccgg gagctgtgac agtggcttgg   120
aaggcagatg gcagcccvgt caaggcggga gtggagacga ccaaaccctc caaacagagc   180
aacaacaagt acgcggccag cagctacctg agcctgacgc cgagcagtg gaagtcccac   240
agaagctaca gctgccaggt cacgcatgaa gggagcaccg tggagaagac agtggcccct   300
acagaatgtt ca                                                      312
```

<210> SEQ ID NO 133
<211> LENGTH: 104
<212> TYPE: PRT
<213> ORGANISM: Homo sapiens

<400> SEQUENCE: 133

```
Pro Lys Ala Asn Pro Thr Val Thr Leu Phe Pro Pro Ser Ser Glu Glu
 1               5                  10                  15

Leu Gln Ala Asn Lys Ala Thr Leu Val Cys Leu Ile Ser Asp Phe Tyr
             20                  25                  30

Pro Gly Ala Val Thr Val Ala Trp Lys Ala Asp Gly Ser Pro Val Lys
         35                  40                  45

Ala Gly Val Glu Thr Thr Lys Pro Ser Lys Gln Ser Asn Asn Lys Tyr
     50                  55                  60

Ala Ala Ser Ser Tyr Leu Ser Leu Thr Pro Glu Gln Trp Lys Ser His
 65                  70                  75                  80

Arg Ser Tyr Ser Cys Gln Val Thr His Glu Gly Ser Thr Val Glu Lys
                 85                  90                  95

Thr Val Ala Pro Thr Glu Cys Ser
            100
```

<210> SEQ ID NO 134
<211> LENGTH: 318
<212> TYPE: DNA
<213> ORGANISM: Homo sapiens

<400> SEQUENCE: 134

```
ggtcagccca aggccaaccc cactgtcact ctgttcccgc cctcctctga ggagctccaa    60
gccaacaagg ccacactagt gtgtctgatc agtgacttct acccgggagc tgtgacagtg   120
gcctggaagg cagatggcag ccccgtcaag gcgggagtgg agaccaccaa accctccaaa   180
cagagcaaca acaagtacgc ggccagcagc tacctgagcc tgacgcccga gcagtggaag   240
tcccacagaa gctacagctg ccaggtcacg catgaaggga gcaccgtgga agacagtg    300
gcccctacag aatgttca                                                318
```

<210> SEQ ID NO 135
<211> LENGTH: 106
<212> TYPE: PRT
<213> ORGANISM: Homo sapiens

<400> SEQUENCE: 135

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 136
<211> LENGTH: 318
<212> TYPE: DNA
<213> ORGANISM: Homo sapiens

<400> SEQUENCE: 136
ggtcagccca aggccaaccc cactgtcact ctgttcccgc cctcctctga ggagctccaa      60
gccaacaagg ccacactagt gtgtctgatc agtgacttct acccgggagc tgtgacagtg     120
gcctggaagg cagatggcag ccccgtcaag gcggagtgg agaccaccaa accctccaaa      180
cagagcaaca acaagtacgc ggccagcagc tacctgagcc tgacgcccga gcagtggaag     240
tcccacagaa gctacagctg ccaggtcacg catgaaggga gcaccgtgga aagacagtg     300 gcccctacag aatgttca                                                  318

<210> SEQ ID NO 137
<211> LENGTH: 318
<212> TYPE: DNA
<213> ORGANISM: Homo sapiens

<400> SEQUENCE: 137
ggccagccta aggccgctcc ttctgtgacc ctgttccccc catcctccga ggaactgcag      60
gctaacaagg ccaccctcgt gtgcctgatc agcgacttct accctggcgc cgtgaccgtg     120
gcctggaagg ctgatagctc tcctgtgaag gccggcgtgg aaaccaccac ccttccaag      180 cagtccaaca caaatacgc cgcctcctcc tacctgtccc tgaccctga gcagtggaag      240 tcccaccggt cctacagctg ccaagtgacc cacgagggct ccaccgtgga aagaccgtg      300 gctcctaccg agtgctcc                                                  318

<210> SEQ ID NO 138
<211> LENGTH: 318
<212> TYPE: DNA
<213> ORGANISM: Homo sapiens

<400> SEQUENCE: 138
ggccagccta aagctgcccc cagcgtcacc ctgtttcctc cctccagcga ggagctccag      60

```
gccaacaagg ccaccctcgt gtgcctgatc tccgacttct atccggcgc tgtgaccgtg    120 gcttggaaag ccgactccag ccctgtcaaa gccggcgtgg agaccaccac accctccaag   180
cagtccaaca caagtacgc cgcctccagc tatctctccc tgaccctga gcagtggaag    240 tcccaccggt cctactcctg tcaggtgacc cacgagggct ccaccgtgga aagaccgtc    300 gcccccaccg agtgctcc                                                 318

<210> SEQ ID NO 139
<211> LENGTH: 106
<212> TYPE: PRT
<213> ORGANISM: Homo sapiens

<400> SEQUENCE: 139

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 140
<211> LENGTH: 318
<212> TYPE: DNA
<213> ORGANISM: Homo sapiens

<400> SEQUENCE: 140
ggtcagccca aggctgcccc ctcggtcact ctgttcccgc cctcctctga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac accctccaaa   180
caaagcaaca caagtacgc ggccagcagc tatctgagcc tgacgcctga gcagtggaag    240
tcccacagaa gctacagctg ccaggtcacg catgaaggga gcaccgtgga agacagtg    300 gccctacag aatgttca                                                  318

<210> SEQ ID NO 141
<211> LENGTH: 106
<212> TYPE: PRT
<213> ORGANISM: Homo sapiens

<400> SEQUENCE: 141

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
50                  55                  60
```

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 142
<211> LENGTH: 312
<212> TYPE: DNA
<213> ORGANISM: Homo sapiens

<400> SEQUENCE: 142
cccaaggctg cccccctcggt cactctgttc ccaccctcct ctgaggagct tcaagccaac     60
aaggccacac tggtgtgtct cataagtgac ttctacccgg gagccgtgac agttgcctgg    120
aaggcagata gcagccccgt caaggcgggg gtggagacca ccacaccctc caaacaaagc    180
aacaacaagt acgcggccag cagctacctg agcctgacgc tgagcagtg gaagtcccac    240 aaaagctaca gctgccaggt cacgcatgaa gggagcaccg tggagaagac agttgcccct    300
acggaatgtt ca                                                       312

<210> SEQ ID NO 143
<211> LENGTH: 104
<212> TYPE: PRT
<213> ORGANISM: Homo sapiens

<400> SEQUENCE: 143

Pro Lys Ala Ala Pro Ser Val Thr Leu Phe Pro Pro Ser Ser Glu Glu
  1               5                  10                  15

Leu Gln Ala Asn Lys Ala Thr Leu Val Cys Leu Ile Ser Asp Phe Tyr
                 20                  25                  30

Pro Gly Ala Val Thr Val Ala Trp Lys Ala Asp Ser Ser Pro Val Lys
             35                  40                  45

Ala Gly Val Glu Thr Thr Thr Pro Ser Lys Gln Ser Asn Asn Lys Tyr
         50                  55                  60

Ala Ala Ser Ser Tyr Leu Ser Leu Thr Pro Glu Gln Trp Lys Ser His
 65                  70                  75                  80

Lys Ser Tyr Ser Cys Gln Val Thr His Glu Gly Ser Thr Val Glu Lys
                 85                  90                  95

Thr Val Ala Pro Thr Glu Cys Ser
            100

<210> SEQ ID NO 144
<211> LENGTH: 318
<212> TYPE: DNA
<213> ORGANISM: Homo sapiens

<400> SEQUENCE: 144
ggtcagccca aggctgcccc ctcggtcact ctgttcccac cctcctctga ggagcttcaa     60
gccaacaagg ccacactggt gtgtctcata agtgacttct acccgggagcc agtgacagtt    120 gcctggaagg cagatagcag ccccgtcaag gcggggtgg agaccaccac accctccaaa    180
caaagcaaca acaagtacgc ggccagcagc tacctgagcc tgacgcctga gcagtggaag    240
tcccacaaaa gctacagctg ccaggtcacg catgaaggga gcaccgtgga gaagacagtg    300
gcccctacgg aatgttca                                                 318

<210> SEQ ID NO 145
<211> LENGTH: 106
<212> TYPE: PRT
<213> ORGANISM: Homo sapiens

<400> SEQUENCE: 145

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Pro Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 146
<211> LENGTH: 318
<212> TYPE: DNA
<213> ORGANISM: Homo sapiens

<400> SEQUENCE: 146
ggtcagccca aggctgcccc ctcggtcact ctgttcccac cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca acaagtacgc ggccagcagc tacctgagcc tgacgcctga gcagtggaag     240
tcccacaaaa gctacagctg ccaggtcacg catgaaggga gcaccgtgga agacagtg       300
gccccctacag aatgttca                                                  318

<210> SEQ ID NO 147
<211> LENGTH: 106
<212> TYPE: PRT
<213> ORGANISM: Homo sapiens

<400> SEQUENCE: 147

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 148

<211> LENGTH: 318
<212> TYPE: DNA
<213> ORGANISM: Homo sapiens

<400> SEQUENCE: 148

```
ggtcagccca aggctgcccc ctcggtcact ctgttcccgc cctcctctga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac accctccaaa   180
caaagcaaca caagtacgc ggccagcagc tacctgagcc tgacgcctga gcagtggaag    240
tcccacagaa gctacagctg ccaggtcacg catgaaggga gcaccgtgga agacagtg     300
gcccctacag aatgttca                                                 318
```

<210> SEQ ID NO 149
<211> LENGTH: 106
<212> TYPE: PRT
<213> ORGANISM: Homo sapiens

<400> SEQUENCE: 149

```
Gly Gln Pro Lys Ala Ala Pro Ser Val Thr Leu Phe Pro Pro Ser Ser
1               5                   10                  15
Glu Glu Leu Gln Ala Asn Lys Ala Thr Leu Val Cys Leu Ile Ser Asp
            20                  25                  30
Phe Tyr Pro Gly Ala Val Thr Val Ala Trp Lys Ala Asp Ser Ser Pro
        35                  40                  45
Val Lys Ala Gly Val Glu Thr Thr Thr Pro Ser Lys Gln Ser Asn Asn
    50                  55                  60
Lys Tyr Ala Ala Ser Ser Tyr Leu Ser Leu Thr Pro Glu Gln Trp Lys
65                  70                  75                  80
Ser His Arg Ser Tyr Ser Cys Gln Val Thr His Glu Gly Ser Thr Val
                85                  90                  95
Glu Lys Thr Val Ala Pro Thr Glu Cys Ser
            100                 105
```

<210> SEQ ID NO 150
<211> LENGTH: 318
<212> TYPE: DNA
<213> ORGANISM: Homo sapiens

<400> SEQUENCE: 150

```
ggtcagccca aggctgcccc atcggtcact ctgttccgc cctcctctga ggagcttcaa     60
gccaacaagg ccacactggt gtgcctgatc agtgacttct acccgggagc tgtgaaagtg   120
gcctggaagg cagatggcag ccccgtcaac acgggagtgg agaccaccac accctccaaa   180
cagagcaaca caagtacgc ggccagcagc tacctgagcc tgacgcctga gcagtggaag    240
tcccacagaa gctacagctg ccaggtcacg catgaaggga gcaccgtgga agacagtg     300
gcccctgcag aatgttca                                                 318
```

<210> SEQ ID NO 151
<211> LENGTH: 106
<212> TYPE: PRT
<213> ORGANISM: Homo sapiens

<400> SEQUENCE: 151

```
Gly Gln Pro Lys Ala Ala Pro Ser Val Thr Leu Phe Pro Pro Ser Ser
1               5                   10                  15
Glu Glu Leu Gln Ala Asn Lys Ala Thr Leu Val Cys Leu Ile Ser Asp
```

```
            20                  25                  30

Phe Tyr Pro Gly Ala Val Lys Val Ala Trp Lys Ala Asp Gly Ser Pro
            35                  40                  45

Val Asn Thr Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Ala Glu Cys Ser
            100                 105

<210> SEQ ID NO 152
<211> LENGTH: 318
<212> TYPE: DNA
<213> ORGANISM: Homo sapiens

<400> SEQUENCE: 152
ggtcagccca aggctgcccc atcggtcact ctgttcccac cctcctctga ggagcttcaa      60
gccaacaagg ccacactggt gtgtctcgta agtgacttct acccgggagc cgtgacagtg     120
gcctggaagg cagatggcag ccccgtcaag gtgggagtgg agaccaccaa accctccaaa     180
caaagcaaca caagtatgc ggccagcagc tacctgagcc tgacgcccga gcagtggaag      240
tcccacagaa gctacagctg ccgggtcacg catgaaggga gcaccgtgga agacagtg      300 gcccctgcag aatgctct                                                   318

<210> SEQ ID NO 153
<211> LENGTH: 106
<212> TYPE: PRT
<213> ORGANISM: Homo sapiens

<400> SEQUENCE: 153

Gly Gln Pro Lys Ala Ala Pro Ser Val Thr Leu Phe Pro Pro Ser Ser
  1               5                  10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
            35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Arg Val Thr His Glu Gly Ser Thr Val
                 85                  90                  95

Glu Lys Thr Val Ala Pro Ala Glu Cys Ser
            100                 105

<210> SEQ ID NO 154
<211> LENGTH: 635
<212> TYPE: PRT
<213> ORGANISM: Homo sapiens

<400> SEQUENCE: 154

Met Gly Trp Ser Cys Ile Ile Leu Phe Leu Val Ala Thr Ala Thr Gly
  1               5                  10                  15

Val His Ser Glu Thr Phe Pro Pro Lys Tyr Leu His Tyr Asp Glu Glu
            20                  25                  30
```

```
Thr Ser His Gln Leu Leu Cys Asp Lys Cys Pro Pro Gly Thr Tyr Leu
        35                  40                  45

Lys Gln His Cys Thr Ala Lys Trp Lys Thr Val Cys Ala Pro Cys Pro
        50                  55                  60

Asp His Tyr Tyr Thr Asp Ser Trp His Thr Ser Asp Glu Cys Leu Tyr
65                  70                  75                  80

Cys Ser Pro Val Cys Lys Glu Leu Gln Tyr Val Lys Gln Glu Cys Asn
                85                  90                  95

Arg Thr His Asn Arg Val Cys Glu Cys Lys Glu Gly Arg Tyr Leu Glu
                100                 105                 110

Ile Glu Phe Cys Leu Lys His Arg Ser Cys Pro Pro Gly Phe Gly Val
        115                 120                 125

Val Gln Ala Gly Thr Pro Glu Arg Asn Thr Val Cys Lys Arg Cys Pro
        130                 135                 140

Asp Gly Phe Phe Ser Asn Glu Thr Ser Ser Lys Ala Pro Cys Arg Lys
145                 150                 155                 160

His Thr Asn Cys Ser Val Phe Gly Leu Leu Leu Thr Gln Lys Gly Asn
                165                 170                 175

Ala Thr His Asp Asn Ile Cys Ser Gly Asn Ser Glu Ser Thr Gln Lys
        180                 185                 190

Cys Gly Ile Asp Val Thr Leu Cys Glu Glu Ala Phe Phe Arg Phe Ala
        195                 200                 205

Val Pro Thr Lys Phe Thr Pro Asn Trp Leu Ser Val Leu Val Asp Asn
        210                 215                 220

Leu Pro Gly Thr Lys Val Asn Ala Glu Ser Val Glu Arg Ile Lys Arg
225                 230                 235                 240

Gln His Ser Ser Gln Glu Gln Thr Phe Gln Leu Leu Lys Leu Trp Lys
                245                 250                 255

His Gln Asn Lys Asp Gln Asp Ile Val Lys Lys Ile Ile Gln Asp Ile
        260                 265                 270

Asp Leu Cys Glu Asn Ser Val Gln Arg His Ile Gly His Ala Asn Leu
        275                 280                 285

Thr Phe Glu Gln Leu Arg Ser Leu Met Glu Ser Leu Pro Gly Lys Lys
        290                 295                 300

Val Gly Ala Glu Asp Ile Glu Lys Thr Ile Lys Ala Cys Lys Pro Ser
305                 310                 315                 320

Asp Gln Ile Leu Lys Leu Leu Ser Leu Trp Arg Ile Lys Asn Gly Asp
                325                 330                 335

Gln Asp Thr Leu Lys Gly Leu Met His Ala Leu Lys His Ser Lys Thr
        340                 345                 350

Tyr His Phe Pro Lys Thr Val Thr Gln Ser Leu Lys Lys Thr Ile Arg
        355                 360                 365

Phe Leu His Ser Phe Thr Met Tyr Lys Leu Tyr Gln Lys Leu Phe Leu
        370                 375                 380

Glu Met Ile Gly Asn Gln Val Gln Ser Val Lys Ile Ser Cys Leu Ile
385                 390                 395                 400

Glu Gly Arg Met Asp Glu Pro Lys Ser Cys Asp Lys Thr His Thr Cys
                405                 410                 415

Pro Pro Cys Pro Ala Pro Glu Leu Leu Gly Gly Pro Ser Val Phe Leu
        420                 425                 430

Phe Pro Pro Lys Pro Lys Asp Thr Leu Met Ile Ser Arg Thr Pro Glu
        435                 440                 445
```

Val Thr Cys Val Val Asp Val Ser His Glu Asp Pro Glu Val Lys
450                 455                 460

Phe Asn Trp Tyr Val Asp Gly Val Glu Val His Asn Ala Lys Thr Lys
465                 470                 475                 480

Pro Arg Glu Glu Gln Tyr Asn Ser Thr Tyr Arg Val Val Ser Val Leu
            485                 490                 495

Thr Val Leu His Gln Asp Trp Leu Asn Gly Lys Glu Tyr Lys Cys Lys
            500                 505                 510

Val Ser Asn Lys Ala Leu Pro Ala Pro Ile Glu Lys Thr Ile Ser Lys
        515                 520                 525

Ala Lys Gly Gln Pro Arg Glu Pro Gln Val Tyr Thr Leu Pro Pro Ser
530                 535                 540

Arg Asp Glu Leu Thr Lys Asn Gln Val Ser Leu Thr Cys Leu Val Lys
545                 550                 555                 560

Gly Phe Tyr Pro Ser Asp Ile Ala Val Glu Trp Glu Ser Asn Gly Gln
            565                 570                 575

Pro Glu Asn Asn Tyr Lys Thr Thr Pro Pro Val Leu Asp Ser Asp Gly
            580                 585                 590

Ser Phe Phe Leu Tyr Ser Lys Leu Thr Val Asp Lys Ser Arg Trp Gln
        595                 600                 605

Gln Gly Asn Val Phe Ser Cys Ser Val Met His Glu Ala Leu His Asn
610                 615                 620

His Tyr Thr Gln Lys Ser Leu Ser Leu Ser Pro
625                 630                 635

<210> SEQ ID NO 155
<211> LENGTH: 405
<212> TYPE: PRT
<213> ORGANISM: Homo sapiens

<400> SEQUENCE: 155

Met Gly Trp Ser Cys Ile Ile Leu Phe Leu Val Ala Thr Ala Thr Gly
1               5                   10                  15

Val His Ser Glu Thr Phe Pro Pro Lys Tyr Leu His Tyr Asp Glu Glu
            20                  25                  30

Thr Ser His Gln Leu Leu Cys Asp Lys Cys Pro Pro Gly Thr Tyr Leu
        35                  40                  45

Lys Gln His Cys Thr Ala Lys Trp Lys Thr Val Cys Ala Pro Cys Pro
    50                  55                  60

Asp His Tyr Tyr Thr Asp Ser Trp His Thr Ser Asp Glu Cys Leu Tyr
65                  70                  75                  80

Cys Ser Pro Val Cys Lys Glu Leu Gln Tyr Val Lys Gln Glu Cys Asn
                85                  90                  95

Arg Thr His Asn Arg Val Cys Glu Cys Lys Glu Gly Arg Tyr Leu Glu
            100                 105                 110

Ile Glu Phe Cys Leu Lys His Arg Ser Cys Pro Pro Gly Phe Gly Val
        115                 120                 125

Val Gln Ala Gly Thr Pro Glu Arg Asn Thr Val Cys Lys Arg Cys Pro
130                 135                 140

Asp Gly Phe Phe Ser Asn Glu Thr Ser Ser Lys Ala Pro Cys Arg Lys
145                 150                 155                 160

His Thr Asn Cys Ser Val Phe Gly Leu Leu Leu Thr Gln Lys Gly Asn
                165                 170                 175

Ala Thr His Asp Asn Ile Cys Ser Gly Asn Ser Glu Ser Thr Gln Lys
            180                 185                 190

```
Cys Gly Ile Asp Val Thr Leu Cys Glu Glu Ala Phe Phe Arg Phe Ala
        195                 200                 205

Val Pro Thr Lys Phe Thr Pro Asn Trp Leu Ser Val Leu Val Asp Asn
210                 215                 220

Leu Pro Gly Thr Lys Val Asn Ala Glu Ser Val Glu Arg Ile Lys Arg
225                 230                 235                 240

Gln His Ser Ser Gln Glu Gln Thr Phe Gln Leu Leu Lys Leu Trp Lys
                245                 250                 255

His Gln Asn Lys Asp Gln Asp Ile Val Lys Ile Ile Gln Asp Ile
            260                 265                 270

Asp Leu Cys Glu Asn Ser Val Gln Arg His Ile Gly His Ala Asn Leu
                275                 280                 285

Thr Phe Glu Gln Leu Arg Ser Leu Met Glu Ser Leu Pro Gly Lys Lys
        290                 295                 300

Val Gly Ala Glu Asp Ile Glu Lys Thr Ile Lys Ala Cys Lys Pro Ser
305                 310                 315                 320

Asp Gln Ile Leu Lys Leu Leu Ser Leu Trp Arg Ile Lys Asn Gly Asp
                325                 330                 335

Gln Asp Thr Leu Lys Gly Leu Met His Ala Leu Lys His Ser Lys Thr
                340                 345                 350

Tyr His Phe Pro Lys Thr Val Thr Gln Ser Leu Lys Lys Thr Ile Arg
        355                 360                 365

Phe Leu His Ser Phe Thr Met Tyr Lys Leu Tyr Gln Lys Leu Phe Leu
370                 375                 380

Glu Met Ile Gly Asn Gln Val Gln Ser Val Lys Ile Ser Cys Leu His
385                 390                 395                 400

His His His His His
            405

<210> SEQ ID NO 156
<211> LENGTH: 635
<212> TYPE: PRT
<213> ORGANISM: Rattus rattus

<400> SEQUENCE: 156

Met Gly Trp Ser Cys Ile Ile Leu Phe Leu Val Ala Thr Ala Thr Gly
1               5                   10                  15

Val His Ser Glu Thr Phe Pro Pro Lys Tyr Leu His Tyr Asp Pro Glu
            20                  25                  30

Thr Gly Arg Gln Leu Leu Cys Asp Lys Cys Ala Pro Gly Thr Tyr Leu
        35                  40                  45

Lys Gln His Cys Thr Val Arg Arg Lys Thr Leu Cys Val Pro Cys Pro
50                  55                  60

Asp Tyr Ser Tyr Thr Asp Ser Trp His Thr Ser Asp Glu Cys Val Tyr
65                  70                  75                  80

Cys Ser Pro Val Cys Lys Glu Leu Gln Thr Val Lys Gln Glu Cys Asn
                85                  90                  95

Arg Thr His Asn Arg Val Cys Glu Cys Glu Glu Gly Arg Tyr Leu Glu
            100                 105                 110

Leu Glu Phe Cys Leu Lys His Arg Ser Cys Pro Pro Gly Leu Gly Val
        115                 120                 125

Leu Gln Ala Gly Thr Pro Glu Arg Asn Thr Val Cys Lys Arg Cys Pro
130                 135                 140

Asp Gly Phe Phe Ser Gly Glu Thr Ser Ser Lys Ala Pro Cys Arg Lys
```

```
             145                 150                 155                 160
        His Thr Asn Cys Ser Ser Leu Gly Leu Leu Leu Ile Gln Lys Gly Asn
                         165                 170                 175

Ala Thr His Asp Asn Val Cys Ser Gly Asn Arg Glu Ala Thr Gln Asn
                         180                 185                 190

Cys Gly Ile Asp Val Thr Leu Cys Glu Glu Ala Phe Phe Arg Phe Ala
                         195                 200                 205

Val Pro Thr Lys Ile Ile Pro Asn Trp Leu Ser Val Leu Val Asp Ser
                         210                 215                 220

Leu Pro Gly Thr Lys Val Asn Ala Glu Ser Val Glu Arg Ile Lys Arg
        225                 230                 235                 240

Arg His Ser Ser Gln Glu Gln Thr Phe Gln Leu Leu Lys Leu Trp Lys
                         245                 250                 255

His Gln Asn Arg Asp Gln Glu Met Val Lys Lys Ile Ile Gln Asp Ile
                         260                 265                 270

Asp Leu Cys Glu Ser Ser Val Gln Arg His Ile Gly His Ala Asn Leu
                         275                 280                 285

Thr Thr Glu Gln Leu Arg Ile Leu Met Glu Ser Leu Pro Gly Lys Lys
                         290                 295                 300

Ile Ser Pro Asp Glu Ile Glu Arg Thr Arg Lys Thr Cys Lys Pro Ser
        305                 310                 315                 320

Glu Gln Leu Leu Lys Leu Leu Ser Leu Trp Arg Ile Lys Asn Gly Asp
                         325                 330                 335

Gln Asp Thr Leu Lys Gly Leu Met Tyr Ala Leu Lys His Leu Lys Ala
                         340                 345                 350

Tyr His Phe Pro Lys Thr Val Thr His Ser Leu Arg Lys Thr Ile Arg
                         355                 360                 365

Phe Leu His Ser Phe Thr Met Tyr Arg Leu Tyr Gln Lys Leu Phe Leu
                         370                 375                 380

Glu Met Ile Gly Asn Gln Val Gln Ser Val Lys Ile Ser Cys Leu Ile
        385                 390                 395                 400

Glu Gly Arg Met Asp Glu Pro Lys Ser Cys Asp Lys Thr His Thr Cys
                         405                 410                 415

Pro Pro Cys Pro Ala Pro Glu Leu Leu Gly Gly Pro Ser Val Phe Leu
                         420                 425                 430

Phe Pro Pro Lys Pro Lys Asp Thr Leu Met Ile Ser Arg Thr Pro Glu
                         435                 440                 445

Val Thr Cys Val Val Val Asp Val Ser His Glu Asp Pro Glu Val Lys
        450                 455                 460

Phe Asn Trp Tyr Val Asp Gly Val Glu Val His Asn Ala Lys Thr Lys
        465                 470                 475                 480

Pro Arg Glu Glu Gln Tyr Asn Ser Thr Tyr Arg Val Val Ser Val Leu
                         485                 490                 495

Thr Val Leu His Gln Asp Trp Leu Asn Gly Lys Glu Tyr Lys Cys Lys
                         500                 505                 510

Val Ser Asn Lys Ala Leu Pro Ala Pro Ile Glu Lys Thr Ile Ser Lys
                         515                 520                 525

Ala Lys Gly Gln Pro Arg Glu Pro Gln Val Tyr Thr Leu Pro Pro Ser
                         530                 535                 540

Arg Asp Glu Leu Thr Lys Asn Gln Val Ser Leu Thr Cys Leu Val Lys
        545                 550                 555                 560

Gly Phe Tyr Pro Ser Asp Ile Ala Val Glu Trp Glu Ser Asn Gly Gln
                         565                 570                 575
```

```
Pro Glu Asn Asn Tyr Lys Thr Thr Pro Pro Val Leu Asp Ser Asp Gly
            580                 585                 590

Ser Phe Phe Leu Tyr Ser Lys Leu Thr Val Asp Lys Ser Arg Trp Gln
            595                 600                 605

Gln Gly Asn Val Phe Ser Cys Ser Val Met His Glu Ala Leu His Asn
            610                 615                 620

His Tyr Thr Gln Lys Ser Leu Ser Leu Ser Pro
625                 630                 635

<210> SEQ ID NO 157
<211> LENGTH: 405
<212> TYPE: PRT
<213> ORGANISM: Rattus rattus

<400> SEQUENCE: 157

Met Gly Trp Ser Cys Ile Ile Leu Phe Leu Val Ala Thr Ala Thr Gly
1               5                   10                  15

Val His Ser Glu Thr Phe Pro Pro Lys Tyr Leu His Tyr Asp Pro Glu
            20                  25                  30

Thr Gly Arg Gln Leu Leu Cys Asp Lys Cys Ala Pro Gly Thr Tyr Leu
        35                  40                  45

Lys Gln His Cys Thr Val Arg Arg Lys Thr Leu Cys Val Pro Cys Pro
50                  55                  60

Asp Tyr Ser Tyr Thr Asp Ser Trp His Thr Ser Asp Glu Cys Val Tyr
65                  70                  75                  80

Cys Ser Pro Val Cys Lys Glu Leu Gln Thr Val Lys Gln Glu Cys Asn
            85                  90                  95

Arg Thr His Asn Arg Val Cys Glu Cys Glu Glu Gly Arg Tyr Leu Glu
            100                 105                 110

Leu Glu Phe Cys Leu Lys His Arg Ser Cys Pro Pro Gly Leu Gly Val
        115                 120                 125

Leu Gln Ala Gly Thr Pro Glu Arg Asn Thr Val Cys Lys Arg Cys Pro
    130                 135                 140

Asp Gly Phe Phe Ser Gly Glu Thr Ser Ser Lys Ala Pro Cys Arg Lys
145                 150                 155                 160

His Thr Asn Cys Ser Ser Leu Gly Leu Leu Leu Ile Gln Lys Gly Asn
            165                 170                 175

Ala Thr His Asp Asn Val Cys Ser Gly Asn Arg Glu Ala Thr Gln Asn
            180                 185                 190

Cys Gly Ile Asp Val Thr Leu Cys Glu Glu Ala Phe Phe Arg Phe Ala
        195                 200                 205

Val Pro Thr Lys Ile Ile Pro Asn Trp Leu Ser Val Leu Val Asp Ser
    210                 215                 220

Leu Pro Gly Thr Lys Val Asn Ala Glu Ser Val Glu Arg Ile Lys Arg
225                 230                 235                 240

Arg His Ser Ser Gln Glu Gln Thr Phe Gln Leu Leu Lys Leu Trp Lys
            245                 250                 255

His Gln Asn Arg Asp Gln Glu Met Val Lys Lys Ile Ile Gln Asp Ile
            260                 265                 270

Asp Leu Cys Glu Ser Ser Val Gln Arg His Ile Gly His Ala Asn Leu
        275                 280                 285

Thr Thr Glu Gln Leu Arg Ile Leu Met Glu Ser Leu Pro Gly Lys Lys
    290                 295                 300

Ile Ser Pro Asp Glu Ile Glu Arg Thr Arg Lys Thr Cys Lys Pro Ser
```

```
              305                 310                 315                 320
    Glu Gln Leu Leu Lys Leu Leu Ser Leu Trp Arg Ile Lys Asn Gly Asp
                        325                 330                 335

Gln Asp Thr Leu Lys Gly Leu Met Tyr Ala Leu Lys His Leu Lys Ala
                        340                 345                 350

Tyr His Phe Pro Lys Thr Val Thr His Ser Leu Arg Lys Thr Ile Arg
                        355                 360                 365

Phe Leu His Ser Phe Thr Met Tyr Arg Leu Tyr Gln Lys Leu Phe Leu
                        370                 375                 380

Glu Met Ile Gly Asn Gln Val Gln Ser Val Lys Ile Ser Cys Leu His
    385                 390                 395                 400

His His His His His
                        405

<210> SEQ ID NO 158
<211> LENGTH: 405
<212> TYPE: PRT
<213> ORGANISM: Cynomolgus

<400> SEQUENCE: 158

Met Gly Trp Ser Cys Ile Ile Leu Phe Leu Val Ala Thr Ala Thr Gly
    1               5                   10                  15

Val His Ser Glu Thr Phe Pro Pro Lys Tyr Leu His Tyr Asp Gln Glu
                        20                  25                  30

Thr Ser His Gln Leu Leu Cys Asp Lys Cys Pro Pro Gly Thr Tyr Leu
                        35                  40                  45

Lys Gln His Cys Thr Ala Lys Arg Lys Thr Val Cys Ala Pro Cys Pro
                50                  55                  60

Asp His Tyr Tyr Thr Asp Ser Trp His Thr Ser Asp Glu Cys Leu Tyr
    65                  70                  75                  80

Cys Ser Pro Val Cys Lys Glu Leu Gln Tyr Val Lys Gln Glu Cys Asn
                        85                  90                  95

Arg Thr His Asn Arg Val Cys Glu Cys Lys Glu Gly Arg Tyr Leu Glu
                        100                 105                 110

Ile Glu Phe Cys Leu Lys His Arg Ser Cys Pro Pro Gly Phe Gly Val
                        115                 120                 125

Val Gln Ala Gly Thr Pro Glu Arg Asn Thr Val Cys Lys Arg Cys Pro
                130                 135                 140

Asp Gly Phe Phe Ser Asn Glu Thr Ser Ser Lys Ala Pro Cys Arg Lys
    145                 150                 155                 160

His Thr Asn Cys Ser Val Phe Gly Leu Leu Leu Thr Gln Lys Gly Asn
                        165                 170                 175

Ala Thr His Asp Asn Ile Cys Ser Gly Asn Ser Glu Ser Thr Gln Lys
                        180                 185                 190

Cys Gly Ile Asp Val Thr Leu Cys Glu Glu Ala Phe Phe Arg Phe Ala
                        195                 200                 205

Val Pro Thr Lys Phe Thr Pro Asn Trp Leu Ser Val Leu Val Asp Asn
                210                 215                 220

Leu Pro Gly Thr Lys Val Asn Ala Glu Ser Val Glu Arg Ile Lys Arg
    225                 230                 235                 240

Arg His Ser Ser Gln Glu Gln Thr Phe Gln Leu Leu Lys Leu Trp Lys
                        245                 250                 255

His Gln Asn Lys Asp Gln Asp Ile Val Lys Lys Ile Ile Gln Asp Ile
                        260                 265                 270
```

```
Asp Leu Cys Glu Asn Ser Val Gln Arg His Ile Gly His Ala Asn Leu
            275                 280                 285

Thr Phe Glu Gln Leu Arg Ser Leu Met Glu Ser Leu Pro Gly Lys Lys
290                 295                 300

Val Gly Ala Glu Asp Ile Glu Lys Thr Thr Lys Ala Cys Lys Pro Ser
305                 310                 315                 320

Asp Gln Ile Leu Lys Leu Leu Ser Leu Trp Arg Ile Lys Asn Gly Asp
                325                 330                 335

Gln Asp Thr Leu Lys Gly Leu Met His Ala Leu Lys His Ser Lys Thr
            340                 345                 350

Tyr His Phe Pro Lys Thr Val Thr Gln Ser Leu Lys Lys Thr Ile Arg
        355                 360                 365

Phe Leu His Ser Phe Thr Met Tyr Lys Leu Tyr Gln Lys Leu Phe Leu
    370                 375                 380

Glu Met Ile Gly Asn Gln Val Gln Ser Val Lys Ile Ser Cys Leu His
385                 390                 395                 400

His His His His His
            405

<210> SEQ ID NO 159
<211> LENGTH: 635
<212> TYPE: PRT
<213> ORGANISM: Cynomolgus

<400> SEQUENCE: 159

Met Gly Trp Ser Cys Ile Ile Leu Phe Leu Val Ala Thr Ala Thr Gly
1               5                   10                  15

Val His Ser Glu Thr Phe Pro Pro Lys Tyr Leu His Tyr Asp Gln Glu
            20                  25                  30

Thr Ser His Gln Leu Leu Cys Asp Lys Cys Pro Pro Gly Thr Tyr Leu
        35                  40                  45

Lys Gln His Cys Thr Ala Lys Arg Lys Thr Val Cys Ala Pro Cys Pro
    50                  55                  60

Asp His Tyr Tyr Thr Asp Ser Trp His Thr Ser Asp Glu Cys Leu Tyr
65                  70                  75                  80

Cys Ser Pro Val Cys Lys Glu Leu Gln Tyr Val Lys Gln Glu Cys Asn
                85                  90                  95

Arg Thr His Asn Arg Val Cys Glu Cys Lys Glu Gly Arg Tyr Leu Glu
            100                 105                 110

Ile Glu Phe Cys Leu Lys His Arg Ser Cys Pro Pro Gly Phe Gly Val
        115                 120                 125

Val Gln Ala Gly Thr Pro Glu Arg Asn Thr Val Cys Lys Arg Cys Pro
    130                 135                 140

Asp Gly Phe Phe Ser Asn Glu Thr Ser Ser Lys Ala Pro Cys Arg Lys
145                 150                 155                 160

His Thr Asn Cys Ser Val Phe Gly Leu Leu Leu Thr Gln Lys Gly Asn
                165                 170                 175

Ala Thr His Asp Asn Ile Cys Ser Gly Asn Ser Glu Ser Thr Gln Lys
            180                 185                 190

Cys Gly Ile Asp Val Thr Leu Cys Glu Glu Ala Phe Phe Arg Phe Ala
        195                 200                 205

Val Pro Thr Lys Phe Thr Pro Asn Trp Leu Ser Val Leu Val Asp Asn
    210                 215                 220

Leu Pro Gly Thr Lys Val Asn Ala Glu Ser Val Glu Arg Ile Lys Arg
225                 230                 235                 240
```

-continued

Arg His Ser Ser Gln Glu Gln Thr Phe Gln Leu Leu Lys Leu Trp Lys
                245                 250                 255

His Gln Asn Lys Asp Gln Asp Ile Val Lys Ile Ile Gln Asp Ile
            260                 265                 270

Asp Leu Cys Glu Asn Ser Val Gln Arg His Ile Gly His Ala Asn Leu
        275                 280                 285

Thr Phe Glu Gln Leu Arg Ser Leu Met Glu Ser Leu Pro Gly Lys Lys
    290                 295                 300

Val Gly Ala Glu Asp Ile Glu Lys Thr Thr Lys Ala Cys Lys Pro Ser
305                 310                 315                 320

Asp Gln Ile Leu Lys Leu Leu Ser Leu Trp Arg Ile Lys Asn Gly Asp
                325                 330                 335

Gln Asp Thr Leu Lys Gly Leu Met His Ala Leu Lys His Ser Lys Thr
            340                 345                 350

Tyr His Phe Pro Lys Thr Val Thr Gln Ser Leu Lys Lys Thr Ile Arg
        355                 360                 365

Phe Leu His Ser Phe Thr Met Tyr Lys Leu Tyr Gln Lys Leu Phe Leu
    370                 375                 380

Glu Met Ile Gly Asn Gln Val Gln Ser Val Lys Ile Ser Cys Leu Ile
385                 390                 395                 400

Glu Gly Arg Met Asp Glu Pro Lys Ser Cys Asp Lys Thr His Thr Cys
                405                 410                 415

Pro Pro Cys Pro Ala Pro Glu Leu Leu Gly Gly Pro Ser Val Phe Leu
            420                 425                 430

Phe Pro Pro Lys Pro Lys Asp Thr Leu Met Ile Ser Arg Thr Pro Glu
        435                 440                 445

Val Thr Cys Val Val Val Asp Val Ser His Glu Asp Pro Glu Val Lys
    450                 455                 460

Phe Asn Trp Tyr Val Asp Gly Val Glu Val His Asn Ala Lys Thr Lys
465                 470                 475                 480

Pro Arg Glu Glu Gln Tyr Asn Ser Thr Tyr Arg Val Val Ser Val Leu
                485                 490                 495

Thr Val Leu His Gln Asp Trp Leu Asn Gly Lys Glu Tyr Lys Cys Lys
            500                 505                 510

Val Ser Asn Lys Ala Leu Pro Ala Pro Ile Glu Lys Thr Ile Ser Lys
        515                 520                 525

Ala Lys Gly Gln Pro Arg Glu Pro Gln Val Tyr Thr Leu Pro Pro Ser
    530                 535                 540

Arg Asp Glu Leu Thr Lys Asn Gln Val Ser Leu Thr Cys Leu Val Lys
545                 550                 555                 560

Gly Phe Tyr Pro Ser Asp Ile Ala Val Glu Trp Glu Ser Asn Gly Gln
                565                 570                 575

Pro Glu Asn Asn Tyr Lys Thr Thr Pro Pro Val Leu Asp Ser Asp Gly
            580                 585                 590

Ser Phe Phe Leu Tyr Ser Lys Leu Thr Val Asp Lys Ser Arg Trp Gln
        595                 600                 605

Gln Gly Asn Val Phe Ser Cys Ser Val Met His Glu Ala Leu His Asn
    610                 615                 620

His Tyr Thr Gln Lys Ser Leu Ser Leu Ser Pro
625                 630                 635

<210> SEQ ID NO 160
<211> LENGTH: 259

```
<212> TYPE: PRT
<213> ORGANISM: Homo sapiens

<400> SEQUENCE: 160

Met Gly Trp Ser Cys Ile Ile Leu Phe Leu Val Ala Thr Ala Thr Gly
1               5                   10                  15

Val His Ser Asp Tyr Lys Asp Asp Asp Lys Arg Met Lys Gln Ile
                20                  25                  30

Glu Asp Lys Ile Glu Glu Ile Leu Ser Lys Ile Tyr His Ile Glu Asn
            35                  40                  45

Glu Ile Ala Arg Ile Lys Lys Leu Ile Gly Glu Arg Gly Gly Gly Ser
        50                  55                  60

Gly Gly Gly Ser Gly Gly Gly Ser Thr Ser Glu Glu Thr Ile Ser Thr
65                  70                  75                  80

Val Gln Glu Lys Gln Gln Asn Ile Ser Pro Leu Val Arg Glu Arg Gly
                85                  90                  95

Pro Gln Arg Val Ala Ala His Ile Thr Gly Thr Arg Gly Arg Ser Asn
            100                 105                 110

Thr Leu Ser Ser Pro Asn Ser Lys Asn Glu Lys Ala Leu Gly Arg Lys
        115                 120                 125

Ile Asn Ser Trp Glu Ser Ser Arg Ser Gly His Ser Phe Leu Ser Asn
130                 135                 140

Leu His Leu Arg Asn Gly Glu Leu Val Ile His Glu Lys Gly Phe Tyr
                150                 155                 160
145

Tyr Ile Tyr Ser Gln Thr Tyr Phe Arg Phe Gln Glu Glu Ile Lys Glu
                165                 170                 175

Asn Thr Lys Asn Asp Lys Gln Met Val Gln Tyr Ile Tyr Lys Tyr Thr
            180                 185                 190

Ser Tyr Pro Asp Pro Ile Leu Leu Met Lys Ser Ala Arg Asn Ser Cys
        195                 200                 205

Trp Ser Lys Asp Ala Glu Tyr Gly Leu Tyr Ser Ile Tyr Gln Gly Gly
210                 215                 220

Ile Phe Glu Leu Lys Glu Asn Asp Arg Ile Phe Val Ser Val Thr Asn
225                 230                 235                 240

Glu His Leu Ile Asp Met Asp His Glu Ala Ser Phe Phe Gly Ala Phe
                245                 250                 255

Leu Val Gly

<210> SEQ ID NO 161
<211> LENGTH: 182
<212> TYPE: PRT
<213> ORGANISM: Homo sapiens

<400> SEQUENCE: 161

Gly Ser Gln His Ile Arg Ala Glu Lys Ala Met Val Asp Gly Ser Trp
1               5                   10                  15

Leu Asp Leu Ala Lys Arg Ser Lys Leu Glu Ala Gln Pro Phe Ala His
                20                  25                  30

Leu Thr Ile Asn Ala Thr Asp Ile Pro Ser Gly Ser His Lys Val Ser
            35                  40                  45

Leu Ser Ser Trp Tyr His Asp Arg Gly Trp Gly Lys Ile Ser Asn Met
        50                  55                  60

Thr Phe Ser Asn Gly Lys Leu Ile Val Asn Gln Asp Gly Phe Tyr Tyr
65                  70                  75                  80

Leu Tyr Ala Asn Ile Cys Phe Arg His His Glu Thr Ser Gly Asp Leu
```

85                  90                  95
Ala Thr Glu Tyr Leu Gln Leu Met Val Tyr Val Thr Lys Thr Ser Ile
                100                 105                 110

Lys Ile Pro Ser Ser His Thr Leu Met Lys Gly Gly Ser Thr Lys Tyr
            115                 120                 125

Trp Ser Gly Asn Ser Glu Phe His Phe Tyr Ser Ile Asn Val Gly Gly
        130                 135                 140

Phe Phe Lys Leu Arg Ser Gly Glu Glu Ile Ser Ile Glu Val Ser Asn
145                 150                 155                 160

Pro Ser Leu Leu Asp Pro Asp Gln Asp Ala Thr Tyr Phe Gly Ala Phe
                165                 170                 175

Lys Val Arg Asp Ile Asp
                180

<210> SEQ ID NO 162
<211> LENGTH: 315
<212> TYPE: DNA
<213> ORGANISM: Homo sapiens

<400> SEQUENCE: 162
cagcccaagg ctgcccctc  ggtcactctg ttcccaccct cctctgagga gcttcaagcc     60
aacaaggcca cactggtgtg tctcgtaagt gacttcaacc cgggagccgt gacagtggcc    120
tggaaggcag atggcagccc cgtcaaggtg ggagtggaga ccaccaaacc ctccaaacaa    180
agcaacaaca gtatgcggc cagcagctac ctgagcctga cgcccgagca gtggaagtcc    240
cacagaagct acagctgccg ggtcacgcat gaagggagca ccgtggagaa gacagtggcc    300
cctgcagaat gctct                                                    315

<210> SEQ ID NO 163
<211> LENGTH: 105
<212> TYPE: PRT
<213> ORGANISM: Homo sapiens

<400> SEQUENCE: 163

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Val Ser Asp Phe
            20                  25                  30

Asn Pro Gly Ala Val Thr Val Ala Trp Lys Ala Asp Gly Ser Pro Val
        35                  40                  45

Lys Val Gly Val Glu Thr Thr Lys Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Arg Val Thr His Glu Gly Ser Thr Val Glu
                85                  90                  95

Lys Thr Val Ala Pro Ala Glu Cys Ser
            100                 105